US012606850B2

(12) United States Patent
Vemuri et al.

(10) Patent No.: US 12,606,850 B2
(45) **Date of Patent: *Apr. 21, 2026**

(54) SYNTHESIS OF BETA-HYDROXYISOVALERATE AND METHODS OF USE

(71) Applicant: Sasya Inc., Saint Paul, MN (US)

(72) Inventors: Goutham Vemuri, Maple Grove, MN (US); Christopher Lindsay, Saint Paul, MN (US); Kevin Roberg-Perez, Minneapolis, MN (US); Christopher D. Snow, Saint Paul, MN (US); Elizabeth A. Cameron, New Brighton, MN (US)

(73) Assignee: Sasya, Inc., St. Paul, MN (US)

( * ) Notice: Subject to any disclaimer, the term of this patent is extended or adjusted under 35 U.S.C. 154(b) by 94 days.

This patent is subject to a terminal disclaimer.

(21) Appl. No.: 18/594,617

(22) Filed: Mar. 4, 2024

(65) Prior Publication Data

US 2025/0002949 A1 Jan. 2, 2025

Related U.S. Application Data

(63) Continuation of application No. 17/658,217, filed on Apr. 6, 2022, now Pat. No. 11,920,177.
(Continued)

(51) Int. Cl.
*C12P 7/16* (2006.01)
*C12N 1/20* (2006.01)
(Continued)

(52) U.S. Cl.
CPC .................. *C12P 7/16* (2013.01); *C12N 1/20* (2013.01); *C12N 9/0006* (2013.01); *C12N 9/88* (2013.01);
(Continued)

(58) Field of Classification Search
CPC ........... C12P 7/16; C12N 1/20; C12N 9/0006; C12N 9/88; C12N 15/52; C12Y 101/01086
See application file for complete search history.

(56) References Cited

U.S. PATENT DOCUMENTS 10,676,765 B2 6/2020 Philippe et al.
2012/0220001 A1 8/2012 Philippe
(Continued)

FOREIGN PATENT DOCUMENTS

AU 749323 5/1999
CN 109251940 1/2019
(Continued)

OTHER PUBLICATIONS

NP_058929.1; https://www.ncbi.nlm.nih.gov/protein/NP_058929.1?report=genbank&log$=prottop&blast_rank=1&RID=828VXU63015; accessed Jul. 23, 2025 (Year: 2025).*
(Continued)

*Primary Examiner* — Louise W Humphrey
*Assistant Examiner* — Candice Lee Swift
(74) *Attorney, Agent, or Firm* — DeWitt LLP

(57) ABSTRACT

The biological production of beta-hydroxyisovalerate (βHIV) using a non-natural microorganism. The non-natural microorganism for the biologically-derived βHIV provides more beta-hydroxyisovalerate synthase activity than the wild-type parent. The non-natural microorganism can host a non-natural enzyme, such as the non-natural enzyme expressed in a yeast or bacteria, wherein the non-natural microorganism comprises an active βHIV metabolic pathway for the production of βHIV. The biological derivation of βHIV eliminates toxic by-products and impurities that result from the chemical production of βHIV, such that βHIV produced by a non-natural microorganism prior to any
(Continued)

isolation or purification process has not been in substantial contact with any halogen-containing component.

33 Claims, 5 Drawing Sheets

Specification includes a Sequence Listing.

Related U.S. Application Data

(60) Provisional application No. 63/171,418, filed on Apr. 6, 2021.

(51) Int. Cl.
*C12N 9/04* (2006.01)
*C12N 9/88* (2006.01)
*C12N 15/52* (2006.01)

(52) U.S. Cl.
CPC ...... *C12N 15/52* (2013.01); *C12Y 101/01086* (2013.01)

(56) References Cited

U.S. PATENT DOCUMENTS

| | | | |
|---|---|---|---|
| 2022/0315954 | A1 | 10/2022 | Vemuri et al. |
| 2022/0325304 | A1 | 10/2022 | Vemuri et al. |

FOREIGN PATENT DOCUMENTS

| | | |
|---|---|---|
| CN | 111349644 | 6/2020 |
| EP | 2669372 | 7/2016 |
| WO | WO2009144079 | 12/2009 |
| WO | WO2011032934 | 3/2011 |
| WO | WO2012021785 | 2/2012 |

OTHER PUBLICATIONS

Gao, Ruichen, and Zhimin Li. "Biosynthesis of 3-Hydroxy-3-Methylbutyrate from L-Leucine by whole-cell catalysis." Journal of Agricultural and Food Chemistry 69.12 (2021): 3712-3719. (Year: 2021).*

Application and File History for U.S. Appl. No. 17/658,217, filed Apr. 6, 2022, inventors Vemuri et al.

Griswold, A. (2008) Genome packaging in prokaryotes: the circular chromosome of *E. coli.* Nature Education 1(1):57 (Year: 2008).

Kyoto Encyclopedia of Genes and Genomes, Butanoate Metabolism; https://www.genome.jp/pathway/sce00650; accessed Mar. 29, 2023 (Year: 2023).

Schoch CL, et al. NCBI Taxonomy: a comprehensive update on curation, resources and tools. Database (Oxford). 2020: baaa062. PubMed: 32761142 PMC: PMC7408187. (Year: 2023).

Application and File History for U.S. Appl. No. 17/658,214, filed Apr. 6, 2022, inventors Vemuri et al.

Uniprot, Accession No. A0A8J6FY38, 2022, www.uniprot.gov (Year:2022).

Wang et al., Improvement of L-Leucine Production of Corynebacterium Glutamicum, Int. J .Molecular Sciences 20, 2019, 2020 (Year: 2019).

Adlington, Stereochemistry of Hydroxylation During the Conversion of alpha-Ketoisocaproate to beta-Hydroxyisovalerate by 4-Hydroxyphenylpyruvate Dioxygenase, Bioorg. Med. Chem. Lett. 6, 1996, 2721-24 (Year: 1996).

Lee et al., Control of fed-batch fermentations, Biotechnol. Adv. 17, 1999. 29-48 (Year: 1999).

International Search Report and Written Opinion for PCTUS2022023728 date mailed Sep. 9, 2022.

Baldwin et al., "4-Hydroxyphenylpyruvate Dioxygenase Appears to Display α-ketoisocaproate Dioxygenase Activity in Rat Liver", Bioorganic & Medicinal Chemistry Letters, vol. 6, No. 12., pp. 1255-1260, (1995).

Liu et al., "Identification of Key Residues Determining the Binding Specificity of Human 4-hydroxyphenylpyruvate Dioxygenase", European Journal of Pharmaceutical Sciences, (2020).

Extended EP Search Report for EP Application No. 22785397 date mailed Jun. 2, 2025.

* cited by examiner

SYNTHESIS OF BETA-HYDROXYISOVALERATE AND METHODS OF USE

PRIORITY CLAIM

This application is a continuation of U.S. application Ser. No. 17/658,217 filed Apr. 6, 2022 (now U.S. Pat. No. 11,920,177 issued Mar. 5, 2024), which claims the benefit of U.S. Provisional Application No. 63/171,418 filed Apr. 6, 2021, which are hereby incorporated by reference in their entirety.

SEQUENCE LISTING XML INCORPORATION BY REFERENCE

A Sequence Listing is provided herewith this disclosure as a Sequence Listing XML, "Sasya 104115.0012.xml" created on Aug. 14, 2024 and having a size of 528 KB, which contains the same disclosure as ASCII plain text file "0002_SequenceListing_.txt" created on Apr. 6, 2022 and having size of 848 KB, which was originally filed in U.S. application Ser. No. 17/658,217 on Apr. 6, 2022, such that both the Sequence Listing XML and ASCII plain text file contain the same Sequence Listing disclosure, and both of which are incorporated by reference in their entirety herein.

FIELD OF THE INVENTION

The present disclosure generally relates to biological processes of producing beta hydroxyisovalerate, more particularly methods to create non-natural microorganisms comprising non-natural βHIV synthase enzymes and processes for using said microorganisms to produce beta hydroxyisovalerate, and more specifically to non-natural microorganisms that produce beta hydroxyisovalerate.

BACKGROUND

The beta hydroxyisovalerate (βHIV) molecule (shown below), which is also known as 3-hydroxy-3-methylbutric acid, has potential applications ranging from liquid crystals to pharmaceutical ingredients and dietary supplements.

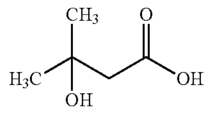

As such, a number of methods to produce β-hydroxyisovalerate are known in the art. They are mainly centered around chemical, organic synthesis starting with 4-hydroxy-4-methyl-2-pentanone. βHIV can be synthesized by the oxidation of 4-hydroxy-4-methyl-2-pentanone. One suitable procedure is described by Coffman et al., J. Am. Chem. Soc. 80: 2882-2887 (1958). See also, for example, U.S. Pat. Nos. 6,248,922, 6,090,978 U.S. 1016471653, U.S. Pat. No. 6,090,918 and U.S. 2014025698. As described therein, βHIV is synthesized by an alkaline sodium hypochlorite oxidation of diacetone alcohol. The product is recovered in free acid form, which can be converted to a salt. For example, βHIV can be prepared as its calcium salt by a procedure similar to that of Coffman et al. (1958) in which the free acid of βHIV is neutralized with calcium hydroxide and recovered by crystallization from an aqueous ethanol solution.

Biological methods to produce βHIV are also known. For example, βHIV can also be prepared by the conversion of 3-methylcrotonate (3-methylbut-2-enoate) by cell-free extracts of *Galactomyces reessii* [Dhar and JPN Rosazza. Journal of Industrial Microbiology & Biotechnology 2002, 28, 81-87]. Cell free extracts of *Galactomyces reessii* contain an enoyl CoA hydratase that can catalyze the transformation of 3-methylcrotonic acid to βHIV. Resting cells of *Galactomyces reessii* could convert β-methylbutyrate into β-hydroxyisovalerate [Lee I Y, Nissen S L, Rosazza J P. Applied and environmental microbiology 1997, 63(11): 4191-4195; Lee I Y, Rosazza J P. Arch. Microbiol., 1998 March; 169(3):257-62]. Using a two-step fed-batch fermentation process where biomass was first produced to sufficient density in the first step, followed by the addition of β-methylbutyrate to the washed biomass in the second step, Lee et al. reported producing 38 g/L of βHIV. U.S. Pat. No. 10,676,765B2 describes an alternative enzymatic method to produce βHIV through the conversion of 3-methylcrotonyl-CoA into βHIV via 3-hydroxy-3-methylbutyryl-CoA. The availability of 3-methylcrotonic acid or β-methylbutyrate in economically viable quantities for in vitro or in vivo production of βHIV is still a challenge that needs to be overcome before this process can become commercially viable.

Indeed, βHIV is synthesized in humans through the metabolism of L-leucine (see for example Nutrient Metabolism, Martin Kohlmeier, Academic Press, 2015) as a result of the conversion of its keto acid, α-ketoisocaproate (KIC) by the promiscuous action of 4-hydroxyphenylpyruvate dioxygenase (HPPD). Dioxygenases are enzymes that incorporate diatomic oxygen to form oxo-intermediates. To reduce diatomic oxygen, these enzymes require a source of electrons as well as a cofactor capable of one-electron chemistry. The ferrous ion is the most common cofactor capable of localizing substrates by acting as a conduit to transfer the electrons from the substrates to oxygen. Common coordinated reductant for the ferrous ion is the α-keto acid moiety and α-keto acid dependent oxygenases are very versatile and play a key role in the secondary metabolism [Purpero and Moran, J. Biol. Inorg. Chem. 12 (2007) 587-601].

A majority of the α-keto acid dependent oxygenases have three substrates—oxygen, α-ketoglutarate (the source of the α-keto acid) and the substrate, whose transformation is the catalytic objective [Hausinger, Crit. Rev. Biochem. Mol. Biol. 39 (2004) 21-68]. HPPD and hydroxymandelate synthase (HMS) are an exception to this general principal by having only two substrates. HPPD and HMS receive electrons from their common α-keto acid substrate, 4-hydroxyphenylpyruvate (HPP), and also transform it into their hydroxylated and decarboxylated products homogentisate and hydroxymandelate, respectively, without the need for α-ketoglutarate. These two enzymes are believed to have evolved from an entirely different lineage than all other α-keto acid oxygenases [Moran, G. M., Archives of Biochemistry and Biophysics 544 (2014) 58-68] although their core catalytic mechanism is consistent with the enzyme family.

There is a large body of literature on HPPD, owing to its importance in agriculture and medicine. The primary product of HPPD reaction is homogentisate, which is the precursor to plastoquinone and tocopherols in plants and archaea. They are intimately involved in electron transport in the photosynthetic system, serve as antioxidants and plant hormones. Therefore, inhibiting the synthesis of homogentisate is commonly used to inhibit the growth of plants and weeds. A number of molecules such as leptospermone and usnic acid and their similars inhibit HPPD activity and are used as ingredients in herbicides [Beaudegnies et al., Bioorg. Med. Chem. 17 (2009) 4134-4152]. HPPD inhibitors such as NTBC (nitisinone) is used to treat Type 1 tyrosinemia. Inborn genetic errors leading to aberrant metabolic enzymes in the catabolism of homogentisate causes Type 1 tyrosinemia. NTBC has been used as a treatment by repressing the synthesis of homogentisate by inhibiting HPPD [Lindstedt et al., Lancet 340 (1992) 813-817].

Interestingly, HPPD was also shown to produce βHIV as a result of its promiscuity towards α-ketoisocaproate, the keto acid of leucine [Crouch N P, E. Baldwin, M.-H. Lee, C. H. Mackinnon, Z. H. Zhang, Bioorg Med Chem Lett 1996, 6(13):1503-1506]. In addition to its involvement in aromatic amino acid metabolism, HPPD is involved in the metabolism of leucine by converting excess α-ketoisocaproate into βHIV [Crouch N P, Lee M H, Iturriagagoitia-Bueno T, Mackinnon C H. Methods in enzymology 2000, 324:342-355]. Prior to the elucidation of the promiscuity of HPPD, a dedicated dioxygenase to transform α-ketoisocaproate into βHIV was alleged to exist [Sabourin P J, Bieber L L: The Journal of biological chemistry 1982, 257(13):7468-7471; Sabourin P J, Bieber L L: Methods in enzymology 1988, 166:288-297; Sabourin P J, Bieber L L: Metabolism: clinical and experimental 1983, 32(2):160-164; Xu et al., Biochemical and Biophysical Research Communications 276, (2000), 1080-1084]. Baldwin et al., (1995) published early reports of HPPD having several fold higher activity with HPP than with α-ketoisocaproate [Baldwin et al., Bioorganic and Medicinal Chemistry Letters, 5(12) (1995), 1255-1260]. Subsequently, sequence studies and further biochemical analyses by Crouch et al, (1996) and Crouch et al., (2000) confirmed that the alleged dioxygenase was HPPD which catalyzed the conversion of α-ketoisocaproate into βHIV as a result of its promiscuity. Indeed, Crouch et al., 1996 suggested any further reference to HPPD as α-ketoisocaproate dioxygenase be discontinued. The promiscuity of HPPD is also evident by its transformation of 2-keto-4-(methylthio)butyric acid, the keto acid of methionine [Adlington, R. M., et al., Bioorganic & Medicinal Chemistry Letters, Volume 6, Issue 16, 20 Aug. 1996, 2003-2006].

There are several examples in the food, pharmaceutical, animal feed, biofuel, and biopolymer industries of producing ingredients through the use of metabolically engineered microorganisms and employing them in a fermentation process. Not all microorganisms are suited for the production of products. For example, bacteria are conventionally better suited for the production of amino acids, vitamins and enzymes while yeasts are better suited for the production of alcohols and organic acids. Therefore, selecting the appropriate microorganism to produce βHIV is critical. This disclosure relates to methods of selecting a microorganism for βHIV production.

Given that βHIV is produced using chemical processes that are not only energy-intensive, but also result in toxic by-products, there is a clear and urgent need to develop environmentally benign processes that use renewable feedstocks. There is also a need for the production of high quality βHIV that is cost-effective and efficiently produced.

SUMMARY

The subject of the present disclosure satisfies the need and provides related advantages as well. Provided herein are certain embodiments to create non-natural microorganisms to express or overexpress the βHIV metabolic pathway, methods of making these microorganisms, and using the microorganisms to produce βHIV.

Provided herein are methods to select and engineer microorganisms to produce beta hydroxyisovalerate (βHIV) and uses of the engineered, non-natural microorganisms. This disclosure also provides methods of producing βHIV by culturing the genetically modified microorganisms in the presence of at least one carbon source, then isolating βHIV from the culture. In certain embodiments, the carbon source is one or more of glucose, xylose, arabinose, sucrose and lactose.

In some embodiments, a non-natural microorganism comprises a metabolic pathway relating to one or more steps of (i) pyruvate to acetolactate, (ii) acetolactate to 2,3-dihydroxyisovalerate, (iii) 2,3-dihydroxyisovalerate to α-ketoisovalerate, (iv) α-ketoisovalerate to α-isopropylmalate, (v) α-isopropylmalate to β-isopropylmalate, (vi) β-isopropylmalate to α-ketoisocaproate and (vii) α-ketoisocaproate to βHIV. In some aspects, if the non-natural microorganism has different cellular compartments, one or more genes for the one or more steps (i) to (vii) for the metabolic pathway encodes an enzyme that is localized to the cytosol.

In some embodiments, a non-natural microorganism comprises a metabolic pathway relating to one or more steps of (i) pyruvate into acetolactate, (ii) acetolactate into 2,3-dihydroxyisovalerate, (iii) 2,3-dihydroxyisovalerate into α-ketoisovalerate, (iv) α-ketoisovalerate into 2-isopropylmalate, (v) 2-isopropylmalate into 2-isopropylmaleate, (vi) 2-isopropylmaleate into 3-isopropylmalate, (vii) 3-isopropylmalate into 2-isopropyl-3-oxosuccinate, (viii) 2-isopropyl-3-oxosuccinate into α-ketoisocaproate, and (ix) α-ketoisocaproate into βHIV. In some aspects, one or more genes for the one or more steps (i) to (ix) of the metabolic pathway encodes an enzyme that is localized to the cytosol.

In some embodiments, the non-natural microorganism expresses or overexpresses at least one of the genes encoding for acetolactate synthase, keto-acid reductoisomerase, dihydroxyacid dehydratase, 2-isopropylmalate synthase, isopropylmalate isomerase, 3-isopropylmalate dehydrogenase and βHIV synthase. In some aspects, the non-natural microorganism expresses or overexpresses two or more genes encoding for acetolactate synthase, keto-acid reductoisomerase, dihydroxyacid dehydratase, 2-isopropylmalate synthase, isopropylmalate isomerase, 3-isopropylmalate dehydrogenase and βHIV synthase.

In certain embodiments, the non-natural microorganisms having compartmentalized metabolism comprise a βHIV producing metabolic pathway with at least one βHIV pathway enzyme localized in the cytosol. In an exemplary embodiment, the non-natural microorganisms comprise a βHIV producing metabolic pathway with all the βHIV pathway enzymes localized in the cytosol.

In some embodiments, the non-natural eukaryotic microorganism expresses or overexpresses at least one of the genes encoding for cytosolic acetolactate synthase, cytosolic keto-acid reductoisomerase, cytosolic dihydroxyacid dehydratase, cytosolic 2-isopropylmalate synthase, cytosolic isopropylmalate isomerase, cytosolic 3-isopropylmalate dehydrogenase and cytosolic βHIV synthase. In some aspects, the non-natural eukaryotic microorganism expresses or overexpresses two or more genes encoding for cytosolic acetolactate synthase, cytosolic keto-acid reductoisomerase, cytosolic dihydroxyacid dehydratase, cytosolic 2-isopropylmalate synthase, cytosolic isopropylmalate isomerase, cytosolic 3-isopropylmalate dehydrogenase and cytosolic βHIV synthase.

In some embodiments, the non-natural microorganism comprises at least one nucleic acid encoding a polypeptide with beta hydroxyisovalerate synthase activity wherein said polypeptide is at least about 65% identical to at least one polypeptide selected from SEQ ID NOs: 1-3. In certain embodiments, the polypeptide with βHIV synthase activity is derived from *Rattus norvegicus*.

In certain embodiments, the non-natural microorganism comprises at least one nucleic acid encoding a polypeptide with βHIV synthase activity wherein said polypeptide is at least about 65% identical to at least one polypeptide selected from SEQ ID NOs: 4-5. In certain embodiments, the polypeptide with HIV synthase activity is derived from *Yarrowia lipolytica*. In certain embodiments, the non-natural microorganism comprises at least one nucleic acid encoding a polypeptide with βHIV synthase activity wherein said polypeptide is at least about 65% identical to at least one polypeptide selected from SEQ ID NOs: 6-8. In certain embodiments, the polypeptide with βHIV synthase activity is derived from *Homo sapiens*.

In another embodiment, the non-natural microorganism comprises a dioxygenase enzyme which has been modified or mutated to increase the ability of the enzyme to preferentially utilize α-ketoisocaproate as its substrate. According to certain aspects of the present invention, the non-natural enzyme comprises one or more dioxygenase enzymes having one or more modifications or mutations at substrate-specificity positions corresponding to amino acids selected from A361, F336, F347, F364, F368, F371, G362, I227, I252, L224, L289, L323, L367, N187, N241, N363, P239, Q251, Q265, S226, V212, V217, V228 and W210 of SEQ ID NO: 1.

In some aspects, at least one of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 1 has been replaced with one of the corresponding disclosed amino acids to alter the respective substrate-specificity residue.

In some other aspects, two or more of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 1 have been replaced with one of the corresponding disclosed amino acids to alter the respective substrate-specificity residue.

In yet some other aspects, at least 3 and up to 24 of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 1 have been replaced with one of the corresponding disclosed amino acids to alter the respective substrate-specificity residue.

According to certain aspects of the present invention, the non-natural enzyme comprises one or more modifications at substrate-specificity positions corresponding to amino acids selected from A361, F336, F347, F364, F368, F371, G362, I227, I252, L224, L289, L323, L367, N187, N241, N363, P239, Q251, Q265, S226, V212, V217, V228 and W210 of SEQ ID NO: 6.

In some aspects, at least one of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 6 has been replaced with one of the corresponding disclosed amino acids to alter the respective substrate-specificity residue.

In some other aspects, two or more of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 6 have been replaced with one of the corresponding disclosed amino acids to alter the respective substrate-specificity residue.

In yet some other aspects, at least 3 and up to 24 of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 6 have been replaced with one of the corresponding disclosed amino acids to alter the respective substrate-specificity residue.

In certain embodiments, the non-natural microorganisms may be prokaryotic microorganisms. In another embodiment, the non-natural microorganism may be an eukaryotic microorganism. In certain embodiments, the non-natural eukaryotic microorganisms may be non-natural yeast microorganisms. In some embodiments, the non-natural yeast may be Crabtree-negative yeasts. In some embodiments, the non-natural yeast microorganism may be selected from the group consisting of *Saccharomyces, Kluyveromyces, Pichia, Issatchenkia, Hansenula*, or *Candida*.

In another embodiment, the non-natural microorganism may be cultivated in a culture medium containing a feedstock providing the carbon source until a recoverable quantity of βHIV is produced and optionally, recovering the βHIV. In certain embodiments, the non-natural microorganism produces βHIV from a carbon source with a yield of at least about 0.1 percent of theoretical yield. In another aspect, the non-natural microorganism produces βHIV from a carbon source with a yield of at least 1 percent of theoretical yield. In another aspect, the non-natural microorganism produces βHIV from a carbon source with a yield of at least about 5 percent of theoretical yield. In another aspect, the non-natural microorganism produces βHIV from a carbon source with a yield of at least 20 percent of theoretical yield. In another aspect, the non-natural microorganism produces βHIV from a carbon source with a yield of at least 50 percent, at least about 75 percent, at least about 80 percent, or at least about 85 percent of the theoretical yield.

In some aspects, the non-natural microorganism produces βHIV from a carbon source with a yield of at least about 0.1 percent up to 100 percent of theoretical yield, in some aspects at least about 1 percent up to 99.9 percent of theoretical yield, in some aspects at least about 5 percent up to about 99.5 of theoretical yield, in some aspects at least 20 percent up to about 99.5 percent of theoretical yield, in some aspects at least 50 percent up to about 99.5 percent of theoretical yield, in some aspects at least about 75 percent up to about 99.5 percent of theoretical yield, in some aspects at least about 80 percent up to about 99.5 percent of theoretical yield, and in some aspects at least about 85 percent up to about 99.5 percent of theoretical yield.

In some embodiments, the present invention is directed to a composition comprising βHIV produced by a non-natural microorganism, wherein the βHIV prior to any isolation or purification process has not been in substantial contact with any component comprising a halogen-containing component. In some aspects, the halogen-containing component is a chemical derivative produced by a typical chemical production process of βHIV. In some aspects, the halogen-containing component comprises hydrochloric acid and/or chloroform.

The above summary is not intended to describe each illustrated embodiment or every implementation of the subject matter hereof. The figures and the detailed description that follow more particularly exemplify various embodiments.

BRIEF DESCRIPTION OF THE FIGURES

Subject matter hereof may be more completely understood in consideration of the following detailed description of various embodiments in connection with the accompanying figures, in which.

Figure 1:
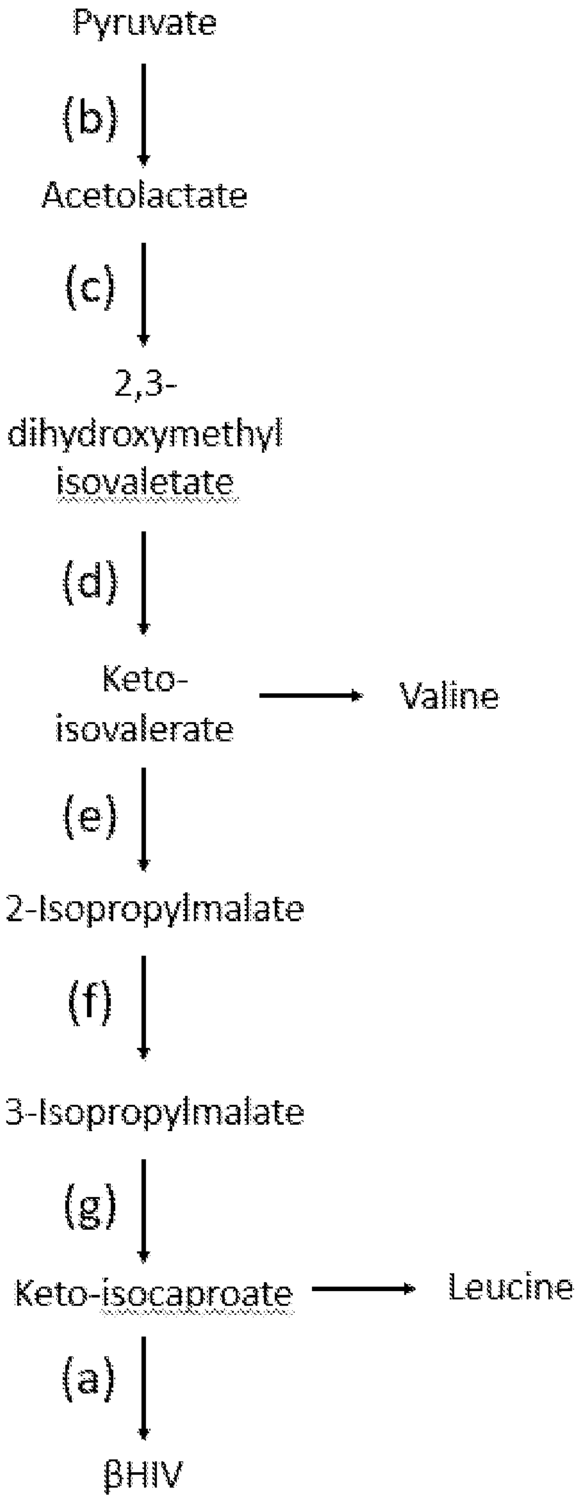
FIG. 1 illustrates a βHIV metabolic pathway, according to certain embodiments of the present invention. According to some aspects this disclosure, the metabolic pathway can also comprise an active transporter to transport βHIV out of the non-natural microorganism.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE INVENTION

The following description of the present disclosure is merely intended to illustrate various embodiments. As such, the specific modifications discussed are not to be construed as limitations on the scope of the present disclosure. It will be apparent to one skilled in the art that various equivalents, changes, and modifications may be made without departing from the scope of the present disclosure, and it is understood that such equivalent embodiments are to be included herein. All references cited herein are incorporated by reference in their entirety.

The present disclosure relates to non-natural microorganisms and the use of said microorganisms in a fermentation process to produce higher value products such as organic acids. More specifically, the present disclosure relates to engineered microorganisms that produce β-hydroxyisovaleric acid (βHIV). As a molecule with unique structure, βHIV has potential applications ranging from liquid crystals to pharmaceutical ingredients and dietary supplements.

As used herein, "β-hydroxyisovalerate" or "beta hydroxyisovalerate" or "βHIV" or "β-hydroxy-β-methylbutyrate" or "3-hydroxy-3-methylbutyric acid" refer to the same compound having the following molecular structures (free acid form on left and conjugate base on the right).

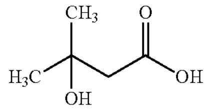

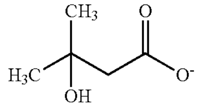

Furthermore, these terms not only include the free acid form or conjugate base, but also the salt form with a cation and derivatives thereof, or any combination of these compounds. For instance, a calcium salt of βHIV includes calcium βHIV hydrate having the following molecular structure.

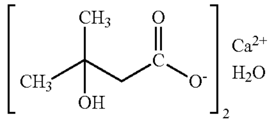

While the foregoing terms mean any form of βHIV, the form of βHIV used within the context of the present disclosure preferably is selected from the group comprising of a free acid, a calcium salt, an ester and a lactone.

As used herein, the term "microorganism" refers to a prokaryote such as a bacterium or a eukaryote such as a yeast or a fungus. As used herein, the term "non-natural microorganism" refers to a microorganism that has at least one genetic alteration not normally found in a naturally occurring strain of the species, including wild-type strains of the reference species. Genetic alterations include, for example, human-intervened modifications introducing expressible nucleic acids encoding polypeptides, other nucleic acid additions, nucleic acid deletions and/or other functional disruption of the microorganism's genetic material. When a microorganism is genetically engineered to overexpress a given enzyme, it is manipulated such that the host cell has the capability to express, and preferably, overexpress an enzyme, thereby increasing the biocatalytic capability of the cell. When a microorganism is engineered to inactivate a gene, it is manipulated such that the host cell has decreased, and preferably, lost the capability to express an enzyme. As used herein, the term "overexpress" refers to increasing the expression of an enzyme to a level greater than the cell normally produces. The term encompasses overexpression of endogenous as well as exogenous enzymes. As used herein, the terms "gene deletion" or "gene knockout" or "gene disruption" refer to the targeted disruption of the gene in vivo resulting in the removal of one or more nucleotides from the genome resulting in decreased or loss of function using genetic manipulation methods such as homologous recombination, directed mutagenesis or directed evolution.

As used herein, the term "gene" refers to a nucleic acid sequence that can be transcribed into messenger RNA and further translated into protein.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

Usually, the nucleotide sequence encoding an enzyme is operably linked to a promoter that causes sufficient expression of the corresponding nucleotide sequence in the host microorganism according to the present disclosure to confer to the cell the ability to produce β-hydroxyisovaleric acid. As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. In order to increase the likelihood that an exogenous gene is translated into an enzyme that is in active form, the corresponding nucleotide sequence may be adapted to optimize its codon usage to that of the chosen host microorganism. Several methods for codon optimization are known in the art and are embedded in computer programs such as CodonW, GenSmart, CodonOpt, etc.

As used herein, the term "promoter" refers to a nucleic acid fragment that functions to control the transcription of one or more genes, located upstream with respect to the direction of transcription of the transcription initiation site of the gene, and is structurally identified by the presence of a binding site for a nucleic acid polymerase, transcription initiation sites and any other DNA sequences known to one of skill in the art. A "constitutive" promoter is a promoter that is active under most environmental and developmental conditions. An "inducible" promoter is a promoter that is active under environmental or developmental regulation.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

The term "enzyme" as used herein is defined as a protein which catalyzes a (bio) chemical reaction in a cell. The interaction of an enzyme with other molecules such as the substrate can be quantified by the Michaelis constant ($K_M$), which indicates the affinity of the substrate to the active site of the enzyme. $K_M$ can be quantified using prior art (see for example, Stryer, Biochemistry, 4th edition, W. H. Freeman, Nelson and Cox, Lehninger Principles of Biochemistry, 6th edition, W. H. Freeman). The rate of biocatalysis or enzymatic activity is defined by $k_{cat}$, which is the enzyme turnover number. Therefore, the ratio of the rate of enzymatic activity to the substrate affinity is widely considered to be representative of an enzyme's catalytic efficiency. As defined herein, the efficiency of an enzyme to act on a specific substrate is quantified by the ratio of $k_{cat}/K_M$. Therefore, an enzyme with higher value of $k_{cat}/K_M$ for a certain substrate can catalyze the reaction more efficiently than another enzyme with a lower value of $k_{cat}/K_M$ for the same substrate. A non-natural enzyme refers to an enzyme that comprises at least one amino acid alteration at the desired position that is not normally found in nature. Amino acid alternations include, for example, human-intervened modifications introducing replacing one naturally occurring amino acid with another, addition or deletion of amino acids such that the modified enzyme has the capability of enhanced catalytic activity.

As used herein, β-hydroxyisovalerate synthase refers to an enzyme that can catalyze the conversion of α-ketoisocaproate into βHIV. One Unit (U) of βHIV synthase activity is defined here as the amount of enzyme needed to convert one micromole of α-ketoisocaproate into βHIV in one minute under the reaction conditions. Accordingly, a variant of βHIV synthase that can convert more α-ketoisocaproate into βHIV than the same amount of another variant is preferred.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product. As used herein, the term "βHIV metabolic pathway" or "βHIV pathway" refers to an enzyme pathway which produces βHIV from pyruvate, as illustrated in FIGS. 1 or FIG. 2.

The present disclosure relates to a non-natural microorganism for producing βHIV. Tolerance to high concentrations of βHIV is an important trait of a suitable microorganism. An ideal microorganism to enable βHIV production is capable of conducting fermentation at low pH levels to decrease downstream recovery costs, resulting in more economical production. Additional characteristics of a suitable microorganism include rapid growth and exhibit overall process robustness.

In some embodiments, the subject of the present disclosure relates to a non-natural microorganism having an active βHIV metabolic pathway from pyruvate to βHIV.

Figure 2:
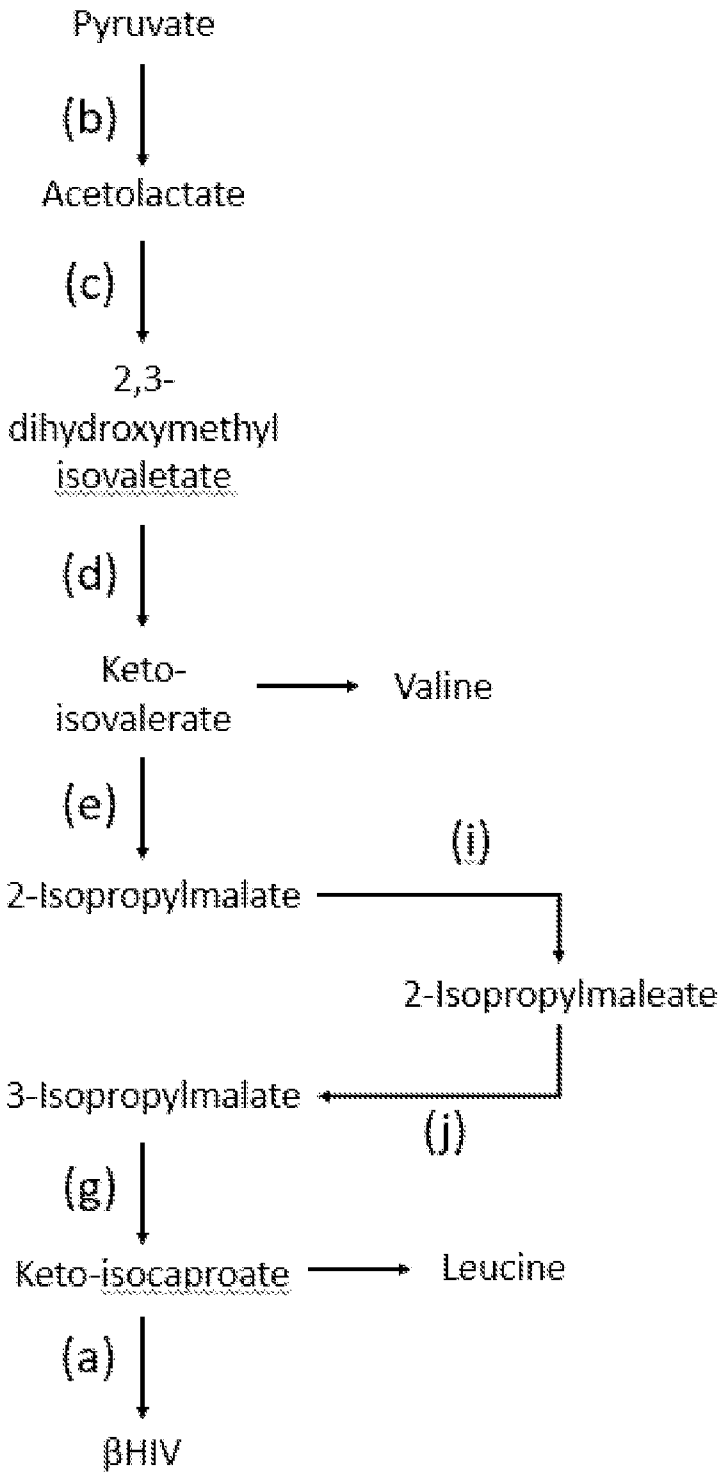
FIG. 2 illustrates another βHIV metabolic pathway, according to certain embodiments of the present invention. According to some aspects of this disclosure, the metabolic pathway can also comprise an active transporter to transport βHIV out of the non-natural microorganism.

A βHIV metabolic pathway is shown in FIG. 1. In some embodiments, βHIV metabolic pathway comprises of the conversion of pyruvate into 2-acetolactate, 2-acetolactate into 2,3-dihydroxy-isovalerate, 2,3-dihydroxy-isovalerate into α-ketoisovalerate, α-ketoisovalerate into 2-isopropylmalate, 2-isopropylmalate into 3-isopropylmalate, 3-isopropylmalate into KIC and KIC into βHIV.

Another βHIV metabolic pathway is shown in FIG. 2. In some embodiments, βHIV metabolic pathway comprises of the conversion of pyruvate into 2-acetolactate, 2-acetolactate into 2,3-dihydroxy-isovalerate, 2,3-dihydroxy-isovalerate into α-ketoisovalerate, α-ketoisovalerate into 2-isopropylmalate, 2-isopropylmalate into 2-isopropylmaleate, 2-isopropylmaleate into 3-isopropylmalate, 3-isopropylmalate into 2-isopropyl-3-oxosuccinate, 2-isopropyl-3-oxosuccinate into KIC, KIC into βHIV.

In some embodiments, the βHIV pathway also comprises a hydroxy acid transporter to facilitate the export of βHIV formed inside the microorganism to extracellular environment.

As used herein, the "theoretical yield" of βHIV refers to the molar ratio of βHIV that is produced extracellularly to the carbon source that is used. The theoretical yield can be calculated based on the biochemical conversion of glucose to pyruvate and the subsequent conversion of pyruvate into βHIV in the βHIV metabolic pathway, taking into consideration of the microorganism's native redox constraints to enable the conversion. For example, in yeast, the theoretical yield of βHIV from glucose is 0.667.

In a first example embodiment, the non-natural microorganism of the present disclosure (a) expresses or overexpresses at least one gene encoding for βHIV synthase, (b) expresses or overexpresses at least one gene encoding for acetolactate synthase, (c) expresses or overexpresses at least one gene encoding for acetohydroxy acid reductoisomerase, (d) expresses or overexpresses at least one gene encoding for 2,3-dihydroxy isovalerate dehydratase, (e) expresses or overexpresses at least one gene encoding for 2-isopropylmalate synthase (f) expresses or overexpresses at least one gene encoding for isopropylmalate isomerase, or (g) expresses or overexpresses at least one gene encoding for 3-isopropylmalate dehydrogenase. In some aspects, the non-natural microorganism of the present disclosure comprises a combination of two or more of (a), (b), (c) (d), (e), (f) and (g).

In a second example embodiment, the non-natural microorganism of the present disclosure (a) expresses or overexpresses at least one gene encoding for βHIV synthase, (b) expresses or overexpresses at least one gene encoding for acetolactate synthase, (c) expresses or overexpresses at least one gene encoding for 2,3-keto-acid reductoisomerase, (d) expresses or overexpresses at least one gene encoding for dihydroxy isovalerate dehydratase, (e) expresses or overexpresses at least one gene encoding for 2-isopropylmalate synthase, (i) expresses or overexpresses at least one gene encoding for 2-isopropylmalate hydrolyase (2-isopropylmaleate-forming), (j) expresses or overexpresses at least one gene encoding for 2-isopropylmalate hydrolyase (3-isopropylmalate-forming), (g) expresses or overexpresses at least one gene encoding for 3-isopropylmalate dehydrogenase. In some aspects, the non-natural organism of the present disclosure comprises a combination of two or more of (a), (b), (c) (d), (e), (i), (j) and (g).

In some embodiments, the non-natural microorganism of the present disclosure expresses or overexpresses at least one gene encoding a polypeptide with acetolactate synthase (EC: 2.2.1.6) activity. For example, acetolactate synthases capable of converting pyruvate to acetolactate may be derived from a variety of sources (e.g., bacterial, yeast, Archaea, etc.), including *B. subtilis* (GenBank Accession No. Q04789.3), *L. lactis* (GenBank Accession No. NP_267340.1), *S. mutans* (GenBank Accession No. NP_721805.1), *K. pneumoniae* (GenBank Accession No. PTD93137.1), *C. glutamicum* (GenBank Accession No. 1238373540), E, cloacae (GenBank Accession No. WP_013097652.1), *M. maripaiudis* (GenBank Accession No. ABX01060.1), P. grisea (GenBank Accession No. AAB81248.1), *T. stipitatus* (GenBank Accession No. XP_002485976.1), or *S. cerevisiae* ILV2 (GenBank Accession No. 1789111829). Additional acetolactate synthases capable of converting pyruvate to acetolactate are described in WO2013016724, which incorporated herein by reference in its entirety. A review article characterizing the biosynthesis of acetolactate from pyruvate via the activity of acetolactate synthases is provided by Chipman et al., 1998, Biochimica et Biophysica Acta 1385: 401-19. Chipman et al, provide an alignment and consensus for the sequences of a representative number of acetolactate synthases. Motifs shared in common between the majority of acetolactate synthases include: SGPG(A/C/V)(T/S)N, GX(P/A)GX (V7A/T), GX(Q/G)(T/A)(IJM)G(Y/F/W)(A/G)X(P/G)(W/A)AX(G/T)(A/V) and GD(G/A)(G/S/C)F, at amino acid positions corresponding to the 163-169, 240-245, 521-535, and 549-553 residues, respectively, of the *S. cerevisiae* ILV2. Thus, a protein harboring one or more of these amino acid motifs can generally be expected to exhibit acetolactate synthase activity. In some embodiments, the non-natural microorganism of the present disclosure expresses or overexpresses at least one gene encoding a polypeptide that is at least about 65% identical to at least one polypeptide selected from SEQ ID NOs: 297-300.

In some embodiments, the non-natural microorganism of the present disclosure expresses or overexpresses at least one gene encoding a polypeptide with acetohydroxy acid reductoisomerase activity (EC: 1.1.1.86). Acetohydroxy acid reductoisomerases capable of converting acetolactate to 2,3-dihydroxyisovaierate may be derived from a variety of sources (e.g., bacterial, yeast, Archaea, etc.), including *E. coli* (GenBank Accession No. EGB30597.1), *L. lactis* (GenBank Accession No. WP_012897822.1), *Shewanella* sp, (GenBank Accession No. WP_011621167.1), *A. fischeri* (GenBank Accession No. WP_005421503.1), *M. maripaludis* (GenBank Accession No. ABO35228.1), *B. subtilis* (GenBank Accession No. CAB14789), *S. pombe* (GenBank Accession No. NP_001018845) or *S. cerevisiae* ILV5 (GenBank Accession No. NP_013459.1). Additional ketol-acid reductoisomerases capable of converting acetolactate to 2,3-dihydroxyisovalerate are described in WO2013016724, incorporated herein by reference in its entirety. Motifs shared between a majority of acetohydroxy acid reductoisomerases include G(Y/C/W)GXQ(G/A), (F/Y/L)(S/A)HG (F/L), V(V/I/F)(M/L/A)(A/C)PK, D(L/I)XGE(Q/R) XXLXG and S(D/NAT)TA(E/Q/R)XG at amino acid positions corresponding to the 89-94, 175-179, 194-200, 282-272, and 459-465 residues, respectively, of the *E. coli* acetohydroxy acid reductoisomerase encoded by ilvC. Thus, a protein harboring one or more of these amino acid motifs can generally be expected to exhibit acetohydroxy acid reductoisomerase activity. The naturally existing acetohydroxy acid reductoisomerases preferentially use NADPH as a cofactor. Cofactor specificity can be switched to preferentially use NADH as a cofactor by means of modifying specific residues. Examples of such acetohydroxy acid reductoisomerases with increased preference for using NADH as a cofactor are described in US Publication No. 2010/0143997. In some embodiments, the non-natural microorganism of the present disclosure expresses or overexpresses at least one gene encoding a polypeptide that is at least about 65% identical to at least one polypeptide selected from SEQ ID NOs: 301-303.

In some embodiments, the non-natural microorganism of the present disclosure expresses or overexpresses at least one gene encoding a polypeptide with 2,3-dihydroxy isovalerate dehydratase activity (EC: 4.2.1.9). Dihydroxy acid dehydratases capable of converting 2,3-dihydroxyisovalerate to α-ketoisovalerate may be derived from a variety of sources (e.g., bacterial, yeast, Archaea, etc.), including *M. tuberculosis* (GenBank Accession No. CLR57443), *L. lactis* (GenBank Accession No. WP_010905837.1), *S. mutans* (GenBank Accession No. WP_002262431.1), *M. stadtma-*

*nae* (GenBank Accession No. WP_011407142.1), *M. tractuosa* (GenBank Accession No. WP_013453775.1), Eubacterium SCB49 (GenBank Accession No. WP_118518751.1), *Y. lipolytica* (GenBank Accession No. QNP96049.1), *N. crassa* (GenBank Accession No. XP_963045.1), or *S. cerevissae* ILV3 (GenBank Accession No. NP_012550.1). Additional dihydroxy acid dehydratases capable of 2,3-dihydroxyisovaierate to α-ketoisovalerate are described in WO2013016724, incorporated herein by reference in its entirety. Motifs shared in common between the majority of 2,3-dihydroxy isovalerate dehydratases include: SLXSRXXIA, CDKXXPG, GXCXGXXTAN, GGSTN, GPXGXPGMRXE, ALXTDGRXSG, and GHXXPEA motifs at amino acid positions corresponding to the 93-101, 122-128, 193-202, 276-280, 482-491, 509-518, and 526-532 residues, respectively, of the *E. coli* 2,3-dihydroxy isovalerate dehydratase. Thus, a protein harboring one or more of these amino acid motifs can generally be expected to exhibit 2,3-dihydroxy isovalerate dehydratase activity. In some embodiments, the non-natural microorganism of the present disclosure expresses or overexpresses at least one gene encoding a polypeptide that is at least about 65% identical to at least one polypeptide selected from SEQ ID NOs: 304-307.

In some embodiments, the non-natural microorganism of the present disclosure expresses or overexpresses at least one gene encoding a polypeptide with 2-isopropylmalate synthase activity (EC: 2.3.3.13). 2-isopropylmalate synthases capable of converting 3-methyl-2-oxobutanoate to (2S)-2-isopropylmalate may be derived from a variety of sources (e.g., bacterial, yeast, Archaea, etc.), including *C. glutamicum* (GenBank Accession No. WP_015439406), *E. coli* (GenBank Accession No. WP_000082850.1), *S. cerevisiae* (GenBank Accession No. NP_014295.1 (Leu4) and NP_014751.1 (Leu9), *M. maripaludis* (GenBank Accession No. WP_011171007.1) or *N. crassa* (GenBank Accession No. XP_964875.1). Motifs shared in common between the majority of the 2-isopropylmalate synthases include: LRDGXQ, IEVXFPXXSXXD, ISXHXHNDXGXXV, AGAXXVEG, GXGERXGNXXL at amino acid positions corresponding to the 12-17, 43-54, 199-211, 220-227, 231-241 residues, respectively, of the *E. coli* 2-isopropylmalate synthase. Thus, a protein harboring one or more of these amino acid motifs can generally be expected to exhibit 2-isopropylmalate synthase activity. In some embodiments, the non-natural microorganism of the present disclosure expresses or overexpresses at least one gene encoding a polypeptide that is at least about 65% identical to at least one polypeptide selected from SEQ ID NOs: 308-313.

In some embodiments, the non-natural microorganism of the present disclosure expresses or overexpresses at least one gene encoding a polypeptide with 2-isopropylmalate isomerase activity (EC: 4.2.1.33). In some embodiments, the isomerization of 2-isopropylmalate into 3-isopropylmalate is catalyzed by an enzyme that is expressed by one gene. Such 2-isopropylmalate isomerases capable of converting 2-isopropylmalate into 3-isopropylmalate may be derived from a variety of sources, including *S. cerevisiae* (GenBank Accession NP_011506.1), *P. kudriavzevii* (GenBank Accession No. XP_029320833.1) or *C. albicans* (GenBank Accession No. XP_718655.1). In some embodiments, the isomerization of 2-isopropylmalate into 3-isopropylmalate is catalyzed by an enzyme that is expressed by two genes, each gene encoding for a different subunit. Such 2-isopropylmalate isomerases capable of converting 2-isopropylmalate into 3-isopropylmalate may be derived from a variety of sources (e.g., bacterial, Archaea, etc.), including *M. tuberculosis* (GenBank Accession No. NP_217504.1), *L. lactis* (GenBank Accession No. WP_095586897.1), *S. mutans* (GenBank Accession No. WP_002262706.1), *C. glutamicum* (GenBank Accession No. WP_003858858.1), *M. maripaludis* (GenBank Accession No. WP_011171424.1) and *E. coli*. MG1655 (GenBank Accession No. NP 414614.1). In some embodiments, the non-natural microorganism of the present disclosure expresses or overexpresses at least one gene encoding a polypeptide with 2-isopropylmalate isomerase activity (EC: 4.2.1.33), containing a subunit with 3-isopropylmalate dehydratase activity. Motifs shared in common between the majority of the enzymes include: HEVTSPQAF, DSHTXTHGAFG, AFGIGTSEVEHVXATQT, CNMXIEXGA, VFXGSCTNXRXXDL, EXCASTSNRNFEGRQG, and GHXXPEA motifs at amino acid positions corresponding to the 33-41, 128-138, 141-157, 220-228, 342-355, and 422-437, residues, respectively, of the *E. coli* 3-isopropylmalate dehydratase. Thus, a protein harboring one or more of these amino acid motifs can generally be expected to exhibit 3-isopropylmalate dehydratase activity. In some embodiments, the non-natural microorganism of the present disclosure expresses or overexpresses at least one gene encoding a polypeptide that is at least about 65% identical to at least one polypeptide selected from SEQ ID NOs: 314-315.

In some embodiments, the non-natural microorganism of the present disclosure expresses or overexpresses at least one gene encoding a polypeptide with 3-isopropylmalate dehydrogenase activity (EC: 1.1.1.85). 3-isopropylmalate dehydrogenase capable of converting (2R,3S)-3-isopropylmalate to 4-Methyl-2-oxopentanoate may be derived from a variety of sources (e.g., bacterial, yeast, Archaea, plant, etc.), including *A. thaliana* (GenBank Accession No. NP_001322636.1), *L. lactis* (GenBank Accession No. WP_095586896.1), *S. mutans* (GenBank Accession No. WP_002262707.1), *C. glutamicum* (GenBank Accession No. WP_011014258.1), *M. maripaludis* (GenBank Accession No. WP_011170483.1), *E. coli*. MG1655 (GenBank Accession No. NP_414615.4), *P. kudriavzevii* (GenBank Accession No. XP_029322355.1), *C. albicans* (GenBank Accession No. XP_720371.1), or *S. cerevisiae* S288C (GenBank Accession No. NP_009911.2). Motifs shared in common between the majority of 3-isopropylmalate hydratases include: DAXLLGAXGXP, VRELXGGIYFG, DKXNVL, TXNXFGDILSDEA, LXEPXHGSAPD, and NPXAXILSXAMXL motifs at amino acid positions corresponding to the 69-79, 137-147, 260-265, 245-257, 279-289, and 297-309 residues, respectively, of the *E. coli* 3-isopropylmalate dehydrogenase. Thus, a protein harboring one or more of these amino acid motifs can generally be expected to exhibit 3-isopropylmalate dehydrogenase activity. In some embodiments, the non-natural microorganism of the present disclosure expresses or overexpresses at least one gene encoding a polypeptide that is at least about 65% identical to at least one polypeptide selected from SEQ ID NOs: 316-320.

In some embodiments, the non-natural microorganism of the present disclosure expresses or overexpresses at least one gene encoding a polypeptide with βHIV synthase activity. The non-natural enzymes disclosed herein have low activity using 4-hydroxyphenylpyruvate, thereby not introducing any undesirable alterations in the metabolism. The present disclosure describes methods of increasing βHIV production through the use of non-natural microorganisms. Accordingly, the present disclosure is directed to an isolated nucleic acid encoding a polypeptide with βHIV synthase activity, wherein the polypeptide sequence is at least 65% identical to at least one polypeptide selected from any of SEQ ID Nos: 1-148. Methods to determine identity and similarity are codified in publicly available computer programs. Example computer program methods to determine identity and similarity between two sequences include BLASTP and BLASTN, publicly available from NCBI and other sources (BLAST Manual, Altschul, S., et al., NCBI NLM NIH Bethesda, Md. 20894). Example parameters for amino acid sequences comparison using BLASTP are gap open 11.0, gap extend 1, Blosum 62 matrix.

In certain embodiments, the polypeptide with βHIV synthase activity is derived from the genus *Rattus*. In an example embodiment, the polypeptide with βHIV synthase activity is derived from *Rattus norvegicus*, F alloantigen *Rattus norvegicus, Rattus* or *Rattus losea*. In another example embodiment, the polypeptide with βHIV synthase activity is selected from at least one of SEQ ID NOS: 1-3.

In some embodiments, the polypeptide with βHIV synthase activity has at least 65% identity to at least one polypeptide selected from any of SEQ ID NOS: 1-148. Further within the scope of the present application are polypeptides with βHIV synthase activity which are at least about 65%, 70%, 75%, 80%, 85%, 90%, 91%, 92%, 93%, 94%, 95%, 98%, 97%, 98%, 99%, or 99.5% identical to at least one polypeptide selected from any of SEQ ID NOS: 1-148. In some embodiments, the non-natural microorganism expresses or overexpresses a nucleic acid encoding at least one polypeptide with βHIV synthase activity selected from any of SEQ ID NOS: 149-288.

The promiscuous activity of HPPD with KIC is indicative of a basal level recognition of the desired substrate and the present disclosure discloses methods to increase KIC/HPP activity by modifying certain amino acids at specific positions in the sequence. Modifying amino acids that play a role in the catalysis can lead to alterations in the enzyme activity. One skilled in the art can recognize the position of these amino acids in homologous protein sequences by aligning the sequences. Two sequences are said to be "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art. The BLOSUM82 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al, (1997) Nucleic Acids Res. 25:3389-3402, and made available to the public at the National Center for Biotechnology Information Website. Optimal alignments, including multiple alignments, can be prepared using, e.g., PSI-BLAST with no compositional adjustments.

As described herein, the present inventors identified polypeptides with βHIV synthase activity. One desirable feature of a polypeptide with βHIV synthase activity is the ability to exhibit high activity for the conversion of KIC into βHIV in the βHIV metabolic pathway. Another desirable property of a polypeptide with βHIV synthase activity is the low activity with HPP, thereby reducing the impact on other aspects of metabolism. The present disclosure identifies several beneficial modifications or mutations which can be made to an existing dioxygenase enzyme to improve the dioxygenase enzyme's ability to catalyze the conversion of KIC to βHIV with higher activity. In some embodiments, the non-natural microorganism expresses or overexpresses at least one gene encoding a polypeptide with increased KIC/HPP activity, wherein the sequence of the polypeptide has at least one modification.

According to certain aspects of the present invention, the non-natural enzyme comprises one or more modifications at substrate-specificity positions corresponding to amino acids selected from A361, F336, F347, F364, F368, F371, G362, I227, I252, L224, L289, L323, L367, N187, N241, N363, P239, Q251, Q265, S226, V212, V217, V228 and W210 of SEQ ID NO: 1.

According to certain aspects of the present invention, the non-natural enzyme comprises one or more modifications at substrate-specificity positions corresponding to amino acids selected from A361, F336, F347, F364, F368, F371, G362, I227, I252, L224, L289, L323, L367, N187, N241, N363, P239, Q251, Q265, S226, V212, V217, V228 and W210 of SEQ ID NO: 6.

In some embodiments, the dioxygenase enzyme has been modified or mutated to alter one or more substrate-specificity residues. In certain embodiments, the dioxygenase enzyme is modified, wherein the residue corresponding to position 361 of SEQ ID NO: 1 is replaced with a residue selected from methionine, leucine and isoleucine. In another embodiment, the dioxygenase enzyme is modified, wherein the residue corresponding to position 336 of SEQ ID NO: 1 is replaced with leucine, methionine, isoleucine and tryptophan. In another embodiment, the dioxygenase enzyme is modified, wherein the residue corresponding to position 347 of SEQ ID NO: 1 is replaced with tryptophan, tyrosine and isoleucine. In another embodiment, the dioxygenase enzyme is modified, wherein the residue corresponding to position 364 of SEQ ID NO: 1 is replaced with methionine, alanine, isoleucine, leucine and tryptophan. In another embodiment, the dioxygenase enzyme is modified, wherein the residue corresponding to position 368 of SEQ ID NO: 1 is replaced with tyrosine, tryptophan, leucine, isoleucine and methionine. In another embodiment, the dioxygenase enzyme is modified, wherein the residue corresponding to position 371 of SEQ ID NO: 1 is replaced with methionine, leucine and isoleucine. In another embodiment, the dioxygenase enzyme is modified, wherein the residue corresponding to position 362 of SEQ ID NO: 1 is replaced with methionine, leucine and isoleucine. In another embodiment, the dioxygenase enzyme is modified, wherein the residue corresponding to position 227 of SEQ ID NO: 1 is replaced with methionine, leucine and isoleucine. In another embodiment, the dioxygenase enzyme is modified, wherein the residue corresponding to position 252 of SEQ ID NO: 1 is replaced with methionine, leucine and valine. In another embodiment, the dioxygenase enzyme is modified, wherein the residue corresponding to position 361 of SEQ ID NO: 1 is replaced with threonine. In another embodiment, the dioxygenase enzyme is modified, wherein the residue corresponding to position 224 of SEQ ID NO: 1 is replaced with methionine, phenylalanine and tryptophan. In another embodiment, the dioxygenase enzyme is modified, wherein the residue corresponding to position 289 of SEQ ID NO: 1 is replaced with methionine, leucine and isoleucine. In another embodiment, the dioxygenase enzyme is modified, wherein the residue corresponding to position 323 of SEQ ID NO: 1 is replaced with tryptophan, tyrosine and isoleucine. In another embodiment, the dioxygenase enzyme is modified, wherein the residue corresponding to position 367 of SEQ ID NO: 1 is replaced with methionine, leucine, isoleucine and tryptophan. In another embodiment, the dioxygenase enzyme is modified, wherein the residue corresponding to position 187 of SEQ ID NO: 1 is replaced with methionine, phenylalanine and tryptophan. In another embodiment, the dioxygenase enzyme is modified, wherein the residue corresponding to position 241 of SEQ ID NO: 1 is replaced with methionine, phenylalanine and tryptophan. In another embodiment, the dioxygenase enzyme is modified, wherein the residue corresponding to position 363 of SEQ ID NO: 1 is replaced with methionine, isoleucine and valine. In another embodiment, the dioxygenase enzyme is modified, wherein the residue corresponding to position 239 of SEQ ID NO: 1 is replaced with leucine. In another embodiment, the dioxygenase enzyme is modified, wherein the residue corresponding to position 251 of SEQ ID NO: 1 is replaced with methionine, isoleucine and proline. In another embodiment, the dioxygenase enzyme is modified, wherein the residue corresponding to position 265 of SEQ ID NO: 1 is replaced with methionine, isoleucine and proline. In another embodiment, the dioxygenase enzyme is modified, wherein the residue corresponding to position 226 of SEQ ID NO: 1 is replaced with methionine, valine, isoleucine and leucine. In another embodiment, the dioxygenase enzyme is modified, wherein the residue corresponding to position 212 of SEQ ID NO: 1 is replaced with phenylalanine, leucine, isoleucine or tryptophan. In another embodiment, the dioxygenase enzyme is modified, wherein the residue corresponding to position 217 of SEQ ID NO: 1 is replaced with methionine, isoleucine or leucine. In another embodiment, the dioxygenase enzyme is modified, wherein the residue corresponding to position 228 of SEQ ID NO: 1 is replaced with methionine, isoleucine or leucine. In another embodiment, the dioxygenase enzyme is modified, wherein the residue corresponding to position 210 of SEQ ID NO: 1 is replaced with leucine.

In some aspects, at least one of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 1 has been replaced with one of the corresponding disclosed amino acids to alter the respective substrate-specificity residue.

In some other aspects, two or more of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 1 have been replaced with one of the corresponding disclosed amino acids to alter the respective substrate-specificity residue.

In yet some other aspects, at least 3 and up to 24 of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 1 have been replaced with one of the corresponding disclosed amino acids to alter the respective substrate-specificity residue.

In some embodiments, the dioxygenase enzyme has been modified or mutated to alter one or more one of the substrate-specificity residues. In certain embodiments, the dioxygenase enzyme is modified, wherein the residue corresponding to position 361 of SEQ ID NO: 6 is replaced with a residue selected from methionine, leucine and isoleucine. In another embodiment, the dioxygenase enzyme is modified, wherein the residue corresponding to position 336 of SEQ ID NO: 6 is replaced with leucine, methionine, isoleucine and tryptophan. In another embodiment, the dioxygenase enzyme is modified, wherein the residue corresponding to position 347 of SEQ ID NO: 6 is replaced with tryptophan, tyrosine and isoleucine. In another embodiment, the dioxygenase enzyme is modified, wherein the residue corresponding to position 364 of SEQ ID NO: 6 is replaced with methionine, alanine, isoleucine, leucine and tryptophan. In another embodiment, the dioxygenase enzyme is modified, wherein the residue corresponding to position 368 of SEQ ID NO: 6 is replaced with tyrosine, tryptophan, leucine, isoleucine and methionine. In another embodiment, the dioxygenase enzyme is modified, wherein the residue corresponding to position 371 of SEQ ID NO: 6 is replaced with methionine, leucine and isoleucine. In another embodiment, the dioxygenase enzyme is modified, wherein the residue corresponding to position 362 of SEQ ID NO: 6 is replaced with methionine, leucine and isoleucine. In another embodiment, the dioxygenase enzyme is modified, wherein the residue corresponding to position 227 of SEQ ID NO: 6 is replaced with methionine, leucine and isoleucine. In another embodiment, the dioxygenase enzyme is modified, wherein the residue corresponding to position 252 of SEQ ID NO: 6 is replaced with methionine, leucine and valine. In another embodiment, the dioxygenase enzyme is modified, wherein the residue corresponding to position 361 of SEQ ID NO: 6 is replaced with threonine. In another embodiment, the dioxygenase enzyme is modified, wherein the residue corresponding to position 224 of SEQ ID NO: 6 is replaced with methionine, phenylalanine and tryptophan. In another embodiment, the dioxygenase enzyme is modified, wherein the residue corresponding to position 289 of SEQ ID NO: 6 is replaced with methionine, leucine and isoleucine. In another embodiment, the dioxygenase enzyme is modified, wherein the residue corresponding to position 323 of SEQ ID NO: 6 is replaced with tryptophan, tyrosine and isoleucine. In another embodiment, the dioxygenase enzyme is modified, wherein the residue corresponding to position 367 of SEQ ID NO: 6 is replaced with methionine, leucine, isoleucine and tryptophan. In another embodiment, the dioxygenase enzyme is modified, wherein the residue corresponding to position 187 of SEQ ID NO: 6 is replaced with methionine, phenylalanine and tryptophan. In another embodiment, the dioxygenase enzyme is modified, wherein the residue corresponding to position 241 of SEQ ID NO: 6 is replaced with methionine, phenylalanine and tryptophan. In another embodiment, the dioxygenase enzyme is modified, wherein the residue corresponding to position 363 of SEQ ID NO: 6 is replaced with methionine, isoleucine and valine. In another embodiment, the dioxygenase enzyme is modified, wherein the residue corresponding to position 239 of SEQ ID NO: 6 is replaced with leucine. In another embodiment, the dioxygenase enzyme is modified, wherein the residue corresponding to position 251 of SEQ ID NO: 6 is replaced with methionine, isoleucine and proline. In another embodiment, the dioxygenase enzyme is modified, wherein the residue corresponding to position 265 of SEQ ID NO: 6 is replaced with methionine, isoleucine and proline. In another embodiment, the dioxygenase enzyme is modified, wherein the residue corresponding to position 226 of SEQ ID NO: 6 is replaced with methionine, valine, isoleucine and leucine. In another embodiment, the dioxygenase enzyme is modified, wherein the residue corresponding to position 212 of SEQ ID NO: 6 is replaced with phenylalanine, leucine, isoleucine or tryptophan. In another embodiment, the dioxygenase enzyme is modified, wherein the residue corresponding to position 217 of SEQ ID NO: 6 is replaced with methionine, isoleucine or leucine. In another embodiment, the dioxygenase enzyme is modified, wherein the residue corresponding to position 228 of SEQ ID NO: 6 is replaced with methionine, isoleucine or leucine. In another embodiment, the dioxygenase enzyme is modified, wherein the residue corresponding to position 210 of SEQ ID NO: 6 is replaced with leucine.

In some aspects, at least one of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 6 has been replaced with one of the corresponding disclosed amino acids to alter the respective substrate-specificity residue.

In some other aspects, two or more of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 6 have been replaced with one of the corresponding disclosed amino acids to alter the respective substrate-specificity residue.

In yet some other aspects, at least 3 and up to 24 of the substrate-specificity positions corresponding to amino acids selected from the group consisting of A361, F336, F347, F364, F368, F371, G362, I227, I252, L224, L289, L323, L367, N187, N241, N363, P239, Q251, Q265, S226, V212, V217, V228 and W210 of SEQ ID NO: 6 have been replaced with one of the corresponding disclosed amino acids to alter the respective substrate-specificity residue.

In an exemplary embodiment, the modified dioxygenase enzyme is derived from a corresponding unmodified dioxygenase that is at least about 65%, 70%, 75%, 80%, 85%, 90%, 91%, 92%, 93%, 94%, 95%, 96%, 97%, 98%, 99%, or 99.5% identical to a polypeptide selected from SEQ ID NOS: 1-8.

In some embodiments, the present disclosure relates to a polypeptide with increased βHIV synthase activity, wherein the polypeptide sequence is derived from *Yarrowia lipolytica* and is at least 65% identical to a polypeptide selected from either of SEQ ID NOs: 4-5 and has been modified or mutated to alter one or more one the substrate-specificity residues. In certain embodiments, the polypeptide is modified at one or more positions corresponding to amino acids selected from A374, F349, F360, F377, F381, I384, G375, V240, 1265, A374, L237, 1302, L336, L380, N200, N254, N377, P252, Q264, Q278, S239, V225, I230, V241 and W223. In an exemplary embodiment, the modified decarboxylase enzyme is derived from a corresponding unmodified decarboxylase that is at least about 65%, 70%, 75%, 80%, 85%, 90%, 91%, 92%, 93%, 94%, 95%, 96%, 97%, 98%, 99%, or 99.5% identical to a polypeptide selected from either of SEQ ID NOs: 4-5.

Corresponding amino acids in other decarboxylases are easily identified by visual inspection of the amino acid sequences or by using commercially available homology software programs. Thus, given the defined regions for changes and the assays described in the present application, one with skill in the art can make one or a number of modifications which would result in an increased ability to specifically catalyze the conversion of KIC to βHIV, in any homologous dioxygenase enzyme of interest. The modified polypeptides can be optimally aligned with the corresponding unmodified, wild-type dioxygenase enzymes to generate a similarity score which is at least about 50%, more preferably at least about 60%, more preferably at least about 70%, more preferably at least about 80%, more preferably at least about 90%, or most preferably at least about 95% of the score for the reference sequence using the BLOSUM82 matrix, with a gap existence penalty of 11 and a gap extension penalty of 1.

In some embodiments, the non-natural microorganism expresses or overexpresses a nucleic acid encoding fragments of the disclosed polypeptides which comprises at least 25, 30, 40, 50, 100, 150, 200, 250, 300 or 375 amino acids and retain βHIV synthase activity. Such fragments may be obtained by deletion mutation, by recombinant techniques that are routine and well-known in the art, or by enzymatic digestion of the polypeptides of interest using any of a number of well-known proteolytic enzymes.

In some embodiments, the non-natural microorganism comprises at least one nucleic acid molecule encoding a polypeptide with βHIV synthase activity, wherein said polypeptide is at least about 65% identical to a polypeptide selected from SEQ ID NOS: 1-148 Further within the scope of present disclosure are recombinant microorganisms comprising at least one nucleic acid molecule encoding a polypeptide with βHIV synthase activity, wherein said polypeptide is at least about 70%, 75%, 80%, 85%, 90%, 91%, 92%, 93%, 94%, 95%, 96%, 97%, 98%, 99%, or 99.5% identical to a polypeptide selected from SEQ ID NOS: 1-149.

In accordance with the present disclosure, any number of mutations can be made to the βHIV synthase enzymes, and in certain embodiments, multiple mutations can be made to result in an increased ability to catalyze the conversion of KIC to βHIV with high catalytic efficiency. Such mutations can include point mutations, frame shift mutations, deletions, and insertions. In certain embodiments, one or more (e.g., one, two, three, four, five, six, seven, eight, nine, ten or more, etc.) point mutations may be preferred.

In some embodiments, the βHIV synthase will have an intact C-terminus. As defined herein, the C-terminus of HPPD is the stretch of residues that include the C-terminal α-helix that shields the active site. For example, in SEQ ID NO: 1, the stretch of amino acids from 361 to 393 are considered the C-terminus. In some embodiments, the residues comprising the C-terminus are modified to allow increased activity with KIC. In some embodiments, the C-terminus of the HPPD is in a conformation to have the highest specificity for KIC.

In one embodiment, the βHIV metabolic pathway is localized to the cytosol of the non-natural microorganism. In one embodiment, the non-natural microorganism comprises a βHIV metabolic pathway with at least one pathway enzyme localized in the cytosol.

In some embodiments, the non-natural microorganism belongs to a genus selected from the group consisting of *Escherichia, Corynebacterium, Lactobacillus, Lactococcus* and *Bacillus*. In some embodiments, the non-natural microorganism belongs to a genus selected from the group consisting of *Saccharomyces, Kluyveromyces, Issatchenkia, Galactomyces, Pichia* and *Candida*.

In some embodiments where the non-natural microorganism is a eukaryote, the βHIV metabolic pathway is expressed or overexpressed in its cytosol.

In certain embodiments, the non-natural microorganism comes in contact with a carbon source in a fermenter to produce βHIV and introducing into the fermenter sufficient nutrients where the final concentration of β-hydroxyisovalerate concentration in the fermentation broth is greater than about 10 mg/L (for example, greater than about 100 mg/L, for example, greater than about 1 g/L, greater than about 5 g/L, greater than about 10 g/L, greater than about 20 g/L, greater than about 40 g/L, greater than 50 g/L), but usually below 150 g/L. In certain embodiments, the carbon source is selected from the group consisting of glucose, xylose, arabinose, sucrose, fructose, lactose, glycerol, and mixtures thereof.

In some embodiments, βHIV thus produced is optionally recovered from the fermentation broth by first removing the cells, followed by separating the aqueous phase from the clarified fermentation broth along with the other by-products of the fermentation. In some embodiments, the βHIV is co-purified with other fermentation-derived products, wherein the composition comprises at least one fermentation-derived impurity. In some embodiments, fermentation-derived products are selected from the group consisting of organic acids and amino acids. In some embodiments, βHIV synthesized according to the present disclosure is substantially devoid of chloroform or hydrochloric acid.

The object of the present disclosure is further illustrated by the following examples that should not be construed as limiting. Examples are provided for clarity of understanding. While the object of the present disclosure has been described in connection with embodiments thereof, it will be understood that it is capable of further modifications and this disclosure is intended to cover variations, user or adaptations of the present disclosure following, in general, the principles of the present disclosure and including such departures from the present disclosure as come within known or customary practice within the art to which the present disclosure pertains and as may be applied to the essential features hereinbefore set forth and as follows in the scope of the appended claims. The contents of all references, patents, and published patent applications cited throughout this application, as well as the Figures and the Sequence Listings, are incorporated herein by reference for all purposes.

EXAMPLES

Example 1: Selection of Microorganisms

This example illustrates a method to select microorganisms that are a priori suited to produce βHIV. Several bacteria and yeasts were tested for their ability to grow in the presence of βHIV. Bacterial strains—*Corynebacterium glutamicum* NRRL B-2784, *Escherichia coli* MG1655 and yeast strains—*Saccharomyces cerevisiae* CENPK.2, *Kluyveromyces marxianus* NRRL Y-318, NRRL Y-6373, *Pichia kudriavzevii* NRRL Y-7551, NRRL Y-5396 were selected as exemplary microorganism to evaluate their ability to grow in the presence of βHIV. Growth is considered an indicator of overall metabolic activity. The bacterial strains were started in LB medium and the yeast strains were started in YPD medium at conditions that are reportedly ideal for optimal growth. For example, *E. coli* strain was started from cryo-vials in LB medium at 37° C. and *S. cerevisiae* was started from cryo-vials in YPD medium at 30° C.

Figure 3:
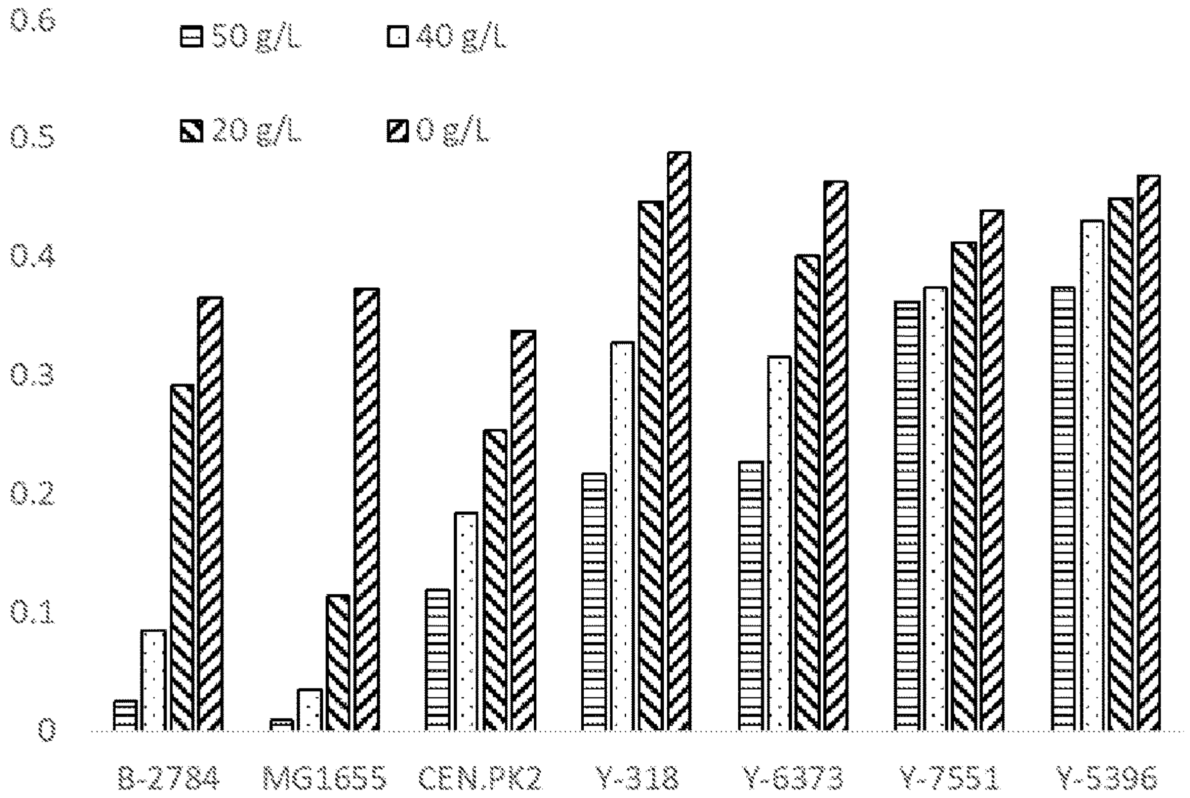
FIG. 3 illustrates the growth of microorganisms as maximum specific growth rate in the presence of various concentrations of βHIV in the media as an indicator of metabolic activity.

Seed cultures of all the strains were transferred into minimal mineral salts medium, supplemented with 2% glucose. To the same media βHIV was added to a final concentration of 20 g/L, 40 g/L or 50 g/L. Growth of the microorganisms in the presence of βHIV was monitored in BioLector II (m2p Labs, Aachen, Germany) in triplicate. The maximum specific growth rate of these microorganisms in the presence of various concentrations of βHIV was calculated and shown in FIG. 3. Typically yeasts grew faster than bacteria at higher concentrations of βHIV, suggesting faster glucose uptake. Specifically, Y-6373, Y-7551 and Y-5396 exhibited the fastest growth and are potential candidates to host the βHIV metabolic pathway. This example illustrates a method to screen and select appropriate host microorganisms for producing βHIV.

Example 2: Production of βHIV in Bacteria

Figure 4:
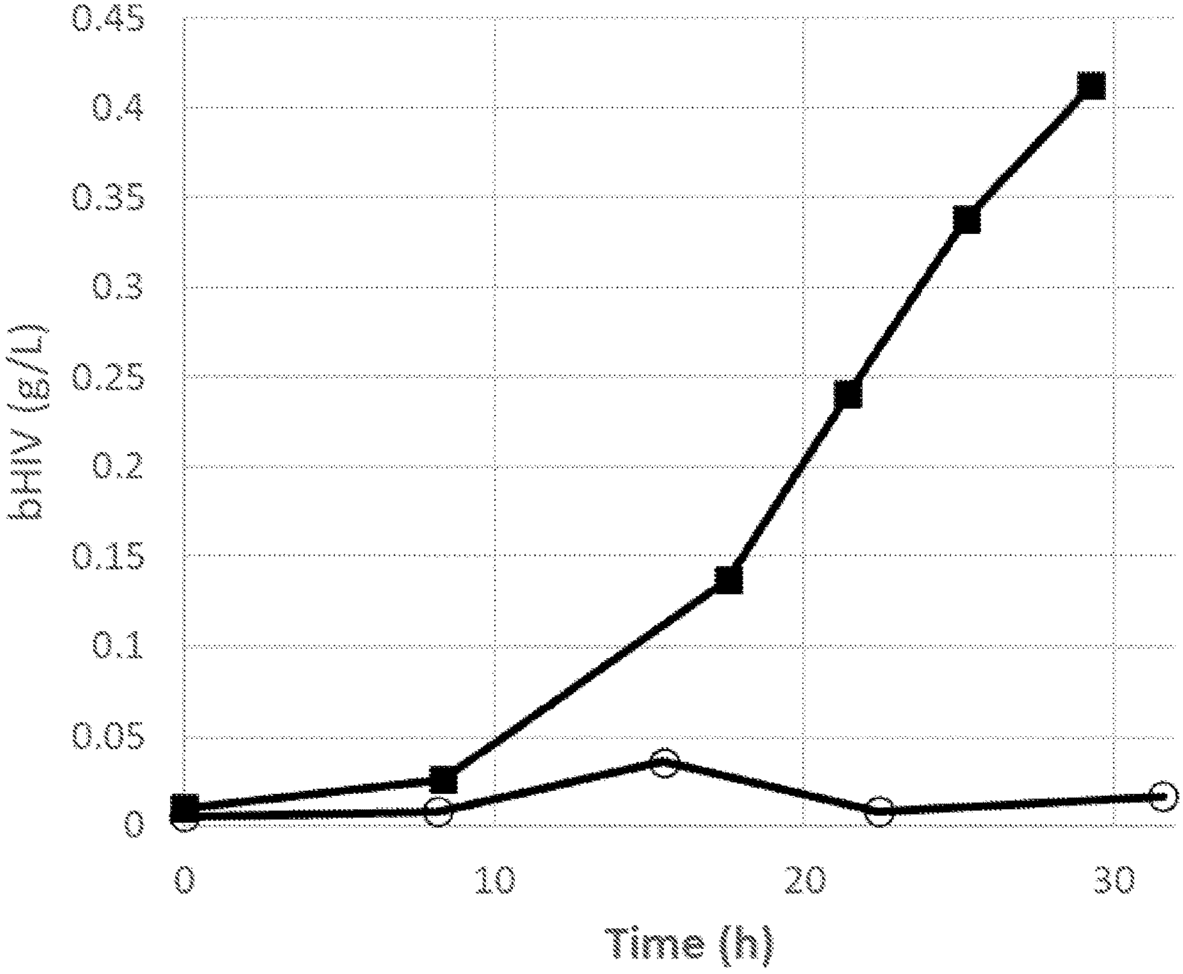
FIG. 4 illustrates the production of βHIV using non-natural bacteria.

This example illustrates the production of βHIV in bacteria and yeast. A strain of *Corynebacterium glutamicum* MV-KICF1 (Applied Microbiol, Microb Biotech, 8, 351-360) that was metabolically modified to produce α-ketoisocaproate was used to introduce a gene that encodes for a polypeptide encoding SEQ ID NO: 1. The codons in the nucleic acid sequence of the gene were optimized according to the codon usage of the bacterium and the DNA was cloned into pZ8-ptac vector (Cleto et al., ACS Synth Biol. 2016 May 20; 5(5): 375-385) and transformed into MV-KICF1 by electroporation. The non-natural bacterial strain endowed with the capability to produce βHIV was propagated in Brain-Heart Infusion medium and cultivated in CGXII medium (Hoffman et al., J Appl Microbiol., 2014, 117: 663-678) using glucose as the main carbon source to evaluate the βHIV production. Substrate consumption and product formation was evaluated on Agilent 1200 HPLC using 5 mM H2SO4 as the mobile phase with Aminex HPX-87c column (BioRad, Hercules, CA). As illustrated in FIG. 4, the non-natural bacterium comprising βHIV synthase produced more βHIV than its parent wild-type.

Example 3: Assembling βHIV Metabolic Pathway in Yeast Cytosol

This example provides methods to assemble βHIV metabolic pathway shown in FIG. 1 in Y-5396 yeast. The example also provides methods for discriminating between enzymes (genes) that perform the same function. All DNA modifications were performed based on a reference genome that is available publicly (Douglass et al., 2018, PLOS Pathog, 14(7):e1007138). To facilitate use of URA3 as a selection marker, both alleles of URA3 in the diploid yeast Y-5396 were deleted. The first URA3 allele was replaced by a KanMX cassette conferring Geneticin resistance and flanked by loxP sites by transforming a KanMX cassette flanked by ~500 bases of homology upstream and downstream of URA3 into Y-5396. Transformants were selected on media containing Geneticin and insertion of the cassette in the URA3 locus confirmed by PCR, creating strain SB500. To delete the second URA3 allele ~500 bases upstream and ~500 bases downstream of URA3 were joined via overlap extension PCR to create a clean deletion construct and transformed into SB500. Transformants were plated on 5-fluorootic acid to select for mutants that had lost both alleles of URA3. The clean deletion of the second allele was confirmed by PCR and the KanMX cassette insertion was re-confirmed, to create strain SB501. Finally, the KanMX cassette was removed by transient expression of Cre recombinase from an unstable plasmid that conferred resistance to Hygromycin. Colonies were then screened for loss of Geneticin resistance (loss of KanMX), loss of Hygromycin resistance (plasmid marker), and ability to grow on 5-FOA (double deletion of URA3). Genomic DNA at the URA3 locus was PCR-amplified and sequenced to confirm the deletions had occurred as expected. The resulting strain called SB502, which has the two copies of the URA3 gene deleted to facilitate the use of uracil for selection.

Genes encoding for enzymes in the βHIV metabolic pathway were inserted in the chromosome at intergenic loci using homologous recombination. Chromosomal integration of heterologous genes to assemble the βHIV metabolic pathway is illustrated for α-isopropylmalate synthase (IPMS) as an example. One plasmid (p1) was constructed containing the integration site 5' homology arm, IPMS expression cassette, and the 3' two-thirds of the URA3 cassette. A second plasmid (p2) was constructed with the 5' two-thirds of the URA3 cassette (such that there was ~500 bases overlap with p1) and the integration site 3' homology arm. This strategy decreases the rate of unwanted recombination events because only when both halves integrate into the same site will a functional URA3 cassette be formed. All PCR reactions were performed using NEB Q5 high fidelity polymerase according to manufacturer's instructions. Plasmids were assembled using NEBuilder HiFi assembly mix according to manufacturer's instructions, routinely using 30 base pair overlaps to facilitate assembly. The URA3 cassette is flanked by loxP sites to facilitate removal of the marker by expression of Cre recombinase. Genes encoding for enzymes with SEQ ID NOS: 308-312 were evaluated for their IPMS activity.

Plasmids shown in Table 1 were assembled using NEBuilder HiFi assembly mix according to manufacturer's instructions, routinely using 30 base pair overlaps to facilitate assembly. IPMS genes were inserted into two separate intergenic loci on chromosome A (NC_042506). Intergenic locus A2193833 (aka igA2.2) and A1207782 (aka igA1.2).

TABLE 1

Relevant plasmids used to modify strains in this example

| Plasmid | Use | Genotype/relevant genes |
|---|---|---|
| pSB011 | Insert IPMS cassette and ura3 marker into io intergenic locus igA2.2 | 5' HA igA2.2, ioTDH3p-SEQ ID NO: 308-ioTKLt; lox66-ioTALt-ura3 3' |
| pSB012 | Insert IPMS cassette and ura3 marker into io intergenic locus igA2.2 | 5' HA igA2.2, ioTDH3p-SEQ ID NO: 309-ioTKLt; lox66-ioTALt-ura3 3'v |
| pSB013 | Insert IPMS cassette and ura3 marker into io intergenic locus igA2.2 | 5' HA igA2.2, ioTDH3p-SEQ ID NO: 310-ioTKLt; lox66-ioTALt-ura3 3'v |
| pSB014 | Insert IPMS cassette and ura3 marker into io intergenic locus igA2.2 | 5' HA igA2.2, ioTDH3p-SEQ ID NO: 311-ioTKLt; lox66-ioTALt-ura3 3' |
| pSB015 | Insert IPMS cassette and ura3 marker into io intergenic locus igA2.2 | 5' HA igA2.2, ioTDH3p-SEQ ID NO: 312-ioTKLt; lox66-ioTALt-ura3 3'v |
| pSB017 | Insert IPMS cassette and ura3 marker into io intergenic locus igA2.2 | Ura3 5'-ioPGKp-lox71, 3' HA igA2.2 |
| pSB019 | Insert IPMS cassette and ura3 marker into io intergenic locus igA1.2 | 5' HA igA1.2, ioTDH3p-*C. glutamicum* leuA B018-ioTKLt; lox66-ioTALt-ura3 3' |
| pSB020 | Insert IPMS cassette and ura3 marker into io intergenic locus igA1.2 | 5' HA igA1.2, ioTDH3p-*C. glutamicum* leuA CP-ioTKLt; lox66-ioTALt-ura3 3' |
| pSB021 | Insert IPMS cassette and ura3 marker into io intergenic locus igA1.2 | Ura3 5'-ioPGKp-lox71, 3' HA igA1.2 |
| pEC010 | Express Cre recombinase in io strains | ioPGKp-cre-CYC1t; KanMX, ioCEN0.8, ioARS |

To construct pSB011-15 the 5' homology arm and ioTDH3 promoter were PCR amplified with primers shown in SEQ ID NO: 321 and SEQ ID NO: 322 and SEQ ID NO: 323 and SEQ ID NO: 324 respectively, using SB502 genomic DNA as template. The IPMS genes were codon optimized for *Issatchenkia orientalis* and synthesized as gene fragments by Twist Biosciences (San Francisco, CA). The genes needed to be split into two fragments because of their length and complexity. The ioTKL terminator & 3' portion of the URA3 cassette and vector backbone (pTwist-Kan high copy), were PCR amplified from a plasmid synthesized by Twist Biosciences. To construct pSB017 the 3' homology arm was amplified using primers SEQ ID NO: 325 and SEQ ID NO: 326 and SB502 genomic DNA as template. The 5' portion of the URA3 cassette and vector backbone was amplified using primers ig2.2p2 gib vec F+R and plasmid ig1.6p2 as template. Clones were screened by PCR and/or restriction digest for proper assembly and sequences were confirmed via Sanger sequencing. The p1 and p2 inserts were liberated from their vector backbones via restriction digest and inserts purified via gel extraction (NEB Monarch gel purification kit) to be transformed into suitable yeast strain.

All transformations were performed using the lithium acetate method as described in Geitz & Schiestl, 2007, Nature Protocols, 31-34. Individual transformants were screened using colony PCR to confirm correct integration of the 5' flank (using primers SEQ ID NO: 327 and SEQ ID NO: 328) and 3' flank (using primers SEQ ID NO: 329 and SEQ ID NO: 330) and to confirm correct assembly of the ura3 marker (using primers SEQ ID NO: 331 and SEQ ID NO: 332) and presence of the gene of interest (SEQ ID NO: 333 and SEQ ID NO: 334). Primers amplifying the native integration site (SEQ ID NO: 327 and SEQ ID NO: 329) were also used to identify any heterozygosity. The resulting strains containing a single copy of a gene encoding enzymes with SED ID NOs: 308-312, designated SB507-SB511, respectively, were assayed for IPMS activity. The activity was determined by measuring the amount of free CoA liberated as described in Kohlhaw and Leary, 1969, Vol. 244, No. 8 pp. 2218-2225. Total protein concentration in cell lysates was measured using Bradford assay. The recorded activity from these strains is expressed in nmol/mg prot/min and shown in Table 2.

TABLE 2

Enzyme activity in yeast strains

| Strain | Sequence | Activity |
|---|---|---|
| SB507 | SEQ ID NO: 308 | 86.5 |
| SB508 | SEQ ID NO: 309 | 56.0 |
| SB509 | SEQ ID NO: 310 | 25.5 |
| SB510 | SEQ ID NO: 311 | 89.3 |
| SB511 | SEQ ID NO: 312 | 5.4 |
| SB512 | Control | 5.5 |

As illustrated in Table 2, even a single copy of the gene could significantly enhance enzyme activity. Strains SB507 and SB510 were selected for inserting a second copy of the gene to make the locus homozygous. These strains were transformed with 1 μg of pEC010 plasmid containing a Cre expression cassette and KanMX cassette conferring resistance to Geneticin. Transformants were plated on YPD+500 ug/mL G418-sulfate. A single colony was used to inoculate YPD broth+500 ug/mL G418-sulfate and grown overnight. The G418 culture was then used to inoculate SC+1 g/L 5-FOA which selected for clones that had lost the ura3 marker. The 5-FOA culture was grown for 24-48 hours until visible growth was observed then cells were streaked for isolation onto a YPD plate. Single colonies were replica plated onto YPD, YPD+G418500 and SC-Ura plates. Clones that did not grow in the presence of G418 (had lost pEC010) or SC-Ura (lacked URA3) were screened via colony PCR to confirm URA3 loop-out. The second copy of the gene was integrated in a second round of transformation using the same p1 and p2 constructs. Successful integration and homozygosity were confirmed using colony PCR. The resulting strain was rendered auxotrophic for uracil by repeating the method described above, to facilitate further modification. In the manner described above, the other genes in the βHIV metabolic pathway shown in FIG. 1 were inserted subsequently. Sequences of exemplary enzymes that catalyze various steps of the βHIV metabolic pathway are step (b): SEQ ID NO: 297, SEQ ID NO: 298, SEQ ID NO: 299, SEQ ID NO: 300 step (c): SEQ ID NO: 301, SEQ ID NO: 302, SEQ ID NO: 303, step (d): SEQ ID NO: 304, SEQ ID NO: 305, SEQ ID NO: 306, SEQ ID NO: 307, step (f): SEQ ID NO: 314, SEQ ID NO: 315 and step (g): SEQ ID NO: 316, SEQ ID NO: 317, SEQ ID NO: 318, SEQ ID NO: 319, SEQ ID NO: 320. Therefore, the resulting yeast strains have the multiple variations of the βHIV metabolic pathway leading up to KIC.

A strain, designated SB553, comprising homozygous integration of genes that encode for SEQ ID NO: 299, SEQ ID NO: 301, SEQ ID NO: 304, SEQ ID NO: 308, SEQ ID NO: 315 and SEQ ID NO: 319, was grown in 50 mL of yeast minimal salts medium supplemented with 40 mg/L of uracil, trace metals, vitamins and glucose as the carbon source (Verduyn, et al. Yeast 8, 7:501-517, 1992). After 44 h of growth, the yeast culture was harvested and centrifuged to remove the yeast cells. The clarified supernatants were analyzed for residual glucose and βHIV synthesis via HPLC as described in Example 2. The strain SB502 was also grown under identical conditions to serve as a control. SB502 produced only 0.32 g/L of KIC while SB553 produced 1.84 g/L of KIC. Increased KIC production is clearly illustrative of the increased activity of all the enzymes expressed or overexpressed in the yeast cytosol.

Example 4: Production of βHIV in Yeast

Figure 5:
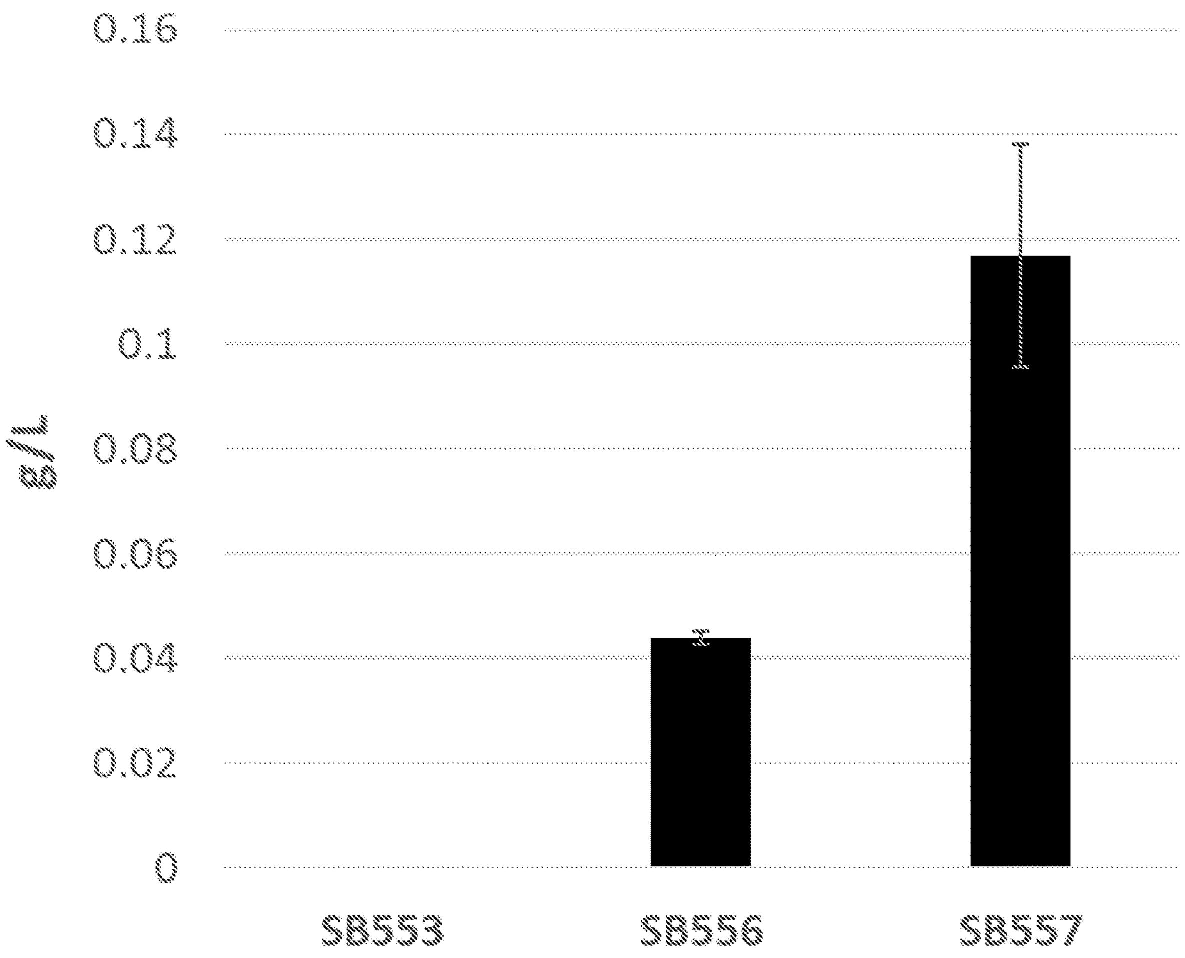
FIG. 5 is a bar graph illustrating the accumulation of βHIV by non-natural yeast microorganism harboring an unmodified dioxygenase enzyme (SB556) or an improved βHIV synthase (SB557), according to certain embodiments of the present invention.

This example will illustrate the integration of the complete βHIV metabolic pathway that will result in βHIV production by a non-natural yeast. All genetic manipulations were carried out using the methods described in Example 3. Step (a) of the βHIV metabolic pathway shown in FIG. 1, encoding for βHIV synthase, was assembled in strain SB553. Codon-optimized sequences of genes that encode for βHIV synthase variants corresponding to SEQ ID NO: 1 and SEQ ID NO: 335 were chromosomally integrated in SB553 to result in strains SB556 and SB557. The three strains were grown under identical conditions using minimal salts medium described in Example 3. After 42 h of growth, the culture was harvested, and cells separated by centrifugation. The clarified supernatant was analyzed for βHIV using an HPLC as described in Example 3. As illustrated in FIG. 5, supernatant from SB553 did not have any detectable βHIV. However, SB556 supernatant had 0.04 g/L of βHIV and SB557 supernatant had 0.12 g/L of βHIV. The result confirms the conversion of glucose into βHIV in SB556 and SB557 yeast using the metabolic pathway shown in FIG. 1 and the ability of the yeast cell to export βHIV into the medium using a transporter. Furthermore, the result also illustrates increased βHIV production using different variants of βHIV.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A non-natural enzyme capable of producing beta-hydroxyisovalerate (βHIV), the non-natural enzyme comprising one or more amino acid substitutions relative to a wild-type enzyme consisting of SEQ ID NO: 1 or 6, wherein the non-natural enzyme comprises one or more amino acid substitutions at substrate-specificity positions corresponding to amino acids selected from N187, W210, V212, V217, L224, S226, I227, V228, P239, N241, Q251, I252, Q265, L289, L323, F336, F347, A361, G362, N363, F364, L367, F368, and F371, of SEQ ID NO: 1 or SEQ ID NO: 6, wherein the non-natural enzyme preferentially utilizes α-ketoisocaproate as its substrate to produce βHIV, and wherein the non-natural enzyme provides more beta-hydroxyisovalerate (βHIV) synthase activity than the wild-type enzyme consisting of SEQ ID NO: 1 or 6.

2. The non-natural enzyme of claim 1, wherein the non-natural enzyme provides a greater conversion of α-ketoisocaproate into the βHIV than the wild-type enzyme consisting of SEQ ID NO: 1 or 6.

3. The non-natural enzyme of claim 1, wherein the non-natural enzyme is at least 65% identical to at least one polypeptide selected from the group consisting of SEQ ID NOS: 1-148.

4. The non-natural enzyme of claim 1, wherein the non-natural enzyme is at least 65% identical to at least one polypeptide selected from the group consisting of SEQ ID NOS: 1-6.

5. The non-natural enzyme of claim 1, wherein the one or more amino acid substitutions are at substrate-specificity positions selected from the group of leucine, isoleucine or methionine at position 361, leucine, isoleucine, methionine or tryptophan at position 336, tryptophan, tyrosine or isoleucine at position 347, alanine, leucine, isoleucine, methionine or tryptophan at position 364, tyrosine, tryptophan, leucine, isoleucine or methionine at position 368, leucine, isoleucine or methionine at position 371, leucine, isoleucine or methionine at position 362, leucine, valine or methionine at position 227, leucine, valine or methionine at position 252, phenylalanine, tryptophan or methionine at position 224, valine or methionine at position 289, tryptophan, tyrosine or isoleucine at position 323, isoleucine, tryptophan or methionine at position 367, phenylalanine, tryptophan or methionine at position 187, phenylalanine, tryptophan or methionine at position 241, isoleucine, methionine or valine at position 363, leucine at position 239, methionine, isoleucine or praline at position 251, methionine, isoleucine or praline at position 265, valine, methionine, isoleucine or leucine at position 226, phenylalanine, leucine, isoleucine or tryptophan at position 212, isoleucine, leucine or methionine at position 217, isoleucine, leucine or methionine at position 228, and leucine at position 210, of SEQ ID NO: 1 or SEQ ID NO: 6.

6. A modified microorganism expressing the non-natural enzyme of claim 1, wherein the modified microorganism expresses or overexpresses at least one gene encoding for βHIV synthase having at least 65% identity to the group consisting of SEQ ID NOS: 1-148, wherein the modified microorganism comprises a βHIV metabolic pathway in the cytosol, and wherein the modified microorganism comprises an active βHIV metabolic pathway from pyruvate to βHIV comprising (i) pyruvate into acetolactate, (ii) acetolactate into 2,3-dihydroxyisovalerate, (iii) 2,3-dihydroxyisovalerate into α-ketoisovalerate, (iv) α-ketoisovalerate into α-isopropylmalate, (v) α-isopropylmalate into β-isopropylmalate, (vi) β-isopropylmalate into α-ketoisocaproate, and (vii) α-ketoisocaproate into βHIV.

7. A modified microorganism expressing the non-natural enzyme of claim 1, wherein the modified microorganism expresses or overexpresses at least one gene encoding for βHIV synthase having at least 65% identity to the group consisting of SEQ ID NOS: 1-148, wherein the modified microorganism comprises a βHIV metabolic pathway in the cytosol, and wherein the modified microorganism comprises an active βHIV metabolic pathway from pyruvate to βHIV comprising (i) pyruvate into acetolactate, (ii) acetolactate into 2,3-dihydroxyisovalerate, (iii) 2,3-dihydroxyisovalerate into α-ketoisovalerate, (iv) α-ketoisovalerate into 2-isopropylmalate, (v) 2-isopropylmalate into 2-isopropylmaleate, (vi) 2-isopropylmaleate into 3-isopropylmalate, (vii) 3-isopropylmalate into 2-isopropyl-3-oxosuccinate, (viii) 2-isopropyl-3-oxosuccinate into α-ketoisocaproate, and (ix) α-ketoisocaproate into βHIV.

8. The modified microorganism of claim 7, wherein the modified microorganism is a yeast or a bacteria.

9. The modified microorganism of claim 7, wherein the modified microorganism is a yeast selected from the group consisting of *Saccharomyces, Kluyveromyces, Pichia, Issatchenkia, Hansenula*, or *Candida.*

10. The modified microorganism of claim 7, wherein the modified microorganism is a prokaryotic or eukaryotic bacteria, wherein the bacteria is selected from a Gram-positive bacteria or a Gram-negative bacteria, the Gram-positive bacteria comprising *Corynebacterium, Lactobacillus, Lactococcus* or *Bacillus*, and the Gram-negative bacteria comprising *Escherichia* or *Pseudomonas.*

11. A method of producing beta-hydroxyisovalerate (βHIV) using a modified microorganism expressing the non-natural enzyme of claim 1, the method comprising:

cultivating the modified microorganism in a culture containing a feedstock of a carbon source and oxygen until a recoverable quantity of βHIV is produced; and recovering the recoverable quantity of produced βHIV.

12. The method of claim 11, further comprising purifying the recoverable quantity of βHIV.

13. The method of claim 11, wherein the carbon source is selected from the group consisting of glucose, xylose, arabinose, sucrose, fructose, lactose, glycerol, and mixtures thereof.

14. The method of claim 11, wherein the modified microorganism comprises a βHIV metabolic pathway in contact with the carbon source and oxygen in a fermenter to produce βHIV, wherein the fermenter introduces sufficient nutrients such that a final βHIV concentration in a fermentation broth is greater than about 10 mg/L.

15. The method of claim 11, further comprising providing the modified microorganism in a fermenter in the presence of the at least one carbon source, wherein the recoverable quantity of βHIV produced is provided in a fermentation-derived composition comprising βHIV, and wherein the recovering step comprises isolating βHIV from the fermentation-derived composition.

16. The method of claim 15, wherein the fermentation-derived composition comprising βHIV prior to isolation is substantially devoid of a chemically derived inorganic residue chosen from chloroform, hydrochloric acid, and a halogen derivative.

17. The method of claim 16, wherein the βHIV prior to the isolation step has not been in substantial contact with chloroform, hydrochloric acid, or any halogen derivative.

18. The method of claim 15, further comprising introducing into the fermenter one or more nutrients in a quantity sufficient that a final concentration of βHIV in the fermentation-derived composition is greater than about 10 mg/L.

19. The method of claim 18, wherein the final concentration of βHIV in the fermentation-derived composition is greater than about 100 mg/L and less than 150 g/L.

20. The method of claim 18, wherein the final concentration of βHIV in the fermentation-derived composition is greater than about 1 g/L and less than 150 g/L.

21. The method of claim 18, wherein the final concentration of βHIV in the fermentation-derived composition is greater than about 10 g/L and less than 150 g/L.

22. The method of claim 18, wherein the final concentration of HIV in the fermentation-derived composition is greater than about 50 g/L and less than 150 g/L.

23. The method of claim 15, wherein the step of isolating βHIV from the fermentation-derived composition comprises removing the cells by centrifugation, followed by separating an aqueous phase from a clarified fermentation-derived composition and one or more optional by-products.

24. The method of claim 11, wherein the modified microorganism comprises a metabolic pathway for producing βHIV, the metabolic pathway comprises one or more steps of (i) pyruvate to acetolactate, (ii) acetolactate to 2,3-dihydroxyisovalerate, (iii) 2,3-dihydroxyisovalerate to α-ketoisovalerate, (iv) α-ketoisovalerate to α-isopropylmalate, (v) α-isopropylmalate to β-isopropylmalate, (vi) β-isopropylmalate to α-ketoisocaproate and (vii) α-ketoisocaproate to βHIV.

25. The method of claim 11, wherein the modified microorganism comprises a metabolic pathway for producing βHIV, the metabolic pathway comprises one or more steps of (i) pyruvate into acetolactate, (ii) acetolactate into 2,3-dihydroxyisovalerate, (iii) 2,3-dihydroxyisovalerate into α-ketoisovalerate, (iv) α-ketoisovalerate into 2-isopropylmalate, (v) 2-isopropylmalate into 2-isopropylmaleate, (vi) 2-isopropylmaleate into 3-isopropylmalate, (vii) 3-isopropylmalate into 2-isopropyl-3-oxosuccinate, (viii) 2-isopropyl-3-oxosuccinate into α-ketoisocaproate, and (ix) α-ketoisocaproate into βHIV.

26. The method of claim 11, wherein the modified microorganism is a eukaryote, and wherein the metabolic pathway hosts at least one βHIV pathway enzyme selected from the group consisting of acetolactate synthase having at least 80% identity to the group consisting of SEQ ID NOs: 297-300, cytosolic keto-acid reductoisomerase having at least 80% identity to the group consisting of SEQ ID NOs: 301-303, cytosolic dihydroxyacid dehydratase having at least 80% identity to the group consisting of SEQ ID NOs: 304-307, cytosolic 2-isopropylmalate synthase having at least 80% identity to the group consisting of SEQ ID NOs: 308-313, cytosolic isopropylmalate isomerase having at least 80% identity to the group consisting of SEQ ID NOs: 314-315, cytosolic 3-isopropylmalate dehydrogenase having at least 80% identity to the group consisting of SEQ ID NOs: 316-320, and cytosolic βHIV synthase having at least 65% identity to the group consisting of SEQ ID NOS: 1-148.

27. The method of claim 11, wherein the modified microorganism comprises at least one nucleic acid encoding a polypeptide with βHIV synthase activity derived from the group consisting of *Rattus norvegicus, Yarrowia lipolytica*, and *Homo sapiens*.

28. The method of claim 11, wherein the non-natural enzyme comprises one or more amino acid substitutions are at substrate-specificity positions selected from the group consisting of leucine, isoleucine or methionine at position 361, leucine, isoleucine, methionine or tryptophan at position 336, tryptophan, tyrosine or isoleucine at position 347, alanine, leucine, isoleucine, methionine or tryptophan at position 364, tyrosine, tryptophan, leucine, isoleucine or methionine at position 368, leucine, isoleucine or methionine at position 371, leucine, isoleucine or methionine at position 362, leucine, valine or methionine at position 227, leucine, valine or methionine at position 252, phenylalanine, tryptophan or methionine at position 224, valine or methionine at position 289, tryptophan, tyrosine or isoleucine at position 323, isoleucine, tryptophan or methionine at position 367, phenylalanine, tryptophan or methionine at position 187, phenylalanine, tryptophan or methionine at position 241, isoleucine, methionine or valine at position 363, leucine at position 239, methionine, isoleucine or proline at position 251, methionine, isoleucine or proline at position 265, valine, methionine, isoleucine or leucine at position 226, phenylalanine, leucine, isoleucine or tryptophan at position 212, isoleucine, leucine or methionine at position 217, isoleucine, leucine or methionine at position 228, and leucine at position 210 of SEQ ID NO: 1 or SEQ ID NO: 6.

29. The method of claim 11, wherein the modified microorganism is a prokaryotic microorganism or an eukaryotic microorganism.

30. The method of claim 29, wherein the modified microorganism comprises a yeast or a bacteria.

31. The method of claim 30, wherein the modified microorganism is a yeast selected from the group consisting of *Saccharomyces, Kluyveromyces, Pichia, Issatchenkia, Hansenula*, and *Candida*.

32. The method of claim 30, wherein the modified microorganism is Gram-positive bacteria or a Gram-negative bacteria, the Gram-positive bacteria selected from the group comprising of *Corynebacterium, Lactobacillus, Lactococcus* and *Bacillus*, and the Gram-negative bacteria selected from the group comprising of *Escherichia* and *Pseudomonas*.

33. The method of claim 11, wherein the modified microorganism expresses or overexpresses at least one gene encoding for an enzyme chosen from the group consisting of βHIV synthase, acetolactate synthase, acetohydroxy acid reductoisomerase, 2,3-keto-acid reductoisomerase, dihydroxy isovalerate dehydratase, 2,3-dihydroxy isovalerate dehydratase, 2-isopropylmalate synthase, isopropylmalate isomerase, 2-isopropylmalate hydrolyase, 3-isopropylmalate dehydrogenase, or a combination thereof.

* * * * *

SEQUENCE LISTING

```
Sequence total quantity: 335
SEQ ID NO: 1            moltype = AA  length = 393
FEATURE                 Location/Qualifiers
source                  1..393
                        mol_type = protein
                        organism = Rattus norvegicus
SEQUENCE: 1
MTTYSNKGPK PERGRFLHFH SVTFWVGNAK QAASFYCNKM GFEPLAYKGL ETGSREVVSH  60
VIKQGKIVFV LCSALNPWNK EMGDHLVKHG DGVKDIAFEV EDCEHIVQKA RERGAKIVRE  120
PWVEEDKFGK VKFAVLQTYG DTTHTLVEKI NYTGRFLPGF EAPTYKDTLL PKLPSCNLEI  180
IDHIVGNQPD QEMESASEWY LKNLQFHRFW SVDDTQVHTE YSSLRSIVVA NYEESIKMPI  240
NEPAPGRKKS QIQEYVDYNG GAGVQHIALR TEDIITTIRH LRERGMEFLA VPSSYYRLLR  300
ENLKTSKIQV KENMDVLEEL KILVDYDEKG YLLQIFTKPM QDRPTLFLEV IQRHNHQGFG  360
AGNFNSLFKA FEEEQALRGN LTDLETNGVR SGM                               393

SEQ ID NO: 2            moltype = AA  length = 377
FEATURE                 Location/Qualifiers
source                  1..377
                        mol_type = protein
                        organism = Rattus norvegicus
SEQUENCE: 2
MYWDKGPKPE RGRFLHFHSV TFWVGNAKQA ASFYCNKMGF EPLAYKGLET GSREVVSHVI  60
KQGKIVFVLC SALNPWNKEM GDHLVKHGDG VKDIAFEVED CEHIVQKARE RGAKIVREPW  120
VEEDKFGKVK FAVLQTYGDT THTLVEKINY TGRFLPGFEA PTYKDTLLPK LPSCNLEIID  180
HIVGNQPDQE MESASEWYLK NLQFHRFWSV DDTQVHTEYS SLRSIVVANY EESIKMPINE  240
PAPGRKKSQI QEYVDYNGGA GVQHIALRTE DIITTIRHLR ERGMEFLAVP SSYYRLLREN  300
LKTSKIQVKE NMDVLEELKI LVDYDEKGYL LQIFTKPMQD RPTLFLEVIQ RHNHQGFGAG  360
NFNSLFKAFE EEQALRG                                                 377

SEQ ID NO: 3            moltype = AA  length = 354
FEATURE                 Location/Qualifiers
source                  1..354
                        mol_type = protein
                        organism = Rattus norvegicus
SEQUENCE: 3
MGFEPLAYKG LETGSREVVS HVIKQGKIVF VLCSALNPWN KEMGDHLVKH GDGVKDIAFE  60
VEDCEHIVQK ARERGAKIVR EPWVEEDKFG KVKFAVLQTY GDTTHTLVEK INYTGRFLPG  120
FEAPRYKDTL LPKLPSCNLE IIDHIVGNQP DQEMESASEW YLKNLQFHRF WSVDDTQVHT  180
EYSSLRSIVV ANYEESIKMP INEPAPGRKK SQIQEYVDYN GGAGVQHIAL RTEDIITTIR  240
HLRERGMEFL AVPPSYYRLL RENLKSAKIQ VKEDMDVLEE LKILVDYDEK GYLLQIFTKP  300
MQDRPTLFLE VIQRHNHQGF GAGNFNSLFK AFEEEQALRG NLTDLETNGV RSGM        354

SEQ ID NO: 4            moltype = AA  length = 394
FEATURE                 Location/Qualifiers
source                  1..394
                        mol_type = protein
```

-continued

```
                         organism = Yarrowia lipolytica
SEQUENCE: 4
MSPSVEVTPA HTPTSYEVTN SLDSYRGYDH VHWYVGNAKQ AASFYITRMG FSPIAYKGLE  60
TGSRDVTTHV VGNGQVRFAF SSALRTGEPQ ADEIHAHLVK HGDAVKDVAF EVDNVEQLFS  120
AAVKKGVRVI SEPKVLKDAH GSVTYAVIST YGDTTHTLIE RGSYEGAFLP GFVDTSANKD  180
PIAAFLPNIE LMHIDHCVGN QDWNEMDNAC KYYEETLGFH RFWSVDDKDI CTEFSALKSV  240
VMASPNEKIK MPVNEPAVGK KKSQIEEYID FYDGPGIQHI ALRTDCILDT VRDLRARGVE  300
FISVPGSYYE NMKERLAKSS LKLEEKFEDI QALNILIDFD EGGYLLQLFT KPLMDRPTVF  360
IEIIQRRNFE GFGAGNFKSL FEAIEREQAK RGNL                            394

SEQ ID NO: 5             moltype = AA  length = 394
FEATURE                  Location/Qualifiers
source                   1..394
                         mol_type = protein
                         organism = Yarrowia lipolytica
SEQUENCE: 5
MSPSVEVTPA HTPTSYEVTN SLDSYRGYDH VHWYVGNAKQ AASFYITRMG FSPIAYKGLE  60
TGSRDVTTHV VGNGQVRFAF SSALRTGEPQ ADEIHAHLVK HGDAVKDVAF EVDNVEQLFS  120
AAVKKGVRVI SEPKVLKDAQ GSVTYAVIST YGDTTHTLIE RGSYEGAFLP GFVDTSANKD  180
PIAAFLPNIE LMHIDHCVGN QDWNEMDNAC KYYEETLGFH RFWSVDDKDI CTEFSALKSV  240
VMASPNEKIK MPVNEPAVGK KKSQIEEYID FYDGPGIQHI ALRTDCILDT VRDLRARGVE  300
FISVPGSYYE NMKERLAKSS LKLEEKFEDI QALNILIDFD EGGYLLQLFT KPLMDRPTVF  360
IEIIQRRNFE GFGAGNFKSL FEAIEREQAK RGNL                            394

SEQ ID NO: 6             moltype = AA  length = 393
FEATURE                  Location/Qualifiers
source                   1..393
                         mol_type = protein
                         organism = Homo sapiens
SEQUENCE: 6
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIMRE  120
PWVEQDKFGK VKFAVLQTYG DTTHTLVEKM NYIGQFLPGY EAPAFMDPLL PKLPKCSLEM  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYKQLR  300
EKLKTAKIKV KENIDALEEL KILVDYDEKG YLLQIFTKPV QDRPTLFLEV IQRHNHQGFG  360
AGNFNSLFKA FEEEQNLRGN LTNMETNGVV PGM                             393

SEQ ID NO: 7             moltype = AA  length = 377
FEATURE                  Location/Qualifiers
source                   1..377
                         mol_type = protein
                         organism = Homo sapiens
SEQUENCE: 7
WYWDKGPKPE RGRFLHFHSV TFWVGNAKQA ASFYCNKMGF EPLAYKGLET GSREVVSHVV  60
KQGKIVFVLC SALNPWNKEM GDHLVKHGDG VKDIAFEVED CEHIVQKARE RGAKIVREPW  120
VEEDKFGKVK FAVLQTYGDT THTLVEKINY TGRFLPGFEA PTYKDTLLPK LPSCNLEIID  180
HIVGNQPDQE MESASEWYLK NLQFHRFWSV DDTQVHTEYS SLRSIVVANY EESIKMPINE  240
PAPGRKKSQI QEYVDYNGGA GVQHIALRTE DIITTICHLR ERGMEFLAVP SSYYRLLREN  300
LKTSKIQVKE NMDVLEELKI LVDYDEKGYL LQIFTKPMQD RPTLFLEVIQ RHNHQGFGAG  360
NFNSLFKAFE EEQALRG                                               377

SEQ ID NO: 8             moltype = AA  length = 375
FEATURE                  Location/Qualifiers
source                   1..375
                         mol_type = protein
                         organism = Homo sapiens
SEQUENCE: 8
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIMRE  120
PWVEQDKFGK VKFAVLQTYG DTTHTLVEKM NYIGQFLPGY EAPAFMDPLL PKLPKCSLEM  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYKQLR  300
EKLKTAKIKV KENIDALEVR PVQDRPTLFL EVIQRHNHQG FGAGNFNSLF KAFEEEQNLR  360
GNLTNMETNG VVPGM                                                 375

SEQ ID NO: 9             moltype = AA  length = 376
FEATURE                  Location/Qualifiers
source                   1..376
                         mol_type = protein
                         organism = Rattus norvegicus
SEQUENCE: 9
YWDKGPKPER GRFLHFHSVT FWVGNAKQAA SFYCNKMGFE PLAYKGLETG SREVVSHVIK  60
QGKIVFVLCS ALNPWNKEMG DHLVKHGDGV KDIAFEVEDC EHIVQKARER GAKIVREPWV  120
EEDKFGKVKF AVLQTYGDTT HTLVEKINYT GRFLPGFEAP TYKDTLLPKL PSCNLEIIDH  180
IVGNQPDQEM ESASEWYLKN LQFHRFWSVD DTQVHTEYSS LRSIVVANYE ESIKMPINEP  240
APGRKKSQIQ EYVDYNGGAG VQHIALRTED IITTIRHLRE RGMEFLAVPS SYYRLLRENL  300
KTSKIQVKEN MDVLEELKIL VDYDEKGYLL QIFTKPMQDR PTLFLEVIQR HNHQGFGAGN  360
FNSLFKAFEE EQALRG                                                376
```

-continued

```
SEQ ID NO: 10          moltype = AA  length = 393
FEATURE                Location/Qualifiers
source                 1..393
                       mol_type = protein
                       organism = Mus musculus
SEQUENCE: 10
MTTYNNKGPK PERGRFLHFH SVTFWVGNAK QAASFYCNKM GFEPLAYRGL ETGSREVVSH  60
VIKRGKIVFV LCSALNPWNK EMGDHLVKHG DGVKDIAFEV EDCDHIVQKA RERGAKIVRE  120
PWVEQDKFGK VKFAVLQTYG DTTHTLVEKI NYTGRFLPGF EAPTYKDTLL PKLPRCNLEI  180
IDHIVGNQPD QEMQSASEWY LKNLQFHRFW SVDDTQVHTE YSSLRSIVVT NYEESIKMPI  240
NEPAPGRKKS QIQEYVDYNG GAGVQHIALK TEDIITAIRH LRERGTEFLA APSSYYKLLR  300
ENLKSAKIQV KESMDVLEEL HILVDYDEKG YLLQIFTKPM QDRPTLFLEV IQRHNHQGFG  360
AGNFNSLFKA FEEEQALRGN LTDLEPNGVR SGM                                393

SEQ ID NO: 11          moltype = AA  length = 379
FEATURE                Location/Qualifiers
source                 1..379
                       mol_type = protein
                       organism = Mus musculus
SEQUENCE: 11
TVDYWDKGPK PERGRFLHFH SVTFWVGNAK QAASFYCNKM GFEPLAYRGL ETGSREVVSH  60
VIKQGKIVFV LCSALNPWNK EMGDHLVKHG DGVKDIAFEV EDCNHIVQKA RERGAKIVRD  120
AWVEQDKFGK VKFAVLQTYG DTTHTLVEKI NYTGRFLPGF EAPTYKDTLL PKLPRCNLEI  180
IDHIVGNQPD QEMQSASEWY LKNLQFHRFW SVDDTQVHTE YSSLRSIVVT NYEESIKMPI  240
NEPAPGRKKS QIQEYVDYNG GAGVQHIALK TEDIITAIRH LRERGTEFLA APSSYYKLLR  300
ENLKSAKIQV KESMDVLEEL HILVDYDEKG YLLQIFTKPM QDRPTLFLEV IQRHNHQGFG  360
AGNFNSLFKA FEEEQALRG                                                379

SEQ ID NO: 12          moltype = AA  length = 393
FEATURE                Location/Qualifiers
source                 1..393
                       mol_type = protein
                       organism = Homo sapiens
SEQUENCE: 12
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIMRE  120
PWVEQDKFGK VKFAVLQTYG DTTHTLVEKM NYIGQFLPGY EPPAFMDPLL PKLPKCSLEM  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYKQLR  300
EKLKTAKIKV KENIDALEEL KILVDYDEKG YLLQIFTKPV QDRPTLFLEV IQRHNHQGFG  360
AGNFNSLFKA FEEEQNLRGN LTNMETNGVV PGM                                393

SEQ ID NO: 13          moltype = AA  length = 393
FEATURE                Location/Qualifiers
source                 1..393
                       mol_type = protein
                       organism = Rattus norvegicus
SEQUENCE: 13
MTTYSNKGPK PERGRFLHFH SVTFWVGNAK QAASFYCNKM GFEPLAYKGL ETGSREVVSH  60
VIKQGKIVFV LCSALNPWNK EMGDHLVKHG DGVKDIAFEV EDCEHIVQKA RERGAKIVRE  120
PWVEEDKFGK VKFAVLQTYG DTTHTLVEKI NYTGRFLPGF EAPTYKDTLL PKLPSCNLEI  180
IDHIVGNQPD QEMESASEWY LKNLQFHRFW SVDDTQVHTE YSSLRSIVVA NYEESIKMPI  240
NEPAPGRKKS QIQEYVDYNG GAGVQHIALR TEDIITTIRH LRERGMEFLA VPSSYYRLLR  300
ENLKTSKIQV KENMDVLEEL KILVDYDEKG YLLQIFTKPM QDRPTLFLEV IQRHNHQGFG  360
AGNFNSLFKA FEEEQALRGN LTDLETNGVR SGM                                393

SEQ ID NO: 14          moltype = AA  length = 393
FEATURE                Location/Qualifiers
source                 1..393
                       mol_type = protein
                       organism = Mus musculus
SEQUENCE: 14
MTTYNNKGPK PERGRFLHFH SVTFWVGNAK QAASFYCNKM GFEPLAYRGL ETGSREVVSH  60
VIKQGKIVFV LCSALNPWNK EMGDHLVKHG DGVKDIAFEV EDCDHIVQKA RERGAKIVRE  120
PWVEQDKFGK VKFAVLQTYG DTTHTLVEKI NYTGRFLPGF EAPTYKDTLL PKLPRCNLEI  180
IDHIVGNQPD QEMQSASEWY LKNLQFHRFW SVDDTQVHTE YSSLRSIVVT NYEESIKMPI  240
NEPAPGRKKS QIQEYVDYNG GAGVQHIALK TEDIITAIRH LRERGTEFLA APSSYYKLLR  300
ENLKSAKIQV KESMDVLEEL HILVDYDEKG YLLQIFTKPM QDRPTLFLEV IQRHNHQGFG  360
AGNFNSLFKA FEEEQALRGN LTDLEPNGVR SGM                                393

SEQ ID NO: 15          moltype = AA  length = 393
FEATURE                Location/Qualifiers
source                 1..393
                       mol_type = protein
                       organism = Bos taurus
SEQUENCE: 15
MTTYSDKGEK PERGRFLHFH SVTFWVGNAK QAASYYCSKL GFEPLAYKGL ETGSREVVSH  60
VVKQGQIVFV FSSALNPWNK EMGDHLVKHG DGVKDIAFEV EDCDYIVQKA RERGAKIVRE  120
```

-continued

```
PWVEQDKLGK VKFAVLQTYG DTTHTLVEKM NYTGRFLPGF EAPPFMDPQL SKLPSCSLEI  180
IDHIVGNQPD QEMVSASEWY LKNLQFHRFW SVDDTQVHTE YSSLRSVVVA NYEESIKMPI  240
NEPAPGKKKS QIQEYVDYNG GAGVQHIALK TKDIITAIRH LRERGVEFLA VPSTYYKQLR  300
EKLKMAKIRV KENIDILEEL KILVDYDEKG YLLQIFTKPM QDRPTLFLEV IQRHNHQGFG  360
AGNFNSLFKA FEEEQDLRGN LTDMEPNGVV SGM                               393

SEQ ID NO: 16          moltype = AA  length = 393
FEATURE                Location/Qualifiers
source                 1..393
                       mol_type = protein
                       organism = Mus musculus
SEQUENCE: 16
MTTYNNKGPK PERGRFLHFH SVTFWVGNAK QAASFYCNKM GFEPLAYRGL ETGSREVVSH  60
VIKQGKIVFV LCSALNPWNK EMGDHLVKHG DGVKDIAFEV EDCDHIVQKA RERGAKIVRE  120
PWVEQDKFGK VKFAVLQTYG DTTHTLVEKI NYTGRFLPGF EAPTYKDTLL PKLPRCNLEI  180
IDHIVGNQPD QEMQSASEWY LKNLQSHRFW SVDDTQVHTE YSSLRSIVVT NYEESIKMPI  240
NEPAPGRKKS QIQEYVDYNG GAGVQHIALK TEDIITAIRH LRERGTEFLA APSSYYKLLR  300
ENLKSAKIQV KESMDVLEEL HILVDYDEKG YLLQIFTKPM QDRPTLFLEV IQRHNHQGFG  360
AGNFNSLFKA FEEEQALRGN LTDLEPNGVR SGM                               393

SEQ ID NO: 17          moltype = AA  length = 377
FEATURE                Location/Qualifiers
source                 1..377
                       mol_type = protein
                       organism = Homo sapiens
SEQUENCE: 17
WYWDKGPKPE RGRFLHFHSV TFWVGNAKQA ASFYCNKMGF EPLAYKGLET GSREVVSHVV  60
KQGKIVFVLC SALNPWNKEM GDHLVKHGDG VKDIAFEVED CEHIVQKARE RGAKIVREPW  120
VEEDKFGKVK FAVLQTYGDT THTLVEKINY TGRFLPGFEA PTYKDTLLPK LPSCNLEIID  180
HIVGNQPDQE MESASEWYLK NLQFHRFWSV DDTQVHTEYS SLRSIVVANY EESIKMPINE  240
PAPGRKKSQI QEYVDYNGGA GVQHIALRTE DIITTICHLR ERGMEFLAVP SSYYRLLREN  300
LKTSKIQVKE NMDVLEELKI LVDYDEKGYL LQIFTKPMQD RPTLFLEVIQ RHNHQGFGAG  360
NFNSLFKAFE EEQALRG                                                 377

SEQ ID NO: 18          moltype = AA  length = 393
FEATURE                Location/Qualifiers
source                 1..393
                       mol_type = protein
                       organism = Pan troglodytes
SEQUENCE: 18
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIVRE  120
PWVEQDKFGK VKFAVLQTYG DTTHTLVEKM NYIGQFLPGY EAPAFMDPLL PKLPKCSLEM  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYKQLR  300
EKLKTAKIKV KENIDALEEL KILVDYDEKG YLLQIFTKPV QDRPTLFLEV IQRHNHQGFG  360
AGNFNSLFKA FEEEQNLRGN LTNMETNGVV PGM                               393

SEQ ID NO: 19          moltype = AA  length = 393
FEATURE                Location/Qualifiers
source                 1..393
                       mol_type = protein
                       organism = Cricetulus griseus
SEQUENCE: 19
MTTYTNKGPK PERGRFLHFH SVTFWVGNAK QAASFYCNKM GFEPLAYRGL ETGSREVVSH  60
VIKQGKIVFV FCSALNPWNK EMGDHLVKHG DGVKDIAFEV EDCDHIVQKA RERGAKIVRE  120
PWVEEDKFGK VKFAVLQTYG DTTHTLVEKI NYTGRFLPGF EAPTYKDTLL PKLPRCNLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITTIRH LRERGMEFLA VPSSYYKLLR  300
ENLKTAKIQV KESLDVLEEL KILVDYDEKG YLLQIFTKPM QDRPTLFLEV IQRRNHQGFG  360
AGNFNSLFKA FEEEQALRGN LTDMETNGVR SGM                               393

SEQ ID NO: 20          moltype = AA  length = 393
FEATURE                Location/Qualifiers
source                 1..393
                       mol_type = protein
                       organism = Saimiri boliviensis
SEQUENCE: 20
MTTYSDKGAK PERGRFLHFH SVTFWVGNAK QAASFYCTKM GFEPLAYRGL ETGSREVVSH  60
VIKQGKIVFV LSSALNPWNK EMGNHLVKHG DGVKDIAFEV EDCDYIVQKA RERGAKIVRE  120
PWVEEDKFGK VKFAVLQTYG DTTHTLVEKM SYAGRFLPGY EAPAFMDPLL PQLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LRERGMEFLS VPSTYYKQLR  300
EKLKVAKIKV KESIDVLEEL KILVDYDEKG YLLQIFTKPV QDRPTLFLEV IQRHNHQGFG  360
AGNFNSLFKA FEEEQNLRGN LTNMETDGVV PGM                               393

SEQ ID NO: 21          moltype = AA  length = 393
FEATURE                Location/Qualifiers
source                 1..393
```

```
                        mol_type = protein
                        organism = Felis catus
SEQUENCE: 21
MTTYSNKGEK PARGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIAQKA RERGAKIVRE  120
PWIEQDKFGK VKLAVLQTYG DTTHTLVEKM NYTGRFLPGF EAPAFVDPLL SKLPSCSLEI  180
IDHIVGNQPD QEMESASDWY LKNLQFHRFW SVDDTQVHTE YSSLRSIVVA NYEESIKMPI  240
NEPAPGKKKS QIQEYVDYNG GPGVQHIALK TQDIITAIRH LRERGMEFLG VPSTYYKQLR  300
EKLKSAKIRV KENIDVLEEL KILVDYDEKG YLLQIFTKPV QDRPTLFLEV IQRHNHQGFG  360
AGNFNSLFKA FEEEQNLRGN LTDLENNGIV PGM                             393

SEQ ID NO: 22           moltype = AA  length = 393
FEATURE                 Location/Qualifiers
source                  1..393
                        mol_type = protein
                        organism = Ovis aries
SEQUENCE: 22
MTTYSDKGEK PERGRFLHFH SVTFWVGNAK QAASYYCSKL GFEPLAYKGL ETGSREVVSH  60
VVKQGQIVFI FSSALNPWNK EMGDHLVKHG DGVKDIAFEV EDCDYIVQKA RERGAKIVRE  120
PWVEQDKLGK VKFAVLQTYG DTTHTLVEKM NYTGRFLPGF EAPAFMDPQL SKLPNCGLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TKDIITAIRH LRERGVEFLA VPSTYYKQLR  300
EKLKSAKIRV KENIDILEEL KILVDYDEKG YLLQIFTKPM QDRPTLFLEV IQRHNHQGFG  360
AGNFNSLFKA FEEEQDLRGN LTDMEPNGVV SSM                             393

SEQ ID NO: 23           moltype = AA  length = 393
FEATURE                 Location/Qualifiers
source                  1..393
                        mol_type = protein
                        organism = Orcinus orca
SEQUENCE: 23
MTTYSNKGEK PERGRFLHFH SVTFWVGNAK QAASYYCSKM GFESLAYKGL ETGSRETVSH  60
VIKQGKIVFI FSSALNPWNK EMGDHLVKHG DGVKDIAFEV EDCDYIVQKA RERGAKIVRE  120
PWVEQDKFGK VKFAVLQTYG DTTHTLVEKM NYTGWFLPGF EAPAFVDPLL PKLPNCSLER  180
IDHIVGNQPD QEMLSASEWY LKNLQFHRFW SVDDTQVHTE YSSLRSIVVA NYEESIKMPI  240
NEPAPGRKKS QIQEYVDYNG GAGVQHIALK TEDIITAIRH LRERGMEFLA VPSTYYKQLR  300
EKLKSAKIRV KENIDVLEEL KILVDYDEKG YLLQIFTKPM QDRPTLFLEV IQRYNHQGFG  360
AGNFNSLFKA FEEEQDLRGN LTDMETNGTV PSM                             393

SEQ ID NO: 24           moltype = AA  length = 393
FEATURE                 Location/Qualifiers
source                  1..393
                        mol_type = protein
                        organism = Odobenus rosmarus
SEQUENCE: 24
MTTYSDKGRK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIVRE  120
PWIEQDKFGK VKLAVLQTYG DTTHTLVEKM NYSGWFLPGF ETPASVDPLL SKLPTCSLEI  180
IDHIVGNQPD QEMVSASEWY LKNLQFHRFW SVDDTQVHTE YSSLRSIVVA NFEESIKMPI  240
NEPAPGKKKS QIQEYVDYNG GAGVQHIALK TQDIITAIRH LRERGMEFLA VPPTYYKQLR  300
EKLKSAKIRV KESIDILEEL KILVDYDEKG YLLQIFTKPM QDRPTLFLEV IQRHNHQGFG  360
AGNFNSLFKA FEEEQDLRGN LTDLKNTRTL PGM                             393

SEQ ID NO: 25           moltype = AA  length = 393
FEATURE                 Location/Qualifiers
source                  1..393
                        mol_type = protein
                        organism = Dasypus novemcinctus
SEQUENCE: 25
MTTYSDKGVK PERGRFLHFH SVTFWVGNAK QAASFYCNKM GFEPLAYRGL ETGSREVVSH  60
VVKQDKIVFV LSSALNPGNK EMGDHLVKHG DGVKDIAFEV EDCASIVQKA RERGAKIVRE  120
PWVEEDKFGK VKFAVLQTYG DTTHTLVEKM NYTGRFLPGF EAPVITDPLL AKLPSCRLEI  180
IDHIVGNQPD QEMVSASEWY VKNLQFHRFW SVDDTQVHTE YSSLRSIVVA NYEETIKMPI  240
NEPAQGKKKS QIQEYVDYNG GAGVQHIALK TQDIITAIRH LKERGLEFLA VPSTYYRQLR  300
EKLKTAKIKV KESIDILEEL KILVDFDEKG YLLQIFTKPV QDRPTLFLEV IQRHNHQGFG  360
AGNFNSLFKA FEEEQKLRGN LTDLGANGVL PGM                             393

SEQ ID NO: 26           moltype = AA  length = 393
FEATURE                 Location/Qualifiers
source                  1..393
                        mol_type = protein
                        organism = Jaculus jaculus
SEQUENCE: 26
MTTYSDKGPK PERGRFLHFH SVTFWVGNAK QAASFYCNKM GFEPLAYKGL ETGSREVVSH  60
VIKQGKIVFV LSSALNPWNK EMGDHLVKHG DGVKDIAFEV EDCEHIVQKA RERGAKIVRE  120
PWVEQDRFGK VKFAVLQTYG DTTHTLVEKI NYTGRFLPGF EAPMLKDPLL SKLPNCSLEI  180
IDHIVGNQPD QEMESASEWY LKNLQFHRFW SVDDTQVHTE YSSLRSIVVA NYEESIKMPI  240
NEPAPGKKKS QIQEYVDYNG GAGVQHIALK TQDIITTIRH LRERGMEFLA VPSTYYKLLR  300
ENLKSAKIRV KESIDVLEEL KILVDYDENG YLLQIFTKPM QDRPTLFLEV IQRHNHQGFG  360
```

-continued

```
AGNFNSLFKA FEEEQALRGN LTDMETNGVV SGM                             393

SEQ ID NO: 27           moltype = AA  length = 393
FEATURE                 Location/Qualifiers
source                  1..393
                        mol_type = protein
                        organism = Mustela putorius
SEQUENCE: 27
MTTYSDKGKK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYLVQKA REQGAKIVRE  120
PWIEQDKFGK VKLAVLQTYG DTTHTLVEKM NYTGRFLPGF EAPISVDPLL SKLPTCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LKARGMEFLG VPSSYYKQLR  300
EKLKTAKIQV KENIDVLEEL KILVDYDEKG YLLQIFTKPM QDRPTLFLEV IQRHNHQGFG  360
AGNFNALFKA FEEEQDLRGN LTNLETNSSL RGM                             393

SEQ ID NO: 28           moltype = AA  length = 393
FEATURE                 Location/Qualifiers
source                  1..393
                        mol_type = protein
                        organism = Heterocephalus glaber
SEQUENCE: 28
MTTYSDKGAK PERGRFLHFH SVTFWVGNAK QAAAFYCSKM GFEPLAYRGL ETGSREVASH  60
VIKQGQIVFV LSSPLNPWNR EMGEHLVKHG DSVKDIAFEV EDCDYIVQKA RERGAKVVRE  120
PWVEEDKFGK VKLAVLQTYG DTTHTLVEKM SFSGSFLPGF EAPRVKDSLL SKLPSCGLET  180
IDHIVGNQPD QEMVSASEWY LRNLQFHRFW SVDDSQVHTE YSALRSIVVT NYEESIKMPI  240
NEPALGRKKS QIQEYVEYNG GAGVQHIALK TPDIITSIRH LRERGVEFLA VPSTYYKQLR  300
ENLKSAKIRV KESIDMLEEL KILVDYDEKG YLLQVFTKPV QDRPTLFLEV IQRHNHQGFG  360
AGNFNALFKA FEAEQDLRGN LTDTETNGVV SGV                             393

SEQ ID NO: 29           moltype = AA  length = 393
FEATURE                 Location/Qualifiers
source                  1..393
                        mol_type = protein
                        organism = Microtus ochrogaster
SEQUENCE: 29
MTTYTNKGPK PERGRFLHFH SVTFWVGNAK QAASFYCNKM GFEPLAYKGL ETGSREVVSH  60
VIKQGKIVFV LCSALNPWNK EMGDHLVKHG DGVKDIAFEV EDCEHIVQKA RERGAKIVRE  120
PWVEEDKFGK VKFAVLQTYG DTTHTLVEKI NYTGHFLPGF EAPVYKDTLL PKLPRCNLEV  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TDDIITAIHH LRERGMEFLA VPSSYYKLLR  300
ENLKTAKIQV KESMDTLEEL KILVDYDEKG YLLQIFTKPM QDRPTLFLEV IQRHNHQGFG  360
AGNFNSLFKA FEEEQALRGN LTDLETNGVR SGK                             393

SEQ ID NO: 30           moltype = AA  length = 393
FEATURE                 Location/Qualifiers
source                  1..393
                        mol_type = protein
                        organism = Chinchilla lanigera
SEQUENCE: 30
MTTYSDKGAK PERGRFLHFH SVTFWVGNAK QAASFYCSKM GFEPLAYRGL ETGSREVASH  60
VIKQGQIVFV FSSPLNPWNK EMGDHLVKHG DGVKDIAFEV EDCDYIVQKA RERGAKVVRE  120
PWVEQDKSGK VKFAVLQTYG DTTHTLVEKT GYSGSFLPGF EAARAKDSLL SKLPSCGLEI  180
IDHIVGNQPD QEMLSASEWY LRNLQFHRFW SVDDTQVHTE YSSLRSIVVT DYEESIKMPI  240
NEPAPGKKKS QIQEYVDYNG GAGVQHIALK TQDIITAIRH LRERGAEFLA VPSSYYTQLR  300
ENLKSAKVRV KENIDVLEEL KILVDYDEKG YLLQIFTKPM QDRPTLFLEV IQRHNHQGFG  360
AGNFNALFKA FEAEQDLRGN LTDLETNGVA SGM                             393

SEQ ID NO: 31           moltype = AA  length = 393
FEATURE                 Location/Qualifiers
source                  1..393
                        mol_type = protein
                        organism = Macaca fascicularis
SEQUENCE: 31
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA REQGAKIVRE  120
PWVEQDKFGK VKFAVLQTYG DTTHTLVEKM NYTGQFLPGY EAPVFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITTIRH LRERGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LTDLETNGVV PGM                             393

SEQ ID NO: 32           moltype = AA  length = 393
FEATURE                 Location/Qualifiers
source                  1..393
                        mol_type = protein
                        organism = Equus caballus
SEQUENCE: 32
MTTYSNKGEK PEKGRFLHFH SVTFWVGNAK QAASFYCNKL GFEPLAYKGL ETGSREVVSH  60
```

-continued

```
VIKQGKIIFV FSSALNPWNK EMGDHLVKHG DGVKDIAFEV EDCDYIVQKA RERGAKIVRE  120
PWVEQDKFGK VKFAVLQTYG DTTHTLVEKM SYAGRFLPGF EAPAFRDPLL SKLPNCSLEI  180
IDHVVGNQPD HEMESASEWY LKNLQFHRFW SVDDTQVHTE YSSLRSIVVA NYEESIKMPI  240
NEPAPGRKKS QIQEYVDYNG GAGVQHIALK THDIITAIRH LRERGMEFLA VPSSYYRQLQ  300
EKLKSAKIRV KESIDVLEEL KILVDYDEKG YLLQIFTKPT QDRPTLFLEV IQRHNHQGFG  360
AGNFNALFKA FEEEQDLRGN LTDMQTNDLV PGK                               393

SEQ ID NO: 33          moltype = AA  length = 393
FEATURE                Location/Qualifiers
source                 1..393
                       mol_type = protein
                       organism = Bos mutus
SEQUENCE: 33
MTTYSDKGEK PERGRFLHFH SVTFWVGNAK QAASYYCSKL GFEPLAYKGL ETGSREVVSH  60
VVKQGQIVFV FSSALNPWNK EMGDHLVKHG DGVKDIAFEV EDCDYIVQKA RERGAKIVRE  120
PWVEQDKLGK VKFAVLQTYG DTTHTLVEKM NYTGRFLPGF EAPPFMDPQL SKLPSCSLEI  180
IDHIVGNQPD QEMVSASEWY LKNLQFHRFW SVDDTQVHTE YSSLRSVVVA NYEESIKMPI  240
NEPAPGKKKS QIQEYVDYNG GAGVQHIALK TKDIITAIRH LRERGVEFLA VPSTYYKQLR  300
EKLKMAKIRV KENIDILEEL KILVDYDEKG YLLQIFTKPM QDRTTIFLEV IQRHNHQGFG  360
AGNFNSLFKA FEEEQDLRGN LTDMEPNGVV SGM                               393

SEQ ID NO: 34          moltype = AA  length = 390
FEATURE                Location/Qualifiers
source                 1..390
                       mol_type = protein
                       organism = Vicugna pacos
SEQUENCE: 34
MTTYSNKGEK PERGRFLHFH SVTFWVGNAK QAASYYCSKM GFEPLAYKGL ETRSREVVSH  60
VIKQGKIVFV FSSALNPWNK EMGDHLVKHG DGVKDIAFEV EDCDYIVQKA RERGAKIVRE  120
PWVEQDKFGK VKFAVLQTYG DTTHTLVEKM NYTGRFLPGF EAPASTDPLL SKLPNCGLEI  180
IDHIVGNQPD QEMLSASEWY LKNLQFHRFW SVDDTQVHTE YSSLRSIVVA NYEESIKMPI  240
NEPAPGRKKS QIQEYVDYNG GAGVQHIALK TQDIITAIRH LRERGMEFLA VPSTYYKQLR  300
EKLKSAKIRV KENIDVLEEL KILVDYDEKG YLLQIFTKPM QDRPTLFLEV IQRHNHQGFG  360
AGNFNSLFKA FEEEQDLRGN LTDMETSGVV                                   390

SEQ ID NO: 35          moltype = AA  length = 393
FEATURE                Location/Qualifiers
source                 1..393
                       mol_type = protein
                       organism = Myotis davidii
SEQUENCE: 35
MTSYSNKGEK PERGRFLHFH SVTFWVGNAK QAASFYCSKM GFKPIAYKGL ETGSREVVSH  60
VVKQGQIVFV FSSALNPWNK EMGDHLVKHG DGVKDIAFEV EDCDYIVQKA RQRGAKIIRE  120
PWVEQDKFGK VKFAVLQTYG DTTHTLVEKM NYAGFFLPGF EPTTNRDQAL SKLPQSNLEV  180
IDHIVGNQPD QEMLSASDWY LNNLQFHRFW SVDDTQVHTE YSSLRSIVVA NYEESIKMPI  240
NEPAPGRKKS QIQEYVDYNG GAGVQHIALK TQDIITAIRH LRERGMEFLD VPSTYYKQLR  300
EKLKSAKIRV KENLDALEEL KILVDYDENG YLLQIFTKPM QDRPTLFLEV IQRHNHQGFG  360
AGNFNALFKA FEEEQNMRGN LTDLEPNGVI RGM                               393

SEQ ID NO: 36          moltype = AA  length = 393
FEATURE                Location/Qualifiers
source                 1..393
                       mol_type = protein
                       organism = Leptonychotes weddellii
SEQUENCE: 36
MTTYSDKGKK PQRGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIVRE  120
PWIEQDKFGK VKLAVLQTYG DTTHTLVEKM NYSGRFLPGF ETPASVDPLL SKLPSCSLEM  180
IDHIVGNQPD QEMVSASEWY LKNLQFHRFW SVDDTQVHTE YSSLRSIVVA NFEESIKMPI  240
NEPAPGKKKS QIQEYVDYNG GAGVQHIALK TQDIITAIRH LRERGMEFLA VPPMYYKQLR  300
EKLKSAKIRV KESIDTLEEL KILVDYDEKG YLLQIFTKPM QDRPTLFLEV IQRHNHQGFG  360
AGNFNSLFKA FEEEQDLRGN LTDLENTRTL PGM                               393

SEQ ID NO: 37          moltype = AA  length = 393
FEATURE                Location/Qualifiers
source                 1..393
                       mol_type = protein
                       organism = Peromyscus maniculatus
SEQUENCE: 37
MTSYTNKGPK PERGRFLHFH SVTFWVGNAK QAASFYCNKM GFEPLAYKGL ETGSREVVSH  60
VIKQGKIVFV LSSALNPWNK EMGDHLVKHG DGVKDIAFEV EDCEHIVQKA RERGAKIVRE  120
PWVEQDKFGK VKFAVLQTYG DTTHTLVEKI NYTGRFLPGF EAPMHKDTLL SKLPSCNLEV  180
IDHIVGNQPD QEMLSASEWY LKNLQFHRFW SVDDTQVHTE YSSLRSIVVA NYEESIKMPI  240
NEPAPGKKKS QIQEYVDYNG GAGVQHIALK TEDIITTIRH LRERGMEFLA VPSSYYRLLR  300
ENLKTAKIQV KESMDVLEEL KILVDYDEKG YLLQIFTKPM QDRPTLFLEV IQRHNHQGFG  360
AGNFNSLFKA FEEEQALRGN LTDLETNGVR SGM                               393

SEQ ID NO: 38          moltype = AA  length = 393
FEATURE                Location/Qualifiers
```

```
source                1..393
                      mol_type = protein
                      organism = Panthera tigris
SEQUENCE: 38
MTTYSNKGEK PARGRFLHFH SVTFWVGNAK QAASFYCNKM GFEPLAYKGL ETGSREVVSH  60
AIKQGKIVFV FSSALNPWNK EMGDHLVKHG DGVKDIAFEV EDCDYIVQKA RERGAKIVRE  120
PWIEQDKFGK VKLAVLQTYG DTTHTLVEKM NYTGRFLPGF EAPAFVDPLL SKLPSCSLEI  180
IDHIVGNQPD QEMESASDWY LKNLQFHRFW SVDDTQVHTE YSSLRSIVVA NYEESIKMPI  240
NEPAPGKKKS QIQEYVDYNG GPGVQHIALK TQDIITAIRH LRERGMEFLG VPSTYYKQLR  300
EKLKSAKIRV KENIDVLEEL KILVDYDEKG YLLQIFTKPV QDRPTLSLEV IQRHKHQGFG  360
AGNFNSLFKA FEEEQNLRGN LTDLENNGIV PGM                             393

SEQ ID NO: 39         moltype = AA  length = 393
FEATURE               Location/Qualifiers
source                1..393
                      mol_type = protein
                      organism = Physeter catodon
SEQUENCE: 39
MTTYSNKGEK PERGQFLHFH SVTFWVGNAK QAASYYCSKM GFEPLAYKGL ETGSREMVSH  60
VIKQGKIVFI FSSALNPWNK EMGDHLVKHG DGVKDIAFEV EDCDYIVQKA RERGAKIVRE  120
PWVEQDKFGR VKFAVLQTYG DTTHTLVEKM NYTGWFLPGF EAPAFVDPLL SKLPNCSLEI  180
IDHIVGNQPD QEMVSASEWY LKNLQFHRFW SVDDTQVHTE YSSLRSIVVA NYEESIKMPI  240
NEPAPGRKKS QIQEYVDYNG GAGVQHIALK TEDIITAIRH LRERGMEFLA VPFTYYKQLR  300
EKLKSAKIRV KENIDVLEEL KILVDYDEKG YLLQIFTKPM QDRPTLFLEV IQRYNHQGFG  360
AGNFNSLFKA FEEEQDLRGN LTDMETNGVG SGM                             393

SEQ ID NO: 40         moltype = AA  length = 393
FEATURE               Location/Qualifiers
source                1..393
                      mol_type = protein
                      organism = Bubalus bubalis
SEQUENCE: 40
MTTYSDKGEK PERGRFLHFH SVTFWVGNAK QAASYYCSKL GFEPLAYKGL ETGSREVVSH  60
VVKQGQIVFV FSSALNPWNK EMGDHLVKHG DGVKDIAFEV EDCDYIVQKA RERGAKIVRE  120
PWVEQDKLGK VKFAVLQTYG DTTHTLVEKM NYTGRFLPGF EAPPFMDPQL SKLPSCSLEI  180
IDHIVGNQPD QEMVSASEWY LKNLQFHRFW SVDDTQVHTE YSSLRSVVVA NYEESIKMPI  240
NEPAPGKKKS QIQEYVDYNG GAGVQHIALK TKDIITAIRH LRERGVEFLA VPSTYYKQLR  300
EKLKSAKIRV KENIDILEEL KILVDYDEKG YLLQIFTKPM QDRPTLFLEV IQRHNHQGFG  360
AGNFNSLFKA FEEEQDLRGN LTDMEPNGVV SGM                             393

SEQ ID NO: 41         moltype = AA  length = 393
FEATURE               Location/Qualifiers
source                1..393
                      mol_type = protein
                      organism = Balaenoptera acutorostrata
SEQUENCE: 41
MTTYSNKGQK PERGQFLHFH SVTFWVGNAK QAASYYCSKM GFEPLAYKGL ETGSREMVSH  60
VIKQGKIVFI FSSALNPWNK EMGDHLVKHG DGVKDIAFEV EDCDYIVQKA RERGAKIVRE  120
PWVEQDKFGK VKFAVLQTYG DTTHTLVEKM NYTGWFLPGF EAPAFVDPLL SKLPNCSLKI  180
IDHIVGNQPD QEMVSASEWY LKNLQFHRFW SVDDTQVHTE YSSLRSIVVA NYEESIKMPI  240
NEPAPGRKKS QIQEYVDYNG GAGVQHIALK TEDIITAIHH LRERGMEFLA VPSTYYKQLR  300
EKLKTAKIRV KENIDVLEEL KILVDYDEKG YLLQIFTKPM QDRPTLFLEV IQRYNHQGFG  360
AGNFNSLFKA FEEEQDLRGN LTDMETNGLV PGM                             393

SEQ ID NO: 42         moltype = AA  length = 393
FEATURE               Location/Qualifiers
REGION                348..349
                      note = misc_feature - Xaa can be any naturally occurring
                       amino acid
source                1..393
                      mol_type = protein
                      organism = Lipotes vexillifer
SEQUENCE: 42
MTTYSNKGEK PEKGRFLHFH SVTFWVGNAK QAASYYCSKM GFEPLAYKGL ETGSREMVSH  60
VIKQGKIAFI FSSALNPWNK EMGDHLVKHG DGVKDIAFEV EDCDYIVQKA RERGAKIVRE  120
PWVEQDKFGK VKFAVLQTYG DTTHTLVEKM NYTGWFLPGF EAPGFVDPLL SKLPNCSLEI  180
IDHIVGNQPD QEMLSASEWY LKNLQFHRFW SVDDTQVHTE YSSLRSIVVA NYEESIKMPI  240
NEPAPGRKKS QIQEYVDYNG GAGVQHVALK TEDIITAIRH LRERGMEFLA VPSTYYKQLR  300
EKLKSAKIRV KENIDVLEEL KILVDYDEKG YLLQIFTKPM QDRPTLFXXV IQRYNHQGFG  360
AGNFNSLFKA FEEEQDLRGN LTDMETNGTT CGM                             393

SEQ ID NO: 43         moltype = AA  length = 420
FEATURE               Location/Qualifiers
source                1..420
                      mol_type = protein
                      organism = Carlito syrichta
SEQUENCE: 43
MRPRLDQKLP GLGPCRPRLS SRPHEGHQTT YSNKGPKPER GRFLHFHSVT FWVGNAKQAA  60
SFYCNKMGFE PFAYRGLETG AREVVSHVIK QGKIVFVLSS ALNPWNKEMG DHLVKHGDGV  120
```

-continued

```
KDITFEVEDC DSIVQKARER GAKIVREPWV EQDKFGKVKF AVLQTYGDTT HTLVEKVNYT  180
GRFLPGFEAP VMTDPLLSKL PNCHLEIIDH IVGNQPDQEM VSASEWYLKN LQFHRFWSVD  240
DKQVHTEYSS LRSVVVANYE ESIKMPINEP APGKKKSQIQ EFVEYNGGAG VQHIALKTQD  300
IITSIRHLRE RGTEFLAVPS TYYKQIREKL KTAKIKVKEN IDILEELRIL VDYDEKGYLL  360
QIFTKPMQDR PTLFLEIIQR HNHQGFGAGN FNALFKAFEE EQDLRGNLID VNTNGVVPGM  420

SEQ ID NO: 44          moltype = AA  length = 393
FEATURE                Location/Qualifiers
source                 1..393
                       mol_type = protein
                       organism = Oryctolagus cuniculus
SEQUENCE: 44
MTTYSDKGAK PERGRFLHFH SVTFWVGNAK QAASFYCTKM GFEPLAYRGL ETGSRQVVSH  60
VIKQGQIVFV LSSALNPGNK EMGDHLVKHG DGVKDIAFEV EDCDYIVQKA RERGAKILRE  120
PWVEQDKFGK VKFAVLQTYG DTTHTLVEKM NYTGRFLPGF EAPMSKDPLL SKLPSCSLEI  180
IDHIVGNQPE QEMVSASEWY LRNLQFHRFW SVDDTQVHTE YSSLRSIVVA NYEESIKMPI  240
NEPAPGRKKS QIQEYVDYNG GAGVQHIALK THDIISAIRH LRERGMEFLA VPATYYKQLR  300
EKLRSAKIRV TESIDVLEEL KILVDYDEKG YLLQIFTKPM QDRPTLFLEV IQRHNHQGFG  360
AGNFNSLFKA FEEEQNLRGN LTDMETNGVV PGM                                393

SEQ ID NO: 45          moltype = AA  length = 393
FEATURE                Location/Qualifiers
source                 1..393
                       mol_type = protein
                       organism = Galeopterus variegatus
SEQUENCE: 45
MTTYSNKGEK PERGRFLHFH SVTFWVGNAK QAASFYCSKM GFKPLAYKGL ETGSREVVSH  60
VIQQGKIVFV LSSALNPWNT EMGDHLVKHG DGVKDIAFEV EDCDYIVQKA QERGAKIMRE  120
PWVEQDKFGK VKFAVLQTYG DTTHTLVEKM NYSGRFLPGF EAPAFTDPLL SKLPDCCLEI  180
IDHVVGNQPD QEMVSASEWY VKNLQFHRFW SVDDTQVHTE YSSLRSIVVA NYEETIKMPI  240
NEPAQGKKKS QIQEYVDYNG GPGVQHIALK TQDIITAIRH LRERGLEFLG VPSTYYKQLR  300
EKLKSAKIRV KESIDVLEEL KILVDYDEKG YLLQIFTKPM QDRPTLFLEV IQRHNHQGFG  360
AGNFNSLFKA FEEEQDLRGN LTDLETNGVG PGI                                393

SEQ ID NO: 46          moltype = AA  length = 393
FEATURE                Location/Qualifiers
source                 1..393
                       mol_type = protein
                       organism = Nannospalax galili
SEQUENCE: 46
MTTYSNKGPK PERGRFLHFH SVTFWVGNAK QAASFYCNKM GFEPLAYKGL ETGSREVVSH  60
VIKQGKIVFV LCSALNPWNK EMGNHLVKHG DGVKDIAFEV EDCDHIVQKA RERGAKIVRE  120
PWVEQDKFGK VKFAVLQTYG DTTHTLVEKM NYTGCFLPGF EAPTYKDPLL SKLPNCNLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGMEFLA VPSSYYKLLR  300
ENLKTARIQV KESIDVLEEL KILVDYDDKG YLLQIFTKPM QDRPTLFLEV IQRHNHQGFG  360
AGNFNSLFKA FEEEQALRGN LTDTGTNRVM SGM                                393

SEQ ID NO: 47          moltype = AA  length = 393
FEATURE                Location/Qualifiers
source                 1..393
                       mol_type = protein
                       organism = Mesitornis unicolor
SEQUENCE: 47
QTTYTDKGEK PLRGRFIHFH SITFWVGNAK QAASYYCNKL GFEELAYRGL ETGSREVVSH  60
VIKQDKIVFV LSSALNPGNE EMGEHLVKHG DGVKDIAFEV EDCDFIVQKA RERGAVVVKE  120
PWVEEDKFGK VKFAVIQTYG DTTHTLVEKL NYKGLFLPGY HQPLFKDPLL PKLPSAKLSF  180
VDHVVGNQPD LQMVPVADWY QKNLLFHRFW SVDDKQLHTE FSALRSIVVT NYEETIKMPI  240
NEPAFGKKKS QIQEYIDYYG GAGVQHIALN TSDIISAITN LKQRGMQFMD VPSSYYQVLR  300
ERLKTAKIKV KENIDKLAEL KILVDFDEKG YLLQIFTKPV QDRPTVFLEV IQRHNHQGFG  360
AGNFKSLFEA IEMDQDARGN LTILEPNGET KRI                                393

SEQ ID NO: 48          moltype = AA  length = 425
FEATURE                Location/Qualifiers
source                 1..425
                       mol_type = protein
                       organism = Rhinopithecus roxellana
SEQUENCE: 48
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDITFEV EDCDYIVQKA RERGAKIVRE  120
PWVEQDKFGK VKFAVLQTYG DTTHTLVEKM NYTGQFLPGY EAPAFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITAIRH LRERGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LTDLETNGVV PGISASWQPR EGQGGRQRSG TEEPRVPALC  420
QEGSH                                                               425

SEQ ID NO: 49          moltype = AA  length = 393
FEATURE                Location/Qualifiers
```

```
source                  1..393
                        mol_type = protein
                        organism = Fukomys damarensis
SEQUENCE: 49
MTTYSDKGAK PERGRFLHFH SVTFWVGNAK QAAAFYCSKM GFEPLAYRGL ETGSREVASH  60
VIKQGQIVFV LSSPLNPWNR EMGEHLAKHG DSVKDIGFEV EDCDYIVQKA RERGAKVVRE  120
PWVEQDKFGK VKFAVLQTYG DTTHTLVEKV NYSGSFLPGF EAPRAKDPLL AKLPSCSLEM  180
IDHIVGNQPD QEMVSASEWY LRSLQFHRFW SVDDTQVHTE YSSLRSIVVT NYEESIKMPI  240
NEPAPGKKKS QIQEYVDYNG GAGVQHIALG TQDIITSIRH LRERGVEFLA VPSTYYKQLR  300
ENLKSAKVQV KESIDMLEEL KILVDYDEKG YLLQIFTKPV QDRPTLFLEV IQRHNHQGFG  360
AGNFNALFKA FEAEQDLRGN LTDVETNGVE SGL                              393

SEQ ID NO: 50           moltype = AA  length = 407
FEATURE                 Location/Qualifiers
source                  1..407
                        mol_type = protein
                        organism = Colobus angolensis
SEQUENCE: 50
MPFEGQLHLI DSLTKTTYSD KGAKPERGRF LHFHSVTFWV GNAKQAASFY CSKMGFEPLA  60
YRGLETGSRE VVSHVIKQGK IVFVLSSALN PWNKEMGDHL VKHGDGVKDI TFEVEDCDYI  120
VQKARERGAK IVREPWVEQD KFGKVKFAVL QTYGDTTHTL VEKMNYTGQF LPGYEAPVFM  180
DPLLPKLPKC SLEIIDHIVG NQPDQEMVSA SEWYLKNLQF HRFWSVDDTQ VHTEYSSLRS  240
VVVANYEESI KMPINEPAPG KKKSQIQEYV DYNGGAGVQH IALNTQDIIT AIRHLRERGM  300
EFLSVPSTYY KQLREKLKTA KIKVKENIDV LEELKILVDY DEKGYLLQIF TKPVQDRPTL  360
FLEVIQRHNH QGFGAGNFNS LFKAFEEEQN LRGNLTDLET NGVVPGM                407

SEQ ID NO: 51           moltype = AA  length = 393
FEATURE                 Location/Qualifiers
source                  1..393
                        mol_type = protein
                        organism = Colobus angolensis
SEQUENCE: 51
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDITFEV EDCDYIVQKA RERGAKIVRE  120
PWVEQDKFGK VKFAVLQTYG DTTHTLVEKM NYTGQFLPGY EAPVFMDPLL PKLPKCSLEI  180
IDHIVGNQPD QEMVSASEWY LKNLQFHRFW SVDDTQVHTE YSSLRSVVVA NYEESIKMPI  240
NEPAPGKKKS QIQEYVDYNG GAGVQHIALN TQDIITAIRH LRERGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LTDLETNGVV PGM                              393

SEQ ID NO: 52           moltype = AA  length = 393
FEATURE                 Location/Qualifiers
source                  1..393
                        mol_type = protein
                        organism = Mandrillus leucophaeus
SEQUENCE: 52
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIVRE  120
PWVEQDKFGK VKFAVLQTYG DTTHTLVEKM NYTGQFLPGY EAPVFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITAIRH LRERGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LTDLETNGVV PGM                              393

SEQ ID NO: 53           moltype = AA  length = 393
FEATURE                 Location/Qualifiers
source                  1..393
                        mol_type = protein
                        organism = Macaca nemestrina
SEQUENCE: 53
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA REQGAKIVRE  120
PWVEQDKFGK VKFAVLQTYG DTTHTLVEKM NYTGQFLPGY EAPVFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITAIRH LRERGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LTDLETNGVV PGM                              393

SEQ ID NO: 54           moltype = AA  length = 393
FEATURE                 Location/Qualifiers
source                  1..393
                        mol_type = protein
                        organism = Aotus nancymaae
SEQUENCE: 54
MTTYSDKGAK PERGRFLHFH SVTFWVGNAK QAASFYCTKM GFEPLAYRGL ETGSREVVSH  60
VIKQGKIVFV LSSALNPWDK EMGDHLVKHG DGVKDIAFEV EDCDYIVQKA RERGAKIVRE  120
PWVEEDKFGK VKFAVLQTYG DTTHTLVEKM NYAGRFLPGY EAPVFMDPLL PQLPKCSLEV  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LRERGMEFLS VPSTYYKQLR  300
```

```
EKLKVAKIKV KESIDVLEEL KILVDYDEKG YLLQIFTKPV QDRPTLFLEV IQRHNHQGFG  360
AGNFNSLFKA FEEEQNLRGN LTNMETDGVV PGM                               393

SEQ ID NO: 55          moltype = AA  length = 393
FEATURE                Location/Qualifiers
source                 1..393
                       mol_type = protein
                       organism = Propithecus coquereli
SEQUENCE: 55
MTTYSNKGAK PERGRFLHFH SVTFWVGNAK QAAAFYCSKM GFEPLAYRGL ETGSREVVSH  60
AIKQGQIVFV LSSALNPWNK EMGDHLVKHG DGVKDIAFEV EDCDYIVQKA WERGAKIVRE  120
PWVEQDKFGK VKFAVLQTYG DTTHTLVEKM NYTGRFLPGF EAPMFKDLLL SRLPSCSLEI  180
IDHIVGNQPD QEMVPASEWY LKNLQFHRFW SVDDTQVHTE YSSLRSIVVA NYEESIKMPI  240
NEPAPGRKKS QIQEYVDYNG GAGVQHIALK TQDIITAIRH LRERGMEFLA VPSTYYKQLR  300
EKLKTAKIRV KESIDVLEEL KILVDYDEKG YLLQIFTKPV QDRPTLFLEI IQRHNHQGFG  360
AGNFNSLFKA FEEEQDLRGN LTDLETNGAA PGT                               393

SEQ ID NO: 56          moltype = AA  length = 391
FEATURE                Location/Qualifiers
source                 1..391
                       mol_type = protein
                       organism = Otolemur garnettii
SEQUENCE: 56
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA REQGAKIVRE  120
PWVEQDKFGK VKFAVLQTYG DTTHTLVEKM NYTGRFLPGF EAPTFKDPLL SKLPKCSLEI  180
IDHIVGNQPD QEMVPASEWY LKNLQFHRFW SVDDTQVHTE YSSLRSIVVA NYEESIKMPI  240
NEPAPGRKKS QIQEYVDYNG GAGVQHIALK TEDIIMAIRH LRERGMEFLA VPSTYYRQLR  300
ENLKTAKIQV KESIDVLEEL KILVDYDEKG YLLQIFTKPM QDRPTLFLEV IQRRNHQGFG  360
AGNFNSLFKA FEEEQDLRGN LTDLEPNGVV S                                 391

SEQ ID NO: 57          moltype = AA  length = 410
FEATURE                Location/Qualifiers
source                 1..410
                       mol_type = protein
                       organism = Cavia porcellus
SEQUENCE: 57
MPWPPGTVSW EARPRPAMTT YSDKGEKPER GRFLHFHSVT FWVGNAKQAA AFYCSKMGFE  60
PLAYRGLETG SREVASHVIK QGQIVFVFSS PLNPGNKELG DHLVKHGDGV KDIAFEVEDC  120
DYIVQKARER GAKVVREPWV EQDRFGKVKF AVLQTYGDTT HTLVEKTGYT GSFLPGFEAP  180
RVKDSLLSKL PNCGLEIIDH VVGNQPDQEM LSASEWYLKN LQFHRFWSVD DTQVHTEYSS  240
LRSIVVTNYE ESIKMPINEP APGRKKSQIQ EYVDYNGGAG VQHIALKTQD IITAIRHLRE  300
RGAEFLAVPS TYYKQLRENL KSAKVQVKEN IDMLEELRIL VDYDEKGYLL QIFTKPMQDR  360
PTLFLEVIQR HNHQGFGAGN FNALFKAFEA EQDLRGNLTD LEPNGVASGM             410

SEQ ID NO: 58          moltype = AA  length = 393
FEATURE                Location/Qualifiers
source                 1..393
                       mol_type = protein
                       organism = Myotis brandtii
SEQUENCE: 58
MTSYSNKGEK PERGRFLHFH SVTFWVGNAK QAASFYCSKM GFKPIAYKGL ETGSREVVSH  60
VVKQGQIVFV FSSALNPWNK EMGDHLVKHG DGVKDIAFEV EDCDYIVQKA RQRGAKIIRE  120
PWVEQDKFGK VKFAVLQTYG DTTHTLVEKM NYTGFFLPGF EPTTNRDPVL SKLPQSNLEV  180
IDHIVGNQPD QEMLSASARY LNNLQFHRFW SVDDTQVHTE YSSLRSIVVA NYEESIKMPI  240
NEPAPGRKKS QIQEYVDYNG GAGVQHIALK TQDIITAIRH LRERGMEFLD VPSTYYKQLR  300
EKLKSAKIRV KESLDALEEL KILVDYDENG YLLQIFTKPM QDRPTLFLEV IQRHNHQGFG  360
AGNFNALFKA FEEEQNLRGN LTDLEPNGVI RGM                               393

SEQ ID NO: 59          moltype = AA  length = 393
FEATURE                Location/Qualifiers
source                 1..393
                       mol_type = protein
                       organism = Equus asinus
SEQUENCE: 59
MTTYSNKGEK PEKGRFLHFH SVTFWVGNAK QAASFYCNKL GFEPLAYKGL ETGSREVVSY  60
VIKQGKIIFV FSSALNPWNK EMGDHLVKHG DGVKDIAFEV EDCDYIVQKA RERGAKIVRE  120
PWVEQDKFGK VKFAVLQTYG DTTHTLVEKM SYAGRFLPGF EAPAFRDPLL SKLPNCSLEI  180
IDHVVGNQPD HEMESASEWY LKNLQFHRFW SVDDTQVHTE YSSLRSIVVA NYEESIKMPI  240
NEPAPGRKKS QIQEYVDYNG GAGVQHIALK THDIITAIRH LRERGMEFLA VPSSYYRQLQ  300
EKLKSAKIRV KESIDVLEEL KILVDYDEKG YLLQIFTKPM QDRPTLFLEV IQRHNHQGFG  360
AGNFNALFKA FEEEQDLRGN LTDMQTNILA PGK                               393

SEQ ID NO: 60          moltype = AA  length = 384
FEATURE                Location/Qualifiers
source                 1..384
                       mol_type = protein
                       organism = Marmota marmota
SEQUENCE: 60
```

-continued

```
MTTYSDKGAK PERGRFLHFH SVTFWVGNAK QAASFYCSKM GFEPLAYRGL ETGSREVVSH  60
VVKQGKIVFV FSSALNPWNK EMGDHLVKHG DGVKDVAFEV EDCDYVVQKA RERGAKIVRE  120
PWVEEDKFGK VKFAVLQTFG DTTHTLVEKT NYSGQFLPGF KAPLLKDSLL PKLPRCGLEI  180
IDHVVGNLPD QEMLSASEWY LRNLQFHRFW SVDDTQVHTE YSSLRSIVVT NYEETIKMPI  240
NEPAMGMKKS SIQEYVDYNG GAGVQHVGLK TQDIITTIRN LQERGMEFLT VPSTYYKQLR  300
ENLKTAKIRV KESIDVLEEL QILMDYDEKG YILQIFTKPM QDRPTLFLEV IQRHNHQGFG  360
AGNFNSLFKA LEDAQELRGN LTNL                                       384

SEQ ID NO: 61          moltype = AA  length = 393
FEATURE                Location/Qualifiers
source                 1..393
                       mol_type = protein
                       organism = Marmota marmota
SEQUENCE: 61
MTTYSDKGAK PERGRFLHFH SVTFWVGNAK QAASFYCSKM GFEPLAYRGL ETGSREVVSH  60
VVKQGKIVFV FSSALNPWNK EMGDHLVKHG DGVKDVAFEV EDCDYIVQKA RERGAKIVQE  120
PWVEEDKFGK VKFAVLQTYG DTTHTLVEKT NYTGRFLPGF EAPLLKDSLL PKLPKCGLEI  180
IDHVVGNQPD QEMLSASEWY LRNLQFHRFW SVDDTQVHTE YSSLRSIVVT NYEETIKMPI  240
NEPAMGRKKS QIQEYVDYNG GAGVQHIALK TQDIITAIRS LRDRGLEFLS VPSTYYKQLR  300
ENLKTAKIRV KESIDVLEEL KILVDYDEKG YLLQIFTKPM QDRPTLFLEV IQRHNHQGFG  360
AGNFNSLFKA FEEEQAIRGN LTDLEIKGEV SGM                              393

SEQ ID NO: 62          moltype = AA  length = 393
FEATURE                Location/Qualifiers
source                 1..393
                       mol_type = protein
                       organism = Cebus imitator
SEQUENCE: 62
MTTYSDKGAK PERGRFLHFH SVTFWVGNAK QAASFYCNKM GFEPLAYRGL ETGSREVVSH  60
VIKQGKIVFV LSSALNPWNK EMGDHLVKHG DGVKDIAFEV EDCDYIVQKA RERGAKIVRE  120
PWVEEDNFGK VKFAVLQTYG DTTHTLVEKM NYAGRFLPGY KAPAFMDPLL PQLPKCSLEV  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LRGRGMEFLS VPSMYYKQLR  300
EKLKVAKIKV KESIDVLEEL KILVDYDEKG YLLQIFTKPV QDRPTLFLEV IQRHNHQGFG  360
AGNFNSLFKA FEEEQDLRGN LTNMETDGVV PGM                              393

SEQ ID NO: 63          moltype = AA  length = 393
FEATURE                Location/Qualifiers
source                 1..393
                       mol_type = protein
                       organism = Capra hircus
SEQUENCE: 63
MTTYSDKGEK PERGRFLHFH SVTFWVGNAK QAASYYCSKL GFEPLAYKGL ETGSREVVSH  60
VVKQGQIVFI FSSALNPWNK EMGDHLVKHG DGVKDIAFEV EDCDYIVQKA RERGAKIVRE  120
PWVEQDKLGK VKFAVLQTYG DTTHTLVEKM NYTGRFLPGF EAPAFMDPQL SKLPNCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TKDIITAIRH LRERGVEFLA VPSTYYKQLR  300
EKLESAKIRV KENIDILEEL KILVDYDEKG YLLQIFTKPM QDRPTLFLEV IQRHNHQGFG  360
AGNFNSLFKA FEEEQDLRGN LTDMEPNGVV SSM                              393

SEQ ID NO: 64          moltype = AA  length = 393
FEATURE                Location/Qualifiers
source                 1..393
                       mol_type = protein
                       organism = Panthera pardus
SEQUENCE: 64
MTTYSNKGEK PARGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA RERGAKIVRE  120
PWIEQDKFGK VKLAVLQTYG DTTHTLVEKM NYTGRFLPGF EAPAFVDPLL SKLPSCSLEI  180
IDHIVGNQPD QEMESASDWY LKNLQFHRFW SVDDTQVHTE YSSLRSIVVA NYEESIKMPI  240
NEPAPGKKKS QIQEYVDYNG GPGVQHIALK TQDIITAIRH LRERGMEFLG VPSTYYKQLR  300
EKLKSAKIRV KENIDVLEEL KILVDYDEKG YLLQIFTKPV QDRPTLFLEV IQRHNHQGFG  360
AGNFNSLFKA FEEEQNLRGN LTDLENNGIV PGM                              393

SEQ ID NO: 65          moltype = AA  length = 393
FEATURE                Location/Qualifiers
source                 1..393
                       mol_type = protein
                       organism = Hipposideros armiger
SEQUENCE: 65
MTSYSNKGEK PVRGRFLHFH SVTFWVGNAK QAASFYCNKM GFEPLAYKGL ETGSREVVSH  60
VIKQGEIVFV FSSALNPWHK EMGDHLVKHG DGVKDIAFEV EDCDYIVQKA RERGAKIIRE  120
PWVEQDKFGK VKFAVLQTYG DTTHTLVEKM NYTGRFLPGF EAPVFKDPQL SKLPHCKLEV  180
IDHIVGNQPD QEMVSASDWY LNNLQFHRFW SVDDTQVHTE YSSLRSIVVA NYEESIKMPI  240
NEPAPGRKKS QIQEYVDYNG GAGVQHIALK THDIITAIRH LRERGIEFLA VPSTYYKQLR  300
EKLKSAKIRV KENIDILEEL KILVDYDEKG YLLQIFTKPM QDRPTLFLEV IQRHNHQGFG  360
AGNFNSLFKA FEEEQNLRGN LTDMDTNGVI HGM                              393

SEQ ID NO: 66          moltype = AA  length = 393
```

-continued

```
FEATURE               Location/Qualifiers
source                1..393
                      mol_type = protein
                      organism = Crocodylus porosus
SEQUENCE: 66
MTTYTDKGQK PERGRFLHFH SITFWVGNAK QAASYYCNKM GFEEMAYRGL ETGSREVVSH  60
VIRQDKIVFV LSSALNPGNE EMGAHLVKHG DGVKDVAFEV EDCDFIVQEA RERGAAIVKE  120
PWVEEDKHGR VKFAVIQTYG DTTHTLVEKL NYGGLFLPGF EAPLFKDQLL PKLPSTKLRF  180
IDHVVGNQPD LEMVPVAEWY QRNLLFHRFW SVDDKQLHTE FSALRSIVVA NYEETIKMPI  240
NEPAVGKKKS QIQEYIDYYG GPGVQHIALN TSDIISAITN LKQRGMEFMS VPATYYQQLR  300
QRLKTAKIEV KESIDKLEEL KILVDFDEKG YLLQIFTKPV QDRPTLFLEV IQRYNHQGFG  360
AGNFKSLFEA IEADQDARGN LTLLTSNVEN NFI                              393

SEQ ID NO: 67         moltype = AA  length = 393
FEATURE               Location/Qualifiers
source                1..393
                      mol_type = protein
                      organism = Ailuropoda melanoleuca
SEQUENCE: 67
MTTYSDKGKK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGARIVRE  120
PWTEEDKFGK VKLAVLQTYG DTTHTLVEKM NYTGRFLPGF EAPASVDPLL SKLPSCSLEI  180
IDHIVGNQPD QEMVSASEWY LKNLQFHRFW SVDDTQVHTE YSSLRSIVVA NYEESIKMPI  240
NEPALGKKKS QIQEYVDYNG GAGVQHIALK TQDIITAIRH LRERGLEFLA VPSTYYKQLR  300
EKLKSAKIRV KESIDVLEEL KILVDYDEKG YLLQIFTKPM QDRPTLFLEV IQRHNHQGFG  360
AGNFNSLFKA FEEEQDLRGN LTDLETNGIL RGM                              393

SEQ ID NO: 68         moltype = AA  length = 393
FEATURE               Location/Qualifiers
SITE                  155
                      note = misc_feature - Xaa can be any naturally occurring
                       amino acid
SITE                  389
                      note = misc_feature - Xaa can be any naturally occurring
                       amino acid
source                1..393
                      mol_type = protein
                      organism = Bos indicus
SEQUENCE: 68
MTTYSDKGEK PERGRFLHFH SVTFWVGNAK QAASYYCSKL GFEPLAYKGL ETGSREVVSH  60
VVKQGQIVFV FSSALNPWNK EMGDHLVKHG DGVKDIAFEV EDCDYIVQKA RERGAKIVRE  120
PWVEQDKLGK VKFAVLQTYG DTTHTLVEKM NYTGXFLPGF EAPPFMDPQL SKLPSCSLEI  180
IDHIVGNQPD QEMVSASEWY LKNLQFHRFW SVDDTQVHTE YSSLRSVVVA NYEESIKMPI  240
NEPAPGKKKS QIQEYVDYNG GAGVQHIALK TKDIITAIRH LRERGVEFLA VPSTYYKQLR  300
EKLKMAKIRV KENIDILEEL KILVDYDEKG YLLQIFTKPM QDRPTLFLEV IQRHNHQGFG  360
AGNFNSLFKA FEEEQDLRGN LTDMEPNGXV SGM                              393

SEQ ID NO: 69         moltype = AA  length = 393
FEATURE               Location/Qualifiers
source                1..393
                      mol_type = protein
                      organism = Castor canadensis
SEQUENCE: 69
MTTYSDKGQK PEKGRFLHFH SVTFWVGNAK QAASFYCSKM GFEPLAYKGL ETGSREVVSH  60
VIKQGKIVFV LSSALNPWNK EMGDHLVKHG DGVKDIAFEV EDCDYIVQKA RERGAKIVQE  120
PWVEQDKFGK VKFAVLQTYG DTTHTLVEKM NYTGRFLPGF EAPTFKDPLL SKLPNCNLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIIAAIRH LRERGMEFLA VPPTYYKQLR  300
ENLKLAKIQV KENIDVLEEL KILVDYDEKG YLLQIFTKPM QDRPTLFLEV IQRHNHQGFG  360
AGNFNSLFKA FEEEQALRGN LTDLEANGMV SGM                              393

SEQ ID NO: 70         moltype = AA  length = 393
FEATURE               Location/Qualifiers
source                1..393
                      mol_type = protein
                      organism = Sus scrofa
SEQUENCE: 70
MTSYSDKGEK PERGRFLHFH SVTFWVGNAK QAASYYCSKI GFEPLAYKGL ETGSREVVSH  60
VVKQDKIVFV FSSALNPWNK EMGDHLVKHG DGVKDIAFEV EDCDYIVQKA RERGAIIVRE  120
PWIEQDKFGK VKFAVLQTFG DTTHTLVEKM NYTGCFLPGF EAPTFTDPLL SKLPKCGLEI  180
IDHIVGNQPD QEMESASQWY MRNLQFHRFW SVDDTQIHTE YSALRSVVMA NYEESIKMPI  240
NEPAPGKKKS QIQEYVDYNG GAGVQHIALK TEDIITAIRS LRERGVEFLA VPFTYYKQLQ  300
EKLKSAKIRV KESIDVLEEL KILVDYDEKG YLLQIFTKPM QDRPTVFLEV IQRNNHQGFG  360
AGNFNSLFKA FEEEQELRGN LTDTDPNGVA FRL                              393

SEQ ID NO: 71         moltype = AA  length = 393
FEATURE               Location/Qualifiers
source                1..393
                      mol_type = protein
```

```
                        organism = Microcebus murinus
SEQUENCE: 71
MTTYSNKGAK PERGRFLHFH SVTFWVGNAK QAAAFYCSKM GFEPLAYRGL ETGSREVVSH  60
VIKQGQIVFV LSSALNPWNK EMGDHLVKHG DGVKDIAFEV EDCDYIVQKA RERGAKIVRE  120
PWVEQDKFGK VKFAVLQTYG DTTHTLVEKM GYTGRFLPGF EAPAFRDPLL PKLPNCTLEI  180
IDHIVGNQPD QEMVPASEWY LKNLQFHRFW SVDDTQVHTE YSSLRSIVVA NYEESIKMPI  240
NEPAPGKKKS QIQEYVDYNG GAGVQHIALK TQDIITAIRH LRERGTEFLA VPSTYYKQLR  300
EKLKTAKIRV KENIDVLEEL KILVDYDEKG YLLQIFTKPV QDRPTLFLEV IQRHNHQGFG  360
AGNFNSLFKA FEEEQALRGN LTDLETNGVV PGM                             393

SEQ ID NO: 72           moltype = AA  length = 393
FEATURE                 Location/Qualifiers
source                  1..393
                        mol_type = protein
                        organism = Odocoileus virginianus
SEQUENCE: 72
MTTYSDKGEK PERGRFLHFH SVTFWVGNAK QAASYYCSKL GFEPLAYKGL ETGSREVVSH  60
VVKQGQIVFV FSSALNPWNK EMGDHLVKHG DGVKDVAFEV EDCDYIVQKA RERGAKIVRE  120
PWLEQDKLGK VKFAVLQTYG DTTHTLVEKM NYTGRFLPGF EAPAFMDPQL SKLPNCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GPGVQHIALK TKDIITAIRH LRERGVEFLA VPSTYYKQLR  300
EKLKSAKIRV KENIDILEEL KILVDYDEKG YLLQIFTKPM QDRPTLFLEV IQRHNHQGFG  360
AGNFNSLFKA FEEEQDLRGN LTDTEPNGVV SSM                             393

SEQ ID NO: 73           moltype = AA  length = 393
FEATURE                 Location/Qualifiers
source                  1..393
                        mol_type = protein
                        organism = Phascolarctos cinereus
SEQUENCE: 73
MTSYTDRGEK PPRGRFLHFH SITFWVGNAK QAASFYCHKM GFSPLAYRGL ETGSREVASH  60
VVKQGKIIFI FSSALNPGNK EMGDHLVKHG DGVKDISFEV EDCDYIVQKA RERGAIIVKE  120
PWIEQDKFGW VKFAVLQTYG DTTHTLVEKL NYTGPFLPGF EAPFFEDPLL PTLPDCKLAM  180
IDHVVGNQPD QEMVPIADWY KKTLMFHRFW SVDDKQVHTE FSSLRSIVMA NYEETIRMPI  240
NEPAMGRKKS QIQEYVDYYG GAGVQHIAMS TTDIISAITH LRARGMEFLN VPSTYYKQLR  300
ERLKSAKIQV KENMDILEKL KILVDYDEKG YLLQIFTKPV QDRPTVFLEV IQRHNHQGFG  360
AGNFNSLFKA FEEEQNIRGN LTDLAPDGLG TVM                             393

SEQ ID NO: 74           moltype = AA  length = 393
FEATURE                 Location/Qualifiers
source                  1..393
                        mol_type = protein
                        organism = Mus pahari
SEQUENCE: 74
MTSYTNKGPK PERGRFLHFH SVTFWVGNAK QAASFYCNKM GFEPLAYRGL ETGSREVVSH  60
VIKQGKIVFV LCSALNPWNK EMGDHLVKHG DGVKDIAFEV EDCDHIVQKA RERGAKIVRE  120
PWVEQDKFGK VKFAVLQTYG DTTHTLVEKI NYTGRFLPGF EAPTYKDTLL PKLPRCNLEI  180
IDHIVGNQPD QEMQSASEWY LKNLQFHRFW SVDDTQVHTE YSSLRSIVVA NYEESIKMPI  240
NEPAPGKKKS QIQEYVDYNG GAGVQHIALK TEDIITTIRH LRERGMEFLA VPSSYYKLLR  300
ENLKSAKIQV KESMDVLEEL KILVDYDEKG YLLQIFTKPM QDRPTLFLEV IQRHNHQGFG  360
AGNFNSLFKA FEEEQALRGN LTDMETNGVR SGM                             393

SEQ ID NO: 75           moltype = AA  length = 393
FEATURE                 Location/Qualifiers
source                  1..393
                        mol_type = protein
                        organism = Mus caroli
SEQUENCE: 75
MTTYTNKGPK PERGRFLHFH SVTFWVGNAK QAASFYCNKM GFEPLAYRGL ETGSREVVSH  60
VIKQGKIVFV LCSALNPWNK EMGDHLVKHG DGVKDVAFEV EDCDHIVQKA RERGAKIVRE  120
PWVEQDKFGK VKFAVLQTYG DTTHTLVEKI NYTGRFLPGF EAPIYKDTLL PKLPRCNLEI  180
IDHIVGNQPD QEMQSASEWY LKNLQFHRFW SVDDTQVHTE YSSLRSIVVT NYEESIKMPI  240
NEPAPGRKKS QIQEYVDYNG GAGVQHIALK TEDIITAIRH LRERGIEFLA VPSSYYKLLR  300
ENLKSAKIQV KENMDILEEL QILVDYDEKG YLLQIFTKPM QDRPTLFLEV IQRHNHQGFG  360
AGNFNSLFKA FEEEQALRGN LTDLEPNGVR SGM                             393

SEQ ID NO: 76           moltype = AA  length = 393
FEATURE                 Location/Qualifiers
source                  1..393
                        mol_type = protein
                        organism = Mesocricetus auratus
SEQUENCE: 76
MTTYNNKGPK PERGRFLHFH SVTFWVGNAK QAASFYCNKM GFEPLAYKGL ETGSREVVSH  60
AIKQGKIVFV LCSALNPWNK EMGDHLVKHG DGVKDIAFEV EDCDHIVQKA RERGAKIVRE  120
PWVEEDKFGK VKFAVLQTYG DTTHTLVEKI NYTGRFLPGF EAPTYKDTLL PKLPRCNLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITTIRH LRERGMEFLA VPSSYYKLLR  300
ENLKTAKIQV KESLDVLEEL KILVDYDEKG YLLQIFTKPM QDRPTLFLEV IQRHNHQGFG  360
AGNFNSLFKA FEEEQALRGN LTDMETNGVR SGM                             393
```

```
SEQ ID NO: 77            moltype = AA  length = 393
FEATURE                  Location/Qualifiers
source                   1..393
                         mol_type = protein
                         organism = Meriones unguiculatus
SEQUENCE: 77
MTTYSNRGPK PERGQFLHFH SVTFWVGNAK QAASFYCNKM GFEPLAYRGL ETGSREVVSH   60
VIKQGKIVFV LSSALNPWNK EMGDHLVKHG DGVKDIAFEV EDCEHIVQKA RERGAKIVRE  120
PWVEEDKFGK VKFAVLQTYG DTTHTLVEKI NYTGRFLPGF EAPAYKDILL SKLPNCHLEI  180
IDHIVGNQPD QEMESASEWY LKNLQFHRFW SVDDTQVHTE YSSLRSIVVA NYEESIKMPI  240
NEPAPGRKKS QIQEYVDYNG GAGVQHIALK TEDIITTIRH LRERGMEFLA VPSSYYKLLR  300
ENLKTAKIQV KESMNVLEEL KILVDYDEKG YLLQIFTKPM QDRPTLFLEV IQRHNHQGFG  360
AGNFNALFKA FEQEQALRGN LTDLETNGVR SGM                               393

SEQ ID NO: 78            moltype = AA  length = 393
FEATURE                  Location/Qualifiers
source                   1..393
                         mol_type = protein
                         organism = Enhydra lutris
SEQUENCE: 78
MTTYSDRGKK PERGRFLHFH SVTFWVGNAK QAASFYCNKM GFEPLAYKGL ETGSREVVSH   60
VIKQGKIVFV FSSALNPWNK EMGDHLVKHG DGVKDIAFEV EDCDYIVQKA REQGAKIVRE  120
PWIEQDKFGK VKLAVLQTYG DTTHTLVEKM NYTGRFLPGF EAPASVDPLL SKLPTCSLEI  180
IDHIVGNQPD QEMVSASEWY LKNLQFHRFW SVDDTQVHTE YSSLRSIVVT NYEESIKMPI  240
NEPAPGRKKS QIQEYVDYNG GAGVQHIALK TQDIITAIRH LRARGMEFLG VPSSYYKQLR  300
EKLKSAKIQV KESIDVLEEL KILVDYDEKG YLLQIFTKPM QDRPTLFLEV IQRHNHQGFG  360
AGNFNSLFKA FEEEQDLRGN LTDLETNGTL RCM                               393

SEQ ID NO: 79            moltype = AA  length = 393
FEATURE                  Location/Qualifiers
source                   1..393
                         mol_type = protein
                         organism = Delphinapterus leucas
SEQUENCE: 79
MTTYSNKGEK PERGRFLHFH SVTFWVGNAK QAASYYCSKM GFEPLAYKGL ETGSREMVSH   60
VIKQGKIVFI FSSALNPWNK EMGDHLVKHG DGVKDIAFEV EDCDYIVQKA RERGAKIVRE  120
PWVEQDKFGK VKFAVLQTYG DTTHTLVEKM NYTGWFLPGF EAPAFVDPLL SKLPNCSLER  180
IDHIVGNQPD QEMLSASEWY LKNLQFHRFW SVDDTQVHTE YSSLRSIVVA NYEESIKMPI  240
NEPAPGRKKS QIQEYVDYNG GAGVQHIALK TEDIITAIRH LRERGMEFLA VPSTYYKQLR  300
EKLKSAKIRV KENIDVLEEL KILVDYDEKG YLLQIFTKPM QDRPTLFLEV IHRYNHQGFG  360
AGNFNSLFKA FEEEQDLRGN LTDMETNGTV AGM                               393

SEQ ID NO: 80            moltype = AA  length = 394
FEATURE                  Location/Qualifiers
source                   1..394
                         mol_type = protein
                         organism = Loxodonta africana
SEQUENCE: 80
MTTYSDKGVK PERGRFLHFH SVTFWVGNAK QAASFYCSKM GFKPLAYRGL ETGSREVVSH   60
VIKHGKIVFV LSSALNPWNK EMGDHLVKHG DGVKDIAFEV EDCNYIVQKA RERGAKIVRE  120
PWVEQDKCGR VKFAVLQTYG DTTHTLVEKI NYTGCFLPGF EAPTFMDPLL SKLPSCNLEI  180
IDHIVGNQPD QEMASASEWY LKNLQFHRFW SVDDTQVHTE YSSLRSIVVT NYEESIKMPI  240
NEPAPGKKKS QIQEYVDYNG GAGVQHIALR TQDIITAIRH LKERGMEFLA VPSTYYKQLR  300
EKLKSAKVQV KESIDVLEEL KILVDYDEKG YLLQIFTKPV QDRPTLFLEV IQRNNHQGFG  360
AGNFNSLFKA FEEEQNLRGN LTDLESNQPG RARH                              394

SEQ ID NO: 81            moltype = AA  length = 393
FEATURE                  Location/Qualifiers
source                   1..393
                         mol_type = protein
                         organism = Octodon degus
SEQUENCE: 81
MTTYSDKGAK PERGRFLHFH SVTFWVGNAK QAAAYYCSKM GFELLAYRGL ETGSREVASH   60
VIKQGQIVFV FSSPLNPWNK EMGDHLVKHG DGVKDIAFEV QDCDYIVQKA RERGAKVVRE  120
PWVEQDKFGK VKFAVLQTYG DTTHTLVEKM SYTGSFLPGF EAPRVKDALL FKLPSCGLEI  180
IDHIVGNQPD QEMASASEWY LRNLQFHRFW SVDDTQVHTE YSSLRSIVVT NYEESIKMPI  240
NEPAPGRKKS QIQEYVDYNG GAGVQHIALK TQDIITAIRH LRERGAEFLA VPSSYYRQLR  300
ENLKSAKVRV KESIDVLEEL KILVDYDEKG YLLQIFTKPM QDRPTLFLEV IQRHNHQGFG  360
AGNFNALFKA FEAEQDLRGN LTDLETNGEV SGM                               393

SEQ ID NO: 82            moltype = AA  length = 393
FEATURE                  Location/Qualifiers
source                   1..393
                         mol_type = protein
                         organism = Chrysemys picta
SEQUENCE: 82
MTTYTDKGEK PEGGKFLHFH SLTFWVGNAK QAASFYCNKM GFEELAYKGL ETGSREVVSH   60
VIKQDKIIFV LSSALNPENK DMGEHLVKHG DGVKDIAFEV EDCDFIVQKA KERGAVIVKE  120
```

-continued

```
PWVEEDKYGK VKFAVIQTYG DTTHTLIENL NYKGLFLPGF EPPLFKDPLL PKLPSGKLSF  180
IDHVVGNQPD LQMVPVAEWY QKNLLFHRFW SVDDKQLHTQ FSALRSIVVA NYEETIKMPI  240
NEPAVGKKKS QIQEYVEYYG GAGVQHIALN TPDIITAVTN LKQRGIEFMT VPSTYYQQLR  300
EKLKSAKIKV KENIDKLEEL KILVDFDEKG YLLQIFTKPV QDRPTVFLEV IQRHNHQGFG  360
AGNFKSLFQA IEDDQDARGN LTILTANGET NFI                              393

SEQ ID NO: 83          moltype = AA  length = 393
FEATURE                Location/Qualifiers
source                 1..393
                       mol_type = protein
                       organism = Pongo abelii
SEQUENCE: 83
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIVRE  120
PWVEQDKFGK VKFAVLQTYG DTTHTLVEKM NYIGQFLPGY EAPAFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYKQLR  300
EKLKTAKIKV KENIDALEEL KILVDYDEKG YLLQIFTKPV QDRPTLFLEV IQRHNHQGFG  360
AGNFNSLFKA FEEEQNLRGN LTNMETNGVV PGM                              393

SEQ ID NO: 84          moltype = AA  length = 393
FEATURE                Location/Qualifiers
source                 1..393
                       mol_type = protein
                       organism = Terrapene carolina
SEQUENCE: 84
MTTYTDKGEK PEGGKFLHFH SLTFWVGNAK QAASFYCNKM GFEELAYKGL ETGSREVVSH  60
VIKQDKIIFV LSSALNPENK EMGEHLLKHG DGVKDIAFEV EDCDFIVQKA KERGAVIVKE  120
PWVEEDKYGK VKFAVIQTYG DTTHTLIENL NYKGLFLPGF EPPLFKDPLL PKLPSGKLSF  180
IDHVVGNQPD LQMVPVAEWY QKNLLFHRFW SVDDKQLHTQ FSALRSIVVA NYEETIKMPI  240
NEPAMGKKKS QIQEYVEYYG GAGVQHIALN TPDIITAVTN LKQRGMEFMT VPSTYYQQLR  300
EKLKSAKIKV KENIDKLEEL KILVDFDEKG YLLQIFTKPV QDRPTVFLEV IQRHNHQGFG  360
AGNFKSLFQA IEDDQDARGN LTILTANGET NFI                              393

SEQ ID NO: 85          moltype = AA  length = 393
FEATURE                Location/Qualifiers
source                 1..393
                       mol_type = protein
                       organism = Neophocaena asiaeorientalis
SEQUENCE: 85
MTTYSNKGEK PERGRFLHFH SVTFWVGNAK QAASYYCSKM GFESLAYKGL ETGSREVVSH  60
VIKQGKIVFI FSSALNPWNK EMGDHLVKHG DGVKDIAFEV EDCDYIVQKA RERGAKIVRE  120
PWVEQDKFGK VKFAVLQTYG DTTHTLVEKM NYTGWFLPGF EAPAFVDPLL SKLPNCSLER  180
IDHIVGNQPD QEMLSASEWY LKNLQFHRFW SVDDTQVHTE YSSLRSIVVA NYEESIKMPI  240
NEPAPGRKKS QIQEYVDYNG GAGVQHIALK TEDITTAIRH LRERGMEFLA VPSTYYKQLR  300
EKLKSAKIRV KENIDVLEEL KILVDYDEKG YLLQIFTKPM QDRPTLFLEV IQRYNHQGFG  360
AGNFNSLFKA FEEEQDLRGN LTDMETNGTV AGM                              393

SEQ ID NO: 86          moltype = AA  length = 393
FEATURE                Location/Qualifiers
source                 1..393
                       mol_type = protein
                       organism = Theropithecus gelada
SEQUENCE: 86
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIVRE  120
PWVEQDKFGK VKFAVLQTYG DTTHTLVEKM NYTGQFLPGY EAPVFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITAIRH LRQRGMEFLS VPSTYYKQLR  300
EKLKTAKIKV KENIEVLEEL KILVDYDEKG YLLQIFTKPV QDRPTLFLEV IQRHNHQGFG  360
AGNFNSLFKA FEEEQNLRGN LTDLETNGVV PGM                              393

SEQ ID NO: 87          moltype = AA  length = 393
FEATURE                Location/Qualifiers
source                 1..393
                       mol_type = protein
                       organism = Callorhinus ursinus
SEQUENCE: 87
MTTYSDKGRK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIVRE  120
PWIEQDKFGK VKLAVLQTYG DTTHTLVEKM NYSGWFLPGF ETPASVDPLL SKLPTCSLEI  180
IDHIVGNQPD QEMVSASEWY LKNLQFHRFW SVDDTQVHTE YSSLRSIVVA NFEESIKMPI  240
NEPAPGKKKS QIQEYVDYNG GAGVQHIALK TQDIITAIRH LRERGMEFLA VPPTYYKQLR  300
EKLKSAKIRV KESIDTLEEL KILVDYDEKG YLLQIFTKPM QDRPTLFLEV IQRHNHQGFG  360
AGNFNSLFKA FEEEQDLRGN LTDLKNTRTL PGT                              393

SEQ ID NO: 88          moltype = AA  length = 393
FEATURE                Location/Qualifiers
source                 1..393
```

```
                        mol_type = protein
                        organism = Vulpes vulpes
SEQUENCE: 88
MTTYSDKGKK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIVRE  120
PWIEEDKFGK VKLAVLQTYG DTTHTLVEKM NYTGRFLPGF EAPACVDPLL SKLPSCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LRDRGMEFLA VPSTYYKQLR  300
EKLKSAKIQV KESIDVLEEL KILVDYDEKG YLLQIFTKPM QDRPTLFLEV IQRHNHQGFG  360
AGNFNSLFKA FEEEQDLRGN LTDLETNGTM PGM                              393

SEQ ID NO: 89           moltype = AA  length = 384
FEATURE                 Location/Qualifiers
source                  1..384
                        mol_type = protein
                        organism = Urocitellus parryii
SEQUENCE: 89
MTTYTDKGAK PERGRFLHFH SVTFWVGNAK QAASFYCSKM GFEPLAYRGL ETGSREVVSH  60
VVKQGKIVFV FSSALNPWNK EMGDHLVKHG DGVKDVAFEV EDCDYIVQKA RERGAKVVRE  120
PWVEEDKFGK VKFAVLQTFG DTTHTLVEKT NYSGRFLPGF QAPLLKDSLL PKLPKCGLEI  180
IDHVVGNLLD HEMLSASEWY LRNLQFHRFW SVDDTQVHTE YSSLRSIVVT NYEETIKMPI  240
NEPAMGMKKS SIQEYVDYNG GAGVQHVGLK TQDIITTIRN LQERGMEFLT VPSTYYKQLR  300
ENLKTAKIQV KESIDVLEEL QILMDYDEKG YILQIFTRPM QDRPTLFLEV IQRHNHQGFG  360
AGNFNSLFKA LEDAQELRGN LTNL                                        384

SEQ ID NO: 90           moltype = AA  length = 393
FEATURE                 Location/Qualifiers
source                  1..393
                        mol_type = protein
                        organism = Ursus arctos
SEQUENCE: 90
MTTYSDKGKK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIVRE  120
PWIEQDKFGK VKLAMLQTYG DTTHTLVEKM NYTGRFLPGF EAPASVDPLL SKLPSCSLEI  180
IDHIVGNQPD QEMVSASEWY LKNLQFHRFW SVDDTQVHTE YSSLRSIVVA NYEESIKMPI  240
NEPALGKKKS QIQEYVDYNG GAGVQHIALK TQDIITAIRH LRERGLEFLA VPSTYYKQLR  300
EKLKSAKIRV KESIDVLEEL KILVDYDEKG YLLQIFTKPM QDRPTLFLEV IQRHNHQGFG  360
AGNFNSLFKA FEEEQDLRGN LTNLETNGIL RGM                              393

SEQ ID NO: 91           moltype = AA  length = 393
FEATURE                 Location/Qualifiers
source                  1..393
                        mol_type = protein
                        organism = Acinonyx jubatus
SEQUENCE: 91
MTTYSNKGEK PARGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA RERGAKIVRE  120
PWIEQDKFGK VKLAVLQTYG DTTHTLVEKM NYTGRFLPGF EAPAFVDPLL SKLPSCSLEI  180
IDHIVGNQPD QEMESASDWY LKNLQFHRFW SVDDTQVHTE YSSLRSIVVA NYEESIKMPI  240
NEPAPGKKKS QIQEYVDYNG GPGVQHIALK TQDIITAIRH LRERGMEFLA VPSTYYKQLR  300
EKLKSAKIRV KENIDVLEEL KILVDYDEKG YLLQIFTKPV QDRPTLFLEV IQRHNHQGFG  360
AGNFNSLFKA FEEEQNLRGN LTDFENNGIV PGM                              393

SEQ ID NO: 92           moltype = AA  length = 393
FEATURE                 Location/Qualifiers
source                  1..393
                        mol_type = protein
                        organism = Homo sapiens
SEQUENCE: 92
MTTYSDKGAK PERGRFLHFH SVTFWVGNAK QATSFYCSKM GFEPLAYRGL ETGSREVVSH  60
VIKQGKIVFV LSSALNPWNK EMGDHLVKHG DGVKDIAFEV EDCDYIVQKA RERGAKIMRE  120
PWVEQDKFGK VKFAVLQTYG DTTHTLVEKM NYIGQFLPGY EAPAFMDPLL PKLPKCSLEM  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYKQLR  300
EKLKTAKIKV KENIDALEEL KILVDYDEKG YLLQIFTKPV QDRPTLFLEV IQRHNHQGFG  360
AGNFNSLFKA FEEEQNLRGN LTNMETNGVV PGM                              393

SEQ ID NO: 93           moltype = AA  length = 461
FEATURE                 Location/Qualifiers
source                  1..461
                        mol_type = protein
                        organism = Gulo gulo
SEQUENCE: 93
DDITLSTEAA ARSEAPKPGS FQRWCRYHPS LGRPGSKGRD LFGVKYFCPA LHWPLVPISE  60
QEASPRSTMT TYSDKGKKPE RGRFLHFHSV TFWVGNAKQA ASFYCNKMGF EPLAYKGLET  120
GSREVVSHVI KQGKIVFVFS SALNPWNKEM GDHLVKHGDG VKDIAFEVED CDYIVQKARE  180
QGAKIVREPW IEQDKFGKVK LAVLQTYGDT THTLVEKMNY TGRFLPGFEA PASVDPLLSK  240
LPTCSLEIID HIVGNQPDQE MVSASEWYLK NLQFHRFWSV DDTQVHTEYS SLRSIVVANY  300
EESIKMPINE PAPGKKKSQI QEYVDYNGGA GVQHIALKTQ DIITAIRHLR ARGMEFLCVP  360
```

```
STYYKQLREK LKSAKIQVKE SIDVLEELKI LVDYDEKGYL LQIFTKPMQD RPTLFLEVIQ  420
RHNHQGFGAG NFNSLFKAFE EEQDLRGNLT DLQTNGTLRG M                      461

SEQ ID NO: 94          moltype = AA  length = 393
FEATURE                Location/Qualifiers
source                 1..393
                       mol_type = protein
                       organism = Bos indicus
SEQUENCE: 94
MTTYSDKGEK PERGRFLHFH SVTFWVGNAK QAASYYCSKL GFEPLAYKGL ETGSREVVSH  60
VVKQGQIVFV FSSALNPWNK EMGDHLVKHG DGVKDIAFEV EDCDYIVQKA RERGAKIVRE  120
PWVEQDKLGK VKFAVLQTYG DTTHTLVEKM NYTGRFLPGF EAPPFMDPQL SKLPSCSLEI  180
IDHIVGNQPD QEMVSASEWY LKNLQFHRFW SVDDTQVHTE YSSLRSVVVA NYEESIKMPI  240
NEPAPGKKKS QIQEYVDYNG GAGVQHIALK TKDIITAIRH LRERGVEFLA VPSTYYKQLR  300
EKLKMAKIRV KENIDILEEL KILVDYDEKG YLLQIFTKPM QDRPTLFLEV IQRHNHQGFG  360
AGNFNSLFKA FEEEQDLRGN LTDMEPNGGV SGM                               393

SEQ ID NO: 95          moltype = AA  length = 393
FEATURE                Location/Qualifiers
source                 1..393
                       mol_type = protein
                       organism = Tupaia chinensis
SEQUENCE: 95
MTTYSDKGAK PQRGRFLHFH SVTFWVGNAK QAASFYCSKM GFEPLAYKGL ETGSREVVSH  60
VIRQGKIVFV LSSALNPWNK EMGDHLVKHG DGVKDIAFEV EDCDYIVQKA RERGAKIVRE  120
PWVEKDKFGK VKFAVLQTYG DTTHTLVEKM NYTGRFLPGF EAPTYVDPHL AKLPDCNLEI  180
IDHIVGNQPD QEMVSASEWY LRNLQFHRFW SVDDTQVHTE YSSLRSIVVA NYEESIKMPI  240
NEPAPGKKKS QIQEYVDYNG GAGVQHIALK THDIITAIRH LRERGMEFLA VPSTYYRQLR  300
EGLKSAKIQV KESIDALEEL KILVDYDEKG YLLQIFTKPV QDRPTLFLEV IQRHNHQGFG  360
AGNFNSLFKA FEEEQALRGN LTDLETNGVA LGM                               393

SEQ ID NO: 96          moltype = AA  length = 393
FEATURE                Location/Qualifiers
source                 1..393
                       mol_type = protein
                       organism = Vombatus ursinus
SEQUENCE: 96
MTSYTDRGQK PPRGRFLHFH SITFWVGNAK QAASFYCHKM GFSPFAYRGL ETGSRDVASH  60
VVKQGKIIFI FSSALNPGNK EMGDHLVKHG DGVKDISFEV EDCDYIVQKA RERGAIIVKE  120
PWTEQDKFGW VKFAVLQTYG DTTHTLVEKL NYTGPFLPGF EAPLFEDPLL PTLPDCKLAM  180
IDHVVGNQPD QEMVPAADWY KKNLMFHRFW SVDDKQVHTE FSSLRSIVMA NYEETIKMPI  240
NEPAMGRKKS QIQEYVDYYG GAGVQHIAMS TPDIISAITY LRARGLEFLS VPSTYYKQLR  300
EGLKSAKIQV KESIDTLEEL KILVDYDEKG YLLQIFTKPV QDRPTVFLEV IQRHNHQGFG  360
AGNFNSLFKA FEEEQNIRGN LTDLAPNGLG IVM                               393

SEQ ID NO: 97          moltype = AA  length = 393
FEATURE                Location/Qualifiers
source                 1..393
                       mol_type = protein
                       organism = Eptesicus fuscus
SEQUENCE: 97
MTSYTNRGEK PERGRFLHFH SVTFWVGNAK QAASFYCSKM GFKPLAYKGL ETGSREVVSH  60
VVKQGQIVFV FSSALNPWNK EMGDHLVKHG DGVKDIAFEV EDCDYIVQKA RQRGAKIIRE  120
PWVEQDKFGK VKFAVLQTYG DTTHTLVEKM NYTGFFLPGF EPTTNRDPAL SKLPQSNLEV  180
IDHIVGNQPD QEMLSASDWY LNNLQFHRFW SVDDTQVHTE YSSLRSIVVA NYEESIKMPI  240
NEPAPGRKKS QIQEYVDYNG GAGVQHIALK TQDIITAIRH LRERGMEFLD VPSTYYKQLR  300
EKLKSAKIRV KESLDALEEL RILVDYDENG YLLQIFTKPM QDRPTLFLEV IQRHNHQGFG  360
AGNFNALFKA FEEEQNLRGN LTDMETNGVV RGM                               393

SEQ ID NO: 98          moltype = AA  length = 392
FEATURE                Location/Qualifiers
source                 1..392
                       mol_type = protein
                       organism = Sousa chinensis
SEQUENCE: 98
SLAPSLLLQP ERGRFLHFHS VTFWVGNAKQ AASYYCSKMG FEPLAYKGLE TGSRETVSHV  60
IKQGKIVFIF SSALNPWNKE MGDHLVKHGD GVKDIAFEVE DCDYIVQKAR ERGAKIVREP  120
WVEQDKFGKV KFAVLQTYGD TTHTLVEKMN YTGWFLPGFE APAFVDPLLS KLPNCSLERI  180
DHIVGNQPDQ EMLSASEWYL KNLQFHRFWS VDDTQVHTEY SSLRSIVVAN YEESIKMPIN  240
EPAPGRKKSQ IQEYVDYNGG AGVQHIALKT EDIITAIRHL RERGMEFLAV PSTYYKQLRE  300
KLKSAKIRVK ENIDVLEELK ILVDYDEKGY LLQIFTKPMQ DRPTLFLEVI QRYNHQGFGA  360
GNFNSLFKAF EEEQDLRGNL TDMETNGTVP GM                                392

SEQ ID NO: 99          moltype = AA  length = 393
FEATURE                Location/Qualifiers
source                 1..393
                       mol_type = protein
                       organism = Platysternon megacephalum
SEQUENCE: 99
```

-continued

```
MTTYTDKGEK PEGGKFLHFH SLTFWVGNAK QAASFYCNKM GFEELAYKGL ETGSREVVSH  60
VIKQDKIIFV LSSALNPENE EMGEHLVKHG DGVKDIAFEV EDCDFIVQKA KERGAVIVKE  120
PWVEEDKYGK VKFAVIQTYG DTTHTLIENL NYKGLFLPGF EPPLFKDPLL PKLPSGKLSF  180
IDHVVGNQLD LHMVPVAEWY QKNLLFHRFW SVDDKQLHTQ FSSLRSIVVA NYEETIKMPI  240
NEPAMGMKKS QIQEYVEYYG GAGVQHIALN TSDIITAVTN LKQRGMEFMV VPSTYYQQLR  300
EKLKSAKIKV KENIDKLEEL KILVDFDGKG YLLQIFTKPV QDRPTVFLEV IQRHNHQGFG  360
AGNFKSLFQA IEDDQDARGN LTILTANGET NSC                                393

SEQ ID NO: 100         moltype = AA  length = 393
FEATURE                Location/Qualifiers
source                 1..393
                       mol_type = protein
                       organism = Grammomys surdaster
SEQUENCE: 100
MTTYTNKGPK PERGRFLHFH SVTFWVGNAK QAASFYCNKM GFEPLAYRGL ETGSREVVSH  60
VIKQGKIVFV LCSALNPWNK EMGDHLAKHG DGVKDIAFEV EDCEYIVQKA RERGAKIVRE  120
PWVEQDKFGK VKFAVLQTYG DTTHTLVEKV NYTGRFLPGF EAPTYKDNLL PKLPRCNLEI  180
IDHIVGNQPD QEMESASEWY LKNLQFHRFW SVDDTQVHTE YSSLRSIVVA NYEESIKMPI  240
NEPAPGKKKS QIQEYVDYNG GAGVQHIALK TEDIITTIRH LRERGMEFLA VPSSYYKMLR  300
ENLKRAKIQV KESLDVLEEL KILVDYDEKG YLLQIFTKPM QDRPTLFLEV IQRHNHQGFG  360
AGNFNALFKA FEEEQALRGN LTDLETNGVR SGM                                393

SEQ ID NO: 101         moltype = AA  length = 392
FEATURE                Location/Qualifiers
source                 1..392
                       mol_type = protein
                       organism = Monodon monoceros
SEQUENCE: 101
TTYSNKGEKP ERGRFLHFHS VTFWVGNAKQ AASYYCSKMG FEPLAYKGLE TGSREMVSHV  60
IKQGKIVFIF SSALNPWNKE MGDHLVKHGD GVKDIAFEVE DCDYIVQKAR ERGAKIVREP  120
WVEQDKFGKV KFAVLQTYGD TTHTLVEKMN YTGWFLPGFE APAFVDPLLS KLPNCSLERI  180
DHIVGNQPDQ EMLSASEWYL KNLQFHRFWS VDDTQVHTEY SSLRSIVVAN YEESIKMPIN  240
EPAPGRKKSQ IQEYVDYNGG AGVQHIALKT EDIITAIRHL RERGMEFLAV PSTYYKQLRE  300
KLKSAKIRVK ENIDVLEELK ILVDYDEKGY LLQIFTKPMQ DRPTLFLEVI HRYNHQGFGA  360
GNFNSLFKAF EEEQDLRGNL TDMETNGTVA GT                                 392

SEQ ID NO: 102         moltype = AA  length = 393
FEATURE                Location/Qualifiers
source                 1..393
                       mol_type = protein
                       organism = Monodon monoceros
SEQUENCE: 102
MTTYSNKGEK PERGRFLHFH SVTFWVGNAK QAASYYCSKM GFEPLAYKGL ETGSREMVSH  60
VIKQGKIVFI FSSALNPWNK EMGDHLVKHG DGVKDIAFEV EDCDYIVQKA RERGAKIVRE  120
PWVEQDKFGK VKFAVLQTYG DTTHTLVEKM NYTGWFLPGF EAPAFVDPLL SKLPNCSLER  180
IDHIVGNQPD QEMLSASEWY LKNLQFHRFW SVDDTQVHTE YSSLRSIVVA NYEESIKMPI  240
NEPAPGRKKS QIQEYVDYNG GAGVQHIALK TEDIITAIRH LRERGMEFLA VPSTYYKQLR  300
EKLKSAKIRV KENIDVLEEL KILVDYDEKG YLLQIFTKPM QDRPTLFLEV IHRYNHQGFG  360
AGNFNSLFKA FEEEQDLRGN LTDMETNGTA AGT                                393

SEQ ID NO: 103         moltype = AA  length = 393
FEATURE                Location/Qualifiers
source                 1..393
                       mol_type = protein
                       organism = Suricata suricatta
SEQUENCE: 103
MTTYSDKGEK PERGRFLHFH SVTFWVGNAK QAASFYCSKM GFEPLAYKGL ETGSREVVSH  60
AIKQGKIVFV FSSALNPWNK EIGDHLAKHG DGVKDIAFEV EDCDYIVQKA KERGAKVVRE  120
PWIEQDKFGK VKLAVLQTYG DTTHTLVEKM NYTGLFLPGF EAPVFLDPLL SKLPSCSLEI  180
IDHIVGNQPD QEMVSAAEWY LKNLQFHRFW SVDDTQVHTE YSSLRSIVVA NYEENIKMPI  240
NEPAPGKKKS QIQEYVDYNG GPGVQHIALK TQDIITAIRH LRERGMEFLG VPSTYYKQLR  300
ERLKSAKIRV KENIDVLEEL KILVDYDEKG YLLQIFTKPM QDRPTLFLEV IQRHNHQGFG  360
AGNFNSLFKA FEEEQNLRGN LTDLETNGVV PGM                                393

SEQ ID NO: 104         moltype = AA  length = 393
FEATURE                Location/Qualifiers
source                 1..393
                       mol_type = protein
                       organism = Lynx canadensis
SEQUENCE: 104
MTTYSNKGEK PARGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA RERGAKIVRE  120
PWIEQDKFGK VKLAVLQTYG DTTHTLVEKM NYTGRFLPGF EAPTFVDPLL SKLPSCSLEI  180
IDHIVGNQPD QEMESASDWY LKNLQFHRFW SVDDTQVHTE YSSLRSIVVA NYEESIKMPI  240
NEPALGKKKS QIQEYVDYNG GPGVQHIALK TQDIITAIRH LRERGMEFLG VPSTYYKQLR  300
EKLKSAKIRV KENIDVLEEL KILVDYDEKG YLLQIFTKPV QDRPTLFLEV IQRHNHQGFG  360
AGNFNSLFKA FEEEQNLRGN LTDLENNGIV PGM                                393

SEQ ID NO: 105         moltype = AA  length = 384
```

```
FEATURE                Location/Qualifiers
source                 1..384
                       mol_type = protein
                       organism = Marmota monax
SEQUENCE: 105
MTTYSDKGAK PERGRFLHFH SVTFWVGNAK QAASFYCSKM GFEPLAYRGL ETGSREVVSH  60
VVKQGKIVFV FSSALNPWNK EMGDHLVKHG DGVKDVAFEV EDCDYIVQKA REQGAKIVRE  120
PWVEEDKFGK VKFAVLQTFG DTTHTLVEKT NYSGRFLPGF KAPLLKDSLL PKLPRCGLEI  180
IDHVVGNLLD HEMSSASEWY LRNLQFHRFW SVDDTQVHTE YSSLRSIVVT NYEETIKMPI  240
NEPAMGMKKS SIQEYVDYNG GAGVQHVGLK TQDIITTIRN LQERGMEFLT VPSTYYKQLR  300
ENLKTAKIRV KESIDVLEEL QILMDYDEKG YILQIFTKPM QDRPTLFLEV IQRHNHQGFG  360
AGNFNSLFKA LEDAQELRGN LTNL                                         384

SEQ ID NO: 106         moltype = AA  length = 393
FEATURE                Location/Qualifiers
source                 1..393
                       mol_type = protein
                       organism = Nomascus leucogenys
SEQUENCE: 106
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIVRE  120
PWIEQDKFGK VKFAVLQTYG DTTHTLVEKM NYIGQFLPGY EAPAFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYRQLR  300
EQLKTAKIKV KENIDVLEEL KILVDYDEKG YLLQIFTKPV QDRPTLFLEV IQRHNHQGFG  360
AGNFNSLFKA FEEEQNLRGN LTNMETSGVV PGM                               393

SEQ ID NO: 107         moltype = AA  length = 394
FEATURE                Location/Qualifiers
source                 1..394
                       mol_type = protein
                       organism = Rhinopithecus roxellana
SEQUENCE: 107
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDITFEV EDCDYIVQKA RERGAKIVRE  120
PWVEQDKFGK VKFAVLQTYG DTTHTLVEKM NYTGQFLPGY EAPAFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITAIRH LRERGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LTDLETNGVV PGMQ                              394

SEQ ID NO: 108         moltype = AA  length = 393
FEATURE                Location/Qualifiers
source                 1..393
                       mol_type = protein
                       organism = Muntiacus muntjak
SEQUENCE: 108
MTTYSDKGEK PESGRFLHFH SVTFWVGNAK QAASYYCSKL GFEPLAYKGL ETGSREVVSH  60
VVKQGQIVFV FSSALNPWNK EMGDHLVKHG DGVKDIAFEV EDCDYIVQKA RERGAKIVRE  120
PWVEQDKFGK VKFAVLQTYG DTTHTLVEKM NYTGRFLPGF EAPAFMDPQL SKLPNCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GPGVQHIALK TKDIITAIRH LRERGVEFLA VPSTYYKQLR  300
EKLKSAKIRV KENIDILEEL KILVDYDEKG YLLQIFTKPM QDRPTLFLEV IQRHNHQGFG  360
AGNFNALFKA FEEEQDLRGN LTDMEPNGVV PGM                               393

SEQ ID NO: 109         moltype = AA  length = 393
FEATURE                Location/Qualifiers
source                 1..393
                       mol_type = protein
                       organism = Mastomys coucha
SEQUENCE: 109
MTTYTNKGPK PERGRFLHFH SVTFWVGNAK QAASFYCNKM GFEPLAYRGL ETGSREVVSH  60
VIKQGKIVFV LCSALNPWNK EMGDHLVKHG DGVKDIAFEV EDCEHIVQKA RERGAKIVRE  120
PWVEQDKFGK VKFAVLQTYG DTTHTLVEKI DYTGRFLPGF EAPIYKDTLL PKLPRCNLEI  180
IDHIVGNQPD QEMESASEWY LKNLQFHRFW SVDDTQVHTE YSSLRSIVVA NYEESIKMPI  240
NEPAPGRKKS QIQEYVDYNG GAGVQHIALK TEDIITTIRH LRERGMEFLA VPSSYYKLLR  300
ENLKTAKIQV KESMDVLEEL KILVDYDEKG YLLQIFTKPV QDRPTLFLEV IQRHNHQGFG  360
AGNFNSLFKA FEEEQALRGN LTDLETNGVR SGM                               393

SEQ ID NO: 110         moltype = AA  length = 387
FEATURE                Location/Qualifiers
source                 1..387
                       mol_type = protein
                       organism = Camelus dromedarius
SEQUENCE: 110
MTTYSDKGEK PERGRFLHFH SVTFWVGNAK QAASYYCSKM GFEPLAYKGL ETRSRDVVSH  60
VIKQGKIVFV FSSALNPWNK EMGDHLVKHG DGVKDIAFEV EDCDYIVQKA RERGAKIVRE  120
PWVEQDKFGK VKFAVLQTYG DTTHTLVEKM NYTGRFLPGF EAPASTDPLL SKLPNCCLEI  180
IDHIVGNQPD QEMLSASEWY LKNLQFHRFW SVDDTQVHTE YSSLRSIVVA NYEESIKMPI  240
```

-continued

```
NEPAPGRKKS QIQEYVDYNG GAGVQHIALN TQDIITAIRH LRERGMEFLA VPSTYYKQLR  300
EKLKSAKIRV KENIDVLEEL KILVDYDEKG YLLQIFTKPM QDRPTLFLEV IQRHNHQGFG  360
AGNFNSLFKA FEEEQDLRGN LTDMETS                                      387

SEQ ID NO: 111         moltype = AA  length = 393
FEATURE                Location/Qualifiers
source                 1..393
                       mol_type = protein
                       organism = Papio anubis
SEQUENCE: 111
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIVRE  120
PWVEQDKFGK VKFAVLQTYG DTTHTLVEKM NYTGQFLPGY EAPVFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITAIRH LRQRGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LTDLETNGVV PGM                               393

SEQ ID NO: 112         moltype = AA  length = 393
FEATURE                Location/Qualifiers
source                 1..393
                       mol_type = protein
                       organism = Sarcophilus harrisii
SEQUENCE: 112
MTTYTDRGEK PPRGRFLHFH SITFWVGNAK QAASFYCNKM GFSPLAYRGL ETGSREVASH  60
VVKQGKIIFI FSSPLNPGNK EMGDHLVKHG DGVKDISFEV EDCDYIVQKA RERGAVIVKE  120
PWIEQDKFGR VKFAILQTYG DTTHTLVEKL NYTGPFLPGF ETPRFLDPLL PKLPDCKLAM  180
IDHVVGNQPD QEMVTAAEWY KKNLLFHRFW SVDDKQVHTE FSSLRSIVMA NYEETIKMPI  240
NEPAMGRKKS QIQEYVDYYG GAGVQHIAMS TPDIISAITH LKARGMEFLS APATYYKQLR  300
EGLKAAKMQV KENIDKLEEL KILVDYDEKG YLLQIFTKPV QDRPTVFLEV IQRHNHQGFG  360
AGNFNALFKA FEEEQSVRGN LTDLAPNGVG IAM                               393

SEQ ID NO: 113         moltype = AA  length = 393
FEATURE                Location/Qualifiers
source                 1..393
                       mol_type = protein
                       organism = Crocuta crocuta
SEQUENCE: 113
SSLSSSLLLQ PERGRFLHFH SVTFWVGNAK QAASFYCNKM GFEPLAYKGL ETGSREVVSH  60
VIKQGKIVFV FSSALNPWDK EMGDHLVKHG DGVKDIAFEV EDCDYIVQKA KERGAKIVRE  120
PWIEQDKFGK VKLAVLQTYG DTTHTLVEKM NYTGRFLPGF EAPVFIDPIL SKLPSCSLEI  180
IDHIVGNQPD QEMVSASEWY LKNLQFHRFW SVDDTQVHTE YSSLRSIVVA NYEESIKMPI  240
NEPALGKKKS QIQEYVDYNG GPGVQHIALK TQDIITAIRH LRERGMEFLG VPSTYYKQLR  300
EKLKSAKIRV KENIDVLEEL KILVDYDEKG YLLQIFTKPM QDRPTLFLEV IQRHNHQGFG  360
AGNFNSLFKA FEEEQNLRGN LTDLETNGTV RGM                               393

SEQ ID NO: 114         moltype = AA  length = 393
FEATURE                Location/Qualifiers
source                 1..393
                       mol_type = protein
                       organism = Hylobates moloch
SEQUENCE: 114
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIVRE  120
PWVEQDKFGK VKFAVLQTYG DTTHTLVEKM NYIGQFLPGY EAPAFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYRQLR  300
EQLKTAKIKV KENIDVLEEL KILVDYDEKG YLLQIFTKPV QDRPTLFLEV IQRHNHQGFG  360
AGNFNSLFKA FEEEQNLRGN LTNMETSGVV PGM                               393

SEQ ID NO: 115         moltype = AA  length = 393
FEATURE                Location/Qualifiers
source                 1..393
                       mol_type = protein
                       organism = Sapajus apella
SEQUENCE: 115
MTTYSDKGAK PERGRFLHFH SVTFWVGNAK QAASFYCNKM GFEPLAYRGL ETGSREVVSH  60
VIKQGKIVFV LSSALNPWNK EMGDHLVKHG DGVKDIAFEV EDCDYIVQKA RERGAKIVRE  120
PWVEEDKFGK VKFAVLQTYG DTTHTLVEKM NYAGRFLPGY KAPAFMDPLL PQLPKCSLEV  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LRGRGMEFLS VPSTYYKQLR  300
EKLKVAKIKV KESIDVLEEL KILVDYDEKG YLLQIFTKPV QDRPTLFLEV IQRHNHQGFG  360
AGNFNSLFKA FEEEQDLRGN LTNMETDGVV PGM                               393

SEQ ID NO: 116         moltype = AA  length = 393
FEATURE                Location/Qualifiers
source                 1..393
                       mol_type = protein
                       organism = Mustela erminea
```

```
SEQUENCE: 116
MTTYSDKGKK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYLVQKA REQGAKIVRE  120
PWIEQDKFGK VKLAVLQTYG DTTHTLVEKM NYTGRFLPGF EAPVSVDPLL SKLPTCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LKARGMEFLG VPSSYYRQLR  300
EKLKTAKIQV KENIDVLEEL KILVDYDEKG YLLQIFTKPM QDRPTLFLEV IQRHNHQGFG  360
AGNFNALFKA FEEEQDLRGN LTNLETNSSL RGM                             393

SEQ ID NO: 117         moltype = AA  length = 387
FEATURE                Location/Qualifiers
source                 1..387
                       mol_type = protein
                       organism = Camelus ferus
SEQUENCE: 117
MTTYSDKGEK PERGRFLHFH SVTFWVGNAK QAASYYCSKM GFEPLAYKGL ETRSRDVVSH  60
VIKQGKIVFV FSSALNPWNK EMGDHLVKHG DGVKDIAFEV EDCDYIVQKA RERGAKIVRE  120
PWVEQDKFGK VKFAVLHTYG DTTHTLVEKM NYTGRFLPGF EAPASTDPLL SKLPNCCLEI  180
IDHIVGNQPD QEMLSASEWY LKNLQFHRFW SVDDTQVHTE YSSLRSIVVA NYEESIKMPI  240
NEPAPGRKKS QIQEYVDYNG GAGVQHIALN TQDIITAIRH LRERGMEFLA VPSTYYKQLR  300
EKLKSAKIRV KENIDVLEEL KILVDYDEKG YLLQIFTKPM QDRPTLFLEV IQRHNHQGFG  360
AGNFNSLFKA FEEEQDLRGN LTDMETS                                    387

SEQ ID NO: 118         moltype = AA  length = 393
FEATURE                Location/Qualifiers
source                 1..393
                       mol_type = protein
                       organism = Phocoena sinus
SEQUENCE: 118
MTTYSNKGEK PERGRFLHFH SVTFWVGNAK QAASYYCSKM GFESLAYKGL ETGSREMVSH  60
VIKQGKIVFI FSSALNPWNK EMGDHLVKHG DGVKDIAFEV EDCDYIAQKA RERGAKIVRE  120
PWVEQDKFGK VKFAVLQTYG DTTHTLVEKM NYTGWFLPGF EVPAFVDPLL SKLPNCSLER  180
IDHIVGNQPD QEMLSASEWY LKNLQFHRFW SVDDTQVHTE YSSLRSIVVA NYEESIKMPI  240
NEPAPGRKKS QIQEYVDYNG GAGVQHIALK TEDIITAIRH LRERGMEFLA VPSTYYKQLR  300
EKLKSAKIRV KENIDVLEEL KILVDYDEKG YLLQIFTKPM QDRPTLFLEV IQRYNHQGFG  360
AGNFNSLFKA FEEEQDLRGN LTDMETNGTV AGM                             393

SEQ ID NO: 119         moltype = AA  length = 393
FEATURE                Location/Qualifiers
source                 1..393
                       mol_type = protein
                       organism = Lontra canadensis
SEQUENCE: 119
MTTYSDKGKK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIVRE  120
PWIEQDKFGK VKLAVLQTYG DTTHTLVEKM NYTGRFLPGF EAPASVDPLL SKLPTCSLEI  180
IDHIVGNQPD QEMVSASEWY LKNLQFHRFW SVDDTQVHTE YSSLRSIVVA NYEESIKMPI  240
NEPAPGRKKS QIQEYVDYNG GAGVQHIALK TQDIITAIRH LRARGMEFLC VPSSYYKQLR  300
EKLKSAKIQV KESIDVLEEL KILVDYDEKG YLLQIFTKPM QDRPTLFLEV IQRHNHQGFG  360
AGNFNSLFKA FEEEQDLRGN LTDLETNGTL RGM                             393

SEQ ID NO: 120         moltype = AA  length = 393
FEATURE                Location/Qualifiers
source                 1..393
                       mol_type = protein
                       organism = Tyto alba
SEQUENCE: 120
MTTYTDKGEK PLRGRFIHFH SITFWVGNAK QAASYYCNKM GFEELAYRGL ETGSREVVSH  60
VIKQDKIVFV LSSALNPGNE EMGEHLVKHG DGVKDIAFEV EDCDFIVQKA KERGAVVVKE  120
PWVEEDKFGK VKFAVIQTYG DTTHTLIEKL NYKGLFLPGY HPPLFKDPLL PKLPSAKLNF  180
VDHVVGNQPD LQMVPVADWY QKNLLFHRFW SVDDKQLHTE FSALRSIVVT NYEETIKMPI  240
NEPAFGKKKS QIQEYVDYYG GAGVQHIALN TSDIISAITN LKQRGMQFMD VPSSYYQMLR  300
ERLKTAKIKV KENIDKLAEL KILVDFDEKG YLLQIFTKPV QDRPTVFLEV IQRHNHQGFG  360
AGNFKSLFEA IEIDQDARGN LTILEPNGET KRI                             393

SEQ ID NO: 121         moltype = AA  length = 394
FEATURE                Location/Qualifiers
source                 1..394
                       mol_type = protein
                       organism = Trachypithecus francoisi
SEQUENCE: 121
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDLTFEV EDCDYIVQKA RERGAKIVRE  120
PWVEQDKFGK VKFAVLQTYG DTTHTLVEKM NYTGQFLPGY EAPAFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITAIRH LRERGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LTDLETNGVV PGMQ                            394
```

```
SEQ ID NO: 122         moltype = AA  length = 392
FEATURE                Location/Qualifiers
source                 1..392
                       mol_type = protein
                       organism = Mirounga leonina
SEQUENCE: 122
TTYSDKGKKP QRGRFLHFHS VTFWVGNAKQ AASFYCNKMG FEPLAYKGLE TGSREVVSHV  60
IKQGKIVFVF SSALNPWNKE MGDHLVKHGD GVKDIAFEVE DCDYIVQKAR EQGAKIVREP  120
WIEQDKFGKV KLAVLQTYGD TTHTLVEKMN YSGRFLPGFE TPASVDPLLS KLPSCSLEMV  180
DHIVGNQPDQ EMVSASEWYL KNLQFHRFWS VDDTQVHTEY SSLRSIVVAN FEESIKMPIN  240
EPAPGKKKSQ IQEYVDYNGG AGVQHIALKT QDIITAIRHL RERGMEFLAV PPTYYKQLRE  300
KLKSAKIRVK ESIDTLEELK ILVDYDEKGY LLQIFTKPMQ DRPTLFLEVI QRHNHQGFGA  360
GNFNSLFKAF EEEQDLRGNL TDSENTRTLP GM                               392

SEQ ID NO: 123         moltype = AA  length = 393
FEATURE                Location/Qualifiers
source                 1..393
                       mol_type = protein
                       organism = Arvicanthis niloticus
SEQUENCE: 123
MTTYTNKGPK PERGRFLHFH SVTFWVGNAK QAASFYCNKM GFEPLAYRGL ETGSREVVSH  60
VIKQGKIVFV LCSALNPWNK EMGDHLVKHG DGVKDIAFEV EDCEHIVQKA RERGAKIIRE  120
PWVEEDKFGK VKFAVLQTYG DTTHTLVEKI NYTGRFLPGF EAPTYKDNLL PKLSRCKLEV  180
IDHIVGNQPD QEMESASEWY LKNLQFHRFW SVDDTQVHTE YSSLRSIVVA NYEESIKMPI  240
NEPAPGRKKS QIQEYVDYNG GAGVQHIALK TEDIITTIRH LRERGMEFLA VPSSYYKMLR  300
ENLKIAKIQV KESMDVLEEL KILVDYDEKG YLLQIFTKPM QDRPTLFLEV IQRHNHQGFG  360
AGNFNALFKA FEEEQALRGN LTDLETNGVR SGM                              393

SEQ ID NO: 124         moltype = AA  length = 393
FEATURE                Location/Qualifiers
source                 1..393
                       mol_type = protein
                       organism = Trachemys scripta
SEQUENCE: 124
MTTYTDKGEK PEGGKFLHFH SLTFWVGNAK QAASFYCNKM GFEELAYKGL ETGSREVVSH  60
VIKQDKIIFV LSSALNPENK EMGEHLVKHG DGVKDIAFEV EDCDFIVQKA KERGAVIVKE  120
PWVEEDKYGK VKFAVIQTYG DTTHTLIENL NYKGLFLPGF ELPLFKDPLL PKLPSGKLSF  180
IDHVVGNQPD LQMVPVAEWY QKNLLFHRFW SVDDKQLHTQ FSALRSIVVA NYEETIKMPI  240
NEPAVGKKKS QIQEYVEYYG GAGVQHIALN TPDIITAVTN LKQRGMEFMT VPSTYYQQLR  300
EKLKSAKIKV KENIDKLEEL KILVDFDEKG YLLQIFTKPV QDRPTVFLEV IQRHNHQGFG  360
AGNFKSLFQA IEDDQDARGN LTILTANGET NFI                              393

SEQ ID NO: 125         moltype = AA  length = 393
FEATURE                Location/Qualifiers
source                 1..393
                       mol_type = protein
                       organism = Pan paniscus
SEQUENCE: 125
MTTYSDKGAK PERGRFLHFH SVTFWVGNAK QAASFYCSKM GFEPLAYRGL ETGSREVVSH  60
VIKQGKIVFV LSSALNPWNK EMGDHLVKHG DGVKDIAFEV EDCDYIVQKA RERGAKIVRE  120
PWVEQDKFGK VKFAVLQTYG DTTHTLVEKM NYIGQFLPGY EAPAFMDPLL PKLPKCRLEM  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TEDIITAIRH LRERGLEFLS VPSTYYKQLR  300
EKLKTAKIKV KENIDALEEL KILVDYDEKG YLLQIFTKPV QDRPTLFLEV IQRHNHQGFG  360
AGNFNSLFKA FEEEQNLRGN LTNMETNGVV PGM                              393

SEQ ID NO: 126         moltype = AA  length = 393
FEATURE                Location/Qualifiers
source                 1..393
                       mol_type = protein
                       organism = Callithrix jacchus
SEQUENCE: 126
MTTYSDKGAK PERGRFLHFH SVTFWVGNAK QAASFYCTKM GFEPLAYRGL ETGSREVVSH  60
VIKQGKIVFV LSSALNPWNK EMGDHLVKHG DGVKDITFEV EDCDYIVQKA RERGAKIVQE  120
PWVEEDKFGK VKFAVLQTFG DITHTLVEKM SYAGRFLPGY EAPVFMDPLL PQLPKCSLKV  180
IDHIVGNQPD QEMASASEWY LKNLQFHRFW SVDDTQVHTE YSSLRSIVVA NYEESIKMPI  240
NEPAPGKKKS QIQEYVEYNG GAGVQHIALK TQDIITAIRH LRERGLEFLS VPSTYYKQLR  300
EKLKVAKIKV KESIDVLEEL KILVDFDEKG YLLQIFTKPV QDRPTLFLEV IQRHNHQGFG  360
AGNFNSLFKA IEEEQNLRGN LTNRETDGVV PGM                              393

SEQ ID NO: 127         moltype = AA  length = 393
FEATURE                Location/Qualifiers
source                 1..393
                       mol_type = protein
                       organism = Canis lupus dingo
SEQUENCE: 127
MTTYSDKGKK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIVRE  120
PWIEEDKFGK VKLAVLQTYG DTTHTLVEKI NYTGRFLPGF EAPACVDPLL SKLPSCSLEI  180
```

-continued

```
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LRDRGMEFLA VPSTYYKQLR  300
EKLKSAKIQV KESIDVLEEL KILVDYDEKG YLLQIFTKPM QDRPTLFLEV IQRHNHQGFG  360
AGNFNSLFKA FEEEQDLRGN LTDLETNGMM PGM                               393

SEQ ID NO: 128         moltype = AA  length = 430
FEATURE                Location/Qualifiers
source                 1..430
                       mol_type = protein
                       organism = Rhinolophus ferrumequinum
SEQUENCE: 128
MEFLGAAAEL EMGSCPGALS TPASCPVFQA GSLTKINMTT YSDKGQKPER GRFLHFHSVT  60
FWVGNAKQAA SFYCSKMGFE PLAYKGLETG SREVVSHVVK QGEIVFVFCS ALNPWNKEMG  120
DHLVKHGDGV KDIAFEVEDC EYIVQKARER GAKIIREPWV EQDKFGKVKF AVLQTYGDTT  180
HTLVEKMNYT GRFLPGFEAP TFTDPLLSKL PHCKLEIIDH IVGNQPDQEM TSASDWYLKN  240
LQFHRFWSVD DTQVHTEYSS LRSIVVANYE ESIKMPINEP APGRKKSQIQ EYVDYNGGAG  300
VQHIALKTQD IITAIRRLRE RGMEFLAVPS TYYKQLREKL KTAKIRVKEN IDVLEELKIL  360
VDYDEKGYLL QIFTKPMQDR PTLFLEVIQR HNHQGFGAGN FNSLFKAFEE EQNLRGNLTD  420
METNGVITGM                                                         430

SEQ ID NO: 129         moltype = AA  length = 393
FEATURE                Location/Qualifiers
source                 1..393
                       mol_type = protein
                       organism = Rhinolophus ferrumequinum
SEQUENCE: 129
MTTYSDKGQK PERGRFLHFH SVTFWVGNAK QAASFYCSKM GFEPLAYKGL ETGSREVVSH  60
VVKQGEIVFV FCSALNPWNK EMGDHLVKHG DGVKDIAFEV EDCEYIVQKA RERGAKIIRE  120
PWVEQDKFGK VKFAVLQTYG DTTHTLVEKM NYTGRFLPGF EAPAFTDPLL SKLPHCKLEI  180
IDHIVGNQPD QEMTSASDWY LKNLQFHRFW SVDDTQVHTE YSSLRSIVVA NYEESIKMPI  240
NEPAPGRKKS QIQEYVDYNG GAGVQHIALK TQDIITAIRR LRERGMEFLA VPSTYYKQLR  300
EKLKTAKIRV KENIDVLEEL KILVDYDEKG YLLQIFTKPM QDRPTLFLEV IQRHNHQGFG  360
AGNFNSLFKA FEEEQNLRGN LTDMETNGVI TGM                               393

SEQ ID NO: 130         moltype = AA  length = 393
FEATURE                Location/Qualifiers
source                 1..393
                       mol_type = protein
                       organism = Phyllostomus discolor
SEQUENCE: 130
MTSYSDKGQK PERGRFLHFH SVTFWVGNAK QAASFYCSKV GFEPLAYKGL ETGSREVVSH  60
VVKQGQIVFV FSSALNPWNK EMGDHLVKHG DGVKDIAFEV EDCDYIVQKA RERGAKIIRE  120
PWVEQDKFGK VKLAVLQTYG DTTHTLVEKM NYTGCFLPGF EAVDCKDPLL SKLPQCGLEV  180
VDHIVGNQPD QEMQSASEWY LKNLQFHRFW SVDDTQVHTE YSSLRSIVVA NYEESIKMPI  240
NEPAPGRKKS QIQEYVDYNG GAGVQHIALK TGDIISAIRH LRERGMEFLH VPSTYYKQLR  300
EKLKSAKIRV KENLDVLEEL RILVDYDEKG YLLQIFTKPM QDRPTLFLEV IQRHNHQGFG  360
AGNFNALFKA FEEEQALRGN LTDMEINGIA RGM                               393

SEQ ID NO: 131         moltype = AA  length = 393
FEATURE                Location/Qualifiers
source                 1..393
                       mol_type = protein
                       organism = Halichoerus grypus
SEQUENCE: 131
MTTYSDKGKK PQRGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIVRE  120
PWIEQDKFGK VKLAVLQTYG DTTHTLVEKM NYSGRFLPGF ETPASVDPLL SKLPSCSLEM  180
IDHIVGNQPD QEMVSASEWY LKNLQFHRFW SVDDTQVHTE YSSLRSIVVA NFEESIKMPI  240
NEPAPGKKKS QIQEYVDYNG GAGVQHIALK TQDIITAIRH LRERGMEFLA VPPTYYKQLR  300
EKLKSAKIRV KESIDTLEEL KILVDYDEKG YLLQIFTKPM QDRPTLFLEV IQRHNHQGFG  360
AGNFNSLFKA FEEEQDLRGN LTDLENTRTL PGM                               393

SEQ ID NO: 132         moltype = AA  length = 393
FEATURE                Location/Qualifiers
source                 1..393
                       mol_type = protein
                       organism = Onychomys torridus
SEQUENCE: 132
MTSYTNKGPK PERGRFLHFH SVTFWVGNAK QAASFYCNKM GFEPLAYKGL ETGSREVVSH  60
VIKQGKIVFV LCSALNPWNK EMGDHLVKHG DAVKDIAFEV EDCEHIVQKA RERGAKIVRE  120
PWVEQDKFGK VKFAVLQTYG DTTHTLVEKI NYTGRFLPGF EAPTHKDTLL SKLPSCNLEV  180
IDHIVGNQPD QEMTSASEWY LKNLQFHRFW SVDDTQVHTE YSSLRSIVVA NYEESIKMPI  240
NEPAPGKKKS QIQEYVDYNG GAGVQHIALK TEDIITTIRH LRERGMEFLA VPSSYYKLLR  300
GNLKTAKIQV KESMDVLEEL KILVDYDEKG YLLQIFTKPM QDRPTLFLEV IQRHNHQGFG  360
AGNFNSLFKA FEEEQALRGN LTDLETNGVR SGM                               393

SEQ ID NO: 133         moltype = AA  length = 393
FEATURE                Location/Qualifiers
source                 1..393
```

```
                         mol_type = protein
                         organism = Rousettus aegyptiacus
SEQUENCE: 133
MTSYSDKGKK PERGRFLHFH SVTFWVGNAK QAASFYCSKM GFEPLAYRGL ETGSREVASH  60
VIKQGQIVFV FSSALNPWNK EMGDHLVRHG DGVKDVAFEV QDCDSIVQKA QERGAKIIRE  120
PWVEQDKFGK VKFAVLQTFG DTTHTLVEKM NYRGPFLPGF MARAPRDSLL SKLPQCNLEV  180
IDHVVGNQPD QEMLSASEWY LNNLQFHRFW SVDDKELHTE YSSLRSIVVT NYEESIKIPI  240
NEPAPGRKKS QIQEYVDYYG GAGVQHIALK TQDIITTIRS LKERGMEFLN TPPTYYKQLR  300
EKLKSAKIRV QENMDTLEEL KILVDYDENG YLLQIFSKPM QDRPTLFLEV IQRHNHQGFG  360
AGNFNSLFKA LEEEQNLRGN LTDLETNGVV PGM                             393

SEQ ID NO: 134           moltype = AA  length = 393
FEATURE                  Location/Qualifiers
source                   1..393
                         mol_type = protein
                         organism = Molossus molossus
SEQUENCE: 134
MTSYSNKGEK PERGRFLHFH SVTFWVGNAK QAASFYCSKM GFKPLAYRGL ETGSRDVVSH  60
VVKQGQIVFV FSSALNPWNK DMGDHLVKHG DGVKDIAFEV EDCDYIVQKA RERGAKIIRE  120
PWVEQDKFGK VKFAVLQTYG DTTHTLVEKM KYTGFFLPGF EPVAKMDPAL SKLPQCNLEV  180
IDHIVGNQPD QEMESASDWY LNNLQFHRFW SVDDTQVHTE YSSLRSIVVA NYEESIKMPI  240
NEPAPGRKKS QIQEYVEYNG GAGVQHIALK TQDIITAIRH LRERGMEFLD VPSTYYKQLR  300
EKLKSAKIRV KENIEILEEL RILVDYDEKG YLLQIFTKPM QDRPTLFLEV IQRHNHQGFG  360
AGNFNALFKA FEEEQNLRGN LTDMEPNGVL RGM                             393

SEQ ID NO: 135           moltype = AA  length = 393
FEATURE                  Location/Qualifiers
source                   1..393
                         mol_type = protein
                         organism = Myotis myotis
SEQUENCE: 135
MTSYSNKGEK PERGRFLHFH SVTFWVGNAK QAASFYCSKM GFKPIAYKGL ETGSREVVSH  60
VVKQGQIVFV FSSALNPWNK EMGDHLVKHG DGVKDIAFEV EDCDYIVQKA RQRGAKIIRE  120
PWVEQDKFGK VKFAVLQTYG DTTHTLVEKM NYTGFFLPGF EPTTNRDPAL SKLPQSNLEV  180
IDHIVGNQPD QEMLSASDWY LNNLQFHRFW SVDDTQVHTE YSSLRSIVVA NYEESIKMPI  240
NEPAPGRKKS QIQEYVDYNG GAGVQHIALK TQDIITAIRH LRERGMEFLD VPSTYYKQLR  300
EKLKSAKIRV KENLDALEEL KILVDYDENG YLLQIFTKPM QDRPTLFLEV IQRHNHQGFG  360
AGNFNALFKA FEEEQNMRGN LTDLEPNGVI RGM                             393

SEQ ID NO: 136           moltype = AA  length = 393
FEATURE                  Location/Qualifiers
source                   1..393
                         mol_type = protein
                         organism = Pipistrellus kuhlii
SEQUENCE: 136
MTSYTNKGEK PERGRFLHFH SVTFWVGNAK QAASYYCSKM GFKPLAYRGL ETGSREVVSH  60
VVKQGQIVFI FSSALNPWNK EMGDHLVKHG DGVKDIAFEV EDCDYIVQKA RQRGAKIIRE  120
PWVEQDKFGK VKFAVLQTYG DTTHTLVEKM DYTGLFLPGF NPTTHTDSVL SKLPQSNLEV  180
IDHIVGNQPD QEMLSASDWY LNNLQFHRFW SVDDTQVHTE YSSLRSIVVA NYEESIKMPI  240
NEPAPGRKKS QIQEYVDYNG GAGVQHIALK TQDIITAIRH LRERGMEFLD VPATYYRQLR  300
EKLKSAKIRV KESLDTLEEL KILVDYDENG YLLQIFTKPM QDRPTLFLEV IQRHNHQGFG  360
AGNFNALFKA FEEEQNLRGN LTDMETNGVV RGM                             393

SEQ ID NO: 137           moltype = AA  length = 393
FEATURE                  Location/Qualifiers
source                   1..393
                         mol_type = protein
                         organism = Balaenoptera musculus
SEQUENCE: 137
MTTYSNKGQK PERGQFLHFH SVTFWVGNAK QAASYYCSKM GFEPLAYKGL ETGSREMVSH  60
VIKQGKIVFI FSSALNPWNK EMGDHLVKHG DGVKDIAFEV EDCDYIVQKA RERGAKIVRE  120
PWVEQDKFGK VKFAVLQTYG DTTHTLVEKM NYTGWFLPGF EAPAFVDPLL SKLPNCSLKI  180
IDHIVGNQPD QEMVSASEWY LKNLQFHRFW SVDDTQVHTE YSSLRSIVVA NYEESIKMPI  240
NEPAPGRKKS QIQEYVDYNG GAGVQHIALK TEDIITAIHH LRERGMEFLA VPSTYYKQLR  300
EKLKTAKIRV KENIDVLEEL KILVDYDEKG YLLQIFTKPM QDRPTLFLEV IQRYNHQGFG  360
AGNFNSLFKA FEEEQDLRGN LTDMETNGLA PGM                             393

SEQ ID NO: 138           moltype = AA  length = 393
FEATURE                  Location/Qualifiers
source                   1..393
                         mol_type = protein
                         organism = Manis pentadactyla
SEQUENCE: 138
MTTYSNQGEK PERGRFLHFH SVTFWVGNAK QAASFYCSKM GFEPLAYKGL ETGSREVVSH  60
VIKQGKIVFV FSSALNPWNR EMGDHLVKHG DGVKDIAFEV EDCDYIVQKA RERGAKIVQE  120
PWVEQDKFGK VKFAVLQTYG DTTHTLVEKM NYSGCFLPGF EPLVFTDPLL SKLPKCYLEI  180
IDHIVGNQPD QEMVSASEWY LKNLQFHRFW SVDDTQVHTE YSSLRSIVVA NYEESIKMPI  240
NEPAPGRKKS QIQEYVDYNG GAGVQHIALK TQDIITAIRH LRERGLEFLA VPPTYYKQLR  300
EKLKSAKIRV KESIDTLEEL KVLVDYDEKG YLLQIFTKPV QDRPTLFLEV IQRHNHQGFG  360
```

```
AGNFNSLFKA FEEEQDLRGN LTDMEANGSM PGR                         393

SEQ ID NO: 139         moltype = AA  length = 393
FEATURE                Location/Qualifiers
source                 1..393
                       mol_type = protein
                       organism = Manis javanica
SEQUENCE: 139
MTTYSNQGEK PERGRFLHFH SVTFWVGNAK QAASFYCSKM GFEPLAYKGL ETGSREVVSH  60
VIKQGKIVFV FSSALNPWNR EMGNHLVKHG DGVKDIAFEV EDCDYIVQKA RERGAKIVQE  120
PWVEQDKFGK VKFAVLQTYG DTTHTLVEKM NYSGCFLPGF EPLVLTDPLL SKLPKCYLEI  180
IDHIVGNQPD QEMVSASEWY LKNLQFHRFW SVDDTQVHTE YSSLRSIVVA NYEESIKMPI  240
NEPAPGRKKS QIQEYVDYNG GAGVQHIALK TQDIITAIRH LRERGLEFLA VPPTYYKQLR  300
QKLKSAKIRV KESIDTLEEL KVLVDYDEKG YLLQIFTKPV QDRPTLFLEV IQRHNHQGFG  360
AGNFNSLFKA FEEEQDLRGN LTDMEANGSM PGK                         393

SEQ ID NO: 140         moltype = AA  length = 393
FEATURE                Location/Qualifiers
source                 1..393
                       mol_type = protein
                       organism = Sturnira hondurensis
SEQUENCE: 140
MTSYSNKGPK PERGRFVHFH SVTFWVGNAK QAASFYCTRM GFEPLAYRGL ETGSREVVSH  60
VVKQGQIVFV FSSALNPWNK EMGDHLVKHG DGVKDVAFEV EDCDYIVQKA QERGAKIIRE  120
PWVEQDKFGK VKFAVLQTYG DTTHTLVEKM SYTGCFLPGF KGLDSKDALL SKLPHCCLEV  180
IDHIVGNQPD QEMQSASEWY LKNLQFHRFW SVDDTQVHTE YSSLRSIVVT NYEESIKMPI  240
NEPAPGKKKS QIQEYVDFNG GAGVQHIALK TQDIISAIRH LRERGMEFLH VPSTYYKQLR  300
EKLKSAKIRV KENMDVLEEL NILVDYDDKG YLLQIFTKPM QDRPTLFLEI IQRHNHQGFG  360
AGNFNALFEA IEEEQALRGN LTDLETNGVV QGK                         393

SEQ ID NO: 141         moltype = AA  length = 393
FEATURE                Location/Qualifiers
source                 1..393
                       mol_type = protein
                       organism = Talpa occidentalis
SEQUENCE: 141
MTTYSDKGAK PERGRFLHFH SVTFWVGNAK QAASFYCSKM GFEPLAYRGL ETGSREVVSH  60
VVKQGKIVFV LSSALNPWNK EMGDHLVKHG DGVKDIAFEV EDCDYIVQKA RERGAKIVRE  120
PWVEEDKFGK VKFAVLQTYG DTTHTLVEKM NYTGRFLPGF EAPTFMDPLL SKLPSCTLEI  180
IDHIVGNQPD QEMLSASDWY LKNLQFHRFW SVDDTQVHTE YSSLRSIVVA NYEESIKMPI  240
NEPAPGKKKS QIQEYVDYNG GAGVQHIALK TQDIIKAIRH LRERGMEFLA VPSAYYRQLR  300
ENLKTAKIRV KESIDVLEEL KILVDYDEKG YLLQIFTKPM QDRPTLFLEV IQRHNHQGFG  360
AGNFNSLFKA FEEEQDLRGN LTDVETNGLV RGM                         393

SEQ ID NO: 142         moltype = AA  length = 390
FEATURE                Location/Qualifiers
source                 1..390
                       mol_type = protein
                       organism = Choloepus didactylus
SEQUENCE: 142
MTTYSNKGVK PERGQFLHFH SVTFWVGNAK QAASFYCNKM GFEPFAYKGL ETGSREVVSH  60
VIKQGKIVFV FSSALNPWNK EMGDHLVKHG DGVKDIAFEV EDCDYIVQKA RERGAKIVRE  120
SWVEQDKFGK VKFAVLQTYG DTTHTLVEKM GYTGRFLPGF EAPAIKDPLL AKLPSCSLEV  180
IDHIVGNQPD QEMVPVSDWY VKNLQFHRFW SVDDTQVHTE YSSLRSIVVA NYEETIKMPI  240
NEPAQGRKKS QIQEYVDYNG GAGVQHIALK TQDITTTIRH LRERGLEFLA VPSTYYKQLR  300
EKLKTAKIRV KENIDVLEEL KILVDYDEKG YLLQIFTKPV QDRPTLFLEV IQRHNHQGFG  360
AGNFNSLFKA FEDEQNRRGN LTDLGTNGVP                             390

SEQ ID NO: 143         moltype = AA  length = 412
FEATURE                Location/Qualifiers
source                 1..412
                       mol_type = protein
                       organism = Chlorocebus sabaeus
SEQUENCE: 143
MCRQQSFFPG GSLHLRQQGQ QAEGGQGLSS GSPPGWPLDP HEPCCNPVIQ AVSFYCSKMG  60
FEPLAYRGLE TGSREVVSHV IKQGKIVFVL SSALNPWNKE MGDHLAKHGD GVKDIAFEVE  120
DCDYIVQKAR ERGAKIVREP WVEQDKFGKV KFAVLQTYGD TTHTLVEKMN YTGQFLPGYE  180
APVFMDPLLP KLPKCSLEII DHIVGNQPDQ EMVSASEWYL KNLQFHRFWS VDDTQVHTEY  240
SSLRSIVVAN YEESIKMPIN EPAPGKKKSQ IQEYVDYNGG AGVQHIALNT QDIITAIRHL  300
RERGMEFLSV PSTYYKQLRE KLKTAKIKVK ENIDVLEELK ILVDYDEKGY LLQIFTKPVQ  360
DRPTLFLEVI QRHNHQGFGA GNFNSLFKAF EEEQNLRGNL SDLETNGVVP GM        412

SEQ ID NO: 144         moltype = AA  length = 393
FEATURE                Location/Qualifiers
source                 1..393
                       mol_type = protein
                       organism = Chlorocebus sabaeus
SEQUENCE: 144
MTTYSDKGAK PERGRFLHFH SVTFWVGNAK QAVSFYCSKM GFEPLAYRGL ETGSREVVSH  60
```

-continued

```
VIKQGKIVFV LSSALNPWNK EMGDHLAKHG DGVKDIAFEV EDCDYIVQKA RERGAKIVRE  120
PWVEQDKFGK VKFAVLQTYG DTTHTLVEKM NYTGQFLPGY EAPVFMDPLL PKLPKCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALN TQDIITAIRH LRERGMEFLS VPSTYYKQLR  300
EKLKTAKIKV KENIDVLEEL KILVDYDEKG YLLQIFTKPV QDRPTLFLEV IQRHNHQGFG  360
AGNFNSLFKA FEEEQNLRGN LSDLETNGVV PGM                              393

SEQ ID NO: 145         moltype = AA  length = 393
FEATURE                Location/Qualifiers
source                 1..393
                       mol_type = protein
                       organism = Arvicola amphibius
SEQUENCE: 145
MTTYTNKGPK PERGRFLHFH SVTFWVGNAK QAASFYCNKM GFEPLAYRGL ETGSREVVSH  60
VIKQGKIVFV LCSALNPWNK EMGDHLVKHG DGVKDIAFEV EDCEHIVQKA RERGAKIVRE  120
PWVEQDKFGK VKFAVLQTYG DTTHTLVEKI NYTGRFLPGF EAPVYKDTLL PKLPRCNLEV  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TDDIITAIRH LRERGMEFLA VPSSYYKLLR  300
ENLKTAKIQV KESLDVLEEL KILVDYDEKG YLLQIFTKPM QDRPTLFLEV IQRHNHQGFG  360
AGNFNSLFKA FEEEQALRGN LTDLETNGVR SGM                              393

SEQ ID NO: 146         moltype = AA  length = 393
FEATURE                Location/Qualifiers
source                 1..393
                       mol_type = protein
                       organism = Tachyglossus aculeatus
SEQUENCE: 146
MTTYTDKGEK PLRGQFLHFH SVTFWVGNAK QAASFYCNKM GFEPLAYRGL ETGSREVVSH  60
VIKQDKIIFI FSSALNPGNK EMGEHLVKHG DGVKDVAFQV EDCDFIVQKA RERGAAIVKE  120
PWVEQDKNGR VKFAVLQTYG DTTHTLIEKI DYKGPFLPGY EAPLFLDPLL PKLPACKLNF  180
IDHVVGNQPD HEMVPAVEWY QKNLLFHRFW SVDDKQVHTD FSALRSIVVA NYEETIKMPI  240
NEPALGKKKS QIQEYVEYYG GAGVQHIALN TQDIISAIAH LKERGTEFMS VPSTYYTQLR  300
EKLKTAKIRV KENIKQLEEL KILVDYDEKG YLLQIFTKPM QDRPTLFLEV IQRHNHQGFG  360
AGNFTSLFKA IEEDQQARGN LTVLSPNGEV SAM                              393

SEQ ID NO: 147         moltype = AA  length = 393
FEATURE                Location/Qualifiers
source                 1..393
                       mol_type = protein
                       organism = Canis lupus
SEQUENCE: 147
MTTYSDKGKK PERGRFLHFH SVTFWVGNAK QAASFYCNKM GFEPLAYKGL ETGSREVVSH  60
VIKQGKIVFV FSSALNPWNK EMGDHLVKHG DGVKDIAFEV EDCDYIVQKA REQGAKIMRE  120
PWIEEDKFGK VKLAVLQTYG DTTHTLVEKI NYTGRFLPGF EAPACVDPLL SKLPSCSLEI  180
IDHIVGNQPD QEMVSASEWY LKNLQFHRFW SVDDTQVHTE YSSLRSIVVA NYEESIKMPI  240
NEPAPGKKKS QIQEYVDYNG GAGVQHIALK TQDIITAIRH LRDRGMEFLA VPSTYYKQLR  300
EKLKSAKIQV KESIDVLEEL KILVDYDEKG YLLQIFTKPM QDRPTLFLEV IQRHNHQGFG  360
AGNFNSLFKA FEEEQDLRGN LTDLETNGMM PGM                              393

SEQ ID NO: 148         moltype = AA  length = 393
FEATURE                Location/Qualifiers
source                 1..393
                       mol_type = protein
                       organism = Eschrichtius robustus
SEQUENCE: 148
MTTYSNKGQK PERGQFLHFH SVTFWVGNAK QAASYYCSKM GFEPLAYKGL ETGSREMVSH  60
VIKQGKIVFI FSSALNPWNK EMGDHLVKHG DGVKDIAFEV EDCDYIVQKA RERGAKIVRE  120
PWVEQDKFGK VKFAVLQTYG DTTHTLVEKM NYTGWFLPGF EAPAFVDPLL SKLPNCSLEI  180
IDHIVGNQPD QEMVSASEWY LKNLQFHRFW SVDDTQVHTE YSSLRSIVVA NYEESIKMPI  240
NEPAPGRKKS QIQEYVDYNG GAGVQHIALK TEDIITAIHH LRERGMEFLA VPSTYYKQLR  300
EKLKTAKIRV KENIDVLEEL KILVDYDEKG YLLQIFTKPM QDRPTLFLEV IQRYNHQGFG  360
AGNFNSLFKA FEEEQDLRGN LTDMETNGLA PGM                              393

SEQ ID NO: 149         moltype = DNA  length = 1179
FEATURE                Location/Qualifiers
source                 1..1179
                       mol_type = unassigned DNA
                       organism = Rattus norvegicus
SEQUENCE: 149
atgaccacct actctaacaa gggtccaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc catcttgtaa cttggaaatc  540
atcgaccaca tcgttggtaa ccaaccagac caagaaatgg aatctgcttc tgaatggtac  600
```

-continued

```
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaga accgaagaca tcatcaccac catcagacac  840
ttgagagaaa gaggtatgga attcttggct gttccatctt cttactacag attgttgaga  900
gaaaacttga agacctctaa gatccaagtt aaggaaaaca tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttaga tctggtatg                         1179

SEQ ID NO: 150         moltype = DNA  length = 1131
FEATURE                Location/Qualifiers
source                 1..1131
                       mol_type = unassigned DNA
                       organism = Rattus norvegicus
SEQUENCE: 150
atgtactggg acaagggtcc aaagccagaa agaggtagat tcttgcactt ccactctgtt  60
accttctggg ttggtaacgc taagcaagct gcttctttct actgtaacaa gatgggtttc  120
gaaccattgg cttacaaggg tttggaaacc ggttctagag aagttgtttc tcacgttatc  180
aagcaaggta agatcgtttt cgttttgtgt tctgctttga acccatggaa caaggaaatg  240
ggtgaccact tggttaagca cggtgacggt gttaaggaca tcgctttcga agttgaagac  300
tgtgaacaca tcgttcaaaa ggctagagaa agaggtgcta agatcgttag agaaccatgg  360
gttgaagaag acaagttcgg taaggttaag ttcgctgttt tgcaaaccta cggtgacacc  420
acccacacct tggttgaaaa gatcaactac accggtagat tcttgccagg tttcgaagct  480
ccaacctaca aggacacctt gttgccaaag ttgccatctt gtaacttgga aatcatcgac  540
cacatcgttg gtaaccaacc agaccaagaa atggaatctg cttctgaatg gtacttgaag  600
aacttgcaat tccacagatt ctggtctgtt gacgacaccc aagttcacac cgaatactct  660
tctttgagat ctatcgttgt tgctaactac gaagaatcta tcaagatgcc aatcaacgaa  720
ccagctccag gtagaaagaa gtctcaaatc caagaatacg ttgactacaa cggtggtgct  780
ggtgttcaac acatcgcttt gagaaccgaa gacatcatca ccaccatcag acacttgaga  840
gaaagaggta tggaattctt ggctgttcca tcttcttact acagattgtt gagagaaaac  900
ttgaagacct ctaagatcca agttaaggaa aacatggacg ttttggaaga attgaagatc  960
ttggttgact acgacgaaaa gggttacttg ttgcaaatct tcaccaagcc aatgcaagac  1020
agaccaacct tgttcttgga agttatccaa agacacaacc accaaggttt cggtgctggt  1080
aacttcaact ctttgttcaa ggctttcgaa gaagaacaag ctttgagagg t           1131

SEQ ID NO: 151         moltype = DNA  length = 1062
FEATURE                Location/Qualifiers
source                 1..1062
                       mol_type = unassigned DNA
                       organism = Rattus norvegicus
SEQUENCE: 151
atgggtttcg aaccattggc ttacaagggt ttggaaaccg gttctagaga agttgtttct  60
cacgttatca agcaaggtaa gatcgttttc gttttgtgtt ctgctttgaa cccatggaac  120
aaggaaatgg gtgaccactt ggttaagcac ggtgacggtg ttaaggacat cgctttcgaa  180
gttgaagact gtgaacacat cgttcaaaag gctagagaaa gaggtgctaa gatcgttaga  240
gaaccatggg ttgaagaaga caagttcggt aaggttaagt tcgctgtttt gcaaacctac  300
ggtgacacca cccacacctt ggttgaaaag atcaactaca ccggtagatt cttgccaggt  360
ttcgaagctc caagatacaa ggacaccttg ttgccaaagt tgccatcttg taacttggaa  420
atcatcgacc acatcgttgg taaccaacca gaccaagaaa tggaatctgc ttctgaatgg  480
tacttgaaga acttgcaatt ccacagattc tggtctgttg acgacaccca agttcacacc  540
gaatactctt ctttgagatc tatcgttgtt gctaactacg aagaatctat caagatgcca  600
atcaacgaac cagctccagg tagaaagaag tctcaaatcc aagaatacgt tgactacaac  660
ggtggtgctg gtgttcaaca catcgctttg agaaccgaag acatcatcac caccatcaga  720
cacttgagag aaagaggtat ggaattcttg gctgttccac catcttacta cagattgttg  780
agagaaaact tgaagtctgc taagatccaa gttaaggaag acatggacgt tttggaagaa  840
ttgaagatct tggttgacta cgacgaaaag ggttacttgt tgcaaatctt caccaagcca  900
atgcaagaca gaccaacctt gttcttggaa gttatccaaa gacacaacca ccaaggtttc  960
ggtgctggta acttcaactc tttgttcaag gctttcgaag aagaacaagc tttgagaggt  1020
aacttgaccg acttggaaac caacggtgtt agatctggta tg                     1062

SEQ ID NO: 152         moltype = DNA  length = 1182
FEATURE                Location/Qualifiers
source                 1..1182
                       mol_type = unassigned DNA
                       organism = Yarrowia lipolytica
SEQUENCE: 152
atgtctccat ctgttgaagt taccccagct cacaccccaa cctcttacga agttaccaac  60
tctttggact cttacagagg ttacgaccac gttcactggt acgttggtaa cgctaagcaa  120
gctgcttctt tctacatcac cagaatgggt ttctctccaa tcgcttacaa gggtttggaa  180
accggttcta gagacgttac cacccacgtt gttggtaacg gtcaagttag attcgctttc  240
tcttctgctt tgagaaccgg tgaaccacaa gctgacgaaa tccacgctca cttggttaag  300
cacggtgacg ctgttaagga cgttgctttc gaagttgaca acgttgaaca attgttctct  360
gctgctgtta agaagggtgt tagagttatc tctgaaccaa aggttttgaa ggacgctcac  420
ggttctgtta cctacgctgt tatctctacc tacggtgaca ccacccacac cttgatcgaa  480
agaggttctt acgaaggtgc tttcttgcca ggtttcgttg acacctctgc taacaaggac  540
ccaatcgctg ctttcttgcc aaacatcgaa ttgatgcaca tcgaccactg tgttggtaac  600
caagactgga acgaaatgga caacgcttgt aagtactacg aagaaacctt gggtttccac  660
```

-continued

```
agattctggt ctgttgacga caaggacatc tgtaccgaat tctctgcttt gaagtctgtt  720
gttatggctt ctccaaacga aaagatcaag atgccagtta acgaaccagc tgttggtaag  780
aagaagtctc aaatcgaaga atacatcgac ttctacgacg gtccaggtat ccaacacatc  840
gctttgagaa ccgactgtat cttggacacc gttagagact tgagagctag aggtgttgaa  900
ttcatctctg ttccaggttc ttactacgaa aacatgaagg aaagattggc taagtcttct  960
ttgaagttgg aagaaaagtt cgaagacatc caagctttga acatcttgat cgacttcgac  1020
gaaggtggtt acttgttgca attgttcacc aagccattga tggacagacc aaccgttttc  1080
atcgaaatca tccaaagaag aaacttcgaa ggtttcggtg ctggtaactt caagtctttg  1140
ttcgaagcta tcgaaagaga acaagctaag agaggtaact tg                    1182
```

```
SEQ ID NO: 153         moltype = DNA  length = 1182
FEATURE                Location/Qualifiers
source                 1..1182
                       mol_type = unassigned DNA
                       organism = Yarrowia lipolytica
SEQUENCE: 153
atgtctccat ctgttgaagt taccccagct cacaccccaa cctcttacga agttaccaac  60
tctttggact cttacagagg ttacgaccac gttcactggt acgttggtaa cgctaagcaa  120
gctgcttctt tctacatcac cagaatgggt ttctctccaa tcgcttacaa gggtttggaa  180
accggttcta gagacgttac cacccacgtt gttggtaacg gtcaagttag attcgctttc  240
tcttctgctt tgagaaccgg tgaaccacaa gctgacgaaa tccacgctca cttggttaag  300
cacggtgacg ctgttaagga cgttgctttc gaagttgaca acgttgaaca attgttctct  360
gctgctgtta agaagggtgt tagagttatc tctgaaccaa aggttttgaa ggacgctcaa  420
ggttctgtta cctacgctgt tatctctacc tacggtgaca ccacccacac cttgatcgaa  480
agaggttctt acgaaggtgc tttcttgcca ggtttcgttg acacctctgc taacaaggac  540
ccaatcgctg ctttcttgcc aaacatcgaa ttgatgcaca tcgaccactg tgttggtaac  600
caagactgga acgaaatgga caacgcttgt aagtactacg aagaaacctt gggtttccac  660
agattctggt ctgttgacga caaggacatc tgtaccgaat tctctgcttt gaagtctgtt  720
gttatggctt ctccaaacga aaagatcaag atgccagtta acgaaccagc tgttggtaag  780
aagaagtctc aaatcgaaga atacatcgac ttctacgacg gtccaggtat ccaacacatc  840
gctttgagaa ccgactgtat cttggacacc gttagagact tgagagctag aggtgttgaa  900
ttcatctctg ttccaggttc ttactacgaa aacatgaagg aaagattggc taagtcttct  960
ttgaagttgg aagaaaagtt cgaagacatc caagctttga acatcttgat cgacttcgac  1020
gaaggtggtt acttgttgca attgttcacc aagccattga tggacagacc aaccgttttc  1080
atcgaaatca tccaaagaag aaacttcgaa ggtttcggtg ctggtaactt caagtctttg  1140
ttcgaagcta tcgaaagaga acaagctaag agaggtaact tg                    1182
```

```
SEQ ID NO: 154         moltype = DNA  length = 1179
FEATURE                Location/Qualifiers
source                 1..1179
                       mol_type = unassigned DNA
                       organism = Homo sapiens
SEQUENCE: 154
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat catgagagaa  360
ccatgggttg aacaagacaa gttcggtaag gttaagttcg ctgttttgca aacctacggt  420
gacaccaccc acaccttggt tgaaaagatg aactacatcg gtcaattctt gccaggttac  480
gaagctccag ctttcatgga cccattgttg ccaaagttgc caaagtgttc tttggaaatg  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtttgga attcttgtct gttccatcta cctactacaa gcaattgaga  900
gaaaagttga agaccgctaa gatcaaggtt aaggaaaaca tcgacgcttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaaccaa cggtgttgtt ccaggtatg                        1179
```

```
SEQ ID NO: 155         moltype = DNA  length = 1131
FEATURE                Location/Qualifiers
source                 1..1131
                       mol_type = unassigned DNA
                       organism = Homo sapiens
SEQUENCE: 155
tggtactggg acaagggtcc aaagccagaa agaggtagat tcttgcactt ccactctgtt  60
accttctggg ttggtaacgc taagcaagct gcttctttct actgtaacaa gatgggtttc  120
gaaccattgg cttacaaggg tttggaaacc ggttctagag aagttgtttc tcacgttgtt  180
aagcaaggta agatcgtttt cgttttgtgt tctgctttga acccatggaa caaggaaatg  240
ggtgaccact tggttaagca cggtgacggt gttaaggaca tcgctttcga agttgaagac  300
tgtgaacaca tcgttcaaaa ggctagagaa agaggtgcta agatcgttag agaaccatgg  360
gttgaagaag acaagttcgg taaggttaag ttcgctgttt tgcaaaccta cggtgacacc  420
acccacacct tggttgaaaa gatcaactac accggtagat tcttgccagg tttcgaagct  480
ccaacctaca aggacacctt gttgccaaag ttgccatctt gtaacttgga aatcatcgac  540
```

```
cacatcgttg gtaaccaacc agaccaagaa atggaatctg cttctgaatg gtacttgaag  600
aacttgcaat tccacagatt ctggtctgtt gacgacaccc aagttcacac cgaatactct  660
tctttgagat ctatcgttgt tgctaactac gaagaatcta tcaagatgcc aatcaacgaa  720
ccagctccag gtagaaagaa gtctcaaatc caagaatacg ttgactacaa cggtggtgct  780
ggtgttcaac acatcgcttt gagaaccgaa gacatcatca ccaccatctg tcacttgaga  840
gaaagaggta tggaattctt ggctgttcca tcttcttact acagattgtt gagagaaaac  900
ttgaagacct ctaagatcca agttaaggaa aacatggacg ttttggaaga attgaagatc  960
ttggttgact acgacgaaaa gggttacttg ttgcaaatct tcaccaagcc aatgcaagac  1020
agaccaacct tgttcttgga agttatccaa agacacaacc accaaggttt cggtgctggt  1080
aacttcaact ctttgttcaa ggctttcgaa gaagaacaag ctttgagagg t           1131

SEQ ID NO: 156          moltype = DNA  length = 1125
FEATURE                 Location/Qualifiers
source                  1..1125
                        mol_type = unassigned DNA
                        organism = Homo sapiens
SEQUENCE: 156
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat catgagagaa  360
ccatgggttg aacaagacaa gttcggtaag gttaagttcg ctgttttgca aacctacggt  420
gacaccaccc acaccttggt tgaaaagatg aactacatcg gtcaattctt gccaggttac  480
gaagctccag ctttcatgga cccattgttg ccaaagttgc caaagtgttc tttggaaatg  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtttgga attcttgtct gttccatcta cctactacaa gcaattgaga  900
gaaaagttga agaccgctaa gatcaaggtt aaggaaaaca tcgacgcttt ggaagttaga  960
ccagttcaag acagaccaac cttgttcttg gaagttatcc aaagacacaa ccaccaaggt  1020
ttcggtgctg gtaacttcaa ctctttgttc aaggctttcg aagaagaaca aaacttgaga  1080
ggtaacttga ccaacatgga aaccaacggt gttgttccag gtatg                 1125

SEQ ID NO: 157          moltype = DNA  length = 1179
FEATURE                 Location/Qualifiers
source                  1..1179
                        mol_type = unassigned DNA
                        organism = Rattus norvegicus
SEQUENCE: 157
atgaccacct acaccgacaa gggtgaaaag ccattgagag gtagattcat ccacttccac  60
tctatcacct tctgggttgg taacgctaag caagctgctt cttactactg taacaagatg  120
ggtttcgaag aattggctta cagaggtttg gaaaccggtt ctagagaagt tgtttctcac  180
gttatcaagc aagacaagat cgttttcgtt ttgtcttctg ctttgaaccc aggtaacgaa  240
gaaatgggtg aacacttggt taagcacggt gacggtgtta aggacatcgc tttcgaagtt  300
gaagactgtg acttcatcgt tcaaaaggct aaggaaagag gtgctgttgt tgttaaggaa  360
ccatgggttg aagaagacaa gttcggtaag gttaagttcg ctgttatcca aacctacggt  420
gacaccaccc acaccttgat cgaaaagttg aactacaagg gtttgttctt gccaggttac  480
cacccaccat tgttcaagga cccattgttg ccaaagttgc catctgctaa gttgaacttc  540
gttgaccacg ttgttggtaa ccaaccagac ttgcaaatgg ttccagttgc tgactggtac  600
caaaagaact tgttgttcca cagattctgg tctgttgacg acaagcaatt gcacaccgaa  660
ttctctgctt tgagatctat cgttgttacc aactacgaag aaaccatcaa gatgccaatc  720
aacgaaccag ctttcggtaa gaagaagtct caaatccaag aatacgttga ctactacggt  780
ggtgctggtg ttcaacacat cgctttgaac acctctgaca tcatctctgc tatcaccaac  840
ttgaagcaaa gaggtatgca attcatggac gttccatctt cttactacca aatgttgaga  900
gaaagattga agaccgctaa gatcaaggtt aaggaaaaca tcgacaagtt ggctgaattg  960
aagatcttgg ttgacttcga cgaaaagggt tacttgttgc aaatcttcac caagccagtt  1020
caagacagac caaccgtttt cttggaagtt atccaaagac acaaccacca aggtttcggt  1080
gctggtaact tcaagtcttt gttcgaagct atcgaaatcg accaagacgc tagaggtaac  1140
ttgaccatct tggaaccaaa cggtgaaacc aagagaatc                         1179

SEQ ID NO: 158          moltype = DNA  length = 1179
FEATURE                 Location/Qualifiers
source                  1..1179
                        mol_type = unassigned DNA
                        organism = Mus musculus
SEQUENCE: 158
caaaccacct acaccgacaa gggtgaaaag ccattgagag gtagattcat ccacttccac  60
tctatcacct tctgggttgg taacgctaag caagctgctt cttactactg taacaagttg  120
ggtttcgaag aattggctta cagaggtttg gaaaccggtt ctagagaagt tgtttctcac  180
gttatcaagc aagacaagat cgttttcgtt ttgtcttctg ctttgaaccc aggtaacgaa  240
gaaatgggtg aacacttggt taagcacggt gacggtgtta aggacatcgc tttcgaagtt  300
gaagactgtg acttcatcgt tcaaaaggct agagaaagag gtgctgttgt tgttaaggaa  360
ccatgggttg aagaagacaa gttcggtaag gttaagttcg ctgttatcca aacctacggt  420
gacaccaccc acaccttggt tgaaaagttg aactacaagg gtttgttctt gccaggttac  480
caccaaccat tgttcaagga cccattgttg ccaaagttgc catctgctaa gttgtctttc  540
```

-continued

```
gttgaccacg ttgttggtaa ccaaccagac ttgcaaatgg ttccagttgc tgactggtac  600
caaaagaact tgttgttcca cagattctgg tctgttgacg acaagcaatt gcacaccgaa  660
ttctctgctt tgagatctat cgttgttacc aactacgaag aaaccatcaa gatgccaatc  720
aacgaaccag ctttcggtaa gaagaagtct caaatccaag aatacatcga ctactacggt  780
ggtgctggtg ttcaacacat cgctttgaac acctctgaca tcatctctgc tatcaccaac  840
ttgaagcaaa gaggtatgca attcatggac gttccatctt cttactacca agttttgaga  900
gaaagattga agaccgctaa gatcaaggtt aaggaaaaca tcgacaagtt ggctgaattg  960
aagatcttgg ttgacttcga cgaaaagggt tacttgttgc aaatcttcac caagccagtt  1020
caagacagac caaccgtttt cttggaagtt atccaaagac acaaccacca aggtttcggt  1080
gctggtaact tcaagtcttt gttcgaagct atcgaaatgg accaagacgc tagaggtaac  1140
ttgaccatct tggaaccaaa cggtgaaacc aagagaatc                         1179

SEQ ID NO: 159         moltype = DNA  length = 1179
FEATURE                Location/Qualifiers
source                 1..1179
                       mol_type = unassigned DNA
                       organism = Mus musculus
SEQUENCE: 159
atgaccacct acaccgacaa gggtgaaaag ccagaaggtg gtaagttctt gcacttccac  60
tctttgacct tctgggttgg taacgctaag caagctgctt ctttctactg taacaagatg  120
ggtttcgaag aattggctta caagggtttg gaaaccggtt ctagagaagt tgtttctcac  180
gttatcaagc aagacaagat catcttcgtt ttgtcttctg ctttgaaccc agaaaacaag  240
gacatgggtg aacacttggt taagcacggt gacggtgtta aggacatcgc tttcgaagtt  300
gaagactgtg acttcatcgt tcaaaaggct aaggaaagag gtgctgttat cgttaaggaa  360
ccatgggttg aagaagacaa gtacggtaag gttaagttcg ctgttatcca aacctacggt  420
gacaccaccc acaccttgat cgaaaacttg aactacaagg gtttgttctt gccaggtttc  480
gaaccaccat tgttcaagga cccattgttg ccaaagttgc catctggtaa gttgtctttc  540
atcgaccacg ttgttggtaa ccaaccagac ttgcaaatgg ttccagttgc tgaatggtac  600
caaaagaact tgttgttcca cagattctgg tctgttgacg acaagcaatt gcacacccaa  660
ttctctgctt tgagatctat cgttgttgct aactacgaag aaaccatcaa gatgccaatc  720
aacgaaccag ctgttggtaa gaagaagtct caaatccaag aatacgttga atactacggt  780
ggtgctggtg ttcaacacat cgctttgaac accccagaca tcatcaccgc tgttaccaac  840
ttgaagcaaa gaggtatcga attcatgacc gttccatcta cctactacca acaattgaga  900
gaaaagttga agtctgctaa gatcaaggtt aaggaaaaca tcgacaagtt ggaagaattg  960
aagatcttgg ttgacttcga cgaaaagggt tacttgttgc aaatcttcac caagccagtt  1020
caagacagac caaccgtttt cttggaagtt atccaaagac acaaccacca aggtttcggt  1080
gctggtaact tcaagtcttt gttccaagct atcgaagacg accaagacgc tagaggtaac  1140
ttgaccatct tgaccgctaa cggtgaaacc aacttcatc                         1179

SEQ ID NO: 160         moltype = DNA  length = 1179
FEATURE                Location/Qualifiers
source                 1..1179
                       mol_type = unassigned DNA
                       organism = Homo sapiens
SEQUENCE: 160
atgaccacct acaccgacaa gggtgaaaag ccagaaggtg gtaagttctt gcacttccac  60
tctttgacct tctgggttgg taacgctaag caagctgctt ctttctactg taacaagatg  120
ggtttcgaag aattggctta caagggtttg gaaaccggtt ctagagaagt tgtttctcac  180
gttatcaagc aagacaagat catcttcgtt ttgtcttctg ctttgaaccc agaaaacaag  240
gaaatgggtg aacacttggt taagcacggt gacggtgtta aggacatcgc tttcgaagtt  300
gaagactgtg acttcatcgt tcaaaaggct aaggaaagag gtgctgttat cgttaaggaa  360
ccatgggttg aagaagacaa gtacggtaag gttaagttcg ctgttatcca aacctacggt  420
gacaccaccc acaccttgat cgaaaacttg aactacaagg gtttgttctt gccaggtttc  480
gaattgccat tgttcaagga cccattgttg ccaaagttgc catctggtaa gttgtctttc  540
atcgaccacg ttgttggtaa ccaaccagac ttgcaaatgg ttccagttgc tgaatggtac  600
caaaagaact tgttgttcca cagattctgg tctgttgacg acaagcaatt gcacacccaa  660
ttctctgctt tgagatctat cgttgttgct aactacgaag aaaccatcaa gatgccaatc  720
aacgaaccag ctgttggtaa gaagaagtct caaatccaag aatacgttga atactacggt  780
ggtgctggtg ttcaacacat cgctttgaac accccagaca tcatcaccgc tgttaccaac  840
ttgaagcaaa gaggtatgga attcatgacc gttccatcta cctactacca acaattgaga  900
gaaaagttga agtctgctaa gatcaaggtt aaggaaaaca tcgacaagtt ggaagaattg  960
aagatcttgg ttgacttcga cgaaaagggt tacttgttgc aaatcttcac caagccagtt  1020
caagacagac caaccgtttt cttggaagtt atccaaagac acaaccacca aggtttcggt  1080
gctggtaact tcaagtcttt gttccaagct atcgaagacg accaagacgc tagaggtaac  1140
ttgaccatct tgaccgctaa cggtgaaacc aacttcatc                         1179

SEQ ID NO: 161         moltype = DNA  length = 1179
FEATURE                Location/Qualifiers
source                 1..1179
                       mol_type = unassigned DNA
                       organism = Rattus norvegicus
SEQUENCE: 161
atgaccacct acaccgacaa gggtgaaaag ccagaaggtg gtaagttctt gcacttccac  60
tctttgacct tctgggttgg taacgctaag caagctgctt ctttctactg taacaagatg  120
ggtttcgaag aattggctta caagggtttg gaaaccggtt ctagagaagt tgtttctcac  180
gttatcaagc aagacaagat catcttcgtt ttgtcttctg ctttgaaccc agaaaacaag  240
gaaatgggtg aacacttgtt gaagcacggt gacggtgtta aggacatcgc tttcgaagtt  300
gaagactgtg acttcatcgt tcaaaaggct aaggaaagag gtgctgttat cgttaaggaa  360
ccatgggttg aagaagacaa gtacggtaag gttaagttcg ctgttatcca aacctacggt  420
```

-continued

```
gacaccaccc acaccttgat cgaaaacttg aactacaagg gtttgttctt gccaggtttc  480
gaaccaccat tgttcaagga cccattgttg ccaaagttgc catctggtaa gttgtctttc  540
atcgaccacg ttgttggtaa ccaaccagac ttgcaaatgg ttccagttgc tgaatggtac  600
caaaagaact tgttgttcca cagattctgg tctgttgacg acaagcaatt gcacacccaa  660
ttctctgctt tgagatctat cgttgttgct aactacgaag aaaccatcaa gatgccaatc  720
aacgaaccag ctatgggtaa gaagaagtct caaatccaag aatacgttga atactacggt  780
ggtgctggtg ttcaacacat cgctttgaac accccagaca tcatcaccgc tgttaccaac  840
ttgaagcaaa gaggtatgga attcatgacc gttccatcta cctactacca acaattgaga  900
gaaaagttga agtctgctaa gatcaaggtt aaggaaaaca tcgacaagtt ggaagaattg  960
aagatcttgg ttgacttcga cgaaaagggt tacttgttgc aaatcttcac caagccagtt  1020
caagacagac caaccgtttt cttggaagtt atccaaagac acaaccacca aggtttcggt  1080
gctggtaact tcaagtcttt gttccaagct atcgaagacg accaagacgc tagaggtaac  1140
ttgaccatct tgaccgctaa cggtgaaacc aacttcatc                        1179

SEQ ID NO: 162         moltype = DNA  length = 1179
FEATURE                Location/Qualifiers
source                 1..1179
                       mol_type = unassigned DNA
                       organism = Mus musculus
SEQUENCE: 162
atgaccacct acaccgacaa gggtgaaaag ccagaaggtg gtaagttctt gcacttccac  60
tctttgacct tctgggttgg taacgctaag caagctgctt ctttctactg taacaagatg  120
ggtttcgaag aattggctta caagggtttg gaaaccggtt ctagagaagt tgtttctcac  180
gttatcaagc aagacaagat catcttcgtt ttgtcttctg ctttgaaccc agaaaacgaa  240
gaaatgggtg aacacttggt taagcacggt gacggtgtta aggacatcgc tttcgaagtt  300
gaagactgtg acttcatcgt tcaaaaggct aaggaaagag gtgctgttat cgttaaggaa  360
ccatgggttg aagaagacaa gtacggtaag gttaagttcg ctgttatcca aacctacggt  420
gacaccaccc acaccttgat cgaaaacttg aactacaagg gtttgttctt gccaggtttc  480
gaaccaccat tgttcaagga cccattgttg ccaaagttgc catctggtaa gttgtctttc  540
atcgaccacg ttgttggtaa ccaattggac ttgcacatgg ttccagttgc tgaatggtac  600
caaaagaact tgttgttcca cagattctgg tctgttgacg acaagcaatt gcacacccaa  660
ttctcttctt tgagatctat cgttgttgct aactacgaag aaaccatcaa gatgccaatc  720
aacgaaccag ctatgggtat gaagaagtct caaatccaag aatacgttga atactacggt  780
ggtgctggtg ttcaacacat cgctttgaac acctctgaca tcatcaccgc tgttaccaac  840
ttgaagcaaa gaggtatgga attcatggtt gttccatcta cctactacca acaattgaga  900
gaaaagttga agtctgctaa gatcaaggtt aaggaaaaca tcgacaagtt ggaagaattg  960
aagatcttgg ttgacttcga cggtaagggt tacttgttgc aaatcttcac caagccagtt  1020
caagacagac caaccgtttt cttggaagtt atccaaagac acaaccacca aggtttcggt  1080
gctggtaact tcaagtcttt gttccaagct atcgaagacg accaagacgc tagaggtaac  1140
ttgaccatct tgaccgctaa cggtgaaacc aactcttgt                        1179

SEQ ID NO: 163         moltype = DNA  length = 1179
FEATURE                Location/Qualifiers
source                 1..1179
                       mol_type = unassigned DNA
                       organism = Bos taurus
SEQUENCE: 163
atgaccacct acaccgacaa gggtcaaaag ccagaaagag gtagattctt gcacttccac  60
tctatcacct tctgggttgg taacgctaag caagctgctt cttactactg taacaagatg  120
ggtttcgaag aaatggctta cagaggtttg gaaaccggtt ctagagaagt tgtttctcac  180
gttatcagac aagacaagat cgttttcgtt ttgtcttctg ctttgaaccc aggtaacgaa  240
gaaatgggtg ctcacttggt taagcacggt gacggtgtta aggacgttgc tttcgaagtt  300
gaagactgtg acttcatcgt tcaagaagct agagaaagag gtgctgctat cgttaaggaa  360
ccatgggttg aagaagacaa gcacggtaga gttaagttcg ctgttatcca aacctacggt  420
gacaccaccc acaccttggt tgaaaagttg aactacggtg gtttgttctt gccaggtttc  480
gaagctccat tgttcaagga ccaattgttg ccaaagttgc catctaccaa gttgagattc  540
atcgaccacg ttgttggtaa ccaaccagac ttggaaatgg ttccagttgc tgaatggtac  600
caaagaaact tgttgttcca cagattctgg tctgttgacg acaagcaatt gcacaccgaa  660
ttctctgctt tgagatctat cgttgttgct aactacgaag aaaccatcaa gatgccaatc  720
aacgaaccag ctgttggtaa gaagaagtct caaatccaag aatacatcga ctactacggt  780
ggtccaggtg ttcaacacat cgctttgaac acctctgaca tcatctctgc tatcaccaac  840
ttgaagcaaa gaggtatgga attcatgtct gttccagcta cctactacca acaattgaga  900
caaagattga agaccgctaa gatcgaagtt aaggaatcta tcgacaagtt ggaagaattg  960
aagatcttgg ttgacttcga cgaaaagggt tacttgttgc aaatcttcac caagccagtt  1020
caagacagac caaccttgtt cttggaagtt atccaaagat acaaccacca aggtttcggt  1080
gctggtaact tcaagtcttt gttcgaagct atcgaagctg accaagacgc tagaggtaac  1140
ttgaccttgt tgacctctaa cgttgaaaac aacttcatc                        1179

SEQ ID NO: 164         moltype = DNA  length = 1179
FEATURE                Location/Qualifiers
source                 1..1179
                       mol_type = unassigned DNA
                       organism = Mus musculus
SEQUENCE: 164
atgaccacct acaccgacaa gggtgaaaag ccattgagag gtcaattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aagacaagat catcttcatc ttctcttctg ctttgaaccc aggtaacaag  240
gaaatgggtg aacacttggt taagcacggt gacggtgtta aggacgttgc tttccaagtt  300
```

-continued

```
gaagactgtg acttcatcgt tcaaaaggct agagaaagag gtgctgctat cgttaaggaa  360
ccatgggttg aacaagacaa gaacggtaga gttaagttcg ctgttttgca aacctacggt  420
gacaccaccc acaccttgat cgaaaagatc gactacaagg gtccattctt gccaggttac  480
gaagctccat tgttcttgga cccattgttg ccaaagttgc cagcttgtaa gttgaacttc  540
atcgaccacg ttgttggtaa ccaaccagac cacgaaatgg ttccagctgt tgaatggtac  600
caaaagaact tgttgttcca cagattctgg tctgttgacg acaagcaagt tcacaccgac  660
ttctctgctt tgagatctat cgttgttgct aactacgaag aaaccatcaa gatgccaatc  720
aacgaaccag ctttgggtaa gaagaagtct caaatccaag aatacgttga atactacggt  780
ggtgctggtg ttcaacacat cgctttgaac acccaagaca tcatctctgc tatcgctcac  840
ttgaaggaaa gaggtaccga attcatgtct gttccatcta cctactacac ccaattgaga  900
gaaaagttga agaccgctaa gatcagagtt aaggaaaaca tcaagcaatt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcacctcttt gttcaaggct atcgaagaag accaacaagc tagaggtaac  1140
ttgaccgttt tgtctccaaa cggtgaagtt tctgctatg                         1179

SEQ ID NO: 165         moltype = DNA  length = 1179
FEATURE                Location/Qualifiers
source                 1..1179
                       mol_type = unassigned DNA
                       organism = Homo sapiens
SEQUENCE: 165
atgacctctt acaccgacag aggtcaaaag ccaccaagag gtagattctt gcacttccac  60
tctatcacct tctgggttgg taacgctaag caagctgctt ctttctactg tcacaagatg  120
ggtttctctc cattcgctta cagaggtttg gaaaccggtt ctagagacgt tgcttctcac  180
gttgttaagc aaggtaagat catcttcatc ttctcttctg ctttgaaccc aggtaacaag  240
gaaatgggtg accacttggt taagcacggt gacggtgtta aggacatctc tttcgaagtt  300
gaagactgtg actacatcgt tcaaaaggct agagaaagag gtgctatcat cgttaaggaa  360
ccatggaccg aacaagacaa gttcggttgg gttaagttcg ctgttttgca aacctacggt  420
gacaccaccc acaccttggt tgaaaagttg aactacaccg gtccattctt gccaggtttc  480
gaagctccat tgttcgaaga cccattgttg ccaaccttgc cagactgtaa gttggctatg  540
atcgaccacg ttgttggtaa ccaaccagac caagaaatgg ttccagctgc tgactggtac  600
aagaagaact tgatgttcca cagattctgg tctgttgacg acaagcaagt tcacaccgaa  660
ttctcttctt tgagatctat cgttatggct aactacgaag aaaccatcaa gatgccaatc  720
aacgaaccag ctatgggtag aaagaagtct caaatccaag aatacgttga ctactacggt  780
ggtgctggtg ttcaacacat cgctatgtct accccagaca tcatctctgc tatcacctac  840
ttgagagcta gaggtttgga attcttgtct gttccatcta cctactacaa gcaattgaga  900
gaaggtttga agtctgctaa gatccaagtt aaggaatcta tcgacacctt ggaagaattg  960
aagatcttgg ttgactacga cgaaaagggt tacttgttgc aaatcttcac caagccagtt  1020
caagacagac caaccgtttt cttggaagtt atccaaagac acaaccacca aggtttcggt  1080
gctggtaact tcaactcttt gttcaaggct ttcgaagaag aacaaaacat cagaggtaac  1140
ttgaccgact tggctccaaa cggtttgggt atcgttatg                         1179

SEQ ID NO: 166         moltype = DNA  length = 1179
FEATURE                Location/Qualifiers
source                 1..1179
                       mol_type = unassigned DNA
                       organism = Pan troglodytes
SEQUENCE: 166
atgacctctt acaccgacag aggtgaaaag ccaccaagag gtagattctt gcacttccac  60
tctatcacct tctgggttgg taacgctaag caagctgctt ctttctactg tcacaagatg  120
ggtttctctc cattggctta cagaggtttg gaaaccggtt ctagagaagt tgcttctcac  180
gttgttaagc aaggtaagat catcttcatc ttctcttctg ctttgaaccc aggtaacaag  240
gaaatgggtg accacttggt taagcacggt gacggtgtta aggacatctc tttcgaagtt  300
gaagactgtg actacatcgt tcaaaaggct agagaaagag gtgctatcat cgttaaggaa  360
ccatggatcg aacaagacaa gttcggttgg gttaagttcg ctgttttgca aacctacggt  420
gacaccaccc acaccttggt tgaaaagttg aactacaccg gtccattctt gccaggtttc  480
gaagctccat tcttcgaaga cccattgttg ccaaccttgc cagactgtaa gttggctatg  540
atcgaccacg ttgttggtaa ccaaccagac caagaaatgg ttccaatcgc tgactggtac  600
aagaagacct tgatgttcca cagattctgg tctgttgacg acaagcaagt tcacaccgaa  660
ttctcttctt tgagatctat cgttatggct aactacgaag aaaccatcag aatgccaatc  720
aacgaaccag ctatgggtag aaagaagtct caaatccaag aatacgttga ctactacggt  780
ggtgctggtg ttcaacacat cgctatgtct accaccgaca tcatctctgc tatcacccac  840
ttgagagcta gaggtatgga attcttgaac gttccatcta cctactacaa gcaattgaga  900
gaaagattga agtctgctaa gatccaagtt aaggaaaaca tggacatctt ggaaaagttg  960
aagatcttgg ttgactacga cgaaaagggt tacttgttgc aaatcttcac caagccagtt  1020
caagacagac caaccgtttt cttggaagtt atccaaagac acaaccacca aggtttcggt  1080
gctggtaact tcaactcttt gttcaaggct ttcgaagaag aacaaaacat cagaggtaac  1140
ttgaccgact tggctccaga cggtttgggt accgttatg                         1179

SEQ ID NO: 167         moltype = DNA  length = 1179
FEATURE                Location/Qualifiers
source                 1..1179
                       mol_type = unassigned DNA
                       organism = Cricetulus griseus
SEQUENCE: 167
atgaccacct acaccgacag aggtgaaaag ccaccaagag gtagattctt gcacttccac  60
tctatcacct tctgggttgg taacgctaag caagctgctt ctttctactg taacaagatg  120
ggtttctctc cattggctta cagaggtttg gaaaccggtt ctagagaagt tgcttctcac  180
```

-continued

```
gttgttaagc aaggtaagat catcttcatc ttctcttctc cattgaaccc aggtaacaag  240
gaaatgggtg accacttggt taagcacggt gacggtgtta aggacatctc tttcgaagtt  300
gaagactgtg actacatcgt tcaaaaggct agagaaagag gtgctgttat cgttaaggaa  360
ccatggatcg aacaagacaa gttcggtaga gttaagttcg ctatcttgca aacctacggt  420
gacaccaccc acaccttggt tgaaaagttg aactacaccg gtccattctt gccaggtttc  480
gaaaccccaa gattcttgga cccattgttg ccaaagttgc cagactgtaa gttggctatg  540
atcgaccacg ttgttggtaa ccaaccagac caagaaatgg ttaccgctgc tgaatggtac  600
aagaagaact tgttgttcca cagattctgg tctgttgacg acaagcaagt tcacaccgaa  660
ttctcttctt tgagatctat cgttatggct aactacgaag aaaccatcaa gatgccaatc  720
aacgaaccag ctatgggtag aaagaagtct caaatccaag aatacgttga ctactacggt  780
ggtgctggtg ttcaacacat cgctatgtct accccagaca tcatctctgc tatcacccac  840
ttgaaggcta gaggtatgga attcttgtct gctccagcta cctactacaa gcaattgaga  900
gaaggtttga aggctgctaa gatgcaagtt aaggaaaaca tcgacaagtt ggaagaattg  960
aagatcttgg ttgactacga cgaaaagggt tacttgttgc aaatcttcac caagccagtt  1020
caagacagac caaccgtttt cttggaagtt atccaaagac acaaccacca aggtttcggt  1080
gctggtaact tcaacgcttt gttcaaggct ttcgaagaag aacaatctgt tagaggtaac  1140
ttgaccgact tggctccaaa cggtgttggt atcgctatg                        1179

SEQ ID NO: 168         moltype = DNA  length = 1179
FEATURE                Location/Qualifiers
source                 1..1179
                       mol_type = unassigned DNA
                       organism = Saimiri boliviensis
SEQUENCE: 168
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttgttaagc aaggtaagat cgttttcgtt ttctcttctg ctttgaaccc atggaacaag  240
gaaatgggtg accacttggt taagcacggt gacggtgtta aggacgttgc tttcgaagtt  300
gaagactgtg actacatcgt tcaaaaggct agagaaagag gtgctaagat cgttcaagaa  360
ccatgggttg aagaagacaa gttcggtaag gttaagttcg ctgttttgca aacctacggt  420
gacaccaccc acaccttggt tgaaaagacc aactacaccg gtagattctt gccaggtttc  480
gaagctccat tgttgaagga ctctttgttg ccaaagttgc caaagtgtgg tttggaaatc  540
atcgaccacg ttgttggtaa ccaaccagac caagaaatgt tgtctgcttc tgaatggtac  600
ttgagaaact tgcaattcca cagattctgg tctgttgacg acacccaagt tcacaccgaa  660
tactcttctt tgagatctat cgttgttacc aactacgaag aaaccatcaa gatgccaatc  720
aacgaaccag ctatgggtag aaagaagtct caaatccaag aatacgttga ctacaacggt  780
ggtgctggtg ttcaacacat cgctttgaag acccaagaca tcatcaccgc tatcagatct  840
ttgagagaca gaggtttgga attcttgtct gttccatcta cctactacaa gcaattgaga  900
gaaaacttga agaccgctaa gatcagagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagctat cagaggtaac  1140
ttgaccgact tggaaatcaa gggtgaagtt tctggtatg                        1179

SEQ ID NO: 169         moltype = DNA  length = 1152
FEATURE                Location/Qualifiers
source                 1..1152
                       mol_type = unassigned DNA
                       organism = Felis catus
SEQUENCE: 169
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttgttaagc aaggtaagat cgttttcgtt ttctcttctg ctttgaaccc atggaacaag  240
gaaatgggtg accacttggt taagcacggt gacggtgtta aggacgttgc tttcgaagtt  300
gaagactgtg actacatcgt tcaaaaggct agagaacaag gtgctaagat cgttagagaa  360
ccatgggttg aagaagacaa gttcggtaag gttaagttcg ctgttttgca aaccttcggt  420
gacaccaccc acaccttggt tgaaaagacc aactactctg gtagattctt gccaggtttc  480
aaggctccat tgttgaagga ctctttgttg ccaaagttgc caagatgtgg tttggaaatc  540
atcgaccacg ttgttggtaa cttgttggac cacgaaatgt cttctgcttc tgaatggtac  600
ttgagaaact tgcaattcca cagattctgg tctgttgacg acacccaagt tcacaccgaa  660
tactcttctt tgagatctat cgttgttacc aactacgaag aaaccatcaa gatgccaatc  720
aacgaaccag ctatgggtat gaagaagtct tctatccaag aatacgttga ctacaacggt  780
ggtgctggtg ttcaacacgt tggtttgaag acccaagaca tcatcaccac catcagaaac  840
ttgcaagaaa gaggtatgga attcttgacc gttccatcta cctactacaa gcaattgaga  900
gaaaacttga agaccgctaa gatcagagtt aaggaatcta tcgacgtttt ggaagaattg  960
caaatcttga tggactacga cgaaaagggt tacatcttgc aaatcttcac caagccaatg  1020
caagacagac caaccttgtt cttggaagtt atccaaagac acaaccacca aggtttcggt  1080
gctggtaact tcaactcttt gttcaaggct ttggaagacg ctcaagaatt gagaggtaac  1140
ttgaccaact tg                                                     1152

SEQ ID NO: 170         moltype = DNA  length = 1152
FEATURE                Location/Qualifiers
source                 1..1152
                       mol_type = unassigned DNA
                       organism = Ovis aries
SEQUENCE: 170
atgaccacct acaccgacaa gggtgctaag ccagaaagag gtagattctt gcacttccac  60
```

```
tctgttacct tctgggttgg taacgctaag caagctgctt ctttctactg ttctaagatg  120
ggtttcgaac cattggctta cagaggtttg gaaaccggtt ctagagaagt tgtttctcac  180
gttgttaagc aaggtaagat cgttttcgtt ttctcttctg ctttgaaccc atggaacaag  240
gaaatgggtg accacttggt taagcacggt gacggtgtta aggacgttgc tttcgaagtt  300
gaagactgtg actacatcgt tcaaaaggct agagaaagag gtgctaaggt tgttagagaa  360
ccatgggttg aagaagacaa gttcggtaag gttaagttcg ctgttttgca aaccttcggt  420
gacaccaccc acaccttggt tgaaaagacc aactactctg gtagattctt gccaggtttc  480
caagctccat tgttgaagga ctctttgttg ccaaagttgc caaagtgtgg tttggaaatc  540
atcgaccacg ttgttggtaa cttgttggac cacgaaatgt tgtctgcttc tgaatggtac  600
ttgagaaact tgcaattcca cagattctgg tctgttgacg acacccaagt tcacaccgaa  660
tactcttctt tgagatctat cgttgttacc aactacgaag aaaccatcaa gatgccaatc  720
aacgaaccag ctatgggtat gaagaagtct tctatccaag aatacgttga ctacaacggt  780
ggtgctggtg ttcaacacgt tggtttgaag acccaagaca tcatcaccac catcagaaac  840
ttgcaagaaa gaggtatgga attcttgacc gttccatcta cctactacaa gcaattgaga  900
gaaaacttga agaccgctaa gatccaagtt aaggaatcta tcgacgtttt ggaagaattg  960
caaatcttga tggactacga cgaaaagggt tacatcttgc aaatcttcac cagaccaatg  1020
caagacagac caaccttgtt cttggaagtt atccaaagac acaaccacca aggtttcggt  1080
gctggtaact tcaactcttt gttcaaggct ttggaagacg ctcaagaatt gagaggtaac  1140
ttgaccaact tg                                                     1152

SEQ ID NO: 171         moltype = DNA  length = 1152
FEATURE                Location/Qualifiers
source                 1..1152
                       mol_type = unassigned DNA
                       organism = Orcinus orca
SEQUENCE: 171
atgaccacct actctgacaa gggtgctaag ccagaaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttgttaagc aaggtaagat cgttttcgtt ttctcttctg ctttgaaccc atggaacaag  240
gaaatgggtg accacttggt taagcacggt gacggtgtta aggacgttgc tttcgaagtt  300
gaagactgtg actacgttgt tcaaaaggct agagaaagag gtgctaagat cgttagagaa  360
ccatgggttg aagaagacaa gttcggtaag gttaagttcg ctgttttgca aaccttcggt  420
gacaccaccc acaccttggt tgaaaagacc aactactctg gtcaattctt gccaggtttc  480
aaggctccat tgttgaagga ctctttgttg ccaaagttgc caagatgtgg tttggaaatc  540
atcgaccacg ttgttggtaa cttgccagac caagaaatgt tgtctgcttc tgaatggtac  600
ttgagaaact tgcaattcca cagattctgg tctgttgacg acacccaagt tcacaccgaa  660
tactcttctt tgagatctat cgttgttacc aactacgaag aaaccatcaa gatgccaatc  720
aacgaaccag ctatgggtat gaagaagtct tctatccaag aatacgttga ctacaacggt  780
ggtgctggtg ttcaacacgt tggtttgaag acccaagaca tcatcaccac catcagaaac  840
ttgcaagaaa gaggtatgga attcttgacc gttccatcta cctactacaa gcaattgaga  900
gaaaacttga agaccgctaa gatcagagtt aaggaatcta tcgacgtttt ggaagaattg  960
caaatcttga tggactacga cgaaaagggt tacatcttgc aaatcttcac caagccaatg  1020
caagacagac caaccttgtt cttggaagtt atccaaagac acaaccacca aggtttcggt  1080
gctggtaact tcaactcttt gttcaaggct ttggaagacg ctcaagaatt gagaggtaac  1140
ttgaccaact tg                                                     1152

SEQ ID NO: 172         moltype = DNA  length = 1170
FEATURE                Location/Qualifiers
source                 1..1170
                       mol_type = unassigned DNA
                       organism = Odobenus rosmarus
SEQUENCE: 172
atgaccacct actctaacaa gggtgttaag ccagaaagag gtcaattctt gcacttccac  60
tctgttacct tctgggttgg taacgctaag caagctgctt ctttctactg taacaagatg  120
ggtttcgaac cattcgctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
tcttgggttg aacaagacaa gttcggtaag gttaagttcg ctgttttgca aacctacggt  420
gacaccaccc acaccttggt tgaaaagatg ggttacaccg gtagattctt gccaggtttc  480
gaagctccag ctatcaagga cccattgttg gctaagttgc catcttgttc tttggaagtt  540
atcgaccaca tcgttggtaa ccaaccagac caagaaatgg ttccagtttc tgactggtac  600
gttaagaact tgcaattcca cagattctgg tctgttgacg acacccaagt tcacaccgaa  660
tactcttctt tgagatctat cgttgttgct aactacgaag aaaccatcaa gatgccaatc  720
aacgaaccag ctcaaggtag aaagaagtct caaatccaag aatacgttga ctacaacggt  780
ggtgctggtg ttcaacacat cgctttgaag acccaagaca tcaccaccac catcagacac  840
ttgagagaaa gaggtttgga attcttggct gttccatcta cctactacaa gcaattgaga  900
gaaaagttga agaccgctaa gatcagagtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagacg aacaaaacag aagaggtaac  1140
ttgaccgact tgggtaccaa cggtgttcca                                  1170

SEQ ID NO: 173         moltype = DNA  length = 1179
FEATURE                Location/Qualifiers
source                 1..1179
                       mol_type = unassigned DNA
                       organism = Dasypus novemcinctus
```

```
SEQUENCE: 173
atgaccacct actctgacaa gggtgttaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttgttaagc aagacaagat cgttttcgtt ttgtcttctg ctttgaaccc aggtaacaag  240
gaaatgggtg accacttggt taagcacggt gacggtgtta aggacatcgc tttcgaagtt  300
gaagactgtg cttctatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatg aactacaccg gtagattctt gccaggtttc  480
gaagctccag ttatcaccga cccattgttg gctaagttgc catcttgtag attggaaatc  540
atcgaccaca tcgttggtaa ccaaccagac caagaaatgg tttctgcttc tgaatggtac  600
gttaagaact tgcaattcca cagattctgg tctgttgacg acacccaagt tcacaccgaa  660
tactcttctt tgagatctat cgttgttgct aactacgaag aaaccatcaa gatgccaatc  720
aacgaaccag ctcaaggtaa gaagaagtct caaatccaag aatacgttga ctacaacggt  780
ggtgctggtg ttcaacacat cgctttgaag acccaagaca tcatcaccgc tatcagacac  840
ttgaaggaaa gaggtttgga attcttggct gttccatcta cctactacag acaattgaga  900
gaaaagttga agaccgctaa gatcaaggtt aaggaatcta tcgacatctt ggaagaattg  960
aagatcttgg ttgacttcga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaagtt gagaggtaac  1140
ttgaccgact tgggtgctaa cggtgttttg ccaggtatg                        1179

SEQ ID NO: 174          moltype = DNA  length = 1275
FEATURE                 Location/Qualifiers
source                  1..1275
                        mol_type = unassigned DNA
                        organism = Jaculus jaculus
SEQUENCE: 174
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcac cttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ctttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttgtct gttccatcta cctactacaa gcaattgaga  900
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatct ctgcttcttg gcaaccaaga  1200
gaaggtcaag gtggtagaca aagatctggt accgaagaac caagagttcc agctttgtgt  1260
caagaaggtt ctcac                                                  1275

SEQ ID NO: 175          moltype = DNA  length = 1182
FEATURE                 Location/Qualifiers
source                  1..1182
                        mol_type = unassigned DNA
                        organism = Mustela putorius
SEQUENCE: 175
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcac cttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ctttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttgtct gttccatcta cctactacaa gcaattgaga  900
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatgc aa                    1182

SEQ ID NO: 176          moltype = DNA  length = 1182
```

```
FEATURE                Location/Qualifiers
source                 1..1182
                       mol_type = unassigned DNA
                       organism = Heterocephalus glaber
SEQUENCE: 176
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacttgac cttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ctttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttgtct gttccatcta cctactacaa gcaattgaga  900
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatgc aa                    1182

SEQ ID NO: 177         moltype = DNA  length = 1221
FEATURE                Location/Qualifiers
source                 1..1221
                       mol_type = unassigned DNA
                       organism = Microtus ochrogaster
SEQUENCE: 177
atgccattcg aaggtcaatt gcacttgatc gactctttga ccaagaccac ctactctgac  60
aagggtgcta agccagaaag aggtagattc ttgcacttcc actctgttac cttctgggtt  120
ggtaacgcta agcaagctgc ttctttctac tgttctaaga tgggtttcga accattggct  180
tacagaggtt tggaaaccgg ttctagagaa gttgtttctc acgttatcaa gcaaggtaag  240
atcgttttcg ttttgtcttc tgctttgaac ccatggaaca aggaaatggg tgaccacttg  300
gttaagcacg gtgacggtgt taaggacatc accttcgaag ttgaagactg tgactacatc  360
gttcaaaagg ctagagaaag aggtgctaag atcgttagag aaccatgggt tgaacaagac  420
aagttcggta aggttaagtt cgctgttttg caaacctacg gtgacaccac ccacaccttg  480
gttgaaaaga tgaactacac cggtcaattc ttgccaggtt acgaagctcc agttttcatg  540
gacccattgt tgccaaagtt gccaaagtgt tctttggaaa tcatcgacca catcgttggt  600
aaccaaccag accaagaaat ggtttctgct tctgaatggt acttgaagaa cttgcaattc  660
cacagattct ggtctgttga cgacacccaa gttcacaccg aatactcttc tttgagatct  720
gttgttgttg ctaactacga agaatctatc aagatgccaa tcaacgaacc agctccaggt  780
aagaagaagt ctcaaatcca agaatacgtt gactacaacg gtggtgctgg tgttcaacac  840
atcgctttga acacccaaga catcatcacc gctatcagac acttgagaga aagaggtatg  900
gaattcttgt ctgttccatc tacctactac aagcaattga gagaaaagtt gaagaccgct  960
aagatcaagg ttaaggaaaa catcgacgtt ttggaagaat tgaagatctt ggttgactac  1020
gacgaaaagg gttacttgtt gcaaatcttc accaagccag ttcaagacag accaaccttg  1080
ttcttggaag ttatccaaag acacaaccac caaggtttcg gtgctggtaa cttcaactct  1140
ttgttcaagg ctttcgaaga agaacaaaac ttgagaggta acttgaccga cttggaaacc  1200
aacggtgttg ttccaggtat g                                           1221

SEQ ID NO: 178         moltype = DNA  length = 1179
FEATURE                Location/Qualifiers
source                 1..1179
                       mol_type = unassigned DNA
                       organism = Chinchilla lanigera
SEQUENCE: 178
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcac cttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ttttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctgt tgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttgtct gttccatcta cctactacaa gcaattgaga  900
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
```

-continued

```
ttgaccgact tggaaaccaa cggtgttgtt ccaggtatg                         1179

SEQ ID NO: 179         moltype = DNA  length = 1179
FEATURE                Location/Qualifiers
source                 1..1179
                       mol_type = unassigned DNA
                       organism = Macaca fascicularis
SEQUENCE: 179
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ttttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttgtct gttccatcta cctactacaa gcaattgaga  900
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatg                         1179

SEQ ID NO: 180         moltype = DNA  length = 1179
FEATURE                Location/Qualifiers
source                 1..1179
                       mol_type = unassigned DNA
                       organism = Equus caballus
SEQUENCE: 180
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ttttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagacaaa gaggtatgga attcttgtct gttccatcta cctactacaa gcaattgaga  900
gaaaagttga agaccgctaa gatcaaggtt aaggaaaaca tcgaagtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatg                         1179

SEQ ID NO: 181         moltype = DNA  length = 1179
FEATURE                Location/Qualifiers
source                 1..1179
                       mol_type = unassigned DNA
                       organism = Bos mutus
SEQUENCE: 181
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ttttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagacaaa gaggtatgga attcttgtct gttccatcta cctactacaa gcaattgaga  900
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
```

-continued

```
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatg                         1179

SEQ ID NO: 182         moltype = DNA  length = 1179
FEATURE                Location/Qualifiers
source                 1..1179
                       mol_type = unassigned DNA
                       organism = Vicugna pacos
SEQUENCE: 182
atgaccacct actctgacaa gggtgctaag ccagaaagag gtagattctt gcacttccac  60
tctgttacct tctgggttgg taacgctaag caagctgttt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggc taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ttttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttgtct gttccatcta cctactacaa gcaattgaga  900
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgtctgact tggaaaccaa cggtgttgtt ccaggtatg                         1179

SEQ ID NO: 183         moltype = DNA  length = 1179
FEATURE                Location/Qualifiers
source                 1..1179
                       mol_type = unassigned DNA
                       organism = Myotis davidii
SEQUENCE: 183
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ttttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttgtct gttccatcta cctactacaa gcaattgaga  900
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatg                         1179

SEQ ID NO: 184         moltype = DNA  length = 1179
FEATURE                Location/Qualifiers
source                 1..1179
                       mol_type = unassigned DNA
                       organism = Leptonychotes weddellii
SEQUENCE: 184
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtcaattctt gccaggttac  480
gaagctccag ttttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaac acccaagaca tcatcaccac catcagacac  840
ttgagagaaa gaggtatgga attcttgtct gttccatcta cctactacaa gcaattgaga  900
```

```
gaaaagttga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatg                        1179

SEQ ID NO: 185         moltype = DNA  length = 1179
FEATURE                Location/Qualifiers
source                 1..1179
                       mol_type = unassigned DNA
                       organism = Peromyscus maniculatus
SEQUENCE: 185
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat catgagagaa  360
ccatgggttg aacaagacaa gttcggtaag gttaagttcg ctgttttgca aacctacggt  420
gacaccaccc acaccttggt tgaaaagatg aactacatcg gtcaattctt gccaggttac  480
gaaccaccag ctttcatgga cccattgttg ccaaagttgc caaagtgttc tttggaaatg  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtttgga attcttgtct gttccatcta cctactacaa gcaattgaga  900
gaaaagttga agaccgctaa gatcaaggtt aaggaaaaca tcgacgcttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaaccaa cggtgttgtt ccaggtatg                        1179

SEQ ID NO: 186         moltype = DNA  length = 1179
FEATURE                Location/Qualifiers
source                 1..1179
                       mol_type = unassigned DNA
                       organism = Panthera tigris
SEQUENCE: 186
atgaccacct actctgacaa gggtgctaag ccagaaagag gtagattctt gcacttccac  60
tctgttacct tctgggttgg taacgctaag caagctacct ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat catgagagaa  360
ccatgggttg aacaagacaa gttcggtaag gttaagttcg ctgttttgca aacctacggt  420
gacaccaccc acaccttggt tgaaaagatg aactacatcg gtcaattctt gccaggttac  480
gaagctccag ctttcatgga cccattgttg ccaaagttgc caaagtgttc tttggaaatg  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtttgga attcttgtct gttccatcta cctactacaa gcaattgaga  900
gaaaagttga agaccgctaa gatcaaggtt aaggaaaaca tcgacgcttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaaccaa cggtgttgtt ccaggtatg                        1179

SEQ ID NO: 187         moltype = DNA  length = 1179
FEATURE                Location/Qualifiers
source                 1..1179
                       mol_type = unassigned DNA
                       organism = Physeter catodon
SEQUENCE: 187
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacatcg gtcaattctt gccaggttac  480
gaagctccag ctttcatgga cccattgttg ccaaagttgc caaagtgttc tttggaaatg  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
```

```
ggtgctggtg ttcaacacat cgctttgaag accgaagaca tcatcaccgc tatcagacac  840
ttgagagaaa gaggtttgga attcttgtct gttccatcta cctactacaa gcaattgaga  900
gaaaagttga agaccgctaa gatcaaggtt aaggaaaaca tcgacgcttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaaccaa cggtgttgtt ccaggtatg                          1179

SEQ ID NO: 188          moltype = DNA  length = 1179
FEATURE                 Location/Qualifiers
source                  1..1179
                        mol_type = unassigned DNA
                        organism = Bubalus bubalis
SEQUENCE: 188
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacatcg gtcaattctt gccaggttac  480
gaagctccag ctttcatgga cccattgttg ccaaagttgc caaagtgtag attggaaatg  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtttgga attcttgtct gttccatcta cctactacaa gcaattgaga  900
gaaaagttga agaccgctaa gatcaaggtt aaggaaaaca tcgacgcttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaaccaa cggtgttgtt ccaggtatg                          1179

SEQ ID NO: 189          moltype = DNA  length = 1179
FEATURE                 Location/Qualifiers
source                  1..1179
                        mol_type = unassigned DNA
                        organism = Balaenoptera acutorostrata
SEQUENCE: 189
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacatcg gtcaattctt gccaggttac  480
gaagctccag ctttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtttgga attcttgtct gttccatcta cctactacaa gcaattgaga  900
gaaaagttga agaccgctaa gatcaaggtt aaggaaaaca tcgacgcttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaaccaa cggtgttgtt ccaggtatg                          1179

SEQ ID NO: 190          moltype = DNA  length = 1179
FEATURE                 Location/Qualifiers
source                  1..1179
                        mol_type = unassigned DNA
                        organism = Lipotes vexillifer
SEQUENCE: 190
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatggatcg aacaagacaa gttcggtaag gttaagttcg ctgttttgca aacctacggt  420
gacaccaccc acaccttggt tgaaaagatg aactacatcg gtcaattctt gccaggttac  480
gaagctccag ctttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
```

```
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtttgga attcttgtct gttccatcta cctactacag acaattgaga  900
gaacaattga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaacctc tggtgttgtt ccaggtatg                        1179

SEQ ID NO: 191         moltype = DNA  length = 1179
FEATURE                Location/Qualifiers
source                 1..1179
                       mol_type = unassigned DNA
                       organism = Carlito syrichta
SEQUENCE: 191
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacatcg gtcaattctt gccaggttac  480
gaagctccag ctttcatgga cccattgttg ccaaagttgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtttgga attcttgtct gttccatcta cctactacag acaattgaga  900
gaacaattga agaccgctaa gatcaaggtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaacctc tggtgttgtt ccaggtatg                        1179

SEQ ID NO: 192         moltype = DNA  length = 1179
FEATURE                Location/Qualifiers
source                 1..1179
                       mol_type = unassigned DNA
                       organism = Oryctolagus cuniculus
SEQUENCE: 192
atgaccacct actctgacaa gggtgctaag ccagaaagag gtagattctt gcacttccac  60
tctgttacct tctgggttgg taacgctaag caagctgctt ctttctactg taccaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcac cttcgaagtt  300
gaagactgtg actacatcgt tcaaaaggct agagaaagag gtgctaagat cgttcaagaa  360
ccatgggttg aagaagacaa gttcggtaag gttaagttcg ctgttttgca aaccttcggt  420
gacatcaccc acaccttggt tgaaaagatg tcttacgctg gtagattctt gccaggttac  480
gaagctccag ttttcatgga cccattgttg ccacaattgc caaagtgttc tttgaaggtt  540
atcgaccaca tcgttggtaa ccaaccagac caagaaatgg cttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga atacaacggt  780
ggtgctggtg ttcaacacat cgctttgaag acccaagaca tcatcaccgc tatcagacac  840
ttgagagaaa gaggtttgga attcttgtct gttccatcta cctactacaa gcaattgaga  900
gaaaagttga aggttgctaa gatcaaggtt aaggaatcta tcgacgtttt ggaagaattg  960
aagatcttgg ttgacttcga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct atcgaagaag aacaaaactt gagaggtaac  1140
ttgaccaaca gagaaaccga cggtgttgtt ccaggtatg                        1179

SEQ ID NO: 193         moltype = DNA  length = 1179
FEATURE                Location/Qualifiers
source                 1..1179
                       mol_type = unassigned DNA
                       organism = Galeopterus variegatus
SEQUENCE: 193
atgaccacct actctgacaa gggtgctaag ccagaaagag gtagattctt gcacttccac  60
tctgttacct tctgggttgg taacgctaag caagctgctt ctttctactg taccaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atgggacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatg aactacgctg gtagattctt gccaggttac  480
gaagctccag ttttcatgga cccattgttg ccacaattgc caaagtgttc tttggaagtt  540
```

```
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttgtct gttccatcta cctactacaa gcaattgaga  900
gaaaagttga aggttgctaa gatcaaggtt aaggaatcta tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaaccga cggtgttgtt ccaggtatg                         1179

SEQ ID NO: 194         moltype = DNA  length = 1179
FEATURE                Location/Qualifiers
source                 1..1179
                       mol_type = unassigned DNA
                       organism = Nannospalax galili
SEQUENCE: 194
atgaccacct actctgacaa gggtgctaag ccagaaagag gtagattctt gcacttccac  60
tctgttacct tctgggttgg taacgctaag caagctgctt ctttctactg taccaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggta accacttggt taagcacggt gacggtgtta aggacatcgc tttcgaagtt  300
gaagactgtg actacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatg tcttacgctg gtagattctt gccaggttac  480
gaagctccag ctttcatgga cccattgttg ccacaattgc caaagtgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttgtct gttccatcta cctactacaa gcaattgaga  900
gaaaagttga aggttgctaa gatcaaggtt aaggaatcta tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccaaca tggaaaccga cggtgttgtt ccaggtatg                         1179

SEQ ID NO: 195         moltype = DNA  length = 1179
FEATURE                Location/Qualifiers
source                 1..1179
                       mol_type = unassigned DNA
                       organism = Mesitornis unicolor
SEQUENCE: 195
atgaccacct actctgacaa gggtgctaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aagaagacaa cttcggtaag gttaagttcg ctgttttgca aacctacggt  420
gacaccaccc acaccttggt tgaaaagatg aactacgctg gtagattctt gccaggttac  480
aaggctccag ctttcatgga cccattgttg ccacaattgc caaagtgttc tttggaagtt  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagaggta gaggtatgga attcttgtct gttccatcta tgtactacaa gcaattgaga  900
gaaaagttga aggttgctaa gatcaaggtt aaggaatcta tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccaaca tggaaaccga cggtgttgtt ccaggtatg                         1179

SEQ ID NO: 196         moltype = DNA  length = 1179
FEATURE                Location/Qualifiers
source                 1..1179
                       mol_type = unassigned DNA
                       organism = Rhinopithecus roxellana
SEQUENCE: 196
atgaccacct actctgacaa gggtgctaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aagaagacaa gttcggtaag gttaagttcg ctgttttgca aacctacggt  420
```

-continued

```
gacaccaccc acaccttggt tgaaaagatg aactacgctg gtagattctt gccaggttac  480
aaggctccag ctttcatgga cccattgttg ccacaattgc caaagtgttc tttggaagtt  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagaggta gaggtatgga attcttgtct gttccatcta cctactacaa gcaattgaga  900
gaaaagttga aggttgctaa gatcaaggtt aaggaatcta tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccaaca tggaaaccga cggtgttgtt ccaggtatg                        1179

SEQ ID NO: 197         moltype = DNA  length = 1179
FEATURE                Location/Qualifiers
source                 1..1179
                       mol_type = unassigned DNA
                       organism = Fukomys damarensis
SEQUENCE: 197
atgaccacct actctaacaa gggtgctaag ccagaaagag gtagattctt gcacttccac  60
tctgttacct tctgggttgg taacgctaag caagctgctg ctttctactg ttctaagatg  120
ggtttcgaac cattggctta cagaggtttg gaaaccggtt ctagagaagt tgtttctcac  180
gctatcaagc aaggtcaaat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct tgggaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtagattctt gccaggtttc  480
gaagctccaa tgttcaagga cttgttgttg tctagattgc catcttgttc tttggaaatc  540
atcgaccaca tcgttggtaa ccaaccagac caagaaatgg ttccagcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggct gttccatcta cctactacaa gcaattgaga  900
gaaaagttga agaccgctaa gatcagagtt aaggaatcta tcgacgtttt ggaagaattg  960
aagatcttgg ttgactacga cgaaaagggt tacttgttgc aaatcttcac caagccagtt  1020
caagacagac caaccttgtt cttggaaatc atccaaagac acaaccacca aggtttcggt  1080
gctggtaact tcaactcttt gttcaaggct ttcgaagaag aacaagactt gagaggtaac  1140
ttgaccgact tggaaaccaa cggtgctgct ccaggtacc                        1179

SEQ ID NO: 198         moltype = DNA  length = 1179
FEATURE                Location/Qualifiers
source                 1..1179
                       mol_type = unassigned DNA
                       organism = Colobus angolensis
SEQUENCE: 198
atgaccacct actctaacaa gggtgctaag ccagaaagag gtagattctt gcacttccac  60
tctgttacct tctgggttgg taacgctaag caagctgctg ctttctactg ttctaagatg  120
ggtttcgaac cattggctta cagaggtttg gaaaccggtt ctagagaagt tgtttctcac  180
gttatcaagc aaggtcaaat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg ggttacaccg gtagattctt gccaggtttc  480
gaagctccag ctttcagaga cccattgttg ccaaagttgc caaactgtac cttggaaatc  540
atcgaccaca tcgttggtaa ccaaccagac caagaaatgg ttccagcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtaccga attcttggct gttccatcta cctactacaa gcaattgaga  900
gaaaagttga agaccgctaa gatcagagtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttgtt ccaggtatg                        1179

SEQ ID NO: 199         moltype = DNA  length = 1179
FEATURE                Location/Qualifiers
source                 1..1179
                       mol_type = unassigned DNA
                       organism = Colobus angolensis
SEQUENCE: 199
atgaccacct actctaacca aggtgaaaag ccagaaagag gtagattctt gcacttccac  60
tctgttacct tctgggttgg taacgctaag caagctgctt ctttctactg ttctaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaga  240
gaaatgggtg accacttggt taagcacggt gacggtgtta aggacatcgc tttcgaagtt  300
```

-continued

```
gaagactgtg actacatcgt tcaaaaggct agagaaagag gtgctaagat cgttcaagaa  360
ccatgggttg aacaagacaa gttcggtaag gttaagttcg ctgttttgca aacctacggt  420
gacaccaccc acaccttggt tgaaaagatg aactactctg gttgtttctt gccaggtttc  480
gaaccattgg ttttcaccga cccattgttg tctaagttgc caaagtgtta cttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtttgga attcttggct gttccaccaa cctactacaa gcaattgaga  900
gaaaagttga agtctgctaa gatcagagtt aaggaatcta tcgacacctt ggaagaattg  960
aaggttttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaagctaa cggttctatg ccaggtaga                         1179
```

```
SEQ ID NO: 200         moltype = DNA  length = 1179
FEATURE                Location/Qualifiers
source                 1..1179
                       mol_type = unassigned DNA
                       organism = Mandrillus leucophaeus
SEQUENCE: 200
atgaccacct actctaacca aggtgaaaag ccagaaaagag gtagattctt gcacttccac  60
tctgttacct tctgggttgg taacgctaag caagctgctt ctttctactg ttctaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaga  240
gaaatgggta accacttggt taagcacggt gacggtgtta aggacatcgc tttcgaagtt  300
gaagactgtg actacatcgt tcaaaaggct agagaaagag gtgctaagat cgttcaagaa  360
ccatgggttg aacaagacaa gttcggtaag gttaagttcg ctgttttgca aacctacggt  420
gacaccaccc acaccttggt tgaaaagatg aactactctg gttgtttctt gccaggtttc  480
gaaccattgg ttttgaccga cccattgttg tctaagttgc caaagtgtta cttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtttgga attcttggct gttccaccaa cctactacaa gcaattgaga  900
caaaagttga agtctgctaa gatcagagtt aaggaatcta tcgacacctt ggaagaattg  960
aaggttttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaagctaa cggttctatg ccaggtaag                         1179
```

```
SEQ ID NO: 201         moltype = DNA  length = 1179
FEATURE                Location/Qualifiers
source                 1..1179
                       mol_type = unassigned DNA
                       organism = Macaca nemestrina
SEQUENCE: 201
atgaccacct actctaacaa gggtgaaaag ccagaaaagag gtagattctt gcacttccac  60
tctgttacct tctgggttgg taacgctaag caagctgctt ctttctactg ttctaagatg  120
ggtttcaagc cattggctta caagggtttg gaaaccggtt ctagagaagt tgtttctcac  180
gttatccaac aaggtaagat cgttttcgtt ttgtcttctg ctttgaaccc atggaacacc  240
gaaatgggtg accacttggt taagcacggt gacggtgtta aggacatcgc tttcgaagtt  300
gaagactgtg actacatcgt tcaaaaggct caagaaagag gtgctaagat catgagagaa  360
ccatgggttg aacaagacaa gttcggtaag gttaagttcg ctgttttgca aacctacggt  420
gacaccaccc acaccttggt tgaaaagatg aactactctg gtagattctt gccaggtttc  480
gaagctccag ctttcaccga cccattgttg tctaagttgc cagactgttg tttggaaatc  540
atcgaccacg ttgttggtaa ccaaccagac caagaaatgg tttctgcttc tgaatggtac  600
gttaagaact tgcaattcca cagattctgg tctgttgacg acacccaagt tcacaccgaa  660
tactcttctt tgagatctat cgttgttgct aactacgaag aaaccatcaa gatgccaatc  720
aacgaaccag ctcaaggtaa gaagaagtct caaatccaag aatacgttga ctacaacggt  780
ggtccaggtg ttcaacacat cgctttgaag acccaagaca tcatcaccgc tatcagacac  840
ttgagagaaa gaggtttgga attcttgggt gttccatcta cctactacaa gcaattgaga  900
gaaaagttga agtctgctaa gatcagagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaccaa cggtgttggt ccaggtatc                         1179
```

```
SEQ ID NO: 202         moltype = DNA  length = 1179
FEATURE                Location/Qualifiers
source                 1..1179
                       mol_type = unassigned DNA
                       organism = Aotus nancymaae
SEQUENCE: 202
atgaccacct actctgacaa gggtaagaag ccagaaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
```

```
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aacaagacaa gttcggtaag gttaagttgg ctatgttgca aacctacggt  420
gacaccaccc acaccttggt tgaaaagatg aactacaccg gtagattctt gccaggtttc  480
gaagctccag cttctgttga cccattgttg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctttgggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtttgga attcttggct gttccatcta cctactacaa gcaattgaga  900
gaaaagttga agtctgctaa gatcagagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccaact tggaaaccaa cggtatcttg agaggtatg                         1179

SEQ ID NO: 203         moltype = DNA  length = 1179
FEATURE                Location/Qualifiers
source                 1..1179
                       mol_type = unassigned DNA
                       organism = Propithecus coquereli
SEQUENCE: 203
atgaccacct actctgacaa gggtaagaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctagaat cgttagagaa  360
ccatggaccg aagaagacaa gttcggtaag gttaagttgg ctgttttgca aacctacggt  420
gacaccaccc acaccttggt tgaaaagatg aactacaccg gtagattctt gccaggtttc  480
gaagctccag cttctgttga cccattgttg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctttgggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtttgga attcttggct gttccatcta cctactacaa gcaattgaga  900
gaaaagttga agtctgctaa gatcagagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaccaa cggtatcttg agaggtatg                         1179

SEQ ID NO: 204         moltype = DNA  length = 1179
FEATURE                Location/Qualifiers
source                 1..1179
                       mol_type = unassigned DNA
                       organism = Otolemur garnettii
SEQUENCE: 204
atgaccacct actctgacaa gggtaagaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacttggt tcaaaaggct agagaacaag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccaa tctctgttga cccattgttg tctaagttgc caacctgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgaaggcta gaggtatgga attcttgggt gttccatctt cttactacaa gcaattgaga  900
gaaaagttga agaccgctaa gatccaagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaagactt gagaggtaac  1140
ttgaccaact tggaaaccaa ctcttctttg agaggtatg                         1179

SEQ ID NO: 205         moltype = DNA  length = 1179
FEATURE                Location/Qualifiers
source                 1..1179
                       mol_type = unassigned DNA
                       organism = Cavia porcellus
SEQUENCE: 205
atgaccacct actctgacaa gggtaagaag ccagaaagag gtagattctt gcacttccac  60
```

```
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacttggt tcaaaaggct agagaacaag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccag tttctgttga cccattgttg tctaagttgc caacctgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgaaggcta gaggtatgga attcttgggt gttccatctt cttactacag acaattgaga  900
gaaaagttga agaccgctaa gatccaagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaagactt gagaggtaac  1140
ttgaccaact tggaaaccaa ctcttctttg agaggtatg                         1179
```

```
SEQ ID NO: 206         moltype = DNA  length = 1179
FEATURE                Location/Qualifiers
source                 1..1179
                       mol_type = unassigned DNA
                       organism = Myotis brandtii
SEQUENCE: 206
atgaccacct actctgacag aggtaagaag ccagaaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccag cttctgttga cccattgttg tctaagttgc caacctgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttacc aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagcta gaggtatgga attcttgggt gttccatctt cttactacaa gcaattgaga  900
gaaaagttga agtctgctaa gatccaagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaccaa cggtaccttg agatgtatg                         1179
```

```
SEQ ID NO: 207         moltype = DNA  length = 1179
FEATURE                Location/Qualifiers
source                 1..1179
                       mol_type = unassigned DNA
                       organism = Equus asinus
SEQUENCE: 207
atgaccacct actctgacaa gggtaagaag ccagaaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccag cttctgttga cccattgttg tctaagttgc caacctgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagcta gaggtatgga attcttgtgt gttccatctt cttactacaa gcaattgaga  900
gaaaagttga agtctgctaa gatccaagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaccaa cggtaccttg agaggtatg                         1179
```

```
SEQ ID NO: 208         moltype = DNA  length = 1383
FEATURE                Location/Qualifiers
source                 1..1383
                       mol_type = unassigned DNA
                       organism = Marmota marmota
```

```
SEQUENCE: 208
gacgacatca ccttgtctac cgaagctgct gctagatctg aagctccaaa gccaggttct  60
ttccaaagat ggtgtagata ccacccatct ttgggtagac caggttctaa gggtagagac  120
ttgttcggtg ttaagtactt ctgtccagct ttgcactggc cattggttcc aatctctgaa  180
caagaagctt ctccaagatc taccatgacc acctactctg acaagggtaa gaagccagaa  240
agaggtagat tcttgcactt ccactctgtt accttctggg ttggtaacgc taagcaagct  300
gcttctttct actgtaacaa gatgggtttc gaaccattgg cttacaaggg tttggaaacc  360
ggttctagag aagttgtttc tcacgttatc aagcaaggta agatcgtttt cgttttctct  420
tctgctttga acccatggaa caaggaaatg ggtgaccact tggttaagca cggtgacggt  480
gttaaggaca tcgctttcga agttgaagac tgtgactaca tcgttcaaaa ggctagagaa  540
caaggtgcta agatcgttag agaaccatgg atcgaacaag acaagttcgg taaggttaag  600
ttggctgttt tgcaaaccta cggtgacacc acccacacct tggttgaaaa gatgaactac  660
accggtagat tcttgccagg tttcgaagct ccagcttctg ttgacccatt gttgtctaag  720
ttgccaacct gttctttgga aatcatcgac cacatcgttg gtaaccaacc agaccaagaa  780
atggtttctg cttctgaatg gtacttgaag aacttgcaat tccacagatt ctggtctgtt  840
gacgacaccc aagttcacac cgaatactct tctttgagat ctatcgttgt tgctaactac  900
gaagaatcta tcaagatgcc aatcaacgaa ccagctccag gtaagaagaa gtctcaaatc  960
caagaatacg ttgactacaa cggtggtgct ggtgttcaac acatcgcttt gaagacccaa  1020
gacatcatca ccgctatcag acacttgaga gctagaggta tggaattctt gtgtgttcca  1080
tctacctact acaagcaatt gagagaaaag ttgaagtctg ctaagatcca agttaaggaa  1140
tctatcgacg ttttggaaga attgaagatc ttggttgact acgacgaaaa gggttacttg  1200
ttgcaaatct tcaccaagcc aatgcaagac agaccaacct tgttcttgga agttatccaa  1260
agacacaacc accaaggttt cggtgctggt aacttcaact ctttgttcaa ggctttcgaa  1320
gaagaacaag acttgagagg taacttgacc gacttgcaaa ccaacggtac cttgagaggt  1380
atg                                                                1383

SEQ ID NO: 209         moltype = DNA  length = 1179
FEATURE                Location/Qualifiers
source                 1..1179
                       mol_type = unassigned DNA
                       organism = Marmota marmota
SEQUENCE: 209
atgaccacct actctgacaa gggtaagaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat catgagagaa  360
ccatggatcg aagaagacaa gttcggtaag gttaagttgg ctgttttgca aacctacggt  420
gacaccaccc acaccttggt tgaaaagatc aactacaccg gtagattctt gccaggtttc  480
gaagctccag cttgtgttga cccattgttg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaca gaggtatgga attcttggct gttccatcta cctactacaa gcaattgaga  900
gaaaagttga agtctgctaa gatccaagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaccaa cggtatgatg ccaggtatg                         1179

SEQ ID NO: 210         moltype = DNA  length = 1179
FEATURE                Location/Qualifiers
source                 1..1179
                       mol_type = unassigned DNA
                       organism = Cebus imitator
SEQUENCE: 210
atgaccacct actctgacaa gggtaagaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aagaagacaa gttcggtaag gttaagttgg ctgttttgca aacctacggt  420
gacaccaccc acaccttggt tgaaaagatc aactacaccg gtagattctt gccaggtttc  480
gaagctccag cttgtgttga cccattgttg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaca gaggtatgga attcttggct gttccatcta cctactacaa gcaattgaga  900
gaaaagttga agtctgctaa gatccaagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaccaa cggtatgatg ccaggtatg                         1179
```

```
SEQ ID NO: 211         moltype = DNA  length = 1179
FEATURE                Location/Qualifiers
source                 1..1179
                       mol_type = unassigned DNA
                       organism = Capra hircus
SEQUENCE: 211
atgaccacct actctgacaa gggtaagaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aagaagacaa gttcggtaag gttaagttgg ctgttttgca aacctacggt  420
gacaccaccc acaccttggt tgaaaagatg aactacaccg gtagattctt gccaggtttc  480
gaagctccag cttgtgttga cccattgttg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaca gaggtatgga attcttggct gttccatcta cctactacaa gcaattgaga  900
gaaaagttga agtctgctaa gatccaagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaccaa cggtaccatg ccaggtatg                        1179

SEQ ID NO: 212         moltype = DNA  length = 1179
FEATURE                Location/Qualifiers
source                 1..1179
                       mol_type = unassigned DNA
                       organism = Panthera pardus
SEQUENCE: 212
atgaccacct actctgacaa gggtagaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aacaagacaa gttcggtaag gttaagttgg ctgttttgca aacctacggt  420
gacaccaccc acaccttggt tgaaaagatg aactactctg gttggttctt gccaggtttc  480
gaaaccccag cttctgttga cccattgttg tctaagttgc caacctgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aacttcgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggct gttccaccaa cctactacaa gcaattgaga  900
gaaaagttga agtctgctaa gatcagagtt aaggaatcta tcgacacctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tgaagaacac cagaaccttg ccaggtacc                        1179

SEQ ID NO: 213         moltype = DNA  length = 1179
FEATURE                Location/Qualifiers
source                 1..1179
                       mol_type = unassigned DNA
                       organism = Hipposideros armiger
SEQUENCE: 213
atgaccacct actctgacaa gggtagaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aacaagacaa gttcggtaag gttaagttgg ctgttttgca aacctacggt  420
gacaccaccc acaccttggt tgaaaagatg aactactctg gttggttctt gccaggtttc  480
gaaaccccag cttctgttga cccattgttg tctaagttgc caacctgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aacttcgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggct gttccaccaa cctactacaa gcaattgaga  900
gaaaagttga agtctgctaa gatcagagtt aaggaatcta tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
```

```
gctggtaact tcaactcttt gttcaaggct ttcgaagaag aacaagactt gagaggtaac  1140
ttgaccgact tgaagaacac cagaaccttg ccaggtatg                         1179

SEQ ID NO: 214         moltype = DNA  length = 1179
FEATURE                Location/Qualifiers
source                 1..1179
                       mol_type = unassigned DNA
                       organism = Crocodylus porosus
SEQUENCE: 214
atgaccacct actctgacaa gggtaagaag ccacaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aacaagacaa gttcggtaag gttaagttgg ctgttttgca aacctacggt  420
gacaccaccc acaccttggt tgaaaagatg aactactctg gtagattctt gccaggtttc  480
gaaaccccag cttctgttga cccattgttg tctaagttgc catcttgttc tttggaaatg  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aacttcgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggct gttccaccaa tgtactacaa gcaattgaga  900
gaaaagttga agtctgctaa gatcagagtt aaggaatcta tcgacacctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaacac cagaaccttg ccaggtatg                         1179

SEQ ID NO: 215         moltype = DNA  length = 1179
FEATURE                Location/Qualifiers
source                 1..1179
                       mol_type = unassigned DNA
                       organism = Ailuropoda melanoleuca
SEQUENCE: 215
atgaccacct actctgacaa gggtaagaag ccacaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatggatcg aacaagacaa gttcggtaag gttaagttgg ctgttttgca aacctacggt  420
gacaccaccc acaccttggt tgaaaagatg aactactctg gtagattctt gccaggtttc  480
gaaaccccag cttctgttga cccattgttg tctaagttgc catcttgttc tttggaaatg  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aacttcgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggct gttccaccaa cctactacaa gcaattgaga  900
gaaaagttga agtctgctaa gatcagagtt aaggaatcta tcgacacctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgact tggaaaacac cagaaccttg ccaggtatg                         1179

SEQ ID NO: 216         moltype = DNA  length = 1176
FEATURE                Location/Qualifiers
source                 1..1176
                       mol_type = unassigned DNA
                       organism = Bos indicus
SEQUENCE: 216
accacctact ctgacaaggg taagaagcca caaagaggta gattcttgca cttccactct  60
gttaccttct gggttggtaa cgctaagcaa gctgcttctt tctactgtaa caagatgggt  120
ttcgaaccat tggcttacaa gggtttggaa accggttcta gagaagttgt ttctcacgtt  180
atcaagcaag gtaagatcgt tttcgttttc tcttctgctt tgaacccatg gaacaaggaa  240
atgggtgacc acttggttaa gcacggtgac ggtgttaagg acatcgcttt cgaagttgaa  300
gactgtgact acatcgttca aaaggctaga gaacaaggtg ctaagatcgt tagagaacca  360
tggatcgaac aagacaagtt cggtaaggtt aagttggctg ttttgcaaac ctacggtgac  420
accacccaca ccttggttga aaagatgaac tactctggta gattcttgcc aggtttcgaa  480
accccagctt ctgttgaccc attgttgtct aagttgccat cttgttcttt ggaaatggtt  540
gaccacatcg ttggtaacca accagaccaa gaaatggttt ctgcttctga atggtacttg  600
aagaacttgc aattccacag attctggtct gttgacgaca cccaagttca caccgaatac  660
tcttctttga gatctatcgt tgttgctaac ttcgaagaat ctatcaagat gccaatcaac  720
gaaccagctc caggtaagaa gaagtctcaa atccaagaat acgttgacta caacggtggt  780
gctggtgttc aacacatcgc tttgaagacc caagacatca tcaccgctat cagacacttg  840
agagaaagag gtatggaatt cttggctgtt ccaccaacct actacaagca attgagagaa  900
aagttgaagt ctgctaagat cagagttaag gaatctatcg acaccttgga agaattgaag  960
```

-continued

```
atcttggttg actacgacga aaagggttac ttgttgcaaa tcttcaccaa gccaatgcaa  1020
gacagaccaa ccttgttctt ggaagttatc caaagacaca accaccaagg tttcggtgct  1080
ggtaacttca actctttgtt caaggctttc gaagaagaac aagacttgag aggtaacttg  1140
accgactctg aaaacaccag aaccttgcca ggtatg                            1176

SEQ ID NO: 217         moltype = DNA  length = 1179
FEATURE                Location/Qualifiers
source                 1..1179
                       mol_type = unassigned DNA
                       organism = Castor canadensis
SEQUENCE: 217
atgaccacct actctaacaa gggtgaaaag ccagctagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccag ctttcgttga cccattgttg tctaagttgc catcttgttc tttggaaatc  540
atcgaccaca tcgttggtaa ccaaccagac caagaaatgg aatctgcttc tgactggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtccaggtg ttcaacacat cgctttgaag acccaagaca tcatcaccgc tatcagacac  840
ttgagagaaa gaggtatgga attcttgggt gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaacaa cggtatcgtt ccaggtatg                         1179

SEQ ID NO: 218         moltype = DNA  length = 1179
FEATURE                Location/Qualifiers
source                 1..1179
                       mol_type = unassigned DNA
                       organism = Sus scrofa
SEQUENCE: 218
atgaccacct actctaacaa gggtgaaaag ccagctagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgc tcaaaaggct agagaaagag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccag ctttcgttga cccattgttg tctaagttgc catcttgttc tttggaaatc  540
atcgaccaca tcgttggtaa ccaaccagac caagaaatgg aatctgcttc tgactggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtccaggtg ttcaacacat cgctttgaag acccaagaca tcatcaccgc tatcagacac  840
ttgagagaaa gaggtatgga attcttgggt gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaacaa cggtatcgtt ccaggtatg                         1179

SEQ ID NO: 219         moltype = DNA  length = 1179
FEATURE                Location/Qualifiers
source                 1..1179
                       mol_type = unassigned DNA
                       organism = Microcebus murinus
SEQUENCE: 219
atgaccacct actctaacaa gggtgaaaag ccagctagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gctatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccag ctttcgttga cccattgttg tctaagttgc catcttgttc tttggaaatc  540
atcgaccaca tcgttggtaa ccaaccagac caagaaatgg aatctgcttc tgactggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtccaggtg ttcaacacat cgctttgaag acccaagaca tcatcaccgc tatcagacac  840
```

```
ttgagagaaa gaggtatgga attcttgggt gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccagtt  1020
caagacagac caaccttgtc tttggaagtt atccaaagac acaagcacca aggtttcggt  1080
gctggtaact tcaactcttt gttcaaggct ttcgaagaag aacaaaactt gagaggtaac  1140
ttgaccgact tggaaaacaa cggtatcgtt ccaggtatg                        1179

SEQ ID NO: 220         moltype = DNA  length = 1179
FEATURE                Location/Qualifiers
source                 1..1179
                       mol_type = unassigned DNA
                       organism = Odocoileus virginianus
SEQUENCE: 220
atgaccacct actctaacaa gggtgaaaag ccagctagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccaa ccttcgttga cccattgttg tctaagttgc catcttgttc tttggaaatc  540
atcgaccaca tcgttggtaa ccaaccagac caagaaatgg aatctgcttc tgactggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctttgggtaa gaagaagtct caaatccaag aatacgttga ctacaacggt  780
ggtccaggtg ttcaacacat cgctttgaag acccaagaca tcatcaccgc tatcagacac  840
ttgagagaaa gaggtatgga attcttgggt gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaacaa cggtatcgtt ccaggtatg                        1179

SEQ ID NO: 221         moltype = DNA  length = 1179
FEATURE                Location/Qualifiers
source                 1..1179
                       mol_type = unassigned DNA
                       organism = Phascolarctos cinereus
SEQUENCE: 221
atgaccacct actctaacaa gggtgaaaag ccagctagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccag ctttcgttga cccattgttg tctaagttgc catcttgttc tttggaaatc  540
atcgaccaca tcgttggtaa ccaaccagac caagaaatgg aatctgcttc tgactggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtccaggtg ttcaacacat cgctttgaag acccaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tcgaaaacaa cggtatcgtt ccaggtatg                        1179

SEQ ID NO: 222         moltype = DNA  length = 1179
FEATURE                Location/Qualifiers
source                 1..1179
                       mol_type = unassigned DNA
                       organism = Mus pahari
SEQUENCE: 222
tcttctttgt cttcttcttt gttgttgcaa ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttctcttctg ctttgaaccc atgggacaag  240
gaaatgggtg accacttggt taagcacggt gacggtgtta aggacatcgc tttcgaagtt  300
gaagactgtg actacatcgt tcaaaaggct aaggaaagag gtgctaagat cgttagagaa  360
ccatggatcg aacaagacaa gttcggtaag gttaagttgg ctgttttgca aacctacggt  420
gacaccaccc acaccttggt tgaaaagatg aactacaccg gtagattctt gccaggtttc  480
gaagctccag ttttcatcga cccaatcttg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
```

-continued

```
aacgaaccag ctttgggtaa gaagaagtct caaatccaag aatacgttga ctacaacggt  780
ggtccaggtg ttcaacacat cgctttgaag acccaagaca tcatcaccgc tatcagacac  840
ttgagagaaa gaggtatgga attcttgggt gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtaccgtt agaggtatg                         1179

SEQ ID NO: 223          moltype = DNA  length = 1179
FEATURE                 Location/Qualifiers
source                  1..1179
                        mol_type = unassigned DNA
                        organism = Mus caroli
SEQUENCE: 223
atgaccacct actctgacaa gggtgaaaag ccagaaagag gtagattctt gcacttccac  60
tctgttacct tctgggttgg taacgctaag caagctgctt ctttctactg ttctaagatg  120
ggtttcgaac cattggctta caagggtttg gaaaccggtt ctagagaagt tgtttctcac  180
gctatcaagc aaggtaagat cgttttcgtt ttctcttctg ctttgaaccc atggaacaag  240
gaaatcggtg accacttggc taagcacggt gacggtgtta aggacatcgc tttcgaagtt  300
gaagactgtg actacatcgt tcaaaaggct aaggaaagag gtgctaaggt tgttagagaa  360
ccatggatcg aacaagacaa gttcggtaag gttaagttgg ctgttttgca aacctacggt  420
gacaccaccc acaccttggt tgaaaagatg aactacaccg gtttgttctt gccaggtttc  480
gaagctccag ttttcttgga cccattgttg tctaagttgc catcttgttc tttggaaatc  540
atcgaccaca tcgttggtaa ccaaccagac caagaaatgg tttctgctgc tgaatggtac  600
ttgaagaact tgcaattcca cagattctgg tctgttgacg acacccaagt tcacaccgaa  660
tactcttctt tgagatctat cgttgttgct aactacgaag aaaacatcaa gatgccaatc  720
aacgaaccag ctccaggtaa gaagaagtct caaatccaag aatacgttga ctacaacggt  780
ggtccaggtg ttcaacacat cgctttgaag acccaagaca tcatcaccgc tatcagacac  840
ttgagagaaa gaggtatgga attcttgggt gttccatcta cctactacaa gcaattgaga  900
gaaagattga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgact tggaaaccaa cggtgttgtt ccaggtatg                         1179

SEQ ID NO: 224          moltype = DNA  length = 1161
FEATURE                 Location/Qualifiers
source                  1..1161
                        mol_type = unassigned DNA
                        organism = Mesocricetus auratus
SEQUENCE: 224
atgaccacct actctgacaa gggtgaaaag ccagaaagag gtagattctt gcacttccac  60
tctgttacct tctgggttgg taacgctaag caagctgctt cttactactg ttctaagatg  120
ggtttcgaac cattggctta caagggtttg gaaaccagat ctagagacgt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca cacctacggt  420
gacaccaccc acaccttggt tgaaaagatg aactacaccg gtagattctt gccaggtttc  480
gaagctccag cttctaccga cccattgttg tctaagttgc caaactgttg tttggaaatc  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaacctc t                                            1161

SEQ ID NO: 225          moltype = DNA  length = 1161
FEATURE                 Location/Qualifiers
source                  1..1161
                        mol_type = unassigned DNA
                        organism = Meriones unguiculatus
SEQUENCE: 225
atgaccacct actctgacaa gggtgaaaag ccagaaagag gtagattctt gcacttccac  60
tctgttacct tctgggttgg taacgctaag caagctgctt cttactactg ttctaagatg  120
ggtttcgaac cattggctta caagggtttg gaaaccagat ctagagacgt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtagattctt gccaggtttc  480
gaagctccag cttctaccga cccattgttg tctaagttgc caaactgttg tttggaaatc  540
atcgaccaca tcgttggtaa ccaaccagac caagaaatgt tgtctgcttc tgaatggtac  600
```

```
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaac acccaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaacctc t                                          1161

SEQ ID NO: 226         moltype = DNA  length = 1170
FEATURE                Location/Qualifiers
source                 1..1170
                       mol_type = unassigned DNA
                       organism = Enhydra lutris
SEQUENCE: 226
atgaccacct actctaacaa gggtgaaaag ccagaaagag gtagattctt gcacttccac  60
tctgttacct tctgggttgg taacgctaag caagctgctt cttactactg ttctaagatg  120
ggtttcgaac cattggctta caagggtttg gaaaccagat ctagagaagt tgtttctcac  180
gttatcaagc aaggtaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtagattctt gccaggtttc  480
gaagctccag cttctaccga cccattgttg tctaagttgc caaactgtgg tttggaaatc  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaacctc tggtgttgtt                                 1170

SEQ ID NO: 227         moltype = DNA  length = 1176
FEATURE                Location/Qualifiers
source                 1..1176
                       mol_type = unassigned DNA
                       organism = Delphinapterus leucas
SEQUENCE: 227
accacctact ctaacaaggg tgaaaagcca gaaagaggta gattcttgca cttccactct  60
gttaccttct gggttggtaa cgctaagcaa gctgcttctt actactgttc taagatgggt  120
ttcgaaccat tggcttacaa gggtttggaa accggttcta gagaaatggt ttctcacgtt  180
atcaagcaag gtaagatcgt tttcatcttc tcttctgctt tgaacccatg gaacaaggaa  240
atgggtgacc acttggttaa gcacggtgac ggtgttaagg acatcgcttt cgaagttgaa  300
gactgtgact acatcgttca aaaggctaga gaaagaggtg ctaagatcgt tagagaacca  360
tgggttgaac aagacaagtt cggtaaggtt aagttcgctg ttttgcaaac ctacggtgac  420
accacccaca ccttggttga aaagatgaac tacaccggtt ggttcttgcc aggtttcgaa  480
gctccagctt tcgttgaccc attgttgtct aagttgccaa actgttcttt ggaaagaatc  540
gaccacatcg ttggtaacca accagaccaa gaaatgttgt ctgcttctga atggtacttg  600
aagaacttgc aattccacag attctggtct gttgacgaca cccaagttca caccgaatac  660
tcttctttga gatctatcgt tgttgctaac tacgaagaat ctatcaagat gccaatcaac  720
gaaccagctc caggtagaaa gaagtctcaa atccaagaat acgttgacta caacggtggt  780
gctggtgttc aacacatcgc tttgaagacc gaagacatca tcaccgctat cagacacttg  840
agagaaagag gtatggaatt cttggctgtt ccatctacct actacaagca attgagagaa  900
aagttgaagt ctgctaagat cagagttaag gaaaacatcg acgttttgga agaattgaag  960
atcttggttg actacgacga aaagggttac ttgttgcaaa tcttcaccaa gccaatgcaa  1020
gacagaccaa ccttgttctt ggaagttatc cacagataca accaccaagg tttcggtgct  1080
ggtaacttca actctttgtt caaggctttc gaagaagaac aagacttgag aggtaacttg  1140
accgacatgg aaaccaacgg taccgttgct ggtacc                          1176

SEQ ID NO: 228         moltype = DNA  length = 1179
FEATURE                Location/Qualifiers
source                 1..1179
                       mol_type = unassigned DNA
                       organism = Loxodonta africana
SEQUENCE: 228
atgaccacct actctaacaa gggtgaaaag ccagaaagag gtagattctt gcacttccac  60
tctgttacct tctgggttgg taacgctaag caagctgctt cttactactg ttctaagatg  120
ggtttcgaac cattggctta caagggtttg gaaaccggtt ctagagaaat ggtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttggttctt gccaggtttc  480
```

```
gaagctccag ctttcgttga cccattgttg tctaagttgc caaactgttc tttggaaaga  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccacagat acaaccacca aggtttcggt  1080
gctggtaact tcaactcttt gttcaaggct ttcgaagaag aacaagactt gagaggtaac  1140
ttgaccgaca tggaaaccaa cggtaccgct gctggtacc                         1179

SEQ ID NO: 229         moltype = DNA  length = 1179
FEATURE                Location/Qualifiers
source                 1..1179
                       mol_type = unassigned DNA
                       organism = Octodon degus
SEQUENCE: 229
atgaccacct actctaacaa gggtgaaaag ccagaaagag gtagattctt gcacttccac  60
tctgttacct tctgggttgg taacgctaag caagctgctt cttactactg ttctaagatg  120
ggtttcgaac cattggctta caagggtttg gaaaccggtt ctagagaaat ggtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttggttctt gccaggtttc  480
gaagctccag ctttcgttga cccattgttg tctaagttgc caaactgttc tttggaaaga  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccacagat acaaccacca aggtttcggt  1080
gctggtaact tcaactcttt gttcaaggct ttcgaagaag aacaagactt gagaggtaac  1140
ttgaccgaca tggaaaccaa cggtaccgtt gctggtatg                         1179

SEQ ID NO: 230         moltype = DNA  length = 1179
FEATURE                Location/Qualifiers
source                 1..1179
                       mol_type = unassigned DNA
                       organism = Chrysemys picta
SEQUENCE: 230
atgaccacct actctaacaa gggtgaaaag ccagaaagag gtagattctt gcacttccac  60
tctgttacct tctgggttgg taacgctaag caagctgctt cttactactg ttctaagatg  120
ggtttcgaat ctttggctta caagggtttg gaaaccggtt ctagagaaat ggtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgc tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttggttctt gccaggtttc  480
gaagttccag ctttcgttga cccattgttg tctaagttgc caaactgttc tttggaaaga  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagat acaaccacca aggtttcggt  1080
gctggtaact tcaactcttt gttcaaggct ttcgaagaag aacaagactt gagaggtaac  1140
ttgaccgaca tggaaaccaa cggtaccgtt gctggtatg                         1179

SEQ ID NO: 231         moltype = DNA  length = 1179
FEATURE                Location/Qualifiers
source                 1..1179
                       mol_type = unassigned DNA
                       organism = Pongo abelii
SEQUENCE: 231
atgaccacct actctaacaa gggtgaaaag ccagaaagag gtagattctt gcacttccac  60
tctgttacct tctgggttgg taacgctaag caagctgctt cttactactg ttctaagatg  120
ggtttcgaat ctttggctta caagggtttg gaaaccggtt ctagagaagt tgtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
```

```
ccatgggttg aacaagacaa gttcggtaag gttaagttcg ctgttttgca aacctacggt  420
gacaccaccc acaccttggt tgaaaagatg aactacaccg gttggttctt gccaggtttc  480
gaagctccag ctttcgttga cccattgttg tctaagttgc caaactgttc tttggaaaga  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcaccaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagat acaaccacca aggtttcggt  1080
gctggtaact tcaactcttt gttcaaggct ttcgaagaag aacaagactt gagaggtaac  1140
ttgaccgaca tggaaaccaa cggtaccgtt gctggtatg                         1179

SEQ ID NO: 232          moltype = DNA  length = 1179
FEATURE                 Location/Qualifiers
source                  1..1179
                        mol_type = unassigned DNA
                        organism = Terrapene carolina
SEQUENCE: 232
atgaccacct actctaacaa gggtgaaaag ccagaaaagag gtagattctt gcacttccac  60
tctgttacct tctgggttgg taacgctaag caagctgctt cttactactg ttctaagatg  120
ggtttcgaat ctttggctta caagggtttg gaaaccggtt ctagagaaac cgtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttggttctt gccaggtttc  480
gaagctccag ctttcgttga cccattgttg ccaaagttgc caaactgttc tttggaaaga  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagat acaaccacca aggtttcggt  1080
gctggtaact tcaactcttt gttcaaggct ttcgaagaag aacaagactt gagaggtaac  1140
ttgaccgaca tggaaaccaa cggtaccgtt ccatctatg                         1179

SEQ ID NO: 233          moltype = DNA  length = 1176
FEATURE                 Location/Qualifiers
source                  1..1176
                        mol_type = unassigned DNA
                        organism = Neophocaena asiaeorientalis
SEQUENCE: 233
tctttggctc catctttgtt gttgcaacca gaaagaggta gattcttgca cttccactct  60
gttaccttct gggttggtaa cgctaagcaa gctgcttctt actactgttc taagatgggt  120
ttcgaaccat tggcttacaa gggtttggaa accggttcta gagaaaccgt ttctcacgtt  180
atcaagcaag gtaagatcgt tttcatcttc tcttctgctt tgaacccatg gaacaaggaa  240
atgggtgacc acttggttaa gcacggtgac ggtgttaagg acatcgcttt cgaagttgaa  300
gactgtgact acatcgttca aaaggctaga gaaagaggtg ctaagatcgt tagagaacca  360
tgggttgaac aagacaagtt cggtaaggtt aagttcgctg ttttgcaaac ctacggtgac  420
accacccaca ccttggttga aaagatgaac tacaccggtt ggttcttgcc aggtttcgaa  480
gctccagctt tcgttgaccc attgttgtct aagttgccaa actgttcttt ggaaagaatc  540
gaccacatcg ttggtaacca accagaccaa gaaatgttgt ctgcttctga atggtacttg  600
aagaacttgc aattccacag attctggtct gttgacgaca cccaagttca caccgaatac  660
tcttctttga gatctatcgt tgttgctaac tacgaagaat ctatcaagat gccaatcaac  720
gaaccagctc caggtagaaa gaagtctcaa atccaagaat acgttgacta caacggtggt  780
gctggtgttc aacacatcgc tttgaagacc gaagacatca tcaccgctat cagacacttg  840
agagaaagag gtatggaatt cttggctgtt ccatctacct actacaagca attgagagaa  900
aagttgaagt ctgctaagat cagagttaag gaaaacatcg acgttttgga agaattgaag  960
atcttggttg actacgacga aaagggttac ttgttgcaaa tcttcaccaa gccaatgcaa  1020
gacagaccaa ccttgttctt ggaagttatc caaagataca accaccaagg tttcggtgct  1080
ggtaacttca actctttgtt caaggctttc gaagaagaac aagacttgag aggtaacttg  1140
accgacatgg aaaccaacgg taccgttcca ggtatg                            1176

SEQ ID NO: 234          moltype = DNA  length = 1179
FEATURE                 Location/Qualifiers
misc_feature            1042..1047
                        note = n is a, c, g, or t
source                  1..1179
                        mol_type = unassigned DNA
                        organism = Theropithecus gelada
SEQUENCE: 234
atgaccacct actctaacaa gggtgaaaag ccagaaaagg gtagattctt gcacttccac  60
tctgttacct tctgggttgg taacgctaag caagctgctt cttactactg ttctaagatg  120
```

```
ggtttcgaac cattggctta caagggtttg gaaaccggtt ctagagaaat ggtttctcac  180
gttatcaagc aaggtaagat cgctttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttggttctt gccaggtttc  480
gaagctccag gtttcgttga cccattgttg tctaagttgc caaactgttc tttggaaatc  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacgt tgctttgaag accgaagaca tcatcaccgc tatcagacac  840
ttgagagaaa gaggtatgga attcttggct gttccatcta cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cnnnnnngtt atccaaagat acaaccacca aggtttcggt  1080
gctggtaact tcaactcttt gttcaaggct ttcgaagaag aacaagactt gagaggtaac  1140
ttgaccgaca tggaaaccaa cggtaccacc tgtggtatg                        1179

SEQ ID NO: 235          moltype = DNA  length = 1179
FEATURE                 Location/Qualifiers
source                  1..1179
                        mol_type = unassigned DNA
                        organism = Callorhinus ursinus
SEQUENCE: 235
atgaccacct actctaacaa gggtcaaaag ccagaaagag gtcaattctt gcacttccac  60
tctgttacct tctgggttgg taacgctaag caagctgctt cttactactg ttctaagatg  120
ggtttcgaac cattggctta caagggtttg gaaaccggtt ctagagaaat ggtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttggttctt gccaggtttc  480
gaagctccag ctttcgttga cccattgttg tctaagttgc caaactgttc tttgaagatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatccaccac  840
ttgagagaaa gaggtatgga attcttggct gttccatcta cctactacaa gcaattgaga  900
gaaaagttga agaccgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagat acaaccacca aggtttcggt  1080
gctggtaact tcaactcttt gttcaaggct ttcgaagaag aacaagactt gagaggtaac  1140
ttgaccgaca tggaaaccaa cggtttggtt ccaggtatg                        1179

SEQ ID NO: 236          moltype = DNA  length = 1179
FEATURE                 Location/Qualifiers
source                  1..1179
                        mol_type = unassigned DNA
                        organism = Vulpes vulpes
SEQUENCE: 236
atgaccacct actctaacaa gggtcaaaag ccagaaagag gtcaattctt gcacttccac  60
tctgttacct tctgggttgg taacgctaag caagctgctt cttactactg ttctaagatg  120
ggtttcgaac cattggctta caagggtttg gaaaccggtt ctagagaaat ggtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttggttctt gccaggtttc  480
gaagctccag ctttcgttga cccattgttg tctaagttgc caaactgttc tttgaagatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatccaccac  840
ttgagagaaa gaggtatgga attcttggct gttccatcta cctactacaa gcaattgaga  900
gaaaagttga agaccgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagat acaaccacca aggtttcggt  1080
gctggtaact tcaactcttt gttcaaggct ttcgaagaag aacaagactt gagaggtaac  1140
ttgaccgaca tggaaaccaa cggtttggct ccaggtatg                        1179

SEQ ID NO: 237          moltype = DNA  length = 1179
FEATURE                 Location/Qualifiers
source                  1..1179
                        mol_type = unassigned DNA
                        organism = Urocitellus parryii
SEQUENCE: 237
```

-continued

```
atgaccacct actctaacaa gggtcaaaag ccagaaagag gtcaattctt gcacttccac  60
tctgttacct tctgggttgg taacgctaag caagctgctt cttactactg ttctaagatg  120
ggtttcgaac cattggctta caagggtttg gaaaccggtt ctagagaaat ggtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttggttctt gccaggtttc  480
gaagctccag ctttcgttga cccattgttg tctaagttgc caaactgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatccaccac  840
ttgagagaaa gaggtatgga attcttggct gttccatcta cctactacaa gcaattgaga  900
gaaaagttga agaccgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagat acaaccacca aggtttcggt  1080
gctggtaact tcaactcttt gttcaaggct ttcgaagaag aacaagactt gagaggtaac  1140
ttgaccgaca tggaaaccaa cggtttggct ccaggtatg                         1179
```

```
SEQ ID NO: 238          moltype = DNA  length = 1179
FEATURE                 Location/Qualifiers
source                  1..1179
                        mol_type = unassigned DNA
                        organism = Ursus arctos
SEQUENCE: 238
atgaccacct actctaacaa gggtgaaaag ccagaaagag gtcaattctt gcacttccac  60
tctgttacct tctgggttgg taacgctaag caagctgctt cttactactg ttctaagatg  120
ggtttcgaac cattggctta caagggtttg gaaaccggtt ctagagaaat ggtttctcac  180
gttatcaagc aaggtaagat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaga gttaagttcg ctgttttgca aacctacggt  420
gacaccaccc acaccttggt tgaaaagatg aactacaccg gttggttctt gccaggtttc  480
gaagctccag ctttcgttga cccattgttg tctaagttgc caaactgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtatgga attcttggct gttccattca cctactacaa gcaattgaga  900
gaaaagttga agtctgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagat acaaccacca aggtttcggt  1080
gctggtaact tcaactcttt gttcaaggct ttcgaagaag aacaagactt gagaggtaac  1140
ttgaccgaca tggaaaccaa cggtgttggt tctggtatg                         1179
```

```
SEQ ID NO: 239          moltype = DNA  length = 1179
FEATURE                 Location/Qualifiers
source                  1..1179
                        mol_type = unassigned DNA
                        organism = Acinonyx jubatus
SEQUENCE: 239
atgaccacct actctaacaa gggtgaaaag ccagaaaagg gtagattctt gcacttccac  60
tctgttacct tctgggttgg taacgctaag caagctgctt ctttctactg taacaagttg  120
ggtttcgaac cattggctta caagggtttg gaaaccggtt ctagagaagt tgtttcttac  180
gttatcaagc aaggtaagat catcttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg tcttacgctg gtagattctt gccaggtttc  480
gaagctccag ctttcagaga cccattgttg tctaagttgc caaactgttc tttggaaatc  540
atcgaccacg ttgttggtaa ccaaccagac cacgaaatgg aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccacgaca tcatcaccgc tatcagacac  840
ttgagagaaa gaggtatgga attcttggct gttccatctt cttactacag acaattgcaa  900
gaaaagttga agtctgctaa gatcagagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaagactt gagaggtaac  1140
ttgaccgaca tgcaaaccaa catcttggct ccaggtaag                         1179
```

```
SEQ ID NO: 240          moltype = DNA  length = 1179
FEATURE                 Location/Qualifiers
source                  1..1179
                        mol_type = unassigned DNA
```

```
                         organism = Homo sapiens
SEQUENCE: 240
atgaccacct actctaacaa gggtgaaaag ccagaaaagg gtagattctt gcacttccac  60
tctgttacct tctgggttgg taacgctaag caagctgctt ctttctactg taacaagttg  120
ggtttcgaac cattggctta caagggtttg gaaaccggtt ctagagaagt tgtttctcac  180
gttatcaagc aaggtaagat catcttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg tcttacgctg gtagattctt gccaggtttc  480
gaagctccag ctttcagaga cccattgttg tctaagttgc caaactgttc tttggaaatc  540
atcgaccacg ttgttggtaa ccaaccagac cacgaaatgg aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccacgaca tcatcaccgc tatcagacac  840
ttgagagaaa gaggtatgga attcttggct gttccatctt cttactacag acaattgcaa  900
gaaaagttga agtctgctaa gatcagagtt aaggaatcta tcgacgtttt ggaagaattg  960
aagatcttgg ttgactacga cgaaaagggt tacttgttgc aaatcttcac caagccaacc  1020
caagacagac caaccttgtt cttggaagtt atccaaagac acaaccacca aggtttcggt  1080
gctggtaact tcaacgcttt gttcaaggct ttcgaagaag aacaagactt gagaggtaac  1140
ttgaccgaca tgcaaaccaa cgacttggtt ccaggtaag                        1179

SEQ ID NO: 241           moltype = DNA  length = 1179
FEATURE                  Location/Qualifiers
source                   1..1179
                         mol_type = unassigned DNA
                         organism = Gulo gulo
SEQUENCE: 241
atgaccacct actctgacaa gggtgaaaag ccagaaagag gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttgggtaag gttaagttcg ctgttttgca aacctacggt  420
gacaccaccc acaccttggt tgaaaagatg aactacaccg gtagattctt gccaggtttc  480
gaagctccac cattcatgga cccacaattg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctgt tgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accaaggaca tcatcaccgc tatcagacac  840
ttgagagaaa gaggtgttga attcttggct gttccatcta cctactacaa gcaattgaga  900
gaaaagttga agatggctaa gatcagagtt aaggaaaaca tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaccaaa cggtgttgtt tctggtatg                        1179

SEQ ID NO: 242           moltype = DNA  length = 1179
FEATURE                  Location/Qualifiers
source                   1..1179
                         mol_type = unassigned DNA
                         organism = Bos indicus
SEQUENCE: 242
atgaccacct actctgacaa gggtgaaaag ccagaaagag gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttgggtaag gttaagttcg ctgttttgca aacctacggt  420
gacaccaccc acaccttggt tgaaaagatg aactacaccg gtagattctt gccaggtttc  480
gaagctccac cattcatgga cccacaattg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctgt tgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accaaggaca tcatcaccgc tatcagacac  840
ttgagagaaa gaggtgttga attcttggct gttccatcta cctactacaa gcaattgaga  900
gaaaagttga agatggctaa gatcagagtt aaggaaaaca tcgacatctt ggaagaattg  960
aagatcttgg ttgactacga cgaaaagggt tacttgttgc aaatcttcac caagccaatg  1020
caagacagaa ccaccatctt cttggaagtt atccaaagac acaaccacca aggtttcggt  1080
gctggtaact tcaactcttt gttcaaggct ttcgaagaag aacaagactt gagaggtaac  1140
ttgaccgaca tggaaccaaa cggtgttgtt tctggtatg                        1179

SEQ ID NO: 243           moltype = DNA  length = 1179
FEATURE                  Location/Qualifiers
```

-continued

```
source                 1..1179
                       mol_type = unassigned DNA
                       organism = Tupaia chinensis
SEQUENCE: 243
atgaccacct actctgacaa gggtgaaaag ccagaaagag gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttgggtaag gttaagttcg ctgttttgca aacctacggt  420
gacaccaccc acaccttggt tgaaaagatg aactacaccg gtagattctt gccaggtttc  480
gaagctccac cattcatgga cccacaattg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctgt tgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accaaggaca tcatcaccgc tatcagacac  840
ttgagagaaa gaggtgttga attcttggct gttccatcta cctactacaa gcaattgaga  900
gaaaagttga agtctgctaa gatcagagtt aaggaaaaca tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaccaaa cggtgttgtt tctggtatg                          1179

SEQ ID NO: 244         moltype = DNA  length = 1179
FEATURE                Location/Qualifiers
misc_feature           463..465
                       note = n is a, c, g, or t
misc_feature           1165..1167
                       note = n is a, c, g, or t
source                 1..1179
                       mol_type = unassigned DNA
                       organism = Vombatus ursinus
SEQUENCE: 244
atgaccacct actctgacaa gggtgaaaag ccagaaagag gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttgggtaag gttaagttcg ctgttttgca aacctacggt  420
gacaccaccc acaccttggt tgaaaagatg aactacaccg gtnnnttctt gccaggtttc  480
gaagctccac cattcatgga cccacaattg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctgt tgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accaaggaca tcatcaccgc tatcagacac  840
ttgagagaaa gaggtgttga attcttggct gttccatcta cctactacaa gcaattgaga  900
gaaaagttga agatggctaa gatcagagtt aaggaaaaca tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaccaaa cggtnnngtt tctggtatg                          1179

SEQ ID NO: 245         moltype = DNA  length = 1179
FEATURE                Location/Qualifiers
source                 1..1179
                       mol_type = unassigned DNA
                       organism = Eptesicus fuscus
SEQUENCE: 245
atgaccacct actctgacaa gggtgaaaag ccagaaagag gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttgggtaag gttaagttcg ctgttttgca aacctacggt  420
gacaccaccc acaccttggt tgaaaagatg aactacaccg gtagattctt gccaggtttc  480
gaagctccac cattcatgga cccacaattg tctaagttgc catcttgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctgt tgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accaaggaca tcatcaccgc tatcagacac  840
ttgagagaaa gaggtgttga attcttggct gttccatcta cctactacaa gcaattgaga  900
gaaaagttga agatggctaa gatcagagtt aaggaaaaca tcgacatctt ggaagaattg  960
aagatcttgg ttgactacga cgaaaagggt tacttgttgc aaatcttcac caagccaatg  1020
```

-continued

```
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaccaaa cggtggtgtt tctggtatg                         1179

SEQ ID NO: 246          moltype = DNA  length = 1179
FEATURE                 Location/Qualifiers
source                  1..1179
                        mol_type = unassigned DNA
                        organism = Sousa chinensis
SEQUENCE: 246
atgaccacct actctgacaa gggtgaaaag ccagaaagag gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttgggtaag gttaagttcg ctgttttgca aacctacggt  420
gacaccaccc acaccttggt tgaaaagatg aactacaccg gtagattctt gccaggtttc  480
gaagctccag ctttcatgga cccacaattg tctaagttgc caaactgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accaaggaca tcatcaccgc tatcagacac  840
ttgagagaaa gaggtgttga attcttggct gttccatcta cctactacaa gcaattgaga  900
gaaaagttgg aatctgctaa gatcagagtt aaggaaaaca tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaccaaa cggtgttgtt tcttctatg                         1179

SEQ ID NO: 247          moltype = DNA  length = 1179
FEATURE                 Location/Qualifiers
source                  1..1179
                        mol_type = unassigned DNA
                        organism = Platysternon megacephalum
SEQUENCE: 247
atgaccacct actctgacaa gggtgaaaag ccagaaagag gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttgggtaag gttaagttcg ctgttttgca aacctacggt  420
gacaccaccc acaccttggt tgaaaagatg aactacaccg gtagattctt gccaggtttc  480
gaagctccag ctttcatgga cccacaattg tctaagttgc caaactgtgg tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accaaggaca tcatcaccgc tatcagacac  840
ttgagagaaa gaggtgttga attcttggct gttccatcta cctactacaa gcaattgaga  900
gaaaagttga agtctgctaa gatcagagtt aaggaaaaca tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca tggaaccaaa cggtgttgtt tcttctatg                         1179

SEQ ID NO: 248          moltype = DNA  length = 1179
FEATURE                 Location/Qualifiers
source                  1..1179
                        mol_type = unassigned DNA
                        organism = Grammomys surdaster
SEQUENCE: 248
atgaccacct actctgacaa gggtgaaaag ccagaaagag gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacgttgc tttcgaagtt  300
gaagactgtg actacatcgt tcaaaaggct agagaaagag gtgctaagat cgttagagaa  360
ccatggttgg aacaagacaa gttgggtaag gttaagttcg ctgttttgca aacctacggt  420
gacaccaccc acaccttggt tgaaaagatg aactacaccg gtagattctt gccaggtttc  480
gaagctccag ctttcatgga cccacaattg tctaagttgc caaactgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtccaggtg ttcaacacat cgctttgaag accaaggaca tcatcaccgc tatcagacac  840
ttgagagaaa gaggtgttga attcttggct gttccatcta cctactacaa gcaattgaga  900
```

-continued

```
gaaaagttga agtctgctaa gatcagagtt aaggaaaaca tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgaca ccgaaccaaa cggtgttgtt tcttctatg                         1179

SEQ ID NO: 249          moltype = DNA  length = 1179
FEATURE                 Location/Qualifiers
source                  1..1179
                        mol_type = unassigned DNA
                        organism = Monodon monoceros
SEQUENCE: 249
atgaccacct actctgacaa gggtgaaaag ccagaatctg gtagattctt gcacttccac  60
tctgttacct tctgggttgg taacgctaag caagctgctt cttactactg ttctaagttg  120
ggtttcgaac cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtagattctt gccaggtttc  480
gaagctccag ctttcatgga cccacaattg tctaagttgc caaactgttc tttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtccaggtg ttcaacacat cgctttgaag accaaggaca tcatcaccgc tatcagacac  840
ttgagagaaa gaggtgttga attcttggct gttccatcta cctactacaa gcaattgaga  900
gaaaagttga agtctgctaa gatcagagtt aaggaaaaca tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaagactt gagaggtaac  1140
ttgaccgaca tggaaccaaa cggtgttgtt ccaggtatg                         1179

SEQ ID NO: 250          moltype = DNA  length = 1179
FEATURE                 Location/Qualifiers
source                  1..1179
                        mol_type = unassigned DNA
                        organism = Monodon monoceros
SEQUENCE: 250
atgacctctt actctgacaa gggtgaaaag ccagaaagag gtagattctt gcacttccac  60
tctgttacct tctgggttgg taacgctaag caagctgctt cttactactg ttctaagatc  120
ggtttcgaac cattggctta caagggtttg gaaaccggtt ctagagaagt tgtttctcac  180
gttgttaagc aagacaagat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctatcat cgttagagaa  360
ccatggatcg aacaagacaa gttcggtaag gttaagttcg ctgttttgca aaccttcggt  420
gacaccaccc acaccttggt tgaaaagatg aactacaccg gttgtttctt gccaggtttc  480
gaagctccaa ccttcaccga cccattgttg tctaagttgc caaagtgtgg tttggaaatc  540
atcgaccaca tcgttggtaa ccaaccagac caagaaatgg aatctgcttc tcaatggtac  600
atgagaaact tgcaattcca cagattctgg tctgttgacg acacccaaat ccacaccgaa  660
tactctgctt tgagatctgt tgttatggct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagatct  840
ttgagagaaa gaggtgttga attcttggct gttccattca cctactacaa gcaattgcaa  900
gaaaagttga agtctgctaa gatcagagtt aaggaatcta tcgacgtttt ggaagaattg  960
aagatcttgg ttgactacga cgaaaagggt tacttgttgc aaatcttcac caagccaatg  1020
caagacagac caaccgtttt cttggaagtt atccaaagaa acaaccacca aggtttcggt  1080
gctggtaact tcaactcttt gttcaaggct ttcgaagaag aacaagaatt gagaggtaac  1140
ttgaccgaca ccgacccaaa cggtgttgct ttcagattg                         1179

SEQ ID NO: 251          moltype = DNA  length = 1179
FEATURE                 Location/Qualifiers
source                  1..1179
                        mol_type = unassigned DNA
                        organism = Suricata suricatta
SEQUENCE: 251
atgacctctt actctgacaa gggtaagaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgcttctcac  180
gttatcaagc aaggtcaaat cgttttcgtt ttctcttctg ctttgaaccc atggaacaag  240
gaaatgggtg accacttggt tagacacggt gacggtgtta aggacgttgc tttcgaagtt  300
caagactgtg actctatcgt tcaaaaggct caagaaagag gtgctaagat catcagagaa  360
ccatgggttg aacaagacaa gttcggtaag gttaagttcg ctgttttgca aaccttcggt  420
gacaccaccc acaccttggt tgaaaagatg aactacagag gtccattctt gccaggtttc  480
atggctagag ctccaagaga ctctttgttg tctaagttgc cacaatgtaa cttggaagtt  540
atcgaccacg ttgttggtaa ccaaccagac caagaaatgt tgtctgcttc tgaatggtac  600
ttgaacaact tgcaattcca cagattctgg tctgttgacg acaaggaatt gcacaccgaa  660
tactcttctt tgagatctat cgttgttacc aactacgaag aatctatcaa gatcccaatc  720
aacgaaccag ctccaggtag aaagaagtct caaatccaag aatacgttga ctactacggt  780
```

```
ggtgctggtg ttcaacacat cgctttgaag acccaagaca tcatcaccac catcagatct  840
ttgaaggaaa gaggtatgga attcttgaac accccaccaa cctactacaa gcaattgaga  900
gaaaagttga agtctgctaa gatcagagtt caagaaaaca tggacacctt ggaagaattg  960
aagatcttgg ttgactacga cgaaaacggt tacttgttgc aaatcttctc taagccaatg  1020
caagacagac caaccttgtt cttggaagtt atccaaagac acaaccacca aggtttcggt  1080
gctggtaact tcaactcttt gttcaaggct ttggaagaag aacaaaactt gagaggtaac  1140
ttgaccgact tggaaaccaa cggtgttgtt ccaggtatg                         1179

SEQ ID NO: 252          moltype = DNA  length = 1179
FEATURE                 Location/Qualifiers
source                  1..1179
                        mol_type = unassigned DNA
                        organism = Lynx canadensis
SEQUENCE: 252
atgacctctt actctaacaa gggtgaaaag ccagaaagag gtagattctt gcacttccac  60
tctgttacct tctgggttgg taacgctaag caagctgctt ctttctactg ttctaagatg  120
ggtttcaagc caatcgctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agacaaagag gtgctaagat catcagagaa  360
ccatgggttg aacaagacaa gttcggtaag gttaagttcg ctgttttgca aacctacggt  420
gacaccaccc acaccttggt tgaaaagatg aactacgctg gtttcttctt gccaggtttc  480
gaaccaacca ccaacagaga ccaagctttg tctaagttgc cacaatctaa cttggaagtt  540
atcgaccaca tcgttggtaa ccaaccagac caagaaatgt tgtctgcttc tgactggtac  600
ttgaacaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggac gttccatcta cctactacaa gcaattgaga  900
gaaaagttga agtctgctaa gatcagagtt aaggaaaact tggacgcttt ggaagaattg  960
aagatcttgg ttgactacga cgaaaacggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaaaacat gagaggtaac  1140
ttgaccgact tggaaccaaa cggtgttatc agaggtatg                         1179

SEQ ID NO: 253          moltype = DNA  length = 1179
FEATURE                 Location/Qualifiers
source                  1..1179
                        mol_type = unassigned DNA
                        organism = Marmota monax
SEQUENCE: 253
atgacctctt actctaacaa gggtgaaaag ccagaaagag gtagattctt gcacttccac  60
tctgttacct tctgggttgg taacgctaag caagctgctt ctttctactg ttctaagatg  120
ggtttcaagc caatcgctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agacaaagag gtgctaagat catcagagaa  360
ccatgggttg aacaagacaa gttcggtaag gttaagttcg ctgttttgca aacctacggt  420
gacaccaccc acaccttggt tgaaaagatg aactacaccg gtttcttctt gccaggtttc  480
gaaccaacca ccaacagaga cccagctttg tctaagttgc cacaatctaa cttggaagtt  540
atcgaccaca tcgttggtaa ccaaccagac caagaaatgt tgtctgcttc tgactggtac  600
ttgaacaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggac gttccatcta cctactacaa gcaattgaga  900
gaaaagttga agtctgctaa gatcagagtt aaggaaaact tggacgcttt ggaagaattg  960
aagatcttgg ttgactacga cgaaaacggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaaaacat gagaggtaac  1140
ttgaccgact tggaaccaaa cggtgttatc agaggtatg                         1179

SEQ ID NO: 254          moltype = DNA  length = 1179
FEATURE                 Location/Qualifiers
source                  1..1179
                        mol_type = unassigned DNA
                        organism = Nomascus leucogenys
SEQUENCE: 254
atgacctctt actctaacaa gggtgaaaag ccagaaagag gtagattctt gcacttccac  60
tctgttacct tctgggttgg taacgctaag caagctgctt ctttctactg ttctaagatg  120
ggtttcaagc caatcgctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agacaaagag gtgctaagat catcagagaa  360
ccatgggttg aacaagacaa gttcggtaag gttaagttcg ctgttttgca aacctacggt  420
gacaccaccc acaccttggt tgaaaagatg aactacaccg gtttcttctt gccaggtttc  480
gaaccaacca ccaacagaga cccagttttg tctaagttgc cacaatctaa cttggaagtt  540
atcgaccaca tcgttggtaa ccaaccagac caagaaatgt tgtctgcttc tgctagatac  600
ttgaacaact tgcaattcca cagattctgg tctgttgacg acacccaagt tcacaccgaa  660
```

-continued

```
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggac gttccatcta cctactacaa gcaattgaga  900
gaaaagttga agtctgctaa gatcagagtt aaggaatctt tggacgcttt ggaagaattg  960
aagatcttgg ttgactacga cgaaaacggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaaaactt gagaggtaac  1140
ttgaccgact tggaaccaaa cggtgttatc agaggtatg                         1179

SEQ ID NO: 255         moltype = DNA  length = 1179
FEATURE                Location/Qualifiers
source                 1..1179
                       mol_type = unassigned DNA
                       organism = Rhinopithecus roxellana
SEQUENCE: 255
atgacctctt acaccaacag aggtgaaaag ccagaaagag gtagattctt gcacttccac  60
tctgttacct tctgggttgg taacgctaag caagctgctt ctttctactg ttctaagatg  120
ggtttcaagc cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agacaaagag gtgctaagat catcagagaa  360
ccatgggttg aacaagacaa gttcggtaag gttaagttcg ctgttttgca aacctacggt  420
gacaccaccc acaccttggt tgaaaagatg aactacaccg gtttcttctt gccaggtttc  480
gaaccaacca ccaacagaga cccagctttg tctaagttgc cacaatctaa cttggaagtt  540
atcgaccaca tcgttggtaa ccaaccagac caagaaatgt tgtctgcttc tgactggtac  600
ttgaacaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggac gttccatcta cctactacaa gcaattgaga  900
gaaaagttga agtctgctaa gatcagagtt aaggaatctt tggacgcttt ggaagaattg  960
agaatcttgg ttgactacga cgaaaacggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaaaactt gagaggtaac  1140
ttgaccgaca tggaaaccaa cggtgttgtt agaggtatg                         1179

SEQ ID NO: 256         moltype = DNA  length = 1179
FEATURE                Location/Qualifiers
source                 1..1179
                       mol_type = unassigned DNA
                       organism = Muntiacus muntjak
SEQUENCE: 256
atgacctctt acaccaacaa gggtgaaaag ccagaaagag gtagattctt gcacttccac  60
tctgttacct tctgggttgg taacgctaag caagctgctt cttactactg ttctaagatg  120
ggtttcaagc cattggctta cagaggtttg gaaaccggtt ctagagaagt tgtttctcac  180
gttgttaagc aaggtcaaat cgttttcatc ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agacaaagag gtgctaagat catcagagaa  360
ccatgggttg aacaagacaa gttcggtaag gttaagttcg ctgttttgca aacctacggt  420
gacaccaccc acaccttggt tgaaaagatg gactacaccg gtttgttctt gccaggtttc  480
aacccaacca cccacaccga ctctgttttg tctaagttgc cacaatctaa cttggaagtt  540
atcgaccaca tcgttggtaa ccaaccagac caagaaatgt tgtctgcttc tgactggtac  600
ttgaacaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtatgga attcttggac gttccagcta cctactacag acaattgaga  900
gaaaagttga agtctgctaa gatcagagtt aaggaatctt tggacacctt ggaagaattg  960
aagatcttgg ttgactacga cgaaaacggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaaaactt gagaggtaac  1140
ttgaccgaca tggaaaccaa cggtgttgtt agaggtatg                         1179

SEQ ID NO: 257         moltype = DNA  length = 1179
FEATURE                Location/Qualifiers
source                 1..1179
                       mol_type = unassigned DNA
                       organism = Mastomys coucha
SEQUENCE: 257
atgacctctt actctaacaa gggtgaaaag ccagaaagag gtagattctt gcacttccac  60
tctgttacct tctgggttgg taacgctaag caagctgctt ctttctactg ttctaagatg  120
ggtttcaagc cattggctta cagaggtttg gaaaccggtt ctagagacgt tgtttctcac  180
gttgttaagc aaggtcaaat cgttttcgtt ttctcttctg ctttgaaccc atggaacaag  240
gacatgggtg accacttggt taagcacggt gacggtgtta aggacatcgc tttcgaagtt  300
gaagactgtg actacatcgt tcaaaaggct agagaaagag gtgctaagat catcagagaa  360
ccatgggttg aacaagacaa gttcggtaag gttaagttcg ctgttttgca aacctacggt  420
gacaccaccc acaccttggt tgaaaagatg aagtacaccg gtttcttctt gccaggtttc  480
gaaccagttg ctaagatgga cccagctttg tctaagttgc cacaatgtaa cttggaagtt  540
```

-continued

```
atcgaccaca tcgttggtaa ccaaccagac caagaaatgg aatctgcttc tgactggtac  600
ttgaacaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga atacaacggt  780
ggtgctggtg ttcaacacat cgctttgaag acccaagaca tcatcaccgc tatcagacac  840
ttgagagaaa gaggtatgga attcttggac gttccatcta cctactacaa gcaattgaga  900
gaaaagttga agtctgctaa gatcagagtt aaggaaaaca tcgaaatctt ggaagaattg  960
agaatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaaaactt gagaggtaac  1140
ttgaccgaca tggaaccaaa cggtgttttg agaggtatg                         1179

SEQ ID NO: 258         moltype = DNA  length = 1179
FEATURE                Location/Qualifiers
source                 1..1179
                       mol_type = unassigned DNA
                       organism = Camelus dromedarius
SEQUENCE: 258
atgacctctt actctaacaa gggtccaaag ccagaaagag gtagattcgt tcacttccac  60
tctgttacct tctgggttgg taacgctaag caagctgctt ctttctactg taccagaatg  120
ggtttcgaac cattggctta cagaggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacgttgc tttcgaagtt  300
gaagactgtg actacatcgt tcaaaaggct caagaaagag gtgctaagat catcagagaa  360
ccatgggttg aacaagacaa gttcggtaag gttaagttcg ctgttttgca aacctacggt  420
gacaccaccc acaccttggt tgaaaagatg tcttacaccg gttgtttctt gccaggtttc  480
aagggtttgg actctaagga cgctttgttg tctaagttgc cacactgttg tttggaagtt  540
atcgaccaca tcgttggtaa ccaaccagac caagaaatgc aatctgcttc tgaatggtac  600
ttgaagaact tgcaattcca cagattctgg tctgttgacg acacccaagt tcacaccgaa  660
tactcttctt tgagatctat cgttgttacc aactacgaag aatctatcaa gatgccaatc  720
aacgaaccag ctccaggtaa gaagaagtct caaatccaag aatacgttga cttcaacggt  780
ggtgctggtg ttcaacacat cgctttgaag acccaagaca tcatctctgc tatcagacac  840
ttgagagaaa gaggtatgga attcttgcac gttccatcta cctactacaa gcaattgaga  900
gaaaagttga agtctgctaa gatcagagtt aaggaaaaca tggacgtttt ggaagaattg  960
aacatcttgg ttgactacga cgacaagggt tacttgttgc aaatcttcac caagccaatg  1020
caagacagac caaccttgtt cttggaaatc atccaaagac acaaccacca aggtttcggt  1080
gctggtaact tcaacgcttt gttcgaagct atcgaagaag aacaagcttt gagaggtaac  1140
ttgaccgact tggaaaccaa cggtgttgtt caaggtaag                         1179

SEQ ID NO: 259         moltype = DNA  length = 1179
FEATURE                Location/Qualifiers
source                 1..1179
                       mol_type = unassigned DNA
                       organism = Papio anubis
SEQUENCE: 259
atgacctctt actctgacaa gggtcaaaag ccagaaagag gtagattctt gcacttccac  60
tctgttacct tctgggttgg taacgctaag caagctgctt ctttctactg ttctaaggtt  120
ggtttcgaac cattggctta caagggtttg gaaaccggtt ctagagaagt tgtttctcac  180
gttgttaagc aaggtcaaat cgttttcgtt ttctcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat catcagagaa  360
ccatgggttg aacaagacaa gttcggtaag gttaagttgg ctgttttgca aacctacggt  420
gacaccaccc acaccttggt tgaaaagatg aactacaccg gttgtttctt gccaggtttc  480
gaagctgttg actgtaagga cccattgttg tctaagttgc cacaatgtgg tttggaagtt  540
gttgaccaca tcgttggtaa ccaaccagac caagaaatgc aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accggtgaca tcatctctgc tatcagacac  840
ttgagagaaa gaggtatgga attcttgcac gttccatcta cctactacaa gcaattgaga  900
gaaaagttga agtctgctaa gatcagagtt aaggaaaact tggacgtttt ggaagaattg  960
agaatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaagcttt gagaggtaac  1140
ttgaccgaca tggaaatcaa cggtatcgct agaggtatg                         1179

SEQ ID NO: 260         moltype = DNA  length = 1179
FEATURE                Location/Qualifiers
source                 1..1179
                       mol_type = unassigned DNA
                       organism = Sarcophilus harrisii
SEQUENCE: 260
atgacctctt actctaacaa gggtgaaaag ccagttagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtgaaat cgttttcgtt ttctcttctg ctttgaaccc atggcacaag  240
gaaatgggtg accacttggt taagcacggt gacggtgtta aggacatcgc tttcgaagtt  300
gaagactgtg actacatcgt tcaaaaggct agagaaagag gtgctaagat catcagagaa  360
ccatgggttg aacaagacaa gttcggtaag gttaagttcg ctgttttgca aacctacggt  420
```

```
gacaccaccc acaccttggt tgaaaagatg aactacaccg gtagattctt gccaggtttc  480
gaagctccag ttttcaagga cccacaattg tctaagttgc cacactgtaa gttggaagtt  540
atcgaccaca tcgttggtaa ccaaccagac caagaaatgg tttctgcttc tgactggtac  600
ttgaacaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccacgaca tcatcaccgc tatcagacac  840
ttgagagaaa gaggtatcga attcttggct gttccatcta cctactacaa gcaattgaga  900
gaaaagttga agtctgctaa gatcagagtt aaggaaaaca tcgacatctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgaca tggacaccaa cggtgttatc cacggtatg                        1179
```

```
SEQ ID NO: 261         moltype = DNA  length = 1179
FEATURE                Location/Qualifiers
source                 1..1179
                       mol_type = unassigned DNA
                       organism = Crocuta crocuta
SEQUENCE: 261
atgaccacct actctgacaa gggtcaaaag ccagaaagag gtagattctt gcacttccac  60
tctgttacct tctgggttgg taacgctaag caagctgctt ctttctactg ttctaagatg  120
ggtttcgaac cattggctta caagggtttg gaaaccggtt ctagagaagt tgtttctcac  180
gttgttaagc aaggtgaaat cgttttcgtt ttctgttctg ctttgaaccc atggaacaag  240
gaaatgggtg accacttggt taagcacggt gacggtgtta aggacatcgc tttcgaagtt  300
gaagactgtg aatacatcgt tcaaaaggct agagaaagag gtgctaagat catcagagaa  360
ccatgggttg aacaagacaa gttcggtaag gttaagttcg ctgttttgca aacctacggt  420
gacaccaccc acaccttggt tgaaaagatg aactacaccg gtagattctt gccaggtttc  480
gaagctccag ctttcaccga cccattgttg tctaagttgc cacactgtaa gttggaaatc  540
atcgaccaca tcgttggtaa ccaaccagac caagaaatga cctctgcttc tgactggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagaaga  840
ttgagagaaa gaggtatgga attcttggct gttccatcta cctactacaa gcaattgaga  900
gaaaagttga agaccgctaa gatcagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgaca tggaaaccaa cggtgttatc accggtatg                        1179
```

```
SEQ ID NO: 262         moltype = DNA  length = 1290
FEATURE                Location/Qualifiers
source                 1..1290
                       mol_type = unassigned DNA
                       organism = Hylobates moloch
SEQUENCE: 262
atggaattct tgggtgctgc tgctgaattg gaaatgggtt cttgtccagg tgctttgtct  60
accccagctt cttgtccagt tttccaagct ggttctttga ccaagatcaa catgaccacc  120
tactctgaca agggtcaaaa gccagaaaga ggtagattct tgcacttcca ctctgttacc  180
ttctgggttg gtaacgctaa gcaagctgct tctttctact gttctaagat gggtttcgaa  240
ccattggctt acaagggttt ggaaaccggt tctagagaag ttgtttctca cgttgttaag  300
caaggtgaaa tcgttttcgt tttctgttct gctttgaacc catggaacaa ggaaatgggt  360
gaccacttgg ttaagcacgg tgacggtgtt aaggacatcg ctttcgaagt tgaagactgt  420
gaatacatcg ttcaaaaggc tagagaaaga ggtgctaaga tcatcagaga accatgggtt  480
gaacaagaca agttcggtaa ggttaagttc gctgttttgc aaacctacgg tgacaccacc  540
cacaccttgg ttgaaaagat gaactacacc ggtagattct tgccaggttt cgaagctcca  600
accttcaccg acccattgtt gtctaagttg ccacactgta agttggaaat catcgaccac  660
atcgttggta accaaccaga ccaagaaatg acctctgctt ctgactggta cttgaagaac  720
ttgcaattcc acagattctg gtctgttgac gacacccaag ttcacaccga atactcttct  780
ttgagatcta tcgttgttgc taactacgaa gaatctatca agatgccaat caacgaacca  840
gctccaggta gaaagaagtc tcaaatccaa gaatacgttg actacaacgg tggtgctggt  900
gttcaacaca tcgctttgaa gacccaagac atcatcaccg ctatcagaag attgagagaa  960
agaggtatgg aattcttggc tgttccatct acctactaca agcaattgag agaaaagttg  1020
aagaccgcta agatcagagt taaggaaaac atcgacgttt tggaagaatt gaagatcttg  1080
gttgactacg acgaaaaggg ttacttgttg caaatcttca ccaagccaat gcaagacaga  1140
ccaaccttgt tcttggaagt tatccaaaga cacaaccacc aaggtttcgg tgctggtaac  1200
ttcaactctt tgttcaaggc tttcgaagaa gaacaaaact tgagaggtaa cttgaccgac  1260
atggaaacca acggtgttat caccggtatg                                  1290
```

```
SEQ ID NO: 263         moltype = DNA  length = 1236
FEATURE                Location/Qualifiers
source                 1..1236
                       mol_type = unassigned DNA
                       organism = Sapajus apella
SEQUENCE: 263
atgtgtagac aacaatcttt cttcccaggt ggttctttgc acttgagaca acaaggtcaa  60
caagctgaag gtggtcaagg tttgtcttct ggttctccac caggttggcc attggaccca  120
cacgaaccat gttgtaaccc agttatccaa gctgtttctt tctactgttc taagatgggt  180
```

```
ttcgaaccat tggcttacag aggtttggaa accggttcta gagaagttgt ttctcacgtt  240
atcaagcaag gtaagatcgt tttcgttttg tcttctgctt tgaacccatg gaacaaggaa  300
atgggtgacc acttggctaa gcacggtgac ggtgttaagg acatcgcttt cgaagttgaa  360
gactgtgact acatcgttca aaaggctaga gaaagaggtg ctaagatcgt tagagaacca  420
tgggttgaac aagacaagtt cggtaaggtt aagttcgctg ttttgcaaac ctacggtgac  480
accacccaca ccttggttga aaagatgaac tacaccggtc aattcttgcc aggttacgaa  540
gctccagttt tcatggaccc attgttgcca aagttgccaa agtgttcttt ggaaatcatc  600
gaccacatcg ttggtaacca accagaccaa gaaatggttt ctgcttctga atggtacttg  660
aagaacttgc aattccacag attctggtct gttgacgaca cccaagttca caccgaatac  720
tcttctttga gatctatcgt tgttgctaac tacgaagaat ctatcaagat gccaatcaac  780
gaaccagctc caggtaagaa gaagtctcaa atccaagaat acgttgacta caacggtggt  840
gctggtgttc aacacatcgc tttgaacacc caagacatca tcaccgctat cagacacttg  900
agagaaagag gtatggaatt cttgtctgtt ccatctacct actacaagca attgagagaa  960
aagttgaaga ccgctaagat caaggttaag gaaaacatcg acgttttgga agaattgaag  1020
atcttggttg actacgacga aaagggttac ttgttgcaaa tcttcaccaa gccagttcaa  1080
gacagaccaa ccttgttctt ggaagttatc caaagacaca accaccaagg tttcggtgct  1140
ggtaacttca actctttgtt caaggctttc gaagaagaac aaaacttgag aggtaacttg  1200
tctgacttgg aaaccaacgg tgttgttcca ggtatg                           1236
```

```
SEQ ID NO: 264         moltype = DNA  length = 1179
FEATURE                Location/Qualifiers
source                 1..1179
                       mol_type = unassigned DNA
                       organism = Mustela erminea
SEQUENCE: 264
atgaccacct actctgacaa gggtgctaag ccagaaaagag gtagattctt gcacttccac  60
tctgttacct tctgggttgg taacgctaag caagctgctt ctttctactg taccaagatg  120
ggtttcgaac cattggctta cagaggtttg gaaaccggtt ctagacaagt tgtttctcac  180
gttatcaagc aaggtcaaat cgttttcgtt ttgtcttctg ctttgaaccc aggtaacaag  240
gaaatgggtg accacttggt taagcacggt gacggtgtta aggacatcgc tttcgaagtt  300
gaagactgtg actacatcgt tcaaaaggct agagaaagag gtgctaagat cttgagagaa  360
ccatgggttg aacaagacaa gttcggtaag gttaagttcg ctgttttgca aacctacggt  420
gacaccaccc acaccttggt tgaaaagatg aactacaccg gtagattctt gccaggtttc  480
gaagctccaa tgtctaagga cccattgttg tctaagttgc catcttgttc tttggaaatc  540
atcgaccaca tcgttggtaa ccaaccagaa caagaaatgg tttctgcttc tgaatggtac  600
ttgagaaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccacgaca tcatctctgc tatcagacac  840
ttgagagaaa gaggtatgga attcttggct gttccagcta cctactacaa gcaattgaga  900
gaaaagttga gatctgctaa gatcagagtt accgaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaaaactt gagaggtaac  1140
ttgaccgaca tggaaaccaa cggtgttgtt ccaggtatg                        1179
```

```
SEQ ID NO: 265         moltype = DNA  length = 1179
FEATURE                Location/Qualifiers
source                 1..1179
                       mol_type = unassigned DNA
                       organism = Camelus ferus
SEQUENCE: 265
atgaccacct acaccaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc gactacaccg gtagattctt gccaggtttc  480
gaagctccaa tctacaagga caccttgttg ccaaagttgc caagatgtaa cttggaaatc  540
atcgaccaca tcgttggtaa ccaaccagac caagaaatgg aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacaa gttgttgaga  900
gaaaacttga agaccgctaa gatccaagtt aaggaatcta tggacgtttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttaga tctggtatg                        1179
```

```
SEQ ID NO: 266         moltype = DNA  length = 1131
FEATURE                Location/Qualifiers
source                 1..1131
                       mol_type = unassigned DNA
                       organism = Phocoena sinus
SEQUENCE: 266
```

```
tggtactggg acaagggtcc aaagccagaa agaggtagat tcttgcactt ccactctgtt  60
accttctggg ttggtaacgc taagcaagct gcttctttct actgtaacaa gatgggtttc  120
gaaccattgg cttacaaggg tttggaaacc ggttctagag aagttgtttc tcacgttgtt  180
aagcaaggta agatcgtttt cgttttgtgt tctgctttga acccatggaa caaggaaatg  240
ggtgaccact tggttaagca cggtgacggt gttaaggaca tcgctttcga agttgaagac  300
tgtgaacaca tcgttcaaaa ggctagagaa agaggtgcta agatcgttag agaaccatgg  360
gttgaagaag acaagttcgg taaggttaag ttcgctgttt tgcaaaccta cggtgacacc  420
acccacacct tggttgaaaa gatcaactac accggtagat tcttgccagg tttcgaagct  480
ccaacctaca aggacacctt gttgccaaag ttgccatctt gtaacttgga aatcatcgac  540
cacatcgttg gtaaccaacc agaccaagaa atggaatctg cttctgaatg gtacttgaag  600
aacttgcaat tccacagatt ctggtctgtt gacgacaccc aagttcacac cgaatactct  660
tctttgagat ctatcgttgt tgctaactac gaagaatcta tcaagatgcc aatcaacgaa  720
ccagctccag gtagaaagaa gtctcaaatc caagaatacg ttgactacaa cggtggtgct  780
ggtgttcaac acatcgcttt gagaaccgaa gacatcatca ccaccatctg tcacttgaga  840
gaaagaggta tggaattctt ggctgttcca tcttcttact acagattgtt gagagaaaac  900
ttgaagacct ctaagatcca agttaaggaa aacatggacg ttttggaaga attgaagatc  960
ttggttgact acgacgaaaa gggttacttg ttgcaaatct tcaccaagcc aatgcaagac  1020
agaccaacct tgttcttgga agttatccaa agacacaacc accaaggttt cggtgctggt  1080
aacttcaact ctttgttcaa ggctttcgaa gaagaacaag ctttgagagg t           1131
```

```
SEQ ID NO: 267         moltype = DNA  length = 1128
FEATURE                Location/Qualifiers
source                 1..1128
                       mol_type = unassigned DNA
                       organism = Lontra canadensis
SEQUENCE: 267
tactgggaca agggtccaaa gccagaaaga ggtagattct tgcacttcca ctctgttacc  60
ttctgggttg gtaacgctaa gcaagctgct tctttctact gtaacaagat gggtttcgaa  120
ccattggctt acaagggttt ggaaaccggt tctagagaag ttgtttctca cgttatcaag  180
caaggtaaga tcgttttcgt tttgtgttct gctttgaacc catggaacaa ggaaatgggt  240
gaccacttgg ttaagcacgg tgacggtgtt aaggacatcg ctttcgaagt tgaagactgt  300
gaacacatcg ttcaaaaggc tagagaaaga ggtgctaaga tcgttagaga accatgggtt  360
gaagaagaca agttcggtaa ggttaagttc gctgttttgc aaacctacgg tgacaccacc  420
cacaccttgg ttgaaaagat caactacacc ggtagattct tgccaggttt cgaagctcca  480
acctacaagg acaccttgtt gccaaagttg ccatcttgta acttggaaat catcgaccac  540
atcgttggta accaaccaga ccaagaaatg gaatctgctt ctgaatggta cttgaagaac  600
ttgcaattcc acagattctg gtctgttgac gacacccaag ttcacaccga atactcttct  660
ttgagatcta tcgttgttgc taactacgaa gaatctatca agatgccaat caacgaacca  720
gctccaggta gaaagaagtc tcaaatccaa gaatacgttg actacaacgg tggtgctggt  780
gttcaacaca tcgctttgag aaccgaagac atcatcacca ccatcagaca cttgagagaa  840
agaggtatgg aattcttggc tgttccatct tcttactaca gattgttgag agaaaacttg  900
aagacctcta agatccaagt taaggaaaac atggacgttt tggaagaatt gaagatcttg  960
gttgactacg acgaaaaggg ttacttgttg caaatcttca ccaagccaat gcaagacaga  1020
ccaaccttgt tcttggaagt tatccaaaga cacaaccacc aaggtttcgg tgctggtaac  1080
ttcaactctt tgttcaaggc tttcgaagaa gaacaagctt tgagaggt               1128
```

```
SEQ ID NO: 268         moltype = DNA  length = 1179
FEATURE                Location/Qualifiers
source                 1..1179
                       mol_type = unassigned DNA
                       organism = Tyto alba
SEQUENCE: 268
atgaccacct actctaacaa gggtccaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc catcttgtaa cttggaaatc  540
atcgaccaca tcgttggtaa ccaaccagac caagaaatgg aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaga accgaagaca tcatcaccac catcagacac  840
ttgagagaaa gaggtatgga attcttggct gttccatctt cttactacag attgttgaga  900
gaaaacttga agacctctaa gatccaagtt aaggaaaaca tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttaga tctggtatg                         1179
```

```
SEQ ID NO: 269         moltype = DNA  length = 1179
FEATURE                Location/Qualifiers
source                 1..1179
                       mol_type = unassigned DNA
                       organism = Trachypithecus francoisi
SEQUENCE: 269
```

```
atgaccacct acaccaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggc taagcacggt gacggtgtta aggacatcgc tttcgaagtt  300
gaagactgtg aatacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaaggtt aactacaccg gtagattctt gccaggtttc  480
gaagctccaa cctacaagga caacttgttg ccaaagttgc caagatgtaa cttggaaatc  540
atcgaccaca tcgttggtaa ccaaccagac caagaaatgg aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacaa gatgttgaga  900
gaaaacttga agagagctaa gatccaagtt aaggaatctt tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaagcttt gagaggtaac  1140
ttgaccgact tggaaaccaa cggtgttaga tctggtatg                          1179
```

```
SEQ ID NO: 270          moltype = DNA  length = 1179
FEATURE                 Location/Qualifiers
source                  1..1179
                        mol_type = unassigned DNA
                        organism = Mirounga leonina
SEQUENCE: 270
atgaccacct acaccaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat catcagagaa  360
ccatgggttg aagaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caacttgttg ccaaagttgt ctagatgtaa gttggaagtt  540
atcgaccaca tcgttggtaa ccaaccagac caagaaatgg aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacaa gatgttgaga  900
gaaaacttga agatcgctaa gatccaagtt aaggaatcta tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagaag aacaagcttt gagaggtaac  1140
ttgaccgact tggaaaccaa cggtgttaga tctggtatg                          1179
```

```
SEQ ID NO: 271          moltype = DNA  length = 1179
FEATURE                 Location/Qualifiers
source                  1..1179
                        mol_type = unassigned DNA
                        organism = Arvicanthis niloticus
SEQUENCE: 271
atgaccacct acaccaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttctgttctg ctttgaaccc atggaacaag  240
gaaatgggtg accacttggt taagcacggt gacggtgtta aggacatcgc tttcgaagtt  300
gaagactgtg accacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc caagatgtaa cttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacaa gttgttgaga  900
gaaaacttga agaccgctaa gatccaagtt aaggaatctt tggacgtttt ggaagaattg  960
aagatcttgg ttgactacga cgaaaagggt tacttgttgc aaatcttcac caagccaatg  1020
caagacagac caaccttgtt cttggaagtt atccaaagaa gaaaccacca aggtttcggt  1080
gctggtaact tcaactcttt gttcaaggct ttcgaagaag aacaagcttt gagaggtaac  1140
ttgaccgaca tggaaaccaa cggtgttaga tctggtatg                          1179
```

```
SEQ ID NO: 272          moltype = DNA  length = 1179
FEATURE                 Location/Qualifiers
source                  1..1179
                        mol_type = unassigned DNA
```

```
                         organism = Trachemys scripta
SEQUENCE: 272
atgaccacct acaacaacaa gggtccaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gctatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg accacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc caagatgtaa cttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacaa gttgttgaga  900
gaaaacttga agaccgctaa gatccaagtt aaggaatctt tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgaca tggaaaccaa cggtgttaga tctggtatg                         1179

SEQ ID NO: 273           moltype = DNA  length = 1179
FEATURE                  Location/Qualifiers
source                   1..1179
                         mol_type = unassigned DNA
                         organism = Pan paniscus
SEQUENCE: 273
atgacctctt acaccaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg accacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc caagatgtaa cttggaaatc  540
atcgaccaca tcgttggtaa ccaaccagac caagaaatgc aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacaa gttgttgaga  900
gaaaacttga agtctgctaa gatccaagtt aaggaatcta tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgaca tggaaaccaa cggtgttaga tctggtatg                         1179

SEQ ID NO: 274           moltype = DNA  length = 1179
FEATURE                  Location/Qualifiers
source                   1..1179
                         mol_type = unassigned DNA
                         organism = Callithrix jacchus
SEQUENCE: 274
atgacctctt acaccaacaa gggtccaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacgctgtta aggacatcgc tttcgaagtt  300
gaagactgtg aacacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc aactacaccg gtagattctt gccaggtttc  480
gaagctccaa cccacaagga caccttgttg tctaagttgc catcttgtaa cttggaagtt  540
atcgaccaca tcgttggtaa ccaaccagac caagaaatga cctctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacaa gttgttgaga  900
ggtaacttga agaccgctaa gatccaagtt aaggaatcta tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttaga tctggtatg                         1179

SEQ ID NO: 275           moltype = DNA  length = 1179
FEATURE                  Location/Qualifiers
```

-continued

```
source                  1..1179
                        mol_type = unassigned DNA
                        organism = Canis lupus
SEQUENCE: 275
atgacctctt acaccaacaa gggtccaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc aactacaccg gtagattctt gccaggtttc  480
gaagctccaa tgcacaagga caccttgttg tctaagttgc catcttgtaa cttggaagtt  540
atcgaccaca tcgttggtaa ccaaccagac caagaaatgt tgtctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacag attgttgaga  900
gaaaacttga agaccgctaa gatccaagtt aaggaatcta tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttaga tctggtatg                         1179

SEQ ID NO: 276          moltype = DNA  length = 1179
FEATURE                 Location/Qualifiers
source                  1..1179
                        mol_type = unassigned DNA
                        organism = Rhinolophus ferrumequinum
SEQUENCE: 276
atgaccacct acaccaacaa gggtccaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatc aactacaccg gtcacttctt gccaggtttc  480
gaagctccag tttacaagga caccttgttg ccaaagttgc caagatgtaa cttggaagtt  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgacgaca tcatcaccgc tatccaccac  840
ttgagagaaa gaggtatgga attcttggct gttccatctt cttactacaa gttgttgaga  900
gaaaacttga agaccgctaa gatccaagtt aaggaatcta tggacacctt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttaga tctggtaag                         1179

SEQ ID NO: 277          moltype = DNA  length = 1179
FEATURE                 Location/Qualifiers
source                  1..1179
                        mol_type = unassigned DNA
                        organism = Rhinolophus ferrumequinum
SEQUENCE: 277
atgaccacct acaccaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc aactacaccg gtagattctt gccaggtttc  480
gaagctccag tttacaagga caccttgttg ccaaagttgc caagatgtaa cttggaagtt  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgacgaca tcatcaccgc tatcagacac  840
ttgagagaaa gaggtatgga attcttggct gttccatctt cttactacaa gttgttgaga  900
gaaaacttga agaccgctaa gatccaagtt aaggaatctt tggacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttaga tctggtatg                         1179
```

```
SEQ ID NO: 278          moltype = DNA  length = 1179
FEATURE                 Location/Qualifiers
source                  1..1179
                        mol_type = unassigned DNA
                        organism = Phyllostomus discolor
SEQUENCE: 278
atgaccacct acaacaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg accacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc caagatgtaa cttggaaatc  540
atcgaccaca tcgttggtaa ccaaccagac caagaaatgc aatctgcttc tgaatggtac  600
ttgaagaact tgcaatctca cagattctgg tctgttgacg acacccaagt tcacaccgaa  660
tactcttctt tgagatctat cgttgttacc aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtaccga attcttggct gctccatctt cttactacaa gttgttgaga  900
gaaaacttga agtctgctaa gatccaagtt aaggaatcta tggacgtttt ggaagaattg  960
cacatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaccaaa cggtgttaga tctggtatg                         1179

SEQ ID NO: 279          moltype = DNA  length = 1179
FEATURE                 Location/Qualifiers
source                  1..1179
                        mol_type = unassigned DNA
                        organism = Halichoerus grypus
SEQUENCE: 279
atgaccacct acaacaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg accacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc caagatgtaa cttggaaatc  540
atcgaccaca tcgttggtaa ccaaccagac caagaaatgc aatctgcttc tgaatggtac  600
ttgaagaact tgcaattcca cagattctgg tctgttgacg acacccaagt tcacaccgaa  660
tactcttctt tgagatctat cgttgttacc aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtaccga attcttggct gctccatctt cttactacaa gttgttgaga  900
gaaaacttga agtctgctaa gatccaagtt aaggaatcta tggacgtttt ggaagaattg  960
cacatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaccaaa cggtgttaga tctggtatg                         1179

SEQ ID NO: 280          moltype = DNA  length = 1179
FEATURE                 Location/Qualifiers
source                  1..1179
                        mol_type = unassigned DNA
                        organism = Onychomys torridus
SEQUENCE: 280
atgaccacct acaacaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaaga gaggtaagat cgttttcgtt ttgtgttctg ctttgaaccc atggaacaag  240
gaaatgggtg accacttggt taagcacggt gacggtgtta aggacatcgc tttcgaagtt  300
gaagactgtg accacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc caagatgtaa cttggaaatc  540
atcgaccaca tcgttggtaa ccaaccagac caagaaatgc aatctgcttc tgaatggtac  600
ttgaagaact tgcaattcca cagattctgg tctgttgacg acacccaagt tcacaccgaa  660
tactcttctt tgagatctat cgttgttacc aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtaccga attcttggct gctccatctt cttactacaa gttgttgaga  900
gaaaacttga agtctgctaa gatccaagtt aaggaatcta tggacgtttt ggaagaattg  960
cacatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
```

```
ttgaccgact tggaaccaaa cggtgttaga tctggtatg                        1179

SEQ ID NO: 281         moltype = DNA  length = 1137
FEATURE                Location/Qualifiers
source                 1..1137
                       mol_type = unassigned DNA
                       organism = Rousettus aegyptiacus
SEQUENCE: 281
accgttgact actgggacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacatcgc tttcgaagtt  300
gaagactgta accacatcgt tcaaaaggct agagaaagag gtgctaagat cgttagagac  360
gcttgggttg aacaagacaa gttcggtaag gttaagttcg ctgttttgca aacctacggt  420
gacaccaccc acaccttggt tgaaaagatc aactacaccg gtagattctt gccaggtttc  480
gaagctccaa cctacaagga caccttgttg ccaaagttgc caagatgtaa cttggaaatc  540
atcgaccaca tcgttggtaa ccaaccagac caagaaatgc aatctgcttc tgaatggtac  600
ttgaagaact tgcaattcca cagattctgg tctgttgacg acacccaagt tcacaccgaa  660
tactcttctt tgagatctat cgttgttacc aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtaccga attcttggct gctccatctt cttactacaa gttgttgaga  900
gaaaacttga agtctgctaa gatccaagtt aaggaatcta tggacgtttt ggaagaattg  960
cacatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggt     1137

SEQ ID NO: 282         moltype = DNA  length = 1179
FEATURE                Location/Qualifiers
source                 1..1179
                       mol_type = unassigned DNA
                       organism = Molossus molossus
SEQUENCE: 282
atgaccacct acaccaacaa gggtccaaag ccagaaagag gtagattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtgttctg ctttgaaccc atggaacaag  240
gaaatgggtg accacttggt taagcacggt gacggtgtta aggacgttgc tttcgaagtt  300
gaagactgtg accacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatc aactacaccg gtagattctt gccaggtttc  480
gaagctccaa tctacaagga caccttgttg ccaaagttgc caagatgtaa cttggaaatc  540
atcgaccaca tcgttggtaa ccaaccagac caagaaatgc aatctgcttc tgaatggtac  600
ttgaagaact tgcaattcca cagattctgg tctgttgacg acacccaagt tcacaccgaa  660
tactcttctt tgagatctat cgttgttacc aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccgc tatcagacac  840
ttgagagaaa gaggtatcga attcttggct gttccatctt cttactacaa gttgttgaga  900
gaaaacttga agtctgctaa gatccaagtt aaggaaaaca tggacatctt ggaagaattg  960
caaatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaccaaa cggtgttaga tctggtatg                        1179

SEQ ID NO: 283         moltype = DNA  length = 1179
FEATURE                Location/Qualifiers
source                 1..1179
                       mol_type = unassigned DNA
                       organism = Myotis myotis
SEQUENCE: 283
atgaccacct actctaacag aggtccaaag ccagaaagag gtcaattctt gcacttccac  60
tctgttacct tctgggttgg taacgctaag caagctgctt ctttctactg taacaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatc aactacaccg gtagattctt gccaggtttc  480
gaagctccag cttacaagga catcttgttg tctaagttgc caaactgtca cttggaaatc  540
atcgaccaca tcgttggtaa ccaaccagac caagaaatgg aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
ggtgctggtg ttcaacacat cgctttgaag accgaagaca tcatcaccac catcagacac  840
ttgagagaaa gaggtatgga attcttggct gttccatctt cttactacaa gttgttgaga  900
gaaaacttga agaccgctaa gatccaagtt aaggaatcta tgaacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
```

```
gctggtaact tcaacgcttt gttcaaggct ttcgaacaag aacaagcttt gagaggtaac  1140
ttgaccgact tggaaaccaa cggtgttaga tctggtatg                         1179

SEQ ID NO: 284         moltype = DNA  length = 1179
FEATURE                Location/Qualifiers
source                 1..1179
                       mol_type = unassigned DNA
                       organism = Pipistrellus kuhlii
SEQUENCE: 284
atgaccacct actctaacaa gggtccaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttgtgttctg ctttgaaccc atggaacaag  240
gaaatgggta accacttggt taagcacggt gacggtgtta aggacatcgc tttcgaagtt  300
gaagactgtg accacatcgt tcaaaaggct agagaaagag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gttgtttctt gccaggtttc  480
gaagctccaa cctacaagga cccattgttg tctaagttgc caaactgtaa cttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag accgaagaca tcatcaccgc tatcagacac  840
ttgagagaaa gaggtatgga attcttggct gttccatctt cttactacaa gttgttgaga  900
gaaaacttga agaccgctag aatccaagtt aaggaatcta tcgacgtttt ggaagaattg  960
aagatcttgg ttgactacga cgacaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgaca ccggtaccaa cagagttatg tctggtatg                         1179

SEQ ID NO: 285         moltype = DNA  length = 1179
FEATURE                Location/Qualifiers
source                 1..1179
                       mol_type = unassigned DNA
                       organism = Balaenoptera musculus
SEQUENCE: 285
atgaccacct actctgacaa gggtccaaag ccagaaagag gtagattctt gcacttccac  60
tctgttacct tctgggttgg taacgctaag caagctgctt ctttctactg taacaagatg  120
ggtttcgaac cattggctta caagggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg aacacatcgt tcaaaaggct agagaaagag gtgctaagat cgttagagaa  360
ccatgggttg aacaagacag attcggtaag gttaagttcg ctgttttgca aacctacggt  420
gacaccaccc acaccttggt tgaaaagatc aactacaccg gtagattctt gccaggtttc  480
gaagctccaa tgttgaagga cccattgttg tctaagttgc caaactgttc tttggaaatc  540
atcgaccaca tcgttggtaa ccaaccagac caagaaatgg aatctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccac catcagacac  840
ttgagagaaa gaggtatgga attcttggct gttccatcta cctactacaa gttgttgaga  900
gaaaacttga agtctgctaa gatcagagtt aaggaatcta tcgacgtttt ggaagaattg  960
aagatcttgg ttgactacga cgaaaacggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgaca tggaaaccaa cggtgttgtt tctggtatg                         1179

SEQ ID NO: 286         moltype = DNA  length = 1260
FEATURE                Location/Qualifiers
source                 1..1260
                       mol_type = unassigned DNA
                       organism = Manis pentadactyla
SEQUENCE: 286
atgagaccaa gattggacca aaagttgcca ggtttgggtc catgtagacc aagattgtct  60
tctagaccac acgaaggtca ccaaaccacc tactctaaca agggtccaaa gccagaaaga  120
ggtagattct tgcacttcca ctctgttacc ttctgggttg gtaacgctaa gcaagctgct  180
tctttctact gtaacaagat gggtttcgaa ccattcgctt acagaggttt ggaaaccggt  240
gctagagaag ttgtttctca cgttatcaag caaggtaaga tcgttttcgt tttgtcttct  300
gctttgaacc catggaacaa ggaaatgggt gaccacttgg ttaagcacgg tgacggtgtt  360
aaggacatca ccttcgaagt tgaagactgt gactctatcg ttcaaaaggc tagagaaaga  420
ggtgctaaga tcgttagaga accatgggtt gaacaagaca agttcggtaa ggttaagttc  480
gctgttttgc aaacctacgg tgacaccacc cacaccttgg ttgaaaaggt taactacacc  540
ggtagattct tgccaggttt cgaagctcca gttatgaccg acccattgtt gtctaagttg  600
ccaaactgtc acttggaaat catcgaccac atcgttggta accaaccaga ccaagaaatg  660
gtttctgctt ctgaatggta cttgaagaac ttgcaattcc acagattctg gtctgttgac  720
gacaagcaag ttcacaccga atactcttct ttgagatctg ttgttgttgc taactacgaa  780
gaatctatca agatgccaat caacgaacca gctccaggta agaagaagtc tcaaatccaa  840
gaattcgttg aatacaacgg tggtgctggt gttcaacaca tcgctttgaa gacccaagac  900
atcatcacct ctatcagaca cttgagagaa agaggtaccg aattcttggc tgttccatct  960
```

-continued

```
acctactaca agcaaatcag agaaaagttg aagaccgcta agatcaaggt taaggaaaac  1020
atcgacatct tggaagaatt gagaatcttg gttgactacg acgaaaaggg ttacttgttg  1080
caaatcttca ccaagccaat gcaagacaga ccaaccttgt tcttggaaat catccaaaga  1140
cacaaccacc aaggtttcgg tgctggtaac ttcaacgctt tgttcaaggc tttcgaagaa  1200
gaacaagact tgagaggtaa cttgatcgac gttaacacca acggtgttgt tccaggtatg  1260

SEQ ID NO: 287          moltype = DNA  length = 1179
FEATURE                 Location/Qualifiers
source                  1..1179
                        mol_type = unassigned DNA
                        organism = Manis javanica
SEQUENCE: 287
atgaccacct actctgacaa gggtcaaaag ccagaaaagg gtagattctt gcacttccac  60
tctgttacct tctgggttgg taacgctaag caagctgctt ctttctactg ttctaagatg  120
ggtttcgaac cattggctta caagggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttcaagaa  360
ccatgggttg aacaagacaa gttcggtaag gttaagttcg ctgttttgca aacctacggt  420
gacaccaccc acaccttggt tgaaaagatg aactacaccg gtagattctt gccaggtttc  480
gaagctccaa ccttcaagga cccattgttg tctaagttgc caaactgtaa cttggaaatc  540
atcgaccaca tcgttggtaa ccaaccagac caagaaatgg tttctgcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcgctgc tatcagacac  840
ttgagagaaa gaggtatgga attcttggct gttccaccaa cctactacaa gcaattgaga  900
gaaaacttga agttggctaa gatccaagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaagctaa cggtatggtt tctggtatg                        1179

SEQ ID NO: 288          moltype = DNA  length = 1179
FEATURE                 Location/Qualifiers
source                  1..1179
                        mol_type = unassigned DNA
                        organism = Sturnira hondurensis
SEQUENCE: 288
atgaccacct actctgacaa gggtgctaag ccacaaagag gtagattctt gcacttccac  60
tctgttacct tctgggttgg taacgctaag caagctgctt ctttctactg ttctaagatg  120
ggtttcgaac cattggctta caagggtttg gaaaccggtt ctagagaagt tgtttctcac  180
gttatcagac aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aaaaggacaa gttcggtaag gttaagttcg ctgttttgca aacctacggt  420
gacaccaccc acaccttggt tgaaaagatg aactacaccg gtagattctt gccaggtttc  480
gaagctccaa cctacgttga cccacacttg gctaagttgc cagactgtaa cttggaaatc  540
atcgaccaca tcgttggtaa ccaaccagac caagaaatgg tttctgcttc tgaatggtac  600
ttgagaaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccacgaca tcatcaccgc tatcagacac  840
ttgagagaaa gaggtatgga attcttggct gttccatcta cctactacag acaattgaga  900
gaaggtttga agtctgctaa gatccaagtt aaggaatcta tcgacgcttt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaactcttt gttcaaggct ttcgaagaag aacaagcttt gagaggtaac  1140
ttgaccgact tggaaaccaa cggtgttgct ttgggtatg                        1179

SEQ ID NO: 289          moltype = DNA  length = 1173
FEATURE                 Location/Qualifiers
source                  1..1173
                        mol_type = unassigned DNA
                        organism = Talpa occidentalis
SEQUENCE: 289
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttatcaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaacaag gtgctaagat cgttagagaa  360
ccatgggttg aacaagacaa gttcggtaag gttaagttcg ctgttttgca aacctacggt  420
gacaccaccc acaccttggt tgaaaagatg aactacaccg gtagattctt gccaggtttc  480
gaagctccaa ccttcaagga cccattgttg tctaagttgc caaagtgttc tttggaaatc  540
atcgaccaca tcgttggtaa ccaaccagac caagaaatgg ttccagcttc tgaatggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtag aaagaagtct caaatccaag aatacgttga ctacaacggt  780
```

-continued

```
ggtgctggtg ttcaacacat cgctttgaag accgaagaca tcatcatggc tatcagacac  840
ttgagagaaa gaggtatgga attcttggct gttccatcta cctactacag acaattgaga  900
gaaaacttga agaccgctaa gatccaagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagaa gaaaccacca aggtttcggt  1080
gctggtaact tcaactcttt gttcaaggct ttcgaagaag aacaagactt gagaggtaac  1140
ttgaccgact tggaaccaaa cggtgttgtt tct                               1173

SEQ ID NO: 290         moltype = DNA  length = 1179
FEATURE                Location/Qualifiers
source                 1..1179
                       mol_type = unassigned DNA
                       organism = Choloepus didactylus
SEQUENCE: 290
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgtttctcac  180
gttgttaagc aaggtaagat cgttttcgtt ttgtcttctg ctttgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaagat cgttagagaa  360
ccatgggttg aagaagacaa gttcggtaag gttaagttcg ctgttttgca aacctacggt  420
gacaccaccc acaccttggt tgaaaagatg aactacaccg gtagattctt gccaggtttc  480
gaagctccaa ccttcatgga cccattgttg tctaagttgc catcttgtac cttggaaatc  540
atcgaccaca tcgttggtaa ccaaccagac caagaaatgt tgtctgcttc tgactggtac  600
ttgaagaact tgcaattcca cagattctgg tctgttgacg acacccaagt tcacaccgaa  660
tactcttctt tgagatctat cgttgttgct aactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaaggc tatcagacac  840
ttgagagaaa gaggtatgga attcttggct gttccatctg cttactacag acaattgaga  900
gaaaacttga agaccgctaa gatcagagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaactcttt gttcaaggct ttcgaagaag aacaagactt gagaggtaac  1140
ttgaccgacg ttgaaaccaa cggtttggtt agaggtatg                         1179

SEQ ID NO: 291         moltype = DNA  length = 1179
FEATURE                Location/Qualifiers
source                 1..1179
                       mol_type = unassigned DNA
                       organism = Chlorocebus sabaeus
SEQUENCE: 291
atgaccacct actctgacaa gggtgctaag ccagaaagag gtagattctt gcacttccac  60
tctgttacct tctgggttgg taacgctaag caagctgctg ctttctactg ttctaagatg  120
ggtttcgaac cattggctta cagaggtttg gaaaccggtt ctagagaagt tgcttctcac  180
gttatcaagc aaggtcaaat cgttttcgtt ttgtcttctc cattgaaccc atggaacaga  240
gaaatgggtg aacacttggt taagcacggt gactctgtta aggacatcgc tttcgaagtt  300
gaagactgtg actacatcgt tcaaaaggct agagaaagag gtgctaaggt tgttagagaa  360
ccatgggttg aagaagacaa gttcggtaag gttaagttgg ctgttttgca aacctacggt  420
gacaccaccc acaccttggt tgaaaagatg tctttctctg gttctttctt gccaggtttc  480
gaagctccaa gagttaagga ctctttgttg tctaagttgc catcttgtgg tttggaaacc  540
atcgaccaca tcgttggtaa ccaaccagac caagaaatgg tttctgcttc tgaatggtac  600
ttgagaaact tgcaattcca cagattctgg tctgttgacg actctcaagt tcacaccgaa  660
tactctgctt tgagatctat cgttgttacc aactacgaag aatctatcaa gatgccaatc  720
aacgaaccag ctttgggtag aaagaagtct caaatccaag aatacgttga atacaacggt  780
ggtgctggtg ttcaacacat cgctttgaag accccagaca tcatcacctc tatcagacac  840
ttgagagaaa gaggtgttga attcttggct gttccatcta cctactacaa gcaattgaga  900
gaaaacttga agtctgctaa gatcagagtt aaggaatcta tcgacatgtt ggaagaattg  960
aagatcttgg ttgactacga cgaaaagggt tacttgttgc aagttttcac caagccagtt  1020
caagacagac caaccttgtt cttggaagtt atccaaagac acaaccacca aggtttcggt  1080
gctggtaact tcaacgcttt gttcaaggct ttcgaagctg aacaagactt gagaggtaac  1140
ttgaccgaca ccgaaaccaa cggtgttgtt tctggtgtt                         1179

SEQ ID NO: 292         moltype = DNA  length = 1179
FEATURE                Location/Qualifiers
source                 1..1179
                       mol_type = unassigned DNA
                       organism = Chlorocebus sabaeus
SEQUENCE: 292
atgaccacct actctgacaa gggtgctaag ccagaaagag gtagattctt gcacttccac  60
tctgttacct tctgggttgg taacgctaag caagctgctg ctttctactg ttctaagatg  120
ggtttcgaac cattggctta cagaggtttg gaaaccggtt ctagagaagt tgcttctcac  180
gttatcaagc aaggtcaaat cgttttcgtt ttgtcttctc cattgaaccc atggaacaga  240
gaaatgggtg aacacttggc taagcacggt gactctgtta aggacatcgg tttcgaagtt  300
gaagactgtg actacatcgt tcaaaaggct agagaaagag gtgctaaggt tgttagagaa  360
ccatgggttg aacaagacaa gttcggtaag gttaagttcg ctgttttgca aacctacggt  420
gacaccaccc acaccttggt tgaaaaggtt aactactctg gttctttctt gccaggtttc  480
gaagctccaa gagctaagga cccattgttg gctaagttgc catcttgttc tttggaaatg  540
atcgaccaca tcgttggtaa ccaaccagac caagaaatgg tttctgcttc tgaatggtac  600
ttgagatctt tgcaattcca cagattctgg tctgttgacg acacccaagt tcacaccgaa  660
```

```
tactcttctt tgagatctat cgttgttacc aactacgaag aatctatcaa gatgccaatc  720
aacgaaccag ctccaggtaa gaagaagtct caaatccaag aatacgttga ctacaacggt  780
ggtgctggtg ttcaacacat cgctttgggt acccaagaca tcatcacctc tatcagacac  840
ttgagagaaa gaggtgttga attcttggct gttccatcta cctactacaa gcaattgaga  900
gaaaacttga agtctgctaa ggttcaagtt aaggaatcta tcgacatgtt ggaagaattg  960
aagatcttgg ttgactacga cgaaaagggt tacttgttgc aaatcttcac caagccagtt  1020
caagacagac caaccttgtt cttggaagtt atccaaagac acaaccacca aggtttcggt  1080
gctggtaact tcaacgcttt gttcaaggct ttcgaagctg aacaagactt gagaggtaac  1140
ttgaccgacg ttgaaaccaa cggtgttgaa tctggtttg                         1179

SEQ ID NO: 293         moltype = DNA  length = 1230
FEATURE                Location/Qualifiers
source                 1..1230
                       mol_type = unassigned DNA
                       organism = Arvicola amphibius
SEQUENCE: 293
atgccatggc caccaggtac cgtttcttgg gaagctagac caagaccagc tatgaccacc  60
tactctgaca agggtgaaaa gccagaaaga ggtagattct tgcacttcca ctctgttacc  120
ttctgggttg gtaacgctaa gcaagctgct gctttctact gttctaagat gggtttcgaa  180
ccattggctt acagaggttt ggaaaccggt tctagagaag ttgcttctca cgttatcaag  240
caaggtcaaa tcgttttcgt tttctcttct ccattgaacc caggtaacaa ggaattgggt  300
gaccacttgg ttaagcacgg tgacggtgtt aaggacatcg ctttcgaagt tgaagactgt  360
gactacatcg ttcaaaaggc tagagaaaga ggtgctaagg ttgttagaga accatgggtt  420
gaacaagaca gattcggtaa ggttaagttc gctgttttgc aaacctacgg tgacaccacc  480
cacaccttgg ttgaaaagac cggttacacc ggttctttct tgccaggttt cgaagctcca  540
agagttaagg actctttgtt gtctaagttg ccaaactgtg gtttggaaat catcgaccac  600
gttgttggta accaaccaga ccaagaaatg ttgtctgctt ctgaatggta cttgaagaac  660
ttgcaattcc acagattctg gtctgttgac gacacccaag ttcacaccga atactcttct  720
ttgagatcta tcgttgttac caactacgaa gaatctatca agatgccaat caacgaacca  780
gctccaggta gaaagaagtc tcaaatccaa gaatacgttg actacaacgg tggtgctggt  840
gttcaacaca tcgctttgaa gacccaagac atcatcaccg ctatcagaca cttgagagaa  900
agaggtgctg aattcttggc tgttccatct acctactaca agcaattgag agaaaacttg  960
aagtctgcta aggttcaagt taaggaaaac atcgacatgt tggaagaatt gagaatcttg  1020
gttgactacg acgaaaaggg ttacttgttg caaatcttca ccaagccaat gcaagacaga  1080
ccaaccttgt tcttggaagt tatccaaaga cacaaccacc aaggtttcgg tgctggtaac  1140
ttcaacgctt tgttcaaggc tttcgaagct gaacaagact tgagaggtaa cttgaccgac  1200
ttggaaccaa acggtgttgc ttctggtatg                                   1230

SEQ ID NO: 294         moltype = DNA  length = 1179
FEATURE                Location/Qualifiers
source                 1..1179
                       mol_type = unassigned DNA
                       organism = Tachyglossus aculeatus
SEQUENCE: 294
atgaccacct actctgacaa gggtgctaag ccagaaagag gtagattctt gcacttccac  60
tctgttacct tctgggttgg taacgctaag caagctgctt ctttctactg ttctaagatg  120
ggtttcgaac cattggctta cagaggtttg gaaaccggtt ctagagaagt tgcttctcac  180
gttatcaagc aaggtcaaat cgttttcgtt ttctcttctc cattgaaccc atggaacaag  240
gaaatgggtg accacttggt taagcacggt gacggtgtta aggacatcgc tttcgaagtt  300
gaagactgtg actacatcgt tcaaaaggct agagaaagag gtgctaaggt tgttagagaa  360
ccatgggttg aacaagacaa gtctggtaag gttaagttcg ctgttttgca aacctacggt  420
gacaccaccc acaccttggt tgaaaagacc ggttactctg gttctttctt gccaggtttc  480
gaagctgcta gagctaagga ctctttgttg tctaagttgc catcttgtgg tttggaaatc  540
atcgaccaca tcgttggtaa ccaaccagac caagaaatgt tgtctgcttc tgaatggtac  600
ttgagaaact tgcaattcca cagattctgg tctgttgacg acacccaagt tcacaccgaa  660
tactcttctt tgagatctat cgttgttacc gactacgaag aatctatcaa gatgccaatc  720
aacgaaccag ctccaggtaa gaagaagtct caaatccaag aatacgttga ctacaacggt  780
ggtgctggtg ttcaacacat cgctttgaag acccaagaca tcatcaccgc tatcagacac  840
ttgagagaaa gaggtgctga attcttggct gttccatctt cttactacac ccaattgaga  900
gaaaacttga agtctgctaa ggttagagtt aaggaaaaca tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagctg aacaagactt gagaggtaac  1140
ttgaccgact tggaaaccaa cggtgttgct tctggtatg                         1179

SEQ ID NO: 295         moltype = DNA  length = 1179
FEATURE                Location/Qualifiers
source                 1..1179
                       mol_type = unassigned DNA
                       organism = Canis lupus
SEQUENCE: 295
atgaccacct actctgacaa gggtgctaag ccagaaagag gtagattctt gcacttccac  60
tctgttacct tctgggttgg taacgctaag caagctgctg cttactactg ttctaagatg  120
ggtttcgaat tgttggctta cagaggtttg gaaaccggtt ctagagaagt tgcttctcac  180
gttatcaagc aaggtcaaat cgttttcgtt ttctcttctc cattgaaccc atggaacaag  240
gaaatgggtg accacttggt taagcacggt gacggtgtta aggacatcgc tttcgaagtt  300
caagactgtg actacatcgt tcaaaaggct agagaaagag gtgctaaggt tgttagagaa  360
ccatgggttg aacaagacaa gttcggtaag gttaagttcg ctgttttgca aacctacggt  420
gacaccaccc acaccttggt tgaaaagatg tcttacaccg gttctttctt gccaggtttc  480
```

```
gaagctccaa gagttaagga cgctttgttg ttcaagttgc catcttgtgg tttggaaatc  540
atcgaccaca tcgttggtaa ccaaccagac caagaaatgg cttctgcttc tgaatggtac  600
ttgagaaact tgcaattcca cagattctgg tctgttgacg acacccaagt tcacaccgaa  660
tactcttctt tgagatctat cgttgttacc aactacgaag aatctatcaa gatgccaatc  720
aacgaaccag ctccaggtag aaagaagtct caaatccaag aatacgttga ctacaacggt  780
ggtgctggtg ttcaacacat cgctttgaag acccaagaca tcatcaccgc tatcagacac  840
ttgagagaaa gaggtgctga attcttggct gttccatctt cttactacag acaattgaga  900
gaaaacttga agtctgctaa ggttagagtt aaggaatcta tcgacgtttt ggaagaattg  960
aagatcttgg ttgactacga cgaaaagggt tacttgttgc aaatcttcac caagccaatg  1020
caagacagac caaccttgtt cttggaagtt atccaaagac acaaccacca aggtttcggt  1080
gctggtaact tcaacgcttt gttcaaggct ttcgaagctg aacaagactt gagaggtaac  1140
ttgaccgact tggaaaccaa cggtgaagtt tctggtatg                         1179

SEQ ID NO: 296         moltype = DNA  length = 1182
FEATURE                Location/Qualifiers
source                 1..1182
                       mol_type = unassigned DNA
                       organism = Eschrichtius robustus
SEQUENCE: 296
atgaccacct actctgacaa gggtgttaag ccagaaagag gtagattctt gcacttccac  60
tctgttacct tctgggttgg taacgctaag caagctgctt ctttctactg ttctaagatg  120
ggtttcaagc cattggctta cagaggtttg gaaaccggtt ctagagaagt tgtttctcac  180
gttatcaagc acggtaagat cgttttcgtt ttgtcttctg ctttgaaccc atggaacaag  240
gaaatgggtg accacttggt taagcacggt gacggtgtta aggacatcgc tttcgaagtt  300
gaagactgta actacatcgt tcaaaaggct agagaaagag gtgctaagat cgttagagaa  360
ccatgggttg aacaagacaa gtgtggtaga gttaagttcg ctgttttgca aacctacggt  420
gacaccaccc acaccttggt tgaaaagatc aactacaccg gttgtttctt gccaggtttc  480
gaagctccaa ccttcatgga cccattgttg tctaagttgc catcttgtaa cttggaaatc  540
atcgaccaca tcgttggtaa ccaaccagac caagaaatgg cttctgcttc tgaatggtac  600
ttgaagaact tgcaattcca cagattctgg tctgttgacg acacccaagt tcacaccgaa  660
tactcttctt tgagatctat cgttgttacc aactacgaag aatctatcaa gatgccaatc  720
aacgaaccag ctccaggtaa gaagaagtct caaatccaag aatacgttga ctacaacggt  780
ggtgctggtg ttcaacacat cgctttgaga acccaagaca tcatcaccgc tatcagacac  840
ttgaaggaaa gaggtatgga attcttggct gttccatcta cctactacaa gcaattgaga  900
gaaaagttga agtctgctaa ggttcaagtt aaggaatcta tcgacgtttt ggaagaattg  960
aagatcttgg ttgactacga cgaaaagggt tacttgttgc aaatcttcac caagccagtt  1020
caagacagac caaccttgtt cttggaagtt atccaaagaa acaaccacca aggtttcggt  1080
gctggtaact tcaactcttt gttcaaggct ttcgaagaag aacaaaactt gagaggtaac  1140
ttgaccgact tggaatctaa ccaaccaggt agagctagac ac                      1182

SEQ ID NO: 297         moltype = AA  length = 571
FEATURE                Location/Qualifiers
source                 1..571
                       mol_type = protein
                       organism = Bacillus subtilis
SEQUENCE: 297
MLTKATKEQK SLVKNRGAEL VVDCLVEQGV THVFGIPGAK IDAVFDALQD KGPEIIVARH  60
EQNAAFMAQA VGRLTGKPGV VLVTSGPGAS NLATGLLTAN TEGDPVVALA GNVIRADRLK  120
RTHQSLDNAA LFQPITKYSV EVQDVKNIPE AVTNAFRIAS AGQAGAAFVS FPQDVVNEVT  180
NTKNVRAVAA PKLGPAADDA ISAAIAKIQT AKLPVVLVGM KGGRPEAIKA VRKLLKKVQL  240
PFVETYQAAG TLSRDLEDQY FGRIGLFRNQ PGDLLLEQAD VVLTIGYDPI EYDPKFWNIN  300
GDRTIIHLDE IIADIDHAYQ PDLELIGDIP STINHIEHDA VKVEFAEREQ KILSDLKQYM  360
HEGEQVPADW KSDRAHPLEI VKELRNAVDD HVTVTCDIGS HAIWMSRYFR SYEPLTLMIS  420
NGMQTLGVAL PWAIGASLVK PGEKVVSVSG DGGFLFSAME LETAVRLKAP IVHIVWNDST  480
YDMVAFQQLK KYNRTSAVDF GNIDIVKYAE SFGATGLRVE SPDQLADVLR QGMNAEGPVI  540
IDVPVDYSDN INLASDKLPK EFGELMKTKA L                                 571

SEQ ID NO: 298         moltype = AA  length = 571
FEATURE                Location/Qualifiers
source                 1..571
                       mol_type = protein
                       organism = Bacillus subtilis
SEQUENCE: 298
MLTKATKEQK SLVKNRGAEL VVDCLVEQGV THVFGIPGAK IDAVFDALQD KGPEIIVARH  60
EQNAAFMAQA VGRLTGKPGV VLVTSGPGAS NLATGLLTAN TEGDPVVALA GNVIRADRLK  120
RTHQSLDNAA LFQPITKYSV EVQDVKNIPE AVTNAFRIAS AGQAGAAFVS FPQDVVNEVT  180
NTKNVRAVAA PKLGPAADDA ISAAIAKIQT AKLPVVLVGM KGGRPEAIKA VRKLLKKVQL  240
PFVETYQAAG TLSRDLEDQY FGRIGLFRNQ PGDLLLEQAD VVLTIGYDPI EYDPKFWNIN  300
GDRTIIHLDE IIADIDHAYQ PDLELIGDIP STINHIEHDA VKVEFAEREQ KILSDLKQYM  360
HEGEQVPADW KSDRAHPLEI VKELRNAVDD HVTVTCDIGS HAIWMSRYFR SYEPLTLMIS  420
NGMQTLGVAL PWAIGASLVK PGEKVVSVSG DGGFLFSAME LETAVRLKAP IVHIVWNDST  480
YDMVAFAQLK KYNRTSAVDF GNIDIVKYAE SFGATGLRVE SPDQLADVLR QGMNAEGPVI  540
IDVPVDYSDN INLASDKLPK EFGELMKTKA L                                 571

SEQ ID NO: 299         moltype = AA  length = 561
FEATURE                Location/Qualifiers
source                 1..561
                       mol_type = protein
                       organism = Trichoderma atroviride
```

```
SEQUENCE: 299
MTKDTVDILI DSLKAAGVKY VFGVPGAKID SVFNALIDHP DIKLVVCRHE QNAAFIAAAM  60
GKVTGRPGVC IATSGPGTSN LVTGLVTATD EGAPVVAIVG SVKRSQSLQR THQSLRGADL  120
LAPVTKKVVS AVVEDQVAEI MLDAFRVAAA SPPGATAVSL PIDLMTPAKS TSTVTAFPAE  180
CFIPPKYGKS PETTLQAAAD LISAAKAPVL FLGMRVSESD DTISAVHGFL RKHPVPVVET  240
FQAAGAISKE LVHLFYGRIG LFSNQPGDQL LQHADLVIAI GLDQAEYDAN MWNARGTTIL  300
HVDIQPADFV AHYKPKIELV GSLADNMTDL TSRLDTVARL QLTKPGEAIR TNMWEWQNSP  360
EASGRSTGPV HPLHFIRLFQ SIIDPSTTVI SDVGSVYIWL CRYFYSYARR TFLMSNVQQT  420
LGVAMPWAIG VSLSQTPPSS KKVVSISGDG GFMFSSQELV TAVQQGCNIT HFIWNDGKYN  480
MVEFQEVNKY GRSSGVDLGG VDFVKLADSM GAKGLRVSSA GDLEAVMKEA LAYDGVCLVD  540
IEIDYSQNHN LMMDLVTSDV S                                           561

SEQ ID NO: 300         moltype = AA  length = 687
FEATURE                Location/Qualifiers
source                 1..687
                       mol_type = protein
                       organism = Saccharomyces cerevisiae
SEQUENCE: 300
MIRQSTLKNF AIKRCFQHIA YRNTPAMRSV ALAQRFYSSS SRYYSASPLP ASKRPEPAPS  60
FNVDPLEQPA EPSKLAKKLR AEPDMDTSFV GLTGGQIFNE MMSRQNVDTV FGYPGGAILP  120
VYDAIHNSDK FNFVLPKHEQ GAGHMAEGYA RASGKPGVVL VTSGPGATNV VTPMADAFAD  180
GIPMVVFTGQ VPTSAIGTDA FQEADVVGIS RSCTKWNVMV KSVEELPLRI NEAFEIATSG  240
RPGPVLVDLP KDVTAAILRN PIPTKTTLPS NALNQLTSRA QDEFVMQSIN KAADLINLAK  300
KPVLYVGAGI LNHADGPRLL KELSDRAQIP VTTTLQGLGS FDQEDPKSLD MLGMHGCATA  360
NLAVQNADLI IAVGARFDDR VTGNISKFAP EARRAAAEGR GGIIHFEVSP KNINKVVQTQ  420
IAVEGDATTN LGKMMSKIFP VKERSEWFAQ INKWKKEYPY AYMEETPGSK IKPQTVIKKL  480
SKVANDTGRH VIVTTGVGQH QMWAAQHWTW RNPHTFITSG GLGTMGYGLP AAIGAQVAKP  540
ESLVIDIDGD ASFNMTLTEL SSAVQAGTPV KILILNNEEQ GMVTQWQSLF YEHRYSHTHQ  600
LNPDFIKLAE AMGLKGLRVK KQEELDAKLK EFVSTKGPVL LEVEVDKKVP VLPMVAGGSG  660
LDEFINFDPE VERQQTELRH KRTGGKH                                     687

SEQ ID NO: 301         moltype = AA  length = 491
FEATURE                Location/Qualifiers
source                 1..491
                       mol_type = protein
                       organism = Escherichia coli
SEQUENCE: 301
MANYFNTLNL RQQLAQLGKC RFMGRDEFAD GASYLQGKKV VIVGCGAQGL NQGLNMRDSG  60
LDISYALRKE AIAEKRASWR KATENGFKVG TYEELIPQAD LVINLTPDKQ HSDVVRTVQP  120
LMKDGAALGY SHGFNIVEVG EQIRKDITVV MVAPKCPGTE VREEYKRGFG VPTLIAVHPE  180
NDPKGEGMAI AKAWAAATGG HRAGVLESSF VAEVKSDLMG EQTILCGMLQ AGSLLCFDKL  240
VEEGTDPAYA EKLIQFGWET ITEALKQGGI TLMMDRLSNP AKLRAYALSE QLKEIMAPLF  300
QKHMDDIISG EFSSGMMADW ANDDKKLLTW REETGKTAFE TAPQYEGKIG EQEYFDKGVL  360
MIAMVKAGVE LAFETMVDSG IIEESAYYES LHELPLIANT IARKRLYEMN VVISDTAEYG  420
NYLFSYACVP LLKPFMAELQ PGDLGKAIPE GAVDNGQLRD VNEAIRSHAI EQVGKKLRGY  480
MTDMKRIAVA G                                                      491

SEQ ID NO: 302         moltype = AA  length = 342
FEATURE                Location/Qualifiers
source                 1..342
                       mol_type = protein
                       organism = Bacillus subtilis
SEQUENCE: 302
MVKVYYNGDI KENVLAGKTV AVIGYGSQGH AHALNLKESG VDVIVGVRQG KSFTQAQEDG  60
HKVFSVKEAA AQAEIIMVLL PDEQQQKVYE AEIKDELTAG KSLVFAHGFN VHFHQIVPPA  120
DVDVFLVAPK GPGHLVRRTY EQGAGVPALF AIYQDVTGEA RDKALAYAKG IGGARAGVLE  180
TTFKEETETD LFGEQAVLCG GLSALVKAGF ETLTEAGYQP ELAYFECLHE LKLIVDLMYE  240
EGLAGMRYSI SDTAQWGDFV SGPRVVDAKV KESMKEVLKD IQNGTFAKEW IVENQVNRPR  300
FNAINASENE HQIEVVGRKL REMMPFVKQG KKKEAVVSVA QN                    342

SEQ ID NO: 303         moltype = AA  length = 395
FEATURE                Location/Qualifiers
source                 1..395
                       mol_type = protein
                       organism = Saccharomyces cerevisiae
SEQUENCE: 303
MLRTQAARLI CNSRVITAKR TFALATRAAA YSRPAARFVK PMITTRGLKQ INFGGTVETV  60
YERADWPREK LLDYFKNDTF ALIGYGSQGY GQGLNLRDNG LNVIIGVRKD GASWKAAIED  120
GWVPGKNLFT VEDAIKRGSY VMNLLSDAAQ SETWPAIKPL LTKGKTLYFS HGFSPVFKDL  180
THVEPPKDLD VILVAPKGSG RTVRSLFKEG RGINSSYAVW NDVTGKAHEK AQALAVAIGS  240
GYVYQTTFER EVNSDLYGER GCLMGGIHGM FLAQYDVLRE NGHSPSEAFN ETVEEATQSL  300
YPLIGKYGMD YMYDACSTTA RRGALDWYPI FKNALKPVFQ DLYESTKNGT ETKRSLEFNS  360
QPDYREKLEK ELDTIRNMEI WKVGKEVRKL RPENQ                             395

SEQ ID NO: 304         moltype = AA  length = 570
FEATURE                Location/Qualifiers
source                 1..570
                       mol_type = protein
                       organism = Lactococcus lactis
```

```
SEQUENCE: 304
MEFKYNGKVE SVELNKYSKT LTQDPTQPAT QAMYYGIGFK DEDFKKAQVG IVSMDWDGNP  60
CNMHLGTLGS KIKSSVNQTD GLIGLQFHTI GVSDGIANGK LGMRYSLVSR EVIADSIETN  120
AGAEYYDAIV AIPGCDKNMP GSIIGMARLN RPSIMVYGGT IEHGEYKGEK LNIVSAFESL  180
GQKITGNISD EDYHGVICNA IPGQGACGGM YTANTLAAAI ETLGMSLPYS SSNPAVSQEK  240
QEECDEIGLA IKNLLEKDIK PSDIMTKEAF ENAITIVMVL GGSTNAVLHI IAMANAIGVE  300
ITQDDFQRIS DITPVLGDFK PSGKYMMEDL HKIGGLPAVL KYLLKEGKLH GDCLTVTGKT  360
LAENVETALD LDFDSQDIMR PLKNPIKATG HLQILYGNLA QGGSVAKISG KEGEFFKGTA  420
RVFDGEQHFI DGIESGRLHA GDVAVIRNIG PVGGPGMPEM LKPTSALIGA GLGKSCALIT  480
DGRFSGGTHG FVVGHIVPEA VEGGLIGLVE DDDIIEIDAV NNSISLKVSD EEIAKRRANY  540
QKPTPKATRG VLAKFAKLTR PASEGCVTDL                                  570

SEQ ID NO: 305         moltype = AA  length = 640
FEATURE                Location/Qualifiers
source                 1..640
                       mol_type = protein
                       organism = Neurospora crassa
SEQUENCE: 305
MASNQDNKAV APDAAAPAGQ STTTTTTNDN SERNLPKEGE YIQWRTLPAG NPDQLNRWSH  60
FLTREHEFPG AQAMLYGAGV PNKDMMKKAP HVGIATVWWE GNPCNTHLLD LGQKVKKAVE  120
REKMLAWQFN TIGVSDGITM GGEGMRYSLQ SREIIADSIE TVTCAQHHDA NISIPGCDKN  180
MPGVIMAAAR HNRPFVMIYG GTMRGGHSEL LDRPINIVTC YEASGAYTYG RLKPACPNST  240
ATPSDVMDDI EQHACPGAGA CGGMYTANTM ATAIEAMGLT APGSSSFPAS SPEKFRECEK  300
AAEYIKICME KDIRPRDLLT KASFENALVL TMILGGSTNG VLHYLAMANS ADVDLTLDDI  360
NRVSAKTPFL ADMAPSGRYY MEDLYKVGGT PAVLKMLIAA GYIDGTIPTI TGKSLAENVS  420
DWPSLDPDQK IIRPLDNPIK SQGHIRVLYG NFSPGGAVAK ITGKEGLSFT GKARCFNKEF  480
ELDAALKNSE ITLEQGNQVL IVRYEGPKGG PGMPEQLKAS AAIMGAGLTN VALVTDGRYS  540
GASHGFIVGH VVPEAATGGP IALVKDGDLI TIDAVRNRID VVKTVEGVEG EEEIAKVLEE  600
RKKGWKAPKM KPTRGALAKY ARLVGDASHG AVTDLGGDAY                       640

SEQ ID NO: 306         moltype = AA  length = 616
FEATURE                Location/Qualifiers
source                 1..616
                       mol_type = protein
                       organism = Escherichia coli
SEQUENCE: 306
MPKYRSATTT HGRNMAGARA LWRATGMTDA DFGKPIIAVV NSFTQFVPGH VHLRDLGKLV  60
AEQIEAAGGV AKEFNTIAVD DGIAMGHGGM LYSLPSRELI ADSVEYMVNA HCADAMVCIS  120
NCDKITPGML MASLRLNIPV IFVSGGPMEA GKTKLSDQII KLDLVDAMIQ GADPKVSDSQ  180
SDQVERSACP TCGSCSGMFT ANSMNCLTEA LGLSQPGNGS LLATHADRKQ LFLNAGKRIV  240
ELTKRYYEQN DESALPRNIA SKAAFENAMT LDIAMGGSTN TVLHLLAAAQ EAEIDFTMSD  300
IDKLSRKVPQ LCKVAPSTQK YHMEDVHRAG GVIGILGELD RAGLLNRDVK NVLGLTLPQT  360
LEQYDVMLTQ DDAVKNMFRA GPAGIRTTQA FSQDCRWDTL DDDRANGCIR SLEHAYSKDG  420
GLAVLYGNFA ENGCIVKTAG VDDSILKFTG PAKVYESQDD AVEAILGGKV VAGDVVVIRY  480
EGPKGGPGMQ EMLYPTSFLK SMGLGKACAL ITDGRFSGGT SGLSIGHVSP EAASGGSIGL  540
IEDGDLIAID IPNRGIQLQV SDAELAARRE AQDARGDKAW TPKNRERQVS FALRAYASLA  600
TSADKGAVRD KSKLGG                                                 616

SEQ ID NO: 307         moltype = AA  length = 585
FEATURE                Location/Qualifiers
source                 1..585
                       mol_type = protein
                       organism = Saccharomyces cerevisiae
SEQUENCE: 307
MGLLTKVATS RQFSTTRCVA KKLNKYSYII TEPKGQGASQ AMLYATGFKK EDFKKPQVGV  60
GSCWWSGNPC NMHLLDLNNR CSQSIEKAGL KAMQFNTIGV SDGISMGTKG MRYSLQSREI  120
IADSFETIMM AQHYDANIAI PSCDKNMPGV MMAMGRHNRP SIMVYGGTIL PGHPTCGSSK  180
ISKNIDIVSA FQSYGEYISK QFTEEERED VEHACPGPGS CGGMYTANTM ASAAEVLGLT  240
IPNSSSFPAV SKEKLAECDN IGEYIKKTME LGILPRDILT KEAFENAITY VVATGGSTNA  300
VLHLVAVAHS AGVKLSPDDF QRISDTTPLI GDFKPSGKYV MADLINVGGT QSVIKYLYEN  360
NMLHGNTMTV TGDTLAERAK KAPSLPEGQE IIKPLSHPIK ANGHLQILYG SLAPGGAVGK  420
ITGKEGTYFK GRARVFEEEG AFIEALERGE IKKGEKTVVV IRYEGPRGAP GMPEMLKPSS  480
ALMGYGLGKD VALLTDGRFS GGSHGFLIGH IVPEAAEGGP IGLVRDGDEI IIDADNNKID  540
LLVSDKEMAQ RKQSWVAPPP RYTRGTLSKY AKLVSNASNG CVLDA                  585

SEQ ID NO: 308         moltype = AA  length = 616
FEATURE                Location/Qualifiers
source                 1..616
                       mol_type = protein
                       organism = Corynebacterium glutamicum
SEQUENCE: 308
MSPNDAFISA PAKIETPVGP RNEGQPAWNK QRGSSMPVNR YMPFEVEVED ISLPDRTWPD  60
KKITVAPQWC AVDLRDGNQA LIDPMSPERK RRMFELLVQM GFKEIEVGFP SASQTDFDFV  120
REIIEKGMIP DDVTIQVLVQ AREHLIRRTF EACEGAKNVI VHFYNSTSIL QRNVVFRMDK  180
VQVKKLATDA AELIKTIAQD YPDTNWRWQY SPESFTGTEV EYAKEVVDAV VEVMDPTPEN  240
PMIINLPSTV EMITPNVYAD SIEWMHRNLN RRDSIILSLH PHNDRGTGVG AAELGYMAGA  300
DRIEGCLFGN GERTGNVCLV TLALNMLTQG VDPQLDFTDI RQIRSTVEYC NQLRVPERHP  360
YGGDLVFTAF SGSHQDAVNK GLDAMAAKVQ PGASSTEVSW EQLRDTEWEV PYLPIDPKDV  420
GRDYEAVIRV NSQSGKGGVA YIMKTDHGLQ IPRSMQVEFS TVVQNVTDAE GGEVNSKAMW  480
```

```
DIFATEYLER TAPVEQIALR VENAQTENED ASITAELIHN GKDVTVDGHG NDPLAAYANA  540
LEKLGIDVEI QEYNQHARTS GDDAEAAAYV LAEVNGRKVW GVGIAGSITY ASLKAVTSAV  600
NRALDVNHEA VLAGGV                                                   616

SEQ ID NO: 309         moltype = AA  length = 616
FEATURE                Location/Qualifiers
source                 1..616
                       mol_type = protein
                       organism = Corynebacterium glutamicum
SEQUENCE: 309
MSPNDAFISA PAKIETPVGP RNEGQPAWNK QRGSSMPVNR YMPFEVEVED ISLPDRTWPD  60
KKITVAPQWC AVDLRDGNQA LIDPMSPERK RRMFELLVQM GFKEIEVGFP SASQTDFDFV  120
REIIEKDMIP DDVTIQVLVQ AREHLIRRTF EACEGAKNVI VHFYNSTSIL QRNVVFRMDK  180
VQVKKLATDA AELIKTVAQD YPDTNWRWQY SPESFTGTEV EYAKEVVDAV VEVMDPTPEN  240
PMIINLPSTV EMITPNVYAD SIEWMHRNLN RRDSIILSLH PHNDRGTGVG AAELGYMAGA  300
DRIEGCLFGN GERTGNVCLV TLALNMLTQG VDPQLDFTDI RQIRSTVEYC NQLRVPERHP  360
YGGDLVFTAF SGSHQDAVNK GLDAMAAKVQ PGASSTEVSW EQLRDTEWEV PYLPIDPKDV  420
GRDYEAVIRV NSQSGKGGVA YIMKTDHGLQ IPRSMQVEFS TVVQNVTDAE GGEVNSKAMW  480
DIFATEYLER TAPVEQIALR VENAQTENED ASITAELIHN GKDVTVDGHG NGPLAAYANA  540
LEKLGIDVEI QEYNQHARTS DDDAEAAAYV LAEVNGRKVW GVGIAGSITY ASLKAVTSAV  600
NRALDVNHEA VLAGGV                                                   616

SEQ ID NO: 310         moltype = AA  length = 616
FEATURE                Location/Qualifiers
source                 1..616
                       mol_type = protein
                       organism = Corynebacterium glutamicum
SEQUENCE: 310
MSPNDAFISA PAKIETPVGP RNEGQPAWNK QRGSSMPVNR YMPFEVEVED ISLPDRTWPD  60
KKITVAPQWC AVDLRDGNQA LIDPMSPERK RRMFELLVQM GFKEIEVGFP SASQTDFDFV  120
REIIEKGMIP DDVTIQVLVQ AREHLIRRTF EACEGAKNVI VHFYNSTSIL QRNVVFRMDK  180
VQVKKLATDA AELIKTIAQD YPDTNWRWQY SPESFTGTEV EYAKEVVDAV VEVMDPTPEN  240
PMIINLPSTV EMITPNVYAD SIEWMHRNLN RRDSIILSLH PHNDRGTGVG AAELGYMAGA  300
DRIEGCLFGN GERTGNVCLV TLALNMLTQG VDPQLDFTDI RQIRSTVEYC NQLRVPERHP  360
YGGDLVFTAF SGSHQDAVNK GLDAMAAKVQ PGASSTEVSW EQLRDTEWEV PYLPIDPKDV  420
GRDYEAVIRV NSQSGKGGVA YIMKTDHGLQ IPRSMQVEFS TVVQNVTDAE GGEVNSKAMW  480
DIFATEYLER TAPVEQIALR VENAQTENED ASITAELIHN GKDVTVDGRG NGPLAAYANA  540
LEKLGIDVEI QEDNQHARTS GDDAEAAAYV LAEVNGRKVW GVGIAGSITY ASLKAVTSAV  600
NRALDVNHEA VLAGGV                                                   616

SEQ ID NO: 311         moltype = AA  length = 616
FEATURE                Location/Qualifiers
source                 1..616
                       mol_type = protein
                       organism = Corynebacterium glutamicum
SEQUENCE: 311
MSPNDAFISA PAKIETPVGP RNEGQPAWNK QRGSSMPVNR YMPFEVEVED ISLPDRTWPD  60
KKITVAPQWC AVDLRDGNQA LIDPMSPERK RRMFELLVQM GFKEIEVGFP SASQTDFDFV  120
REIIEKDMIP DDVTIQVLVQ AREHLIRRTF EACEGAKNVI VHFYNSTSIL QRNVVFRMDK  180
VQVKKLATDA AELIKTVAQD YPDTNWRWQY SPESFTGTEV EYAKEVVDAV VEVMDPTPEN  240
PMIINLPSTV EMITPNVYAD SIEWMHRNLN RRDSIILSLH PHNDRGTGVG AAELGYMAGA  300
DRIEGCLFGN GERTGNVCLV TLALNMLTQG VDPQLDFTDI RQIRSTVEYC NQLRVPERHP  360
YGGDLVFTAF SGSHQDAVNK GLDAMAAKVQ PGASSTEVSW EQLRDTEWEV PYLPIDPKDV  420
GRDYEAVIRV NSQSGKGGVA YIMKTDHGLQ IPRSMQVEFS TVVQNVTDAE GGEVNSKAMW  480
DIFATEYLER TAPVEQIALR VENAQTENED ASITAELIHN GKDVTVDGHG NGPLAAYANA  540
LEKLGIDVEI QEYNQHAHTS DDDAEAAAYV LAEVNGRKVW GVGIAGSITY ASLKAVTSAV  600
NRALDVNHEA VLAGGV                                                   616

SEQ ID NO: 312         moltype = AA  length = 523
FEATURE                Location/Qualifiers
source                 1..523
                       mol_type = protein
                       organism = Escherichia coli
SEQUENCE: 312
MSQQVIIFDT TLRDGEQALQ ASLSVKEKLQ IALALERMGV DVMEVGFPVS SPGDFESVQT  60
IARQVKNSRV CALARCVEKD IDVAAESLKV AEAFRIHTFI ATSPMHIATK LRSTLDEVIE  120
RAIYMVKRAR NYTDDVEFSC EDAGRTPIAD LARVVEAAIN AGATTINIPD TVGYTMPFEF  180
AGIISGLYER VPNIDKAIIS VHTHDDLGLA VGNSLAAVHA GARQVEGAMN GIGERAGNCS  240
LEEVIMAIKV RKDILNVHTA INHQEIWRTS QLVSQICNMP IPANKAIVGS GAFAHSSGIH  300
QDGVLKNREN YEIMTPESIG LNQIQLNLTS RSGRAAVKHR MDEMGYKESE YNLDNLYDAF  360
LKLADKKGQV FDYDLEALAF IGKQQEEPEH FRLDYFSVQS GSNDIATAAV KLACGEEVKA  420
EAANGNGPVD AVYQAINRIT EYNVELVKYS LTAKGHGKDA LDQVDIVANY NGRRFHGVGL  480
ATDIVESSAK AMVHVLNNIW RAAEVEKELQ RKAQHNENNK ETV                     523

SEQ ID NO: 313         moltype = AA  length = 619
FEATURE                Location/Qualifiers
source                 1..619
                       mol_type = protein
                       organism = Saccharomyces cerevisiae
```

```
SEQUENCE: 313
MVKESIIALA EHAASRASRV IPPVKLAYKN MLKDPSSKYK PFNAPKLSNR KWPDNRITRA  60
PRWLSTDLRD GNQSLPDPMS VEQKKEYFHK LVNIGFKEIE VSFPSASQTD FDFTRYAVEN  120
APDDVSIQCL VQSREHLIKR TVEALTGAKK ATIHTYLATS DMFREIVFNM SREEAISKAV  180
EATKLVRKLT KDDPSQQATR WSYEFSPECF SDTPGEFAVE ICEAVKKAWE PTEENPIIFN  240
LPATVEVASP NVYADQIEYF ATHITEREKV CISTHCHNDR GCGVAATELG MLAGADRVEG  300
CLFGNGERTG NVDLVTVAMN MYTQGVSPNL DFSDLTSVLD VVERCNKIPV SQRAPYGGDL  360
VVCAFSGSHQ DAIKKGFNLQ NKKRAQGETQ WRIPYLPLDP KDIGRDYEAV IRVNSQSGKG  420
GAAWVILRSL GLDLPRNMQI EFSSAVQDHA DSLGRELKSD EISKLFKEAY NYNDEQYQAI  480
SLVNYNVEKF GTERRVFTGQ VKVGDQIVDI EGTGNGPISS LVDALSNLLN VRFAVANYTE  540
HSLGSGSSTQ AASYIHLSYR RNADNEKAYK WGVGVSEDVG DSSVRAIFAT INNIIHSGDV  600
SIPSLAEVEG KNAAASGSA                                              619

SEQ ID NO: 314         moltype = AA  length = 779
FEATURE                Location/Qualifiers
source                 1..779
                       mol_type = protein
                       organism = Saccharomyces cerevisiae
SEQUENCE: 314
MVYTPSKGPR TLYDKVFDAH VVHQDENGSF LLYIDRHLVH EVTSPQAFEG LENAGRKVRR  60
VDCTLATVDH NIPTESRKNF KSLDTFIKQT DSRLQVKTLE NNVKQFGVPY FGMSDARQGI  120
VHTIGPEEGF TLPGTTVVCG DSHTSTHGAF GSLAFGIGTS EVEHVLATQT IIQAKSKNMR  180
ITVNGKLSPG ITSKDLILYI IGLIGTAGGT GCVIEFAGEA IEALSMEARM SMCNMAIEAG  240
ARAGMIKPDE TTFQYTKGRP LAPKGAEWEK AVAYWKTLKT DEGAKFDHEI NIEAVDVIPT  300
ITWGTSPQDA LPITGSVPDP KNVTDPIKKS GMERALAYMG LEPNTPLKSI KVDKVFIGSC  360
TNGRIEDLRS AAAVVRGQKL ASNIKLAMVV PGSGLVKKQA EAEGLDKIFQ EAGFEWREAG  420
CSICLGMNPD ILDAYERCAS TSNRNFEGRQ GALSRTHLMS PAMAAAAGIA GHFVDIREFE  480
YKDQDQSSPK VEVTSEDEKE LESAAYDHAE PVQPEDAPQD IANDELKDIP VKSDDTPAKP  540
SSSGMKPFLT LEGISAPLDK ANVDTDAIIP KQFLKTIKRT GLKKGLFYEW RFRKDDQGKD  600
QETDFVLNVE PWREAEILVV TGDNFGCGSS REHAPWALKD FGIKSIIAPS YGDIFYNNSF  660
KNGLLPIRLD QQIIIDKLIP IANKGGKLCV DLPNQKILDS DGNVLVDHFE IEPFRKHCLV  720
NGLDDIGITL QKEEYISRYE ALRREKYSFL EGGSKLLKFD NVPKRKAVTT TFDKVHQDW   779

SEQ ID NO: 315         moltype = AA  length = 764
FEATURE                Location/Qualifiers
source                 1..764
                       mol_type = protein
                       organism = Pichia kudriavzevii
SEQUENCE: 315
MSTLYDKVFA DHVVHTDESG STLIYIDRHL VHEVTSPQAF EGLTTAGRSV RRPDCTLVTV  60
DHNIPTISRK NFKNVSTFIE QEDSRLQVET LEQNVKDFNL AYFGMSDDRQ GIVHVVGPEQ  120
GFTLPGTTVV CGDSHTSTHG AFGALAFGIG TSEVEHVLAT QTLIQAKSKN MLIRIDGDLK  180
PGITSKDLVL HVIGVIGTAG GTGSVIEFAG KAIRDLSMEA RMSICNMAIE AGARAGMIAP  240
DQITFDYIKG RPLAPQGEEW EKAVKYWKTL YSDENAKFDK EVIIKAEDIV PTITWGNSPQ  300
DALPITGKVP DPKDFKDDIT RSGVEAALEY MGLTANTPLQ EIPIDKVFIG SCTNSRIEDL  360
REAAKVVIGH KKAENVKLAL VVPGSGLVKK QAEKEGLDKI FQAAGFEWRE AGCSMCLGMN  420
PDILDPHERC ASTSNRNFRG RQGALSRTHL MSPAMAAAAG IVGHFTDIRN FKYNTSDAPQ  480
VQLSSGNEEE DKELQDALYE HEKEPIQTVD SSEEINDIPP NPANEPETAA VGGIEKFTIL  540
KSVAAPMERA NIDTDAIIPK QFLKTIKRTG LSKGLFYESR FVKDAQGNDV ATDFVLNVAP  600
FNKANIIVCT GDNFGCGSSR EHAPWALKDF GIKSIIAPSF GDIFYNNSFK NGLLPIRLPQ  660
SIIQEKIYPI AKAEKEITVD LVNQQIRGPD DEVLVEHFDV EPFRKHCLVN GLDDIGITLT  720
KSKFIDEFEA LRKNKFSFIE MGSRKYIPVK GAKKSPYGNT AQEW                  764

SEQ ID NO: 316         moltype = AA  length = 340
FEATURE                Location/Qualifiers
source                 1..340
                       mol_type = protein
                       organism = Corynebacterium glutamicum
SEQUENCE: 316
MKLAVIGGDG IGPEVTAEAL KVLNAVRDDI ETTDYDLGAR RYLKNGELLT DEDLASLREH  60
DAILLGAIGA PGSVPPGILE RGLLLKMRFA LDHHVNLRPS KLYDGVESPL RNPGKIDFVV  120
VREGTEGAYT GNGGAIRVGT PHEIANETSV NTRYGAERVI RYAFELAQSR RKKLTLVHKT  180
NVLVHGGGLW QRTVDEVAKE YPEVAVDYNH IDAATIYLVT DPSRFDVIVT DNLFGDILTD  240
EAGAVSGGIG LAASGNIDAT GTNPSMFEPV HGSAPDIAGQ GIADPTAAIL SAAMLLRHLG  300
DEDNAVRIET AIAADVAGRD NSQPISTTEV GDRIVKALQS                      340

SEQ ID NO: 317         moltype = AA  length = 364
FEATURE                Location/Qualifiers
source                 1..364
                       mol_type = protein
                       organism = Saccharomyces cerevisiae
SEQUENCE: 317
MSAPKKIVVL PGDHVGQEIT AEAIKVLKAI SDVRSNVKFD FENHLIGGAA IDATGVPLPD  60
EALEASKKAD AVLLGAVGGP KWGTGSVRPE QGLLKIRKEL QLYANLRPCN FASDSLLDLS  120
PIKPQFAKGT DFVVVRELVG GIYFGKRKED DGDGVAWDSE QYTVPEVQRI TRMAAFMALQ  180
HEPPLPIWSL DKANVLASSR LWRKTVEETI KNEFPTLKVQ HQLIDSAAMI LVKNPTHLNG  240
IIITSNMFGD IISDEASVIP GSLGLLPSAS LASLPDKNTA FGLYEPCHGS APDLPKNKVN  300
PIATILSAAM MLKLSLNLPE EGKAIEDAVK KVLDAGIRTG DLGGSNSTTE VGDAVAEEVK  360
KILA                                                              364
```

```
SEQ ID NO: 318          moltype = AA  length = 364
FEATURE                 Location/Qualifiers
source                  1..364
                        mol_type = protein
                        organism = Saccharomyces cerevisiae
SEQUENCE: 318
MSAPKKIVVL PGDHVGQEIT AEAIKVLKAI SDVRSNVKFD FENHLIGGAA IDATGVPLPD  60
EALEASKKAD AVLLGAVGGP KWGTGSVRPE QGLLKIRKEL QLYANLRPCN FASDSLLDLS  120
PIKPQFAKGT DFVVVRELVG GIYFGKRKED DGDGVAWDSE QYTVPEVQRI TRMAAFMALQ  180
HEPPLPIWSL DKANVLASSR LWRKTVEETI KNEFPTLKVQ HQLIDSAAMI LVKRPTHLNG  240
IIITSNMFGD IISDEASVIP GSLGLLPSAS LASLPDKNTA FGLYEPCHGS APKYPKNKVN  300
PIATILSAAM MLKLSLNLPE EGKAIEDAVK KVLDAGIRTG DLGGSNSTTE VGDAVAEEVK  360
KILA                                                              364

SEQ ID NO: 319          moltype = AA  length = 363
FEATURE                 Location/Qualifiers
source                  1..363
                        mol_type = protein
                        organism = Escherichia coli
SEQUENCE: 319
MSKNYHIAVL PGDGIGPEVM TQALKVLDAV RNRFAMRITT SHYDVGGAAI DNHGQPLPPA  60
TVEGCEQADA VLFGSVGGPK WEHLPPDQQP ERGALLPLRK HFKLFSNLRP AKLYQGLEAF  120
CPLRADIAAN GFDILCVREL TGGIYFGQPK GREGSGQYEK AFDTEVYHRF EIERIARIAF  180
ESARKRRHKV TSIDKANVLQ SSILWREIVN EIATEYPDVE LAHMYIDNAT MQLIKDPSQF  240
DVLLCSNLFG DILSDECAMI TGSMGMLPSA SLNEQGFGLY EPAGGSAPDI AGKNIANPIA  300
QILSLALLLR YSLDADDAAC AIERAINRAL EEGIRTGDLA RGAAAVSTDE MGDIIARYVA  360
EGV                                                               363

SEQ ID NO: 320          moltype = AA  length = 373
FEATURE                 Location/Qualifiers
source                  1..373
                        mol_type = protein
                        organism = Arabidopsis thaliana
SEQUENCE: 320
MAVASPGKKR YTITLLPGDG IGPEVVSIAK NVLQQAGSLE GVEFNFREMP IGGAALDLVG  60
VPLPEETISA AKESDAVLLG AIGGYKWDNN EKHLRPEKGL LQIRAALKVF ANLRPATVLP  120
QLVDASTLKR EVAEGVDLMV VRELTGGIYF GEPRGIKTNE NGEEVGFNTE VYAAHEIDRI  180
ARVAFETARK RRGKLCSVDK ANVLEASILW RKRVTALASE YPDVELSHMY VDNAAMQLVR  240
DPKQFDTIVT NNIFGDILSD EASMITGSIG MLPSASLSDS GPGLFEPIHG SAPDIAGQDK  300
ANPLATILSA AMLLKYGLGE EKAAKRIEDA VLVALNNGFR TGDIYSAGTK LVGCKEMGEE  360
VLKSVDSQVP ASV                                                    373

SEQ ID NO: 321          moltype = DNA  length = 38
FEATURE                 Location/Qualifiers
source                  1..38
                        mol_type = unassigned DNA
                        organism = Synthetic primer
SEQUENCE: 321
gacctcgcgt taaccctctt gtgtccaccc ttcataag                        38

SEQ ID NO: 322          moltype = DNA  length = 39
FEATURE                 Location/Qualifiers
source                  1..39
                        mol_type = unassigned DNA
                        organism = Synthetic primer
SEQUENCE: 322
ccttcctcaa attgctgtgg aagagggtct ctcaccatg                       39

SEQ ID NO: 323          moltype = DNA  length = 41
FEATURE                 Location/Qualifiers
source                  1..41
                        mol_type = unassigned DNA
                        organism = Synthetic primer
SEQUENCE: 323
gaccctcttc cacagcaatt tgaggaagga ataggagaag g                    41

SEQ ID NO: 324          moltype = DNA  length = 30
FEATURE                 Location/Qualifiers
source                  1..30
                        mol_type = unassigned DNA
                        organism = Synthetic primer
SEQUENCE: 324
tgtgtttgtt tgtgtgtttt gtgtgttttg                                 30

SEQ ID NO: 325          moltype = DNA  length = 53
FEATURE                 Location/Qualifiers
source                  1..53
                        mol_type = unassigned DNA
```

```
                        organism = Synthetic primer
SEQUENCE: 325
gtatagcata cattatacga agttatcatg tatgcatggc tggctatatt ttg        53

SEQ ID NO: 326          moltype = DNA  length = 42
FEATURE                 Location/Qualifiers
source                  1..42
                        mol_type = unassigned DNA
                        organism = Synthetic primer
SEQUENCE: 326
catgataact tcgtataatg tatgctatac gaacggtatt gc                    42

SEQ ID NO: 327          moltype = DNA  length = 25
FEATURE                 Location/Qualifiers
source                  1..25
                        mol_type = unassigned DNA
                        organism = Synthetic primer
SEQUENCE: 327
catggcttga attacatttt caagg                                       25

SEQ ID NO: 328          moltype = DNA  length = 19
FEATURE                 Location/Qualifiers
source                  1..19
                        mol_type = unassigned DNA
                        organism = Synthetic primer
SEQUENCE: 328
gccggtatcg tccttcttg                                              19

SEQ ID NO: 329          moltype = DNA  length = 27
FEATURE                 Location/Qualifiers
source                  1..27
                        mol_type = unassigned DNA
                        organism = Synthetic primer
SEQUENCE: 329
cctctaaagg gccacaattt tttaatc                                     27

SEQ ID NO: 330          moltype = DNA  length = 21
FEATURE                 Location/Qualifiers
source                  1..21
                        mol_type = unassigned DNA
                        organism = Synthetic primer
SEQUENCE: 330
cattgatgtt gccgttgcag c                                           21

SEQ ID NO: 331          moltype = DNA  length = 25
FEATURE                 Location/Qualifiers
source                  1..25
                        mol_type = unassigned DNA
                        organism = Synthetic primer
SEQUENCE: 331
ggtgcagtaa cgaggtagtt taacc                                       25

SEQ ID NO: 332          moltype = DNA  length = 25
FEATURE                 Location/Qualifiers
source                  1..25
                        mol_type = unassigned DNA
                        organism = Synthetic primer
SEQUENCE: 332
cgatggcgtc atacaaagaa agatc                                       25

SEQ ID NO: 333          moltype = DNA  length = 24
FEATURE                 Location/Qualifiers
source                  1..24
                        mol_type = unassigned DNA
                        organism = Synthetic primer
SEQUENCE: 333
gccaccagga tagaattgga tgag                                        24

SEQ ID NO: 334          moltype = DNA  length = 26
FEATURE                 Location/Qualifiers
source                  1..26
                        mol_type = unassigned DNA
                        organism = Synthetic primer
SEQUENCE: 334
ccatcgtttt attggattct tatagg                                      26

SEQ ID NO: 335          moltype = AA  length = 393
FEATURE                 Location/Qualifiers
REGION                  1..393
```

-continued

```
                          note = Engineered protein
source                    1..393
                          mol_type = protein
                          organism = synthetic construct
SEQUENCE: 335
MTTYSNKGPK PERGRFLHFH SVTFWVGNAK QAASFYCNKM GFEPLAYKGL ETGSREVVSH  60
VIKQGKIVFV LCSALNPWNK EMGDHLVKHG DGVKDIAFEV EDCEHIVQKA RERGAKIVRE  120
PWVEEDKFGK VKFAVLQTYG DTTHTLVEKI NYTGRFLPGF EAPTYKDTLL PKLPSCNLEI  180
IDHIVGNQPD QEMESASEWY LKNLQFHRFW SVDDTQVHTE YSSLRSIVVA NYEESIKMPI  240
NEPAPGRKKS PIQEYVDYNG GAGVQHIALR TEDIITTIRH LRERGMEFLA VPSSYYRLLR  300
ENLKTSKIQV KENMDVLEEL KILVDYDEKG YLLQIFTKPM QDRPTLFLEV IQRHNHQGFG  360
AGNFNSLFKA LEEEQALRGN LTDLETNGVR SGM                              393
```